(12) United States Patent
Goodacre et al.

(10) Patent No.: US 7,855,216 B2
(45) Date of Patent: Dec. 21, 2010

(54) AZA-INDOLYL COMPOUNDS AND METHODS OF USE

(75) Inventors: Simon Charles Goodacre, Harlow (GB); Karen Williams, Harlow (GB); Stephen Price, Harlow (GB); Hazel Joan Dyke, Harlow (GB); John Gary Montana, Harlow (GB); Mark S. Stanley, Pacifica, CA (US); Liang Bao, Daly City, CA (US); Wendy Lee, San Ramon, CA (US)

(73) Assignee: Genentech, Inc., South San Francisco, CA (US)

( * ) Notice: Subject to any disclaimer, the term of this patent is extended or adjusted under 35 U.S.C. 154(b) by 76 days.

(21) Appl. No.: 11/947,656

(22) Filed: Nov. 29, 2007

(65) Prior Publication Data

US 2008/0242655 A1  Oct. 2, 2008

Related U.S. Application Data

(60) Provisional application No. 60/944,743, filed on Jun. 18, 2007, provisional application No. 60/917,620, filed on May 11, 2007, provisional application No. 60/868,055, filed on Nov. 30, 2006.

(51) Int. Cl.
| | |
|---|---|
| *C07D 471/04* | (2006.01) |
| *A61K 31/437* | (2006.01) |
| *A61P 29/00* | (2006.01) |
| *A61P 35/00* | (2006.01) |
| *C07D 487/04* | (2006.01) |
| *A61K 31/519* | (2006.01) |
| *A61K 31/5025* | (2006.01) |

(52) U.S. Cl. .......... 514/300; 514/248; 514/265.1; 544/235; 544/253; 546/113

(58) Field of Classification Search .......... 546/113; 514/303, 300

See application file for complete search history.

(56) References Cited

U.S. PATENT DOCUMENTS

| 2005/0058481 | A1* | 3/2005 | Christiansen et al. | .......... 400/70 |
| 2009/0181941 | A1* | 7/2009 | Leblanc et al. | .......... 514/210.21 |

FOREIGN PATENT DOCUMENTS

| WO | WO03/091215 | | 11/2003 |
| WO | WO2005/023251 | | 3/2005 |
| WO | WO 2006/002051 | * | 1/2006 |
| WO | WO 2006/100095 | * | 3/2006 |
| WO | WO 2007/070393 | * | 6/2007 |

OTHER PUBLICATIONS

Kanth, et al., Heterocycles (2005), 65(6), 1415-1423.*

* cited by examiner

*Primary Examiner*—James O Wilson
*Assistant Examiner*—Cecilia M Jaisle
(74) *Attorney, Agent, or Firm*—Brian L. Buckwalter

(57) ABSTRACT

The invention relates to azaindolyl compounds of Formula I with anti-cancer and/or anti-inflammatory activity and more specifically to azaindolyl compounds which inhibit MEK kinase activity. The invention provides compositions and methods useful for inhibiting abnormal cell growth or treating a hyperproliferative disorder, or treating an inflammatory disease in a mammal. The invention also relates to methods of using the compounds for in vitro, in situ, and in vivo diagnosis or treatment of mammalian cells, or associated pathological conditions.

22 Claims, No Drawings

AZA-INDOLYL COMPOUNDS AND METHODS OF USE

CROSS REFERENCE TO RELATED APPLICATIONS

This application claims priority under 35 U.S.C. §119(e), U.S. Provisional Application No. 60/868,055 filed Nov. 30, 2006, and U.S. Provisional Application No. 60/917,620 filed May 11, 2007, and U.S. Provisional Application No. 60/944, 743, filed Jun. 18, 2007, which are incorporated herein by reference.

FIELD OF THE INVENTION

The invention relates to azaindolyl compounds with anti-cancer activity and more specifically to azaindolyl compounds which inhibit MEK kinase activity. The invention also relates to methods of using the compounds for in vitro, in situ, and in vivo diagnosis or treatment of mammalian cells, or associated pathological conditions.

BACKGROUND OF THE INVENTION

In the quest to understand how Ras transmits extracellular growth signals, the MAP (mitogen-activated protein) kinase (MAPK) pathway has emerged as the crucial route between membrane-bound Ras and the nucleus. The MAPK pathway encompasses a cascade of phosphorylation events involving three key kinases, namely Raf, MEK (MAP kinase kinase) and ERK (MAP kinase). Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). Overall, treatment of cells with growth factors leads to the activation of ERK1 and 2 which results in proliferation and, in some cases, differentiation (Lewis et al., *Adv. Cancer Res.* 1998, 74, 49-139).

There has been strong evidence that genetic mutations and/or overexpression of protein kinases involved in the MAP kinase pathway lead to uncontrolled cell proliferation and, eventually, tumor formation, in proliferative diseases. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science* 1993, 260, 1834-1837). Recently, bRaf mutations have been identified in more than 60% of malignant melanoma (Davies, H. et al., *Nature* 2002, 417, 949-954). These mutations in bRaf result in a constitutively active MAP kinase cascade. Studies of primary tumor samples and cell lines have also shown constitutive or over-activation of the MAP kinase pathway in cancers of pancreas, colon, lung, ovary and kidney (Hoshino, R. et al., *Oncogene* 1999, 18, 813-822).

MEK has emerged as an attractive therapeutic target in the MAP kinase cascade pathway. MEK, downstream of Ras and Raf, is highly specific for the phosphorylation of MAP kinase; in fact, the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5 (7), 810-816); Trachet et al., AACR Apr. 6-10, 2002, Poster #5426; Tecle, H. IBC 2.sup.nd International Conference of Protein Kinases, Sep. 9-10, 2002), block static allodynia in animals (WO 01/05390 published Jan. 25, 2001) and inhibit growth of acute myeloid leukemia cells (Milella et al., *J Clin Invest* 2001, 108 (6), 851-859).

Several small molecule MEK inhibitors have also been discussed in, for example, WO02/06213, WO 03/077855 and WO03/077914. There still exists a need for new MEK inhibitors as effective and safe therapeutics for treating a variety of proliferative disease states, such as conditions related to the hyperactivity of MEK, as well as diseases modulated by the MEK cascade.

SUMMARY OF THE INVENTION

The invention relates generally to azaindolyl compounds of Formula I (and/or solvates, hydrates and/or salts thereof) with anti-cancer and/or anti-inflammatory activity, and more specifically with MEK kinase inhibitory activity. Certain hyperproliferative and inflammatory disorders are characterized by the modulation of MEK kinase function, for example by mutations or overexpression of the proteins. Accordingly, the compounds of the invention and compositions thereof are useful in the treatment of hyperproliferative disorders such as cancer and/or inflammatory diseases such as rheumatoid arthritis.

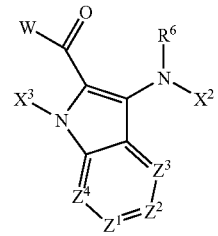

I wherein:
$Z^1$ is $CR^1$ or N;
$Z^2$ is $CR^2$ or N;
$Z^3$ is $CR^3$ or N;
$Z^4$ is $CR^4$ or N;
where one or two of $Z^1$, $Z^2$, $Z^3$, and $Z^4$ are N;
$R^1$, $R^2$, $R^3$ and $R^4$ are independently selected from H, halo, CN, $CF_3$, $-OCF_3$, $-NO_2$, $-(CR^{14}R^{14})_nC(=Y)R^{11}$, $-(CR^{14}R^{15})_nC(=Y)OR^{11}$, $-(CR^{14}R^{15})_nC(=Y)NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y)R^{11}$, $-(CR^{14}R^{15})_nNR^{12}C(=Y)OR^{11}$, $-(CR^{14}R^{15})_nNR^{13}C(=Y)NR^{11}R^{12}$, $-(CR^{14}R^{15})_nNR^{12}SO_2R^{11}$, $-(CR^{14}R^{15})_nOC(=Y)R^{11}$, $-(CR^{14}R^{15})_nOC(=Y)OR^{11}$, $-(CR^{14}R^{15})_nOC(=Y)NR^{11}R^{12}$, $-(CR^{14}R^{15})_nOS(O)_2(OR^{11})$, $-(CR^{14}R^{15})_nOP —(=Y)(OR$^{11}$)(OR$^{12}$), —(CR$^{14}$R$^{15}$)$_n$OP(OR$^{11}$)(OR$^{12}$), —(CR$^{14}$R$^{15}$)$_n$S(O)R$^{11}$, —(CR$^{14}$R$^{15}$)S(O)$_2$R$^{11}$, —(CR$^{14}$R$^{15}$)$_n$S(O)$_2$NR$^{11}$R$^{12}$, —(CR$^{14}$R$^{15}$)$_n$S(O)(OR$^{11}$), —(CR$^{14}$R$^{15}$)$_n$S(O)$_2$(OR$^{11}$), —(CR$^{14}$R$^{15}$)$_n$SC(=Y)R$^{11}$, —(CR$^{14}$R$^{15}$)$_n$SC(=Y)OR$^{11}$, —(CR$^{14}$R$^{15}$)$_n$SC(=Y) NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

W is

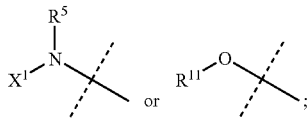

or

R$^5$ and R$^6$ are independently selected from H or C$_1$-C$_{12}$ alkyl;

X$^1$ is selected from R$^{11}$, —OR$^{11}$, —NR$^{11}$R$^{12}$, —S(O)R$^{11}$, and —S(O)$_2$R$^{11}$; when X$^1$ is R$^{11}$ or —OR$^{11}$, R$^{11}$ or —OR$^{11}$ of X$^1$ is optionally taken together with —N—R$^5$ of W to form a 4-7 membered saturated or unsaturated ring having 0-2 additional heteroatoms selected from O, S and N, wherein said ring is optionally substituted with one or more groups selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y') OR$^{16}$, —(CR$^{19}$R$^{20}$)$_n$C(=Y')NR$^{16}$R$^{17}$, —(CR$^{19}$R$^{20}$)$_n$ NR$^{16}$R$^{17}$, —(CR$^{19}$R$^{20}$)$_n$OR$^{16}$, —(CR$^{19}$R$^{20}$)$_n$—SR$^{16}$, —(CR$^{19}$R$^{20}$)$_n$NR$^{16}$C(=Y')R$^{17}$, —(CR$^{19}$R$^{20}$)$_n$NR$^{16}$C(=Y') OR$^{17}$, —(CR$^{19}$R$^{20}$)$_n$NR$^{18}$C(=Y')NR$^{16}$R$^{17}$, —(CR$^{19}$R$^{20}$)$_n$ NR$^{17}$SO$_2$R$^{16}$, —(CR$^{19}$R$^{20}$)$_n$OC(=Y')R$^{16}$, —(CR$^{19}$R$^{20}$)$_n$ OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y') (OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y') NR$^{16}$R$^{17}$, and R$^{21}$;

X$^2$ is selected from carbocyclyl, heterocyclyl, aryl, and heteroaryl;

X$^3$ is selected from H, —(CR$^{23}$R$^{24}$)$_p$R$^{12}$, —(CR$^{23}$R$^{24}$)$_q$ NR$^{11}$R$^{12}$, —(CR$^{23}$R$^{24}$)$_q$OR$^{12}$, —(CR$^{23}$R$^{24}$)$_p$C(O)NR$^{11}$R$^{12}$, —(CR$^{23}$R$^{24}$)$_q$NR$^{11}$C(O)R$^{12}$, —(CR$^{23}$R$^{24}$)$_p$S(O)$_2$NR$^{11}$R$^{12}$, and —(CR$^{23}$R$^{24}$)$_q$NR$^{11}$S(O)$_2$R$^{12}$;

R$^{11}$, R$^{12}$ and R$^{13}$ are independently H, C$_1$-C$_{12}$ alkyl, C$_2$-C$_8$ alkenyl, C$_2$-C$_8$ alkynyl, carbocyclyl, heterocyclyl, aryl, or heteroaryl, or R$^{11}$ and R$^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, CF$_3$, —OCF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O) NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{14}$ and R$^{15}$ are independently selected from H, C$_1$-C$_{12}$ alkyl, aryl, carbocyclyl, heterocyclyl, and heteroaryl;

m and n are independently selected from 0, 1, 2, 3, 4, 5, or 6;

p is 0, 1, 2, or 3;

q is 2 or 3;

Y is independently O, NR$^{11}$, or S;

wherein each said alkyl, alkenyl, alkynyl, carbocyclyl, heterocyclyl, aryl and heteroaryl of R$^1$, R$^2$, R$^3$, R$^4$, R$^5$, R$^6$, X$^1$, X$^2$, R$^{11}$, R$^{12}$, R$^{13}$, R$^{14}$, and R$^{15}$ is independently optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y') OR$^{16}$, —(CR$^{19}$R$^{20}$)$_n$C(=Y')NR$^{16}$R$^{17}$, —(CR$^{19}$R$^{20}$)$_n$ NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y') OR$^{17}$, —(CR$^{19}$R$^{20}$)$_n$NR$^{18}$C(=Y')NR$^{16}$R$^{17}$, —(CR$^{19}$R$^{20}$)$_n$ NR$^{17}$SO$_2$R$^{16}$, —(CR$^{19}$R$^{20}$)$_n$OC(=Y')R$^{16}$—(CR$^{19}$R$^{20}$)$_n$OC (=Y')OR$^{16}$, —(CR$^{19}$R$^{20}$)$_n$OC(=Y')NR$^{16}$R$^{17}$, —(CR$^{19}$R$^{20}$)$_n$ OS(O)$_2$(OR$^{16}$), —(CR$^{19}$R$^{20}$)$_n$OP(=Y') (OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$—(CR$^{19}$R$^{20}$)$_n$SC(=Y')OR$^{16}$, —(CR$^{19}$R$^{20}$)$_n$SC(=Y') NR$^{16}$R$^{17}$, and R$^{21}$;

each R$^{16}$, R$^{17}$ and R$^{18}$ is independently H, C$_1$-C$_{12}$ alkyl, C$_2$-C$_8$ alkenyl, C$_2$-C$_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC (O)N(C$_1$-C$_6$ alkyl)$_2$, —OC(O)O(C$_1$-C$_6$ alkyl), —NHC(O) NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C (O)O(C$_1$-C$_6$ alkyl);

or R$^{16}$ and R$^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O) NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{19}$ and R$^{20}$ are independently selected from H, C$_1$-C$_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, oxo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

each Y' is independently O, NR$^{22}$, or S;

$R^{22}$ is H or $C_1$-$C_{12}$ alkyl; and $R^{23}$ and $R^{24}$ are independently H or $C_1$-$C_6$ alkyl wherein said alkyl is optionally substituted with one or more groups selected from halo, CN, CF$_3$, —OCF$_3$, —NO$_2$, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl).

The present invention includes a composition (e.g., a pharmaceutical composition) comprising a compound of Formula I (and/or solvates, hydrates and/or salts thereof) and a carrier (a pharmaceutically acceptable carrier). The present invention also includes a composition (e.g., a pharmaceutical composition) comprising a compound of Formula I (and/or solvates, hydrates and/or salts thereof) and a carrier (a pharmaceutically acceptable carrier), further comprising a second chemotherapeutic and/or a second anti-inflammatory agent. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of Formula I (and/or solvates and salts thereof) or a composition thereof, alone or in combination with a second chemotherapeutic agent.

The present invention includes a method of treating an inflammatory disease in a mammal (e.g., human) comprising administering to said mammal a therapeutically effective amount of a compound of Formula I (and/or solvates and salts thereof) or a composition thereof, alone or in combination with a second anti-inflammatory agent.

The present invention includes a method of using the present compounds for in vitro, in situ, and in vivo diagnosis or treatment of mammalian cells, organisms, or associated pathological conditions.

DETAILED DESCRIPTION OF EXEMPLARY EMBODIMENTS

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3, 4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "halo" refers to F, Cl, Br or I. The heteroatoms present in heteroaryl or heterocyclcyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "chemotherapeutic agent" is a compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASEL (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

The term "inflammatory diseases" as used in this application includes, but not limited to, rheumatoid arthritis, atherosclerosis, congestive hear failure, inflammatory bowel disease (including, but not limited to, Crohn's disease and ulcerative colitis), chronic obstructive pulmonary disease in the lung, fibrotic disease in the liver and kidney, Crohn's disease, lupus, skin diseases such as psoriasis, eczema and scleroderma, osteoarthritis, multiple sclerosis, asthma, diseases and disorders related to diabetic complications, fibrotic organ failure in organs such as lung, liver, kidney, and inflammatory complications of the cardiovascular system such as acute coronary syndrome.

An "anti-inflammatory agent" is a compound useful in the treatment of inflammation. Examples of anti-inflammatory agents include injectable protein therapeutics such as Enbrel®, Remicade®, Humira® and Kineret®. Other examples of anti-inflammatory agents include non-steroidal anti-inflammatory agents (NSAIDs), such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as Remicade® (infliximab) and Enbrel® (etanercept); fibroblast growth factors; platelet derived growth factors; enzyme blockers such as Arava® (leflunomide); and/or a cartilage protecting agent such as hyaluronic acid, glucosamine, and chondroitin.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the MEK inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and trialkylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention" and "compounds of the present invention" and "compounds of Formula I", unless otherwise indicated, include compounds of Formula I and stereoisomers, geometric isomers, tautomers, solvates, metabolites, salts (e.g., pharmaceutically acceptable salts) and prodrugs thereof.

The present invention provides azaindolyl compounds of Formula I as described above useful as kinase inhibitors, particularly useful as MEK kinase inhibitors. The present invention includes compounds of Formulae I-a, I-b, I-c, I-d, I-e, I-f, I-g, I-h, I-i, II-a, II-b, II-c, II-d, II-e, II-f, II-g, II-h, II-i, III-a, III-b, III-c, III-d, III-e, III-f, III-g, III-h, and III-i, and all other variables are as defined in Formula I.

I-a
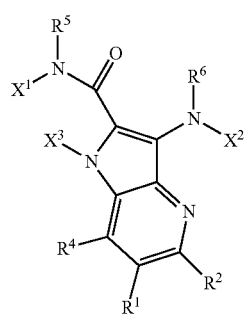

I-b
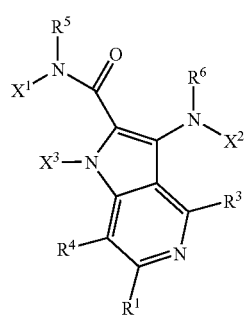

I-c
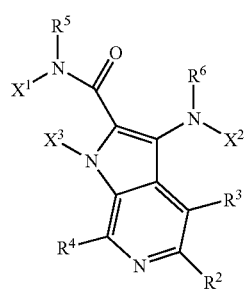

-continued

I-d
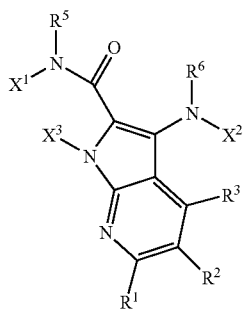

I-e
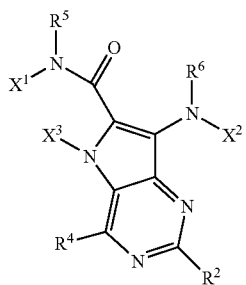

I-f
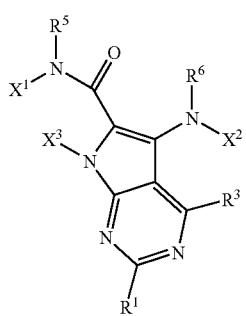

I-g
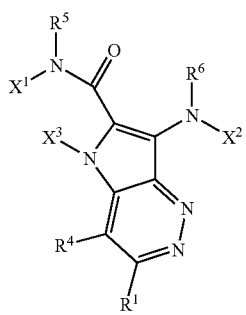

I-h
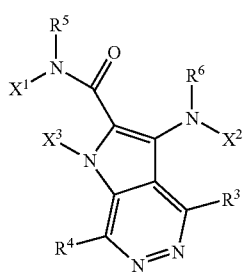

-continued
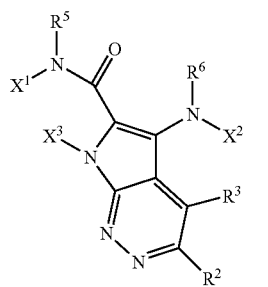
I-i
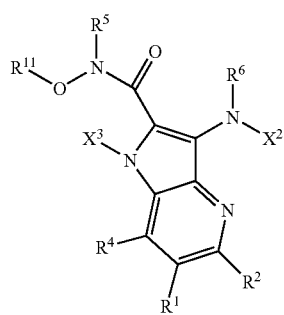
II-a
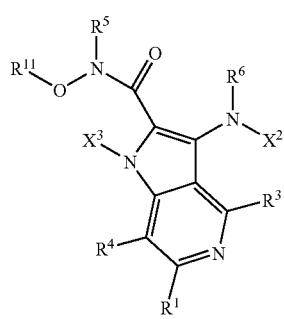
II-b
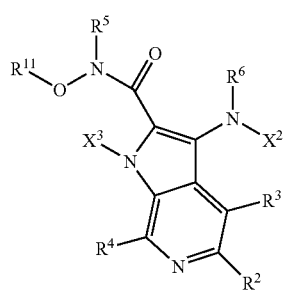
II-c
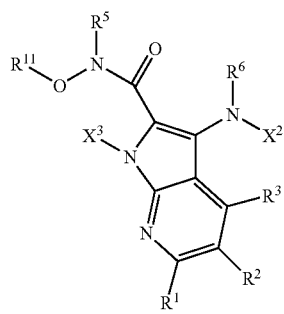
II-d
-continued
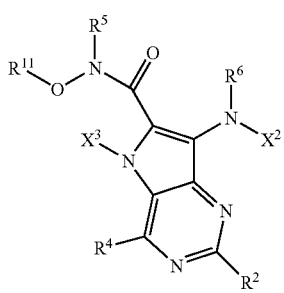
II-e
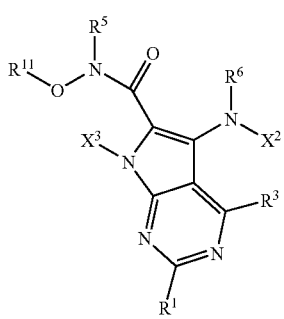
II-f
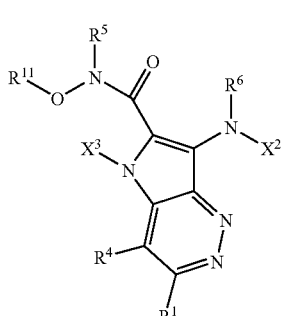
II-g
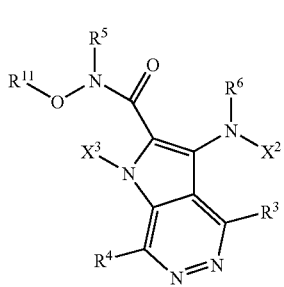
II-h
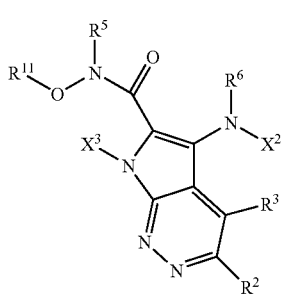
II-i

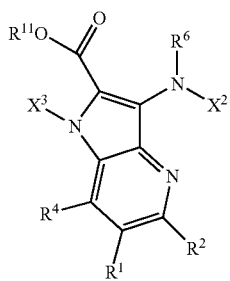

III-a

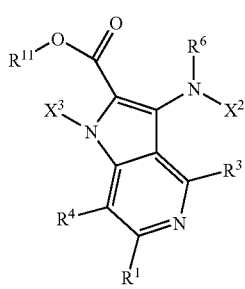

III-b

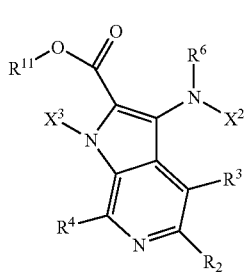

III-c

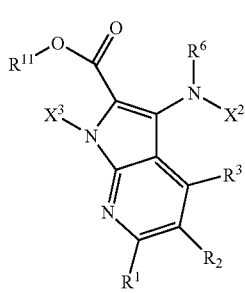

III-d

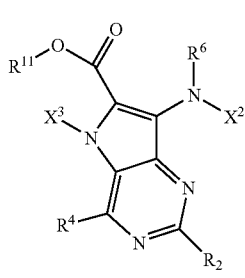

III-e

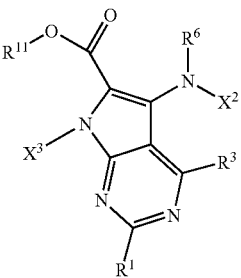

III-f

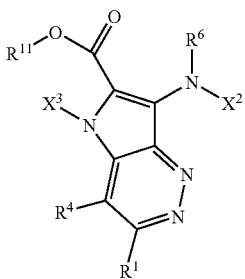

III-g

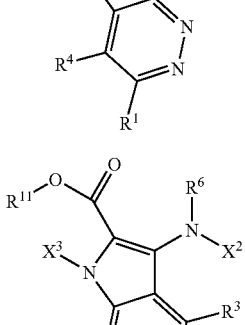

III-h

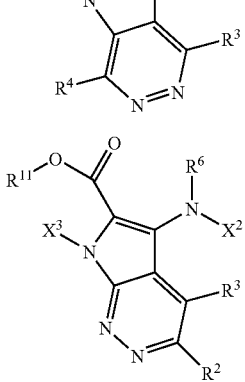

III-i

In an embodiment of the present invention, compounds are of Formulae I-b, I-f, I-g, I-h, II-b, II-f, II-g, II-h, III-b, III-f, III-g, or III-h, and all other variables are as defined in Formula I.

In an embodiment of the present invention, $R^1$ is H, halo, CN, $CF_3$, $-NR^{11}R^{12}$, $-OR^{11}$, $-SR^{11}$, $-C(=O)NR^{11}R^{12}$, or $C_1$-$C_6$ alkyl, and all other variables are as defined in Formula I, I-a, I-b, I-d, I-f, I-g, II-a, II-b, II-d, II-f, II-g, III-a, III-b, III-d, III-f, or III-g.

In another embodiment of the present invention, $R^1$ is H, halo, CN, $CF_3$, $C_1$-$C_6$ alkyl, $-NR^{11}R^{12}$ wherein $R^{11}$ and $R^{12}$ are independently H or $C_1$-$C_6$ alkyl, $-OR^1$ wherein $R^{11}$ is H or $C_1$-$C_6$ alkyl, or $-SR^{11}$ wherein $R^{11}$ is H or $C_1$-$C_6$ alkyl; and all other variables are as defined in Formula I, I-a, I-b, I-d, I-f, I-g, II-a, II-b, II-d, II-f, II-g, III-a, III-b, III-d, III-f, or III-g.

In another embodiment of the present invention, $R^1$ is H, Cl, CN, $CF_3$, methyl, $-NH_2$, $-NH(CH_3)$, $-N(CH_3)_2$, $-OH$, or $-OCH_3$; and all other variables are as defined in Formula I, I-a, I-b, I-d, I-f, I-g, II-a, II-b, II-d, II-f, II-g, III-a, III-b, III-d, III-f, or III-g.

In another embodiment of the present invention, $R^1$ is not H; and all other variables are as defined in Formula I, I-a, I-b, I-d, I-f, I-g, II-a, II-b, II-d, II-f, II-g, III-a, III-b, III-d, III-f, or III-g.

In another embodiment of the present invention, $R^1$ is Cl, CN, $CF_3$, methyl, $-NH_2$, $-NH(CH_3)$, $-N(CH_3)_2$, $-OH$, or $-OCH_3$; and all other variables are as defined in Formula I, I-a, I-b, I-d, I-f, I-g, II-a, II-b, II-d, II-f, II-g, III-a, III-b, III-d, III-f, or III-g.

In an embodiment of the present invention, $R^2$ is H, halo, CN, $CF_3$, $-NR^{11}R^{12}$, $-OR^{11}$, $-SR^{11}$, $-C(=O)NR^{11}R^{12}$, or $C_1$-$C_6$ alkyl, and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^2$ is H, halo, CN, $CF_3$, $C_1$-$C_6$ alkyl, $-NR^{11}R^{12}$ wherein $R^{11}$ and $R^{12}$ are independently H or $C_1$-$C_6$ alkyl, $-OR^{11}$ wherein $R^{11}$ is H or $C_1$-$C_6$ alkyl, or $-SR^{11}$ wherein $R^{11}$ is H or $C_1$-$C_6$ alkyl; and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^2$ is H, Cl, CN, $CF_3$, methyl, $-NH_2$, $-NH(CH_3)$, $-N(CH_3)_2$, $-OH$, or $-OCH_3$; and all other variables are as defined in Formula I, I-a, I-c, I-d, I-e, I-i, II-a, II-c, II-d, II-e, II-i, III-a, III-c, III-d, III-e, or III-i, or as defined above.

In an embodiment of the present invention, $R^3$ is H, halo, CN, $CF_3$, $-NR^{11}R^{12}$, $-OR^{11}$, $-SR^{11}$, $-C(=O)NR^{11}R^{12}$, or $C_1$-$C_6$ alkyl, and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^3$ is H, halo, $CF_3$, $C_1$-$C_6$ alkyl; and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^3$ is H, F, $CF_3$, or methyl; and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^3$ is H, F, Cl, $CF_3$, methyl or CN; and all other variables are as defined in Formula I, I-a, I-c, I-d, I-e, I-i, II-a, II-c, II-d, II-e, II-i, III-a, III-c, III-d, III-e, or III-i, or as defined above.

In another embodiment of the present invention, $R^3$ is H; and all other variables are as defined in Formula I, I-a, I-c, I-d, I-e, I-i, II-a, II-c, II-d, II-e, II-i, III-a, III-c, III-d, III-e, or III-i, or as defined above.

In an embodiment of the present invention, $R^4$ is H, halo, CN, $CF_3$, $-NR^{11}R^{12}$, $-OR^{11}$, $-SR^{11}$, $-C(=O)NR^{11}R^{12}$, or $C_1$-$C_6$ alkyl, and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In another embodiment of the present invention, $R^4$ is H, halo, CN, $CF_3$, $-NR^{11}R^{12}$ or $-C(=O)NR^{11}R^{12}$ wherein $R^{11}$ and $R^{12}$ are independently H or $C_1$-$C_6$ alkyl, $-OR^{11}$ wherein $R^{11}$ is H or $C_1$-$C_6$ alkyl, or $-SR^{11}$ wherein $R^{11}$ is H or $C_1$-$C_6$ alkyl; and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In another embodiment of the present invention, $R^4$ is H, Br, CN, $CF_3$, $-NH_2$, $-NH(CH_3)$, $-N(CH_3)_2$, $-C(O)NH_2$, $-C(O)NHCH_3$, $-C(O)N(CH_3)_2$, $-OH$, or $-OCH_3$; and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In another embodiment of the present invention, $R^4$ is halo, or $C_1$-$C_6$ alkyl optionally substituted by halo, and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In another embodiment of the present invention, $R^4$ is independently H, Cl, Br, Me, Et, F, $CHF_2$, or $CF_3$; and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In another embodiment of the present invention, $R^4$ is independently H or F; and all other variables are as defined in Formula I, I-a, I-b, I-c, I-e, I-g, I-h, II-a, II-b, II-c, II-e, II-g, II-h, III-a, III-b, III-c, III-e, III-g, or III-h, or as defined above.

In an embodiment of the present invention, $R^5$ is H or $C_1$-$C_6$ alkyl; and all other variables are as defined in Formula I, I-a to I-i, or II-a to II-i, or as defined above.

In another embodiment of the present invention, $R^5$ is H or methyl; and all other variables are as defined in Formula I, I-a to I-i, or II-a to II-i, or as defined above.

In another embodiment of the present invention, $R^5$ is H; and all other variables are as defined in Formula I, I-a to I-i, or II-a to II-i, or as defined above.

In another embodiment of the present invention, $R^5$ is methyl; and all other variables are as defined in Formula I, I-a to I-i, or II-a to II-i, or as defined above.

In an embodiment of the present invention, $R^6$ is H or $C_1$-$C_6$ alkyl; and all other variables are as defined in Formula I, I-a to I-i, II-a to II-i, or III-a to III-i, or as defined above.

In another embodiment of the present invention, $R^6$ is H or methyl; and all other variables are as defined in Formula I, I-a to I-i, II-a to II-i, or III-a to III-i, or as defined above.

In another embodiment of the present invention, $R^6$ is H; and all other variables are as defined in Formula I, I-a to I-i, II-a to II-i, or III-a to III-i, or as defined above.

In another embodiment of the present invention, $R^6$ is methyl; and all other variables are as defined in Formula I, I-a to I-i, II-a to II-i, or III-a to III-i, or as defined above.

In an embodiment of the present invention, $X^1$ is $OR^{11}$ (i.e., Formula II-a to II-i); and all other variables are as defined in Formula I or I-a to I-i; or as defined above.

In an embodiment of the present invention, $X^1$ is $OR^{11}$ wherein $R^{11}$ is H; and all other variables are as defined in Formula I or I-a to I-i; or as defined above.

In another embodiment of the present invention, $X^1$ is $OR^{11}$ wherein $R^{11}$ is $C_1$-$C_{12}$ alkyl (e.g., $C_1$-$C_6$ alkyl) substituted with one or more groups independently selected from halo, CN, $CF_3$, $-OCF_3$, $-NO_2$, oxo, $-Si(C_1$-$C_6$ alkyl), $-(CR^{19}R^{20})_nC(=Y')R^{16}$, $-(CR^{19}R^{20})_nC(Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in Formula I or I-a to I-i, or as defined above.

In another embodiment of the present invention, $X^1$ is:
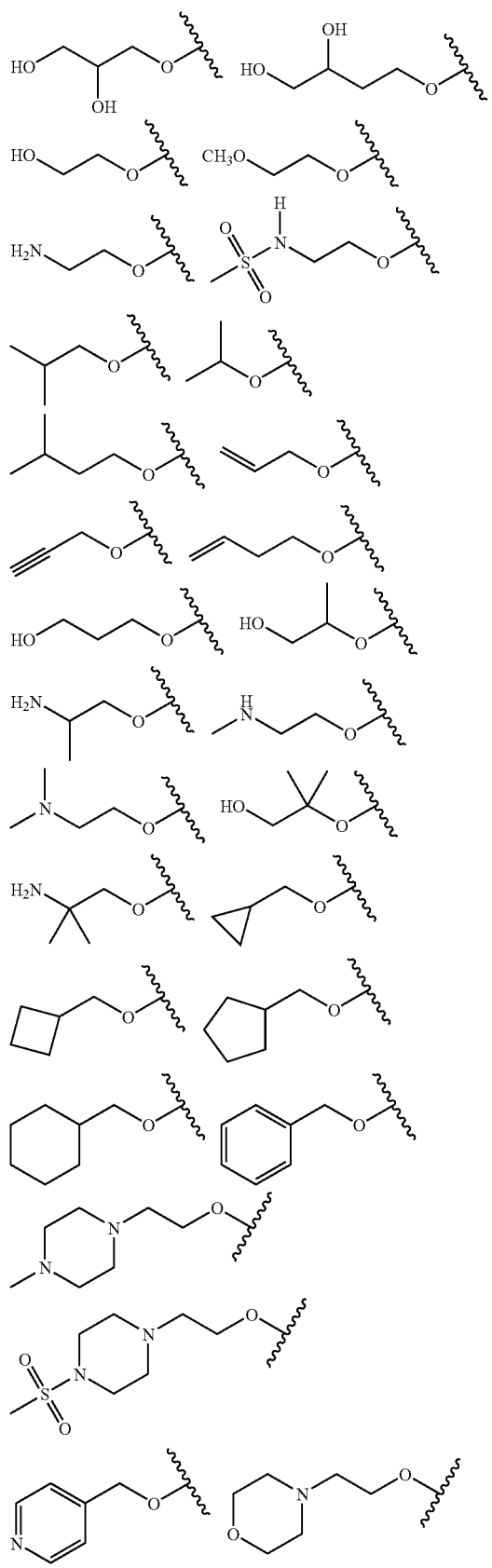
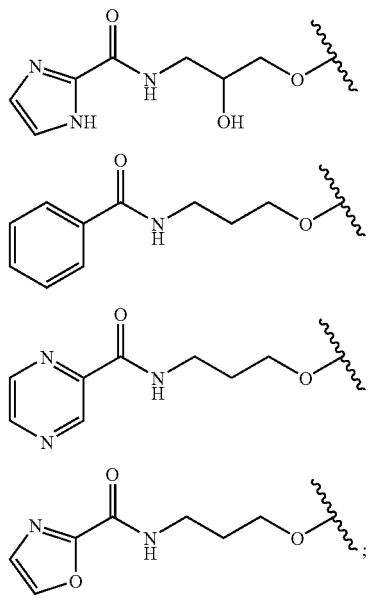
and all other variables are as defined in Formula I or I-a to I-i, or as defined above.
In another embodiment of the present invention, $X^1$ is
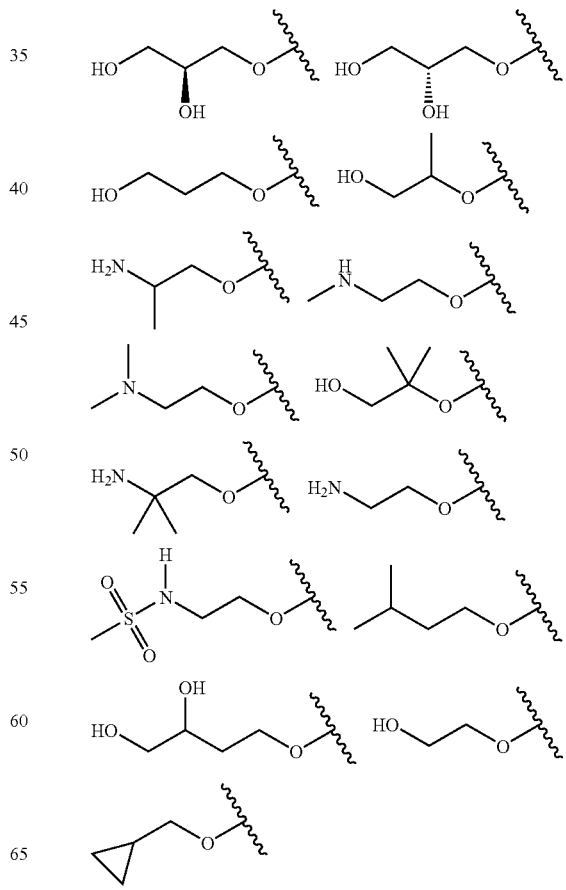

-continued

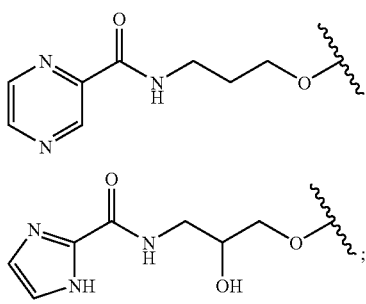

and all other variables are as defined in Formula I or I-a to I-i, or as defined above.

In another embodiment of the present invention, $X^1$ is

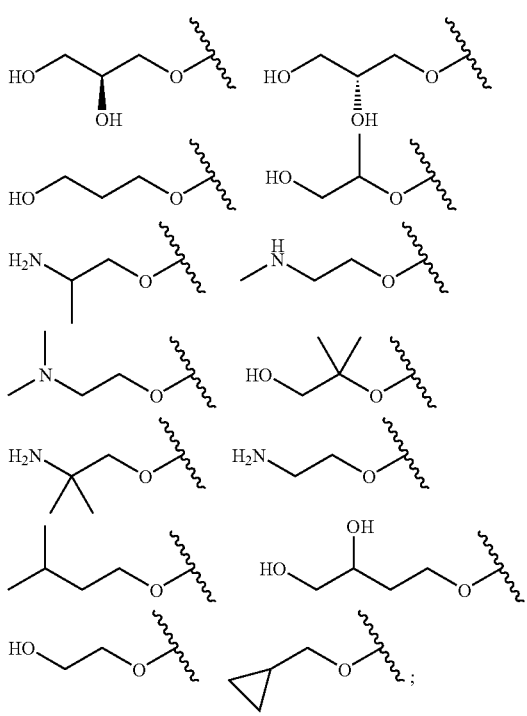

and all other variables are as defined in Formula I or I-a to I-i, or as defined above.

In another embodiment of the present invention, $X^1$ is

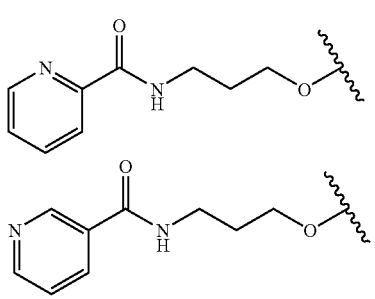

-continued

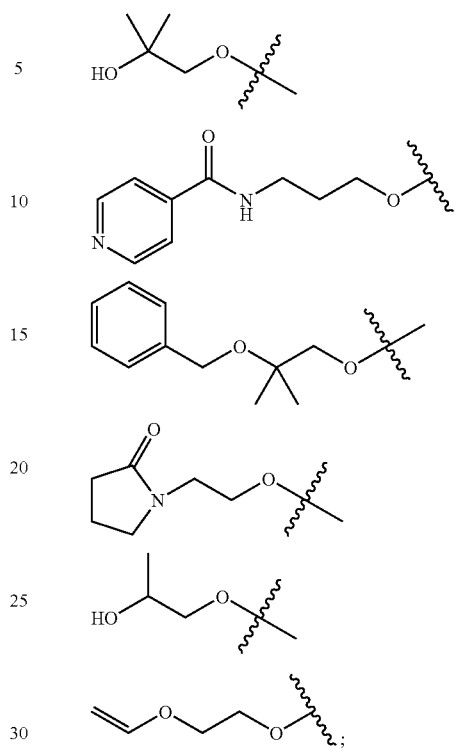

and all other variables are as defined in Formula I or I-a to I-i, or as defined above.

In another embodiment of the present invention, $X^1$ is

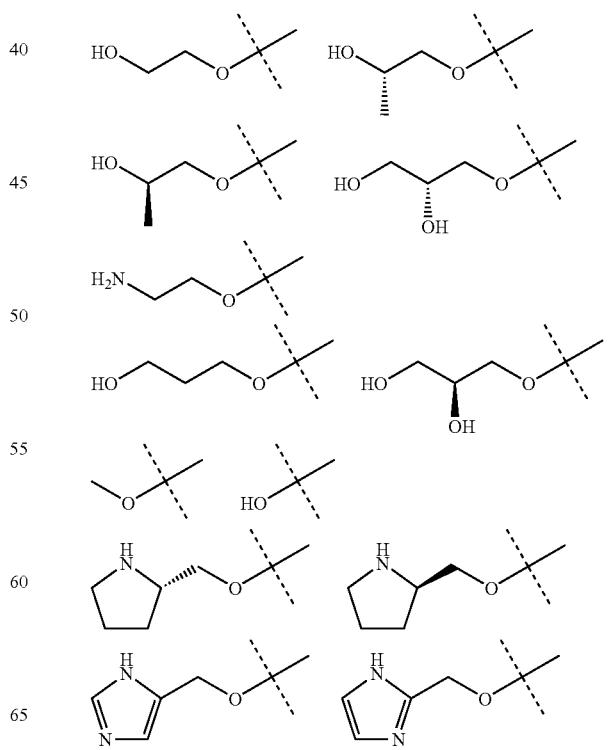

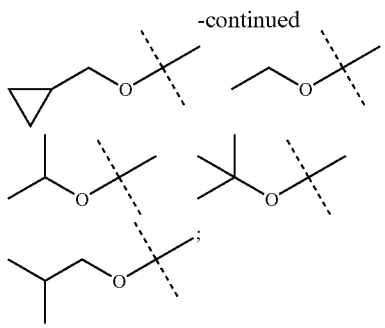

and all other variables are as defined in Formula I or I-a to I-i, or as defined above.

In another embodiment of the present invention, $X^1$ is

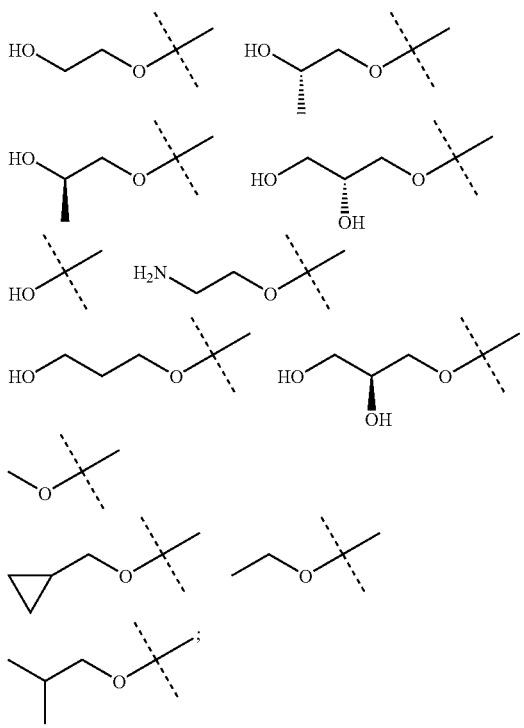

and all other variables are as defined in Formula I or I-a to I-i, or as defined above.

In another embodiment of the present invention, $X^1$ is $OR^{11}$ wherein $R^{11}$ is heterocyclyl (e.g., 4- to 6-membered heterocyclyl) optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y')OR$^{16}$, —(CR$^{19}$R$^{20}$)$_n$C(=Y')NR$^{16}$R$^{17}$, —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$R$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and R$^{21}$; and all other variables are as defined in Formula I or I-a to I-i, or as defined above.

In another embodiment of the present invention, $X^1$ is $OR^{11}$ wherein $R^{11}$ is 4- to 6-membered heterocyclyl having 1 nitrogen ring atom wherein said heterocyclyl is optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y')OR$^{16}$, —(CR$^{19}$R$^{20}$)$_n$C(=Y)NR$^{16}$R$^{17}$, —(CR$^{19}$R$^{20}$)$_n$NR$^{16}$R$^{17}$, (CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, (CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, (CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(=Y')$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), (CR$^{19}$R$^{20}$)$_n$S(O)R$^{16}$, —(CR$^{19}$R$^{20}$)$_n$S(O)$_2$R$^{16}$, —(CR$^{19}$R$^{19}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and; and all other variables are as defined in Formula I or I-a to I-i, or as defined above.

In another embodiment of the present invention, $X^1$ is

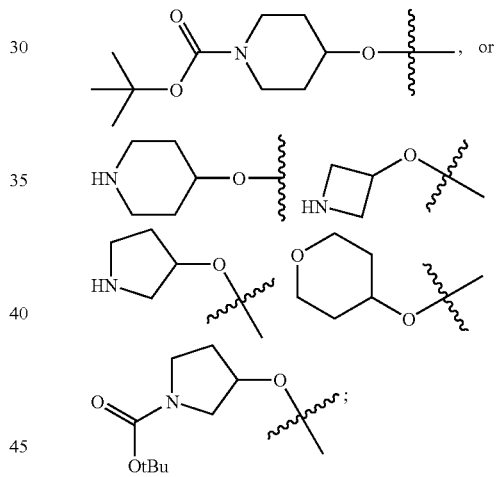

and all other variables are as defined in Formula I or I-a to I-i, or as defined above.

In another embodiment of the present invention, $X^1$ is

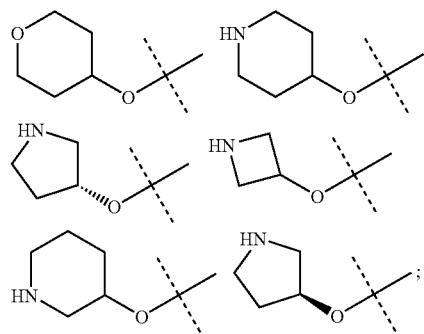

and all other variables are as defined in Formula I or I-a to I-i, or as defined above.

In another embodiment of the present invention, $X^1$ is

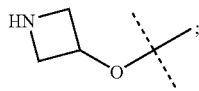

and all other variables are as defined in Formula I or I-a to I-i, or as defined above In an embodiment of the present invention, $X^1$ is $R^{11}$ and $X^1$ is taken together with —N—$R^5$ of W to form a 5-7 membered saturated or unsaturated cyclic ring having 0-2 additional heteroatoms selected from O, S and N, wherein said cyclic ring is optionally substituted with one or more groups selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, $(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I or I-a to I-i, or as defined above.

In another embodiment of the present invention, $X^1$ is $R^{11}$ and $X^1$ is taken together with —N—$R^5$ of W to form a 5-6 membered saturated cyclic ring having 0-2 additional heteroatoms selected from O, S and N, wherein said cyclic ring is optionally substituted with one or more groups selected from halo, CN, $CF_3$, —$OCF_3$, —$NO_2$, OXO, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n—SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(R^{16})(OR^1)$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I or I-a to I-i, or as defined above.

In another embodiment of the present invention, W is:

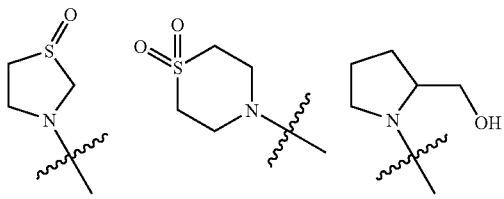

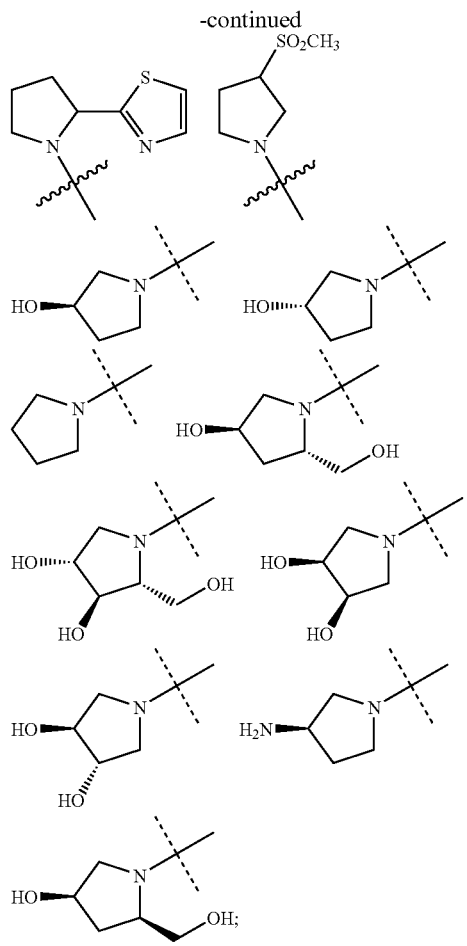

and all other variables are as defined in Formula I or I-a to I-i, or as defined above.

In another embodiment of the present invention, W is:

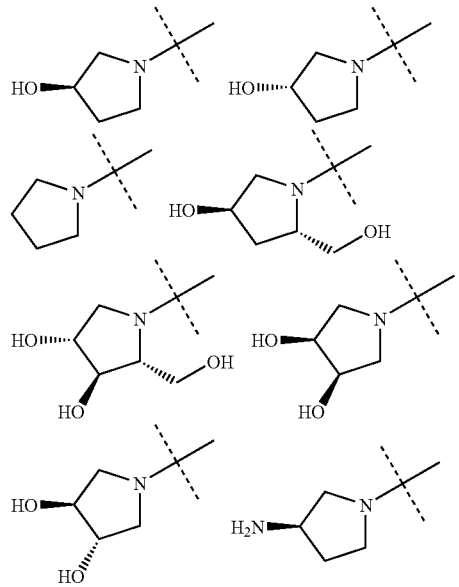

-continued

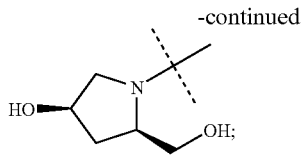

and all other variables are as defined in Formula I or I-a to I-i, or as defined above.

In an embodiment of the present invention, $X^1$ is $R^{11}$ and $X^1$ is taken together with —N—$R^5$ of W to form a 4-membered saturated or unsaturated cyclic ring having 0-1 additional heteroatoms selected from O, S and N, wherein said cyclic ring is optionally substituted with one or more groups selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nC(=Y')R^{16}$, —$(CR^{19}R^{20})_nOC(=Y')OR^{16}$—$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I or I-a to I-i, or as defined above.

In another embodiment of the present invention, W is:

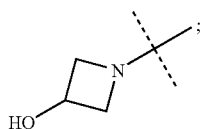

and all other variables are as defined in Formula I or I-a to I-i, or as defined above.

In an embodiment of the present invention, $X^1$ is —$OR^{11}$ and —$OR^{11}$ of $X^1$ is taken together with —N—$R^5$ of W to form a 4-7 membered saturated or unsaturated cyclic ring having 0-2 additional heteroatoms selected from O, S and N, wherein said cyclic ring is optionally substituted with one or more groups selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$—$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nC(=Y')R^{16}$, —$(CR^{19}R^{20})_nOC(=Y')OR^{16}$—$(CR^{19}R^{20})_nOC(=Y')NR^{16}R^{17}$, —$(CR^{19}R^{20})_nOS(O)_2(OR^{16})$, —$(CR^{19}R^{20})_n$ $OP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_n$—$S(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I or I-a to I-i, or as defined above.

In another embodiment of the present invention, $X^1$ is —$OR^{11}$ and —$OR^{11}$ of $X^1$ is taken together with —N—$R^5$ of W to form a 5-7 membered saturated or unsaturated cyclic ring having 0-2 additional heteroatoms selected from O, S and N, wherein said cyclic ring is optionally substituted with one or more groups selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I or I-a to I-i, or as defined above.

In another embodiment of the present invention, W is:

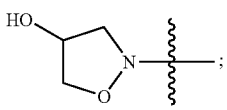

and all other variables are as defined in Formula I or I-a to I-i, or as defined above.

In an embodiment of the present invention, $X^1$ is $R^{11}$; and all other variables are as defined in Formula I, I-a, I-b, I-c, I-d, I-e, I-f, I-g, I-h, or I-i, or as defined above.

In an embodiment of the present invention, $X^1$ is $R^{11}$ wherein $R^{11}$ is H; and all other variables are as defined in Formula I, I-a, I-b, I-c, I-d, I-e, I-f, I-g, I-h, or I-i, or as defined above In another embodiment of the present invention, $X^1$ is $R^{11}$ wherein $R^{11}$ is $C_1$-$C_{12}$ alkyl (e.g., $C_1$-$C_6$ alkyl) substituted with one or more groups independently selected from halo, CN, $CF_3$, —$OCF_3$, —$NO_2$, OXO, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')$ OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and R$^{21}$; and all other variables are as defined in Formula I, I-a, I-b, I-c, I-d, I-e, I-f, I-g, I-h, or I-i, or as defined above.

In another embodiment of the present invention, X$^1$ is

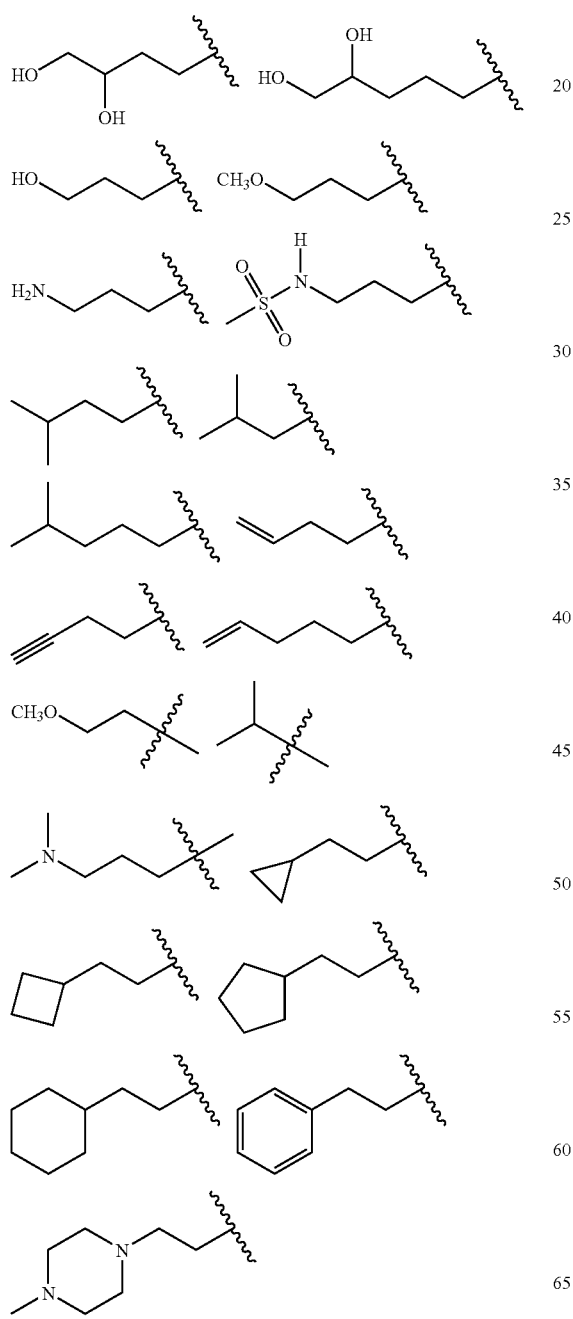

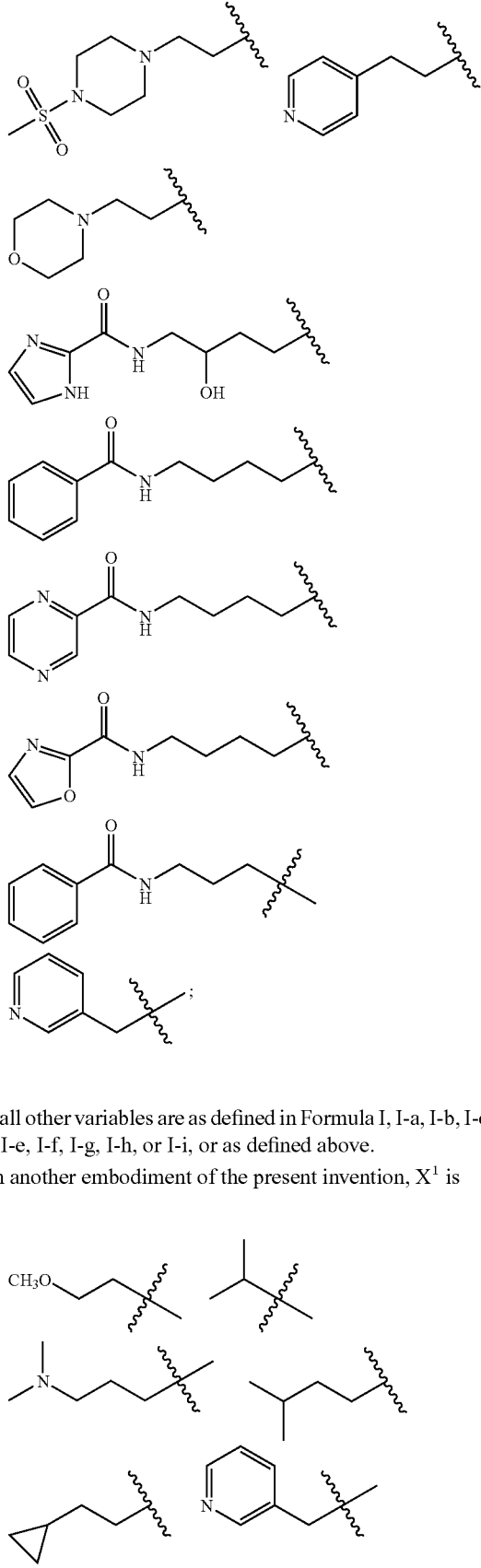

and all other variables are as defined in Formula I, I-a, I-b, I-c, I-d, I-e, I-f, I-g, I-h, or I-i, or as defined above.

In another embodiment of the present invention, X$^1$ is

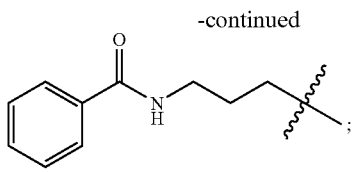

and all other variables are as defined in Formula I, I-a, I-b, I-c, I-d, I-e, I-f, I-g, I-h, or I-i, or as defined above.

In another embodiment of the present invention, $X^1$ is

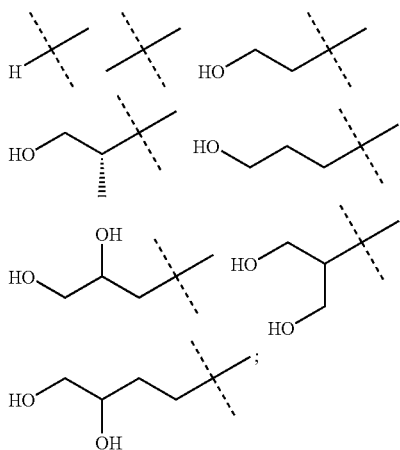

and all other variables are as defined in Formula I, I-a, I-b, I-c, I-d, I-e, I-f, I-g, I-h, or I-i, or as defined above.

In another embodiment of the present invention, $X^1$ is

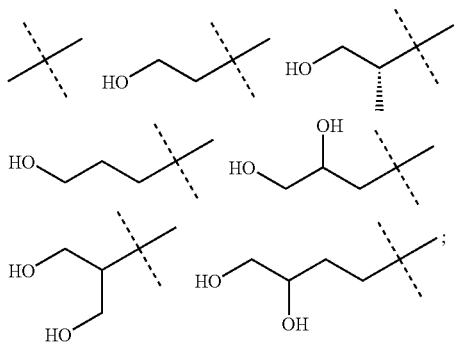

and all other variables are as defined in Formula I, I-a, I-b, I-c, I-d, I-e, I-f, I-g, I-h, or I-i, or as defined above.

In another embodiment of the present invention, $X^1$ is

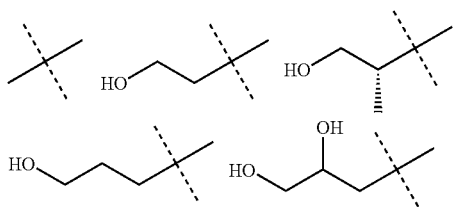

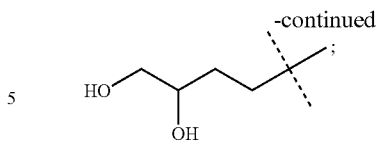

and all other variables are as defined in Formula I, I-a, I-b, I-c, I-d, I-e, I-f, I-g, I-h, or I-i, or as defined above.

In another embodiment of the present invention, $X^1$ is —S(O)$_2$R$^{11}$, and all other variables are as defined in Formula I, I-a, I-b, I-c, I-d, I-e, I-f, I-g, I-h, or I-i, or as defined above.

In another embodiment of the present invention, $X^1$ is —S(O)$_2$R$^{11}$ wherein R$^{11}$ is H or methyl; and all other variables are as defined in Formula I, I-a, I-b, I-c, I-d, I-e, I-f, I-g, I-h, or I-i, or as defined above.

In an embodiment of the present invention, W is —OR$^{11}$ (i.e., Formula III-a, III-b, III-c, III-d, III-e, III-f, III-g, III-h, or III-i) wherein R$^{11}$ of W is H or C$_1$-C$_{12}$ alkyl; and all other variables are as defined above.

In another embodiment of the present invention, W is —OR$^{11}$ (i.e., Formula III-a, III-b, III-c, III-d, III-e, III-f, III-g, III-h, or III-i) wherein R$^{11}$ of W is H; and all other variables are as defined above.

In another embodiment of the present invention, W is —OR$^{11}$ (i.e., Formula III-a, III-b, III-c, III-d, III-e, III-f, III-g, III-h, or III-i) wherein R$^{11}$ of W is C$_1$-C$_6$ alkyl; and all other variables are as defined above.

In an embodiment of the present invention, $X^2$ is aryl (e.g., phenyl), wherein said aryl is optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y')OR$^{16}$, —(CR$^{19}$R$^{20}$)$_n$C(=Y')NR$^{16}$R$^{17}$, —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and R$^{21}$; and all other variables are as defined in Formula I, I-a to I-i, II-a to II-i, or III-a to III-i, or as defined above.

In another embodiment of the present invention, $X^2$ is

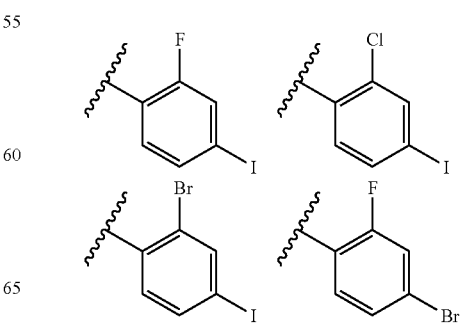

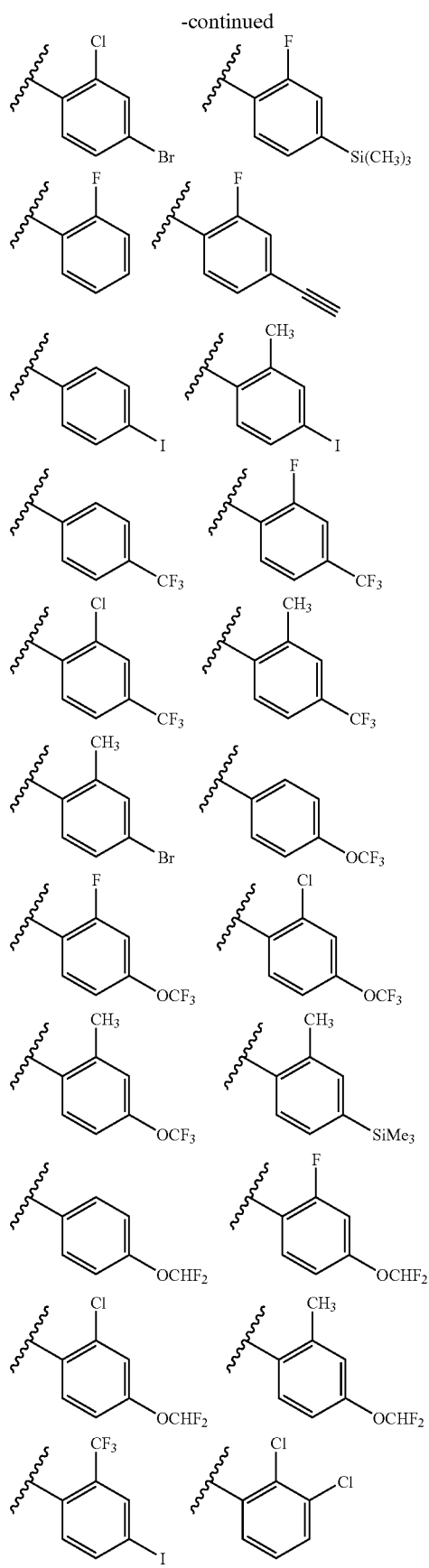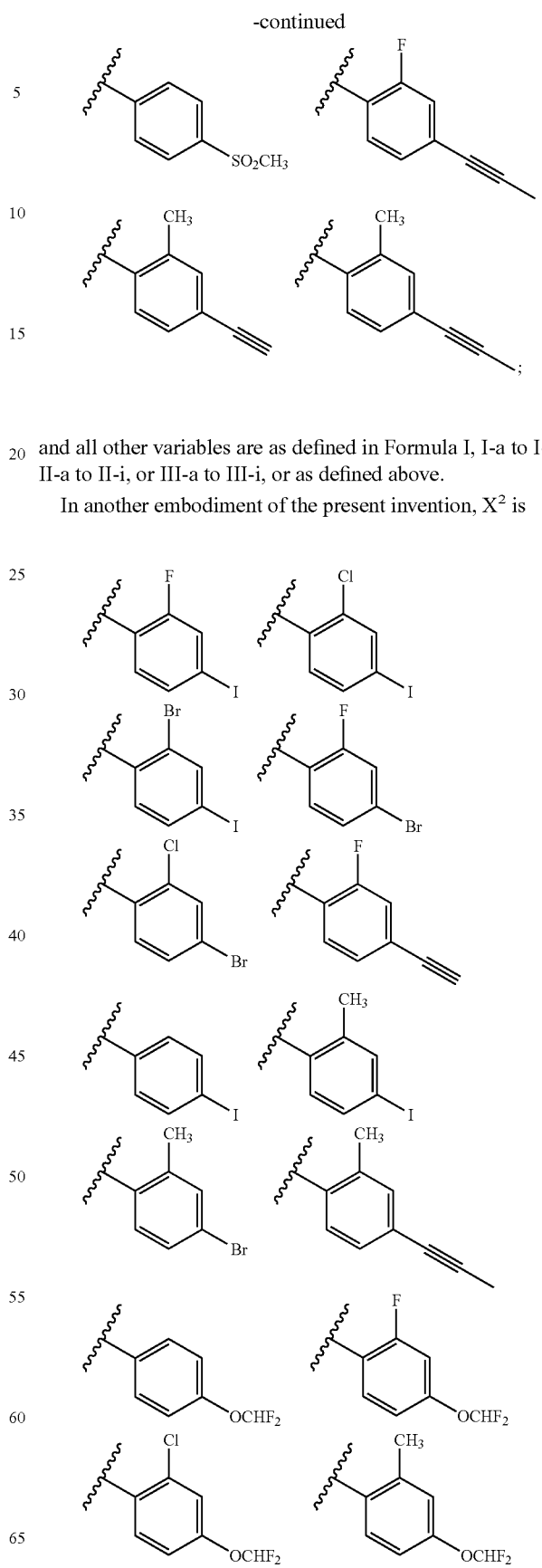
and all other variables are as defined in Formula I, I-a to I-i, II-a to II-i, or III-a to III-i, or as defined above.
In another embodiment of the present invention, $X^2$ is -continued

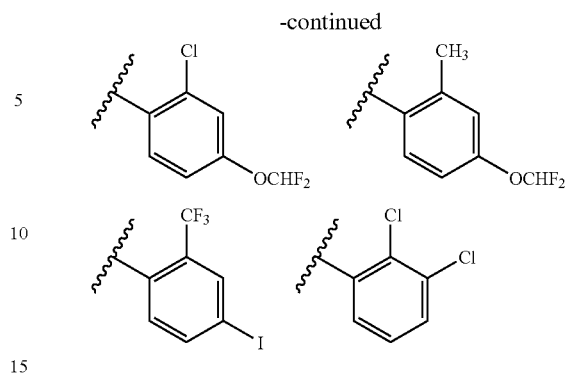

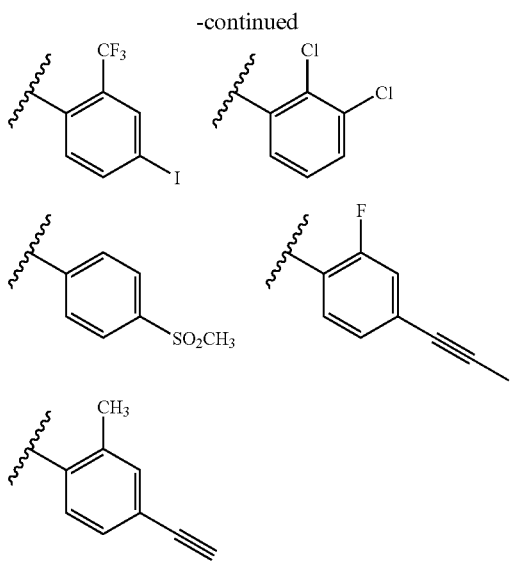

and all other variables are as defined in Formula I, I-a to I-i, II-a to II-i, or III-a to III-i, or as defined above.

In another embodiment of the present invention, $X^2$ is $C_6$-$C_{10}$ aryl substituted with $C_1$-$C_4$ alkyl; and all other variables are as defined in Formula I, I-a to I-i, II-a to II-i, or III-a to III-i, or as defined above.

In another embodiment of the present invention, $X^2$ is

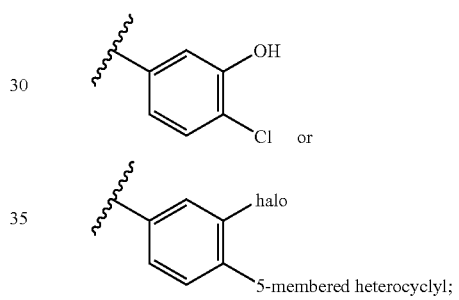

and all other variables are as defined in Formula I, I-a to I-i, II-a to II-i, or III-a to III-i, or as defined above.

In another embodiment of the present invention, $X^2$ is

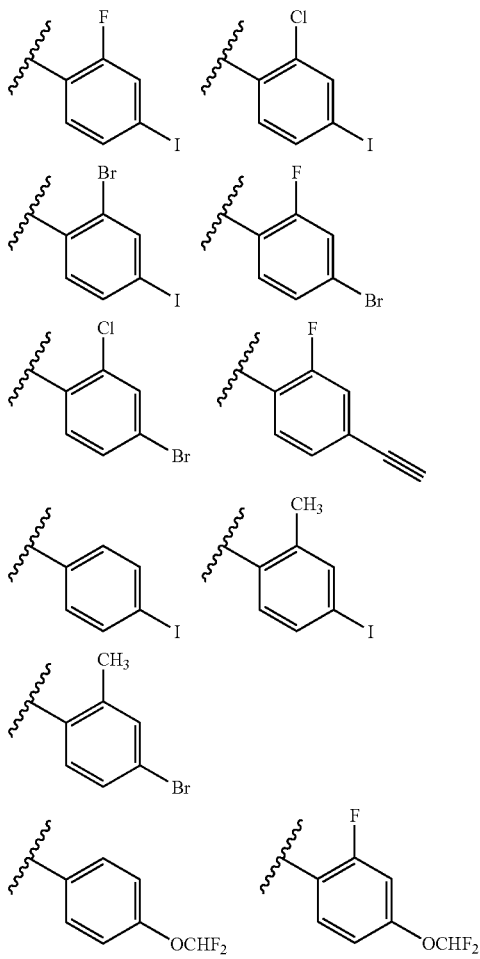

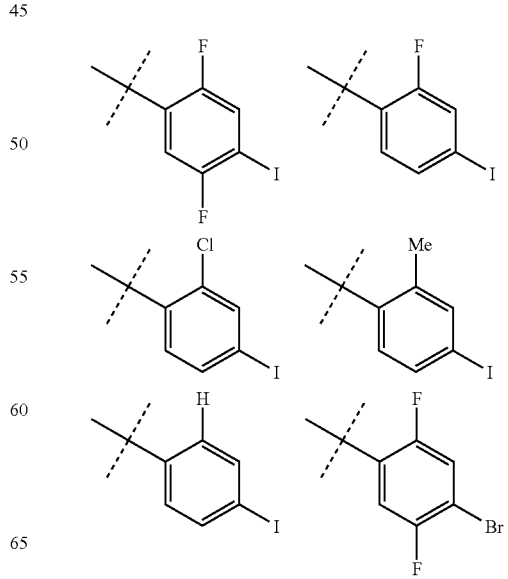

-continued
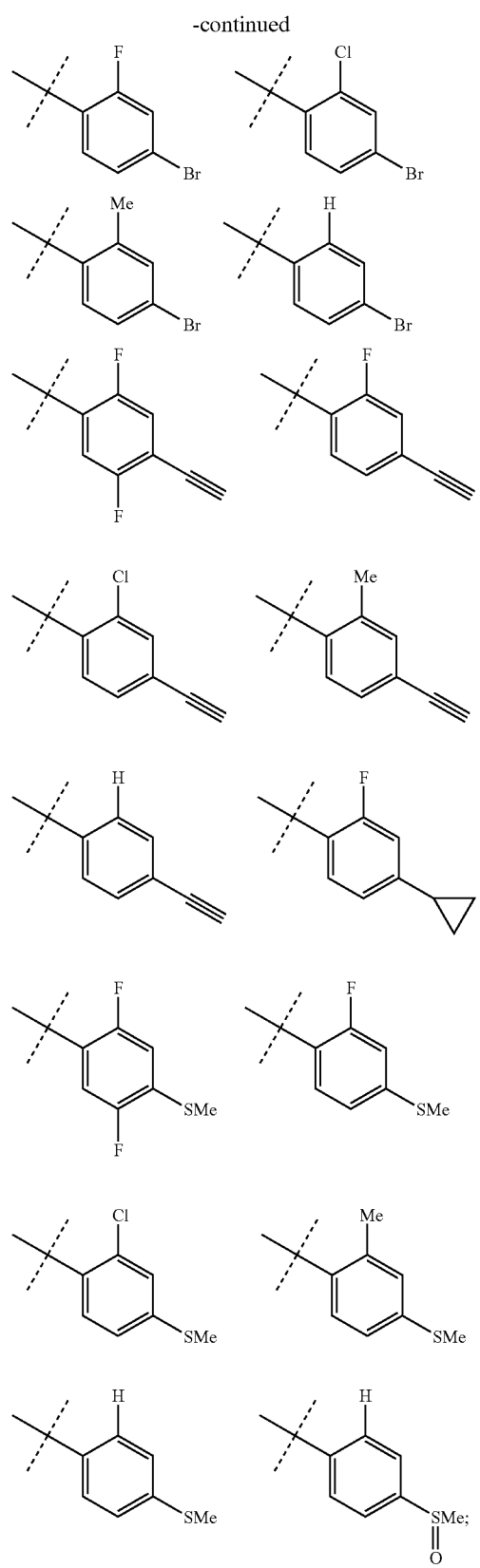
and all other variables are as defined in Formula I, I-a to I-i, II-a to II-i, or III-a to III-i, or as defined above
In another embodiment of the present invention, $X^2$ is
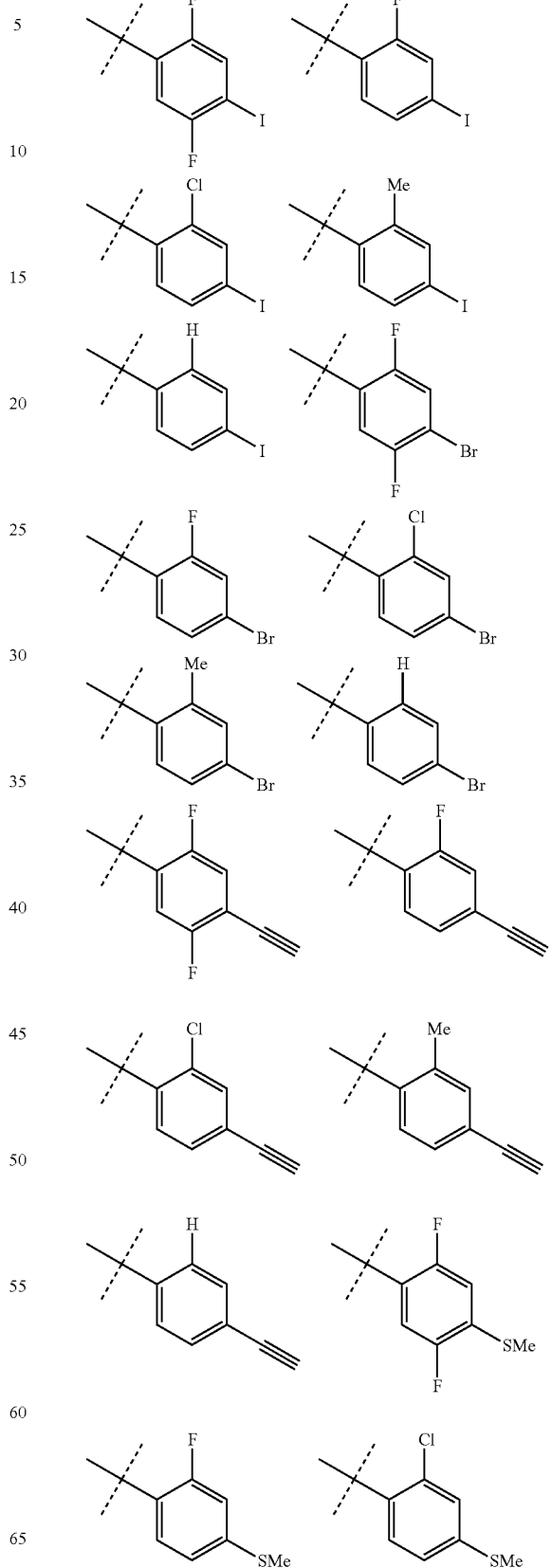

-continued

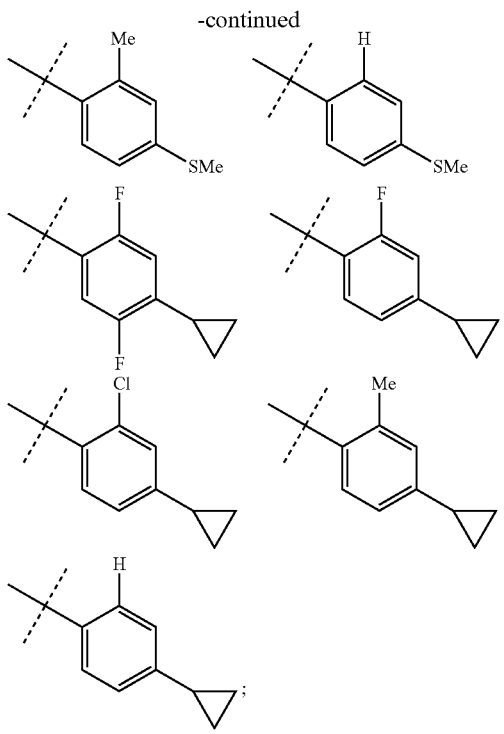

and all other variables are as defined in Formula I, I-a to I-i, II-a to II-i, or III-a to III-i, or as defined above.

In another embodiment of the present invention, $X^2$ is carbocyclyl (e.g., $C_4$-$C_6$ carbocyclyl) or heterocyclyl (e.g., 4- to 6-membered heterocyclyl), wherein said carbocyclyl or heterocyclyl is optionally substituted with one or more groups independently selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_n$—$SR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I, I-a to I-i, II-a to II-i, or III-a to III-i, or as defined above.

In another embodiment of the present invention, X is $C_4$-$C_6$ carbocyclyl wherein said carbocyclyl is substituted with —$C(=Y')R^{16}$; and all other variables are as defined in Formula I, I-a to I-i, II-a to II-i, or III-a to III-i, or as defined above.

In another embodiment of the present invention, $X^2$ is

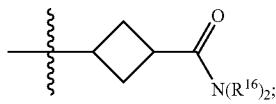

and all other variables are as defined in Formula I, I-a to I-i, II-a to II-i, or III-a to III-i, or as defined in any one of the embodiments above.

In an embodiment of the present invention, X is H, $(CR^{23}R^{24})_pR^{12}$, —$(CR^{23}R^{24})_qNR^{11}R^{12}$, —$(CR^{23}R^{24})_qOR^{12}$, —$(CR^{23}R^{24})C(O)NR^{11}R^{12}$, —$(CR^{23}R^{24})_qNR^{11}C(O)R^{12}$, —$(CR^{23}R^{24})S(O)_2NR^{11}R^{12}$, and —$(CR^{23}R^{24})_qNR^{11}S(O)_2R^{12}$; wherein q is 2; p is 0, 1 or 2; $R^{23}$ and $R^{24}$ are independently H or $C_1$-$C_3$ alkyl; $R^{11}$ of $X^3$ is H, $C_1$-$C_6$ alkyl or aryl; and $R^{12}$ of $X^3$ is H, $C_1$-$C_6$ alkyl, aryl, carbocyclyl, heterocyclyl, or heteroaryl; and wherein said alkyl, aryl, carbocyclyl, heterocyclyl, or heteroaryl of $R^{11}$ and $R^{12}$ is optionally substituted with one or more groups independently selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_n S(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in Formula I, I-a to I-i, II-a to II-i, or III-a to III-i, or as defined in any one of the embodiments above.

In another embodiment of the present invention, $X^3$ is H, —$(CH_2)_pR^{12}$, or —$(CH_2)_qNR^{11}S(O)_2R^{12}$; wherein q is 2; p is 0 or 1; $R^{12}$ of $X^3$ is H, $C_1$-$C_6$ alkyl or aryl; and $R^{11}$ of $X^3$ is $C_1$-$C_6$ alkyl; and wherein said alkyl or aryl of $R^{11}$ and $R^{12}$ is optionally and independently substituted with one or more —$OR^{16}$ groups wherein each $R^{16}$ is independently H or methyl; and all other variables are as defined in Formula I, I-a to I-i, II-a to II-i, or III-a to III-i, or as defined in any one of the embodiments above.

In another embodiment of the present invention, $X^3$ is —$(CH_2)_pR^{12}$ wherein p is 0 or 1 and $R^{12}$ of $X^3$ is carbocyclyl (e.g., $C_3$ carbocyclyl); and all other variables are as defined in Formula I, I-a to I-i, II-a to II-i, or III-a to III-i, or as defined in any one of the embodiments above.

In another embodiment of the present invention, $X^3$ is H, methyl, ethyl, n-propyl, i-propyl, benzyl, —$(CH_2)$-p-methoxyphenyl, —$(CH_2)_3OH$, —$(CH_2)_2CH(OH)CH_2OH$, or —$(CH_2)N(CH_2OH)SO_2CH_3$; and all other variables are as defined in Formula I, I-a to I-i, II-a to II-i, or III-a to III-i, or as defined in any one of the embodiments above.

In another embodiment of the present invention, $X^3$ is H; and all other variables are as defined in Formula I, I-a to I-i, II-a to II-i, or III-a to III-i, or as defined in any one of the embodiments above.

In another embodiment of the present invention, $X^3$ is methyl; and all other variables are as defined in Formula I, I-a to I-i, II-a to II-i, or III-a to III-i, or as defined in any one of the embodiments above.

In another embodiment of the present invention, $X^3$ is ethyl or cyclopropyl; and all other variables are as defined in Formula I, I-a to I-i, II-a to II-i, or III-a to III-i, or as defined in any one of the embodiments above.

In another embodiment of the present invention, $X^{31}$ S
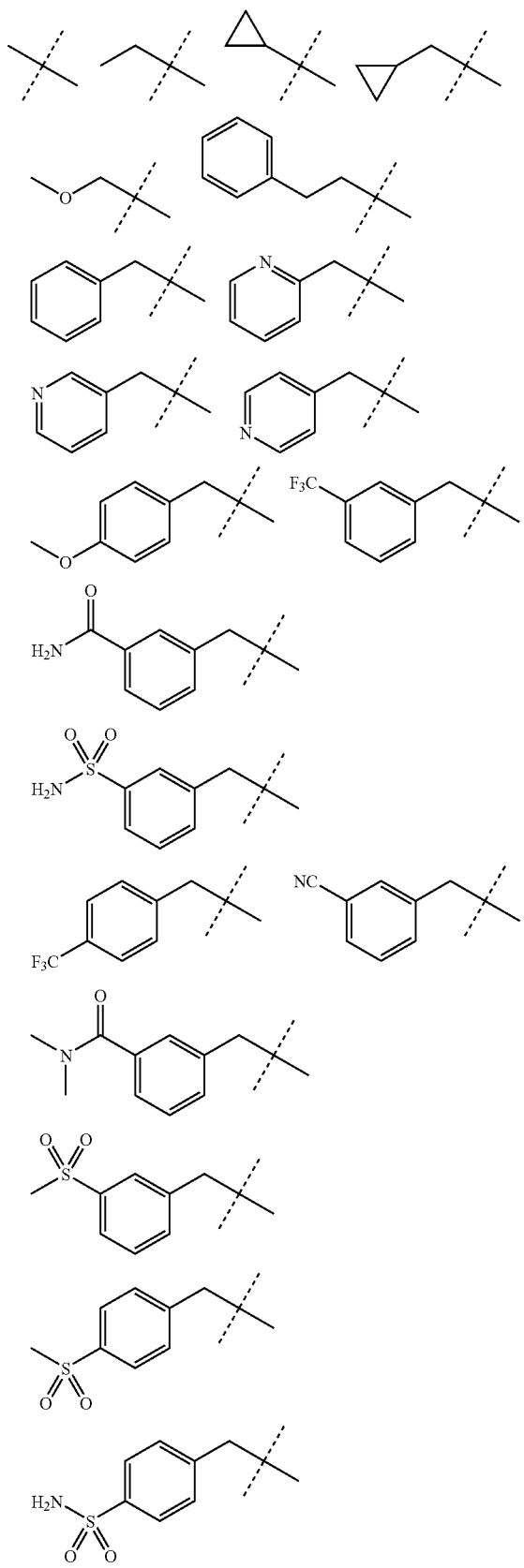
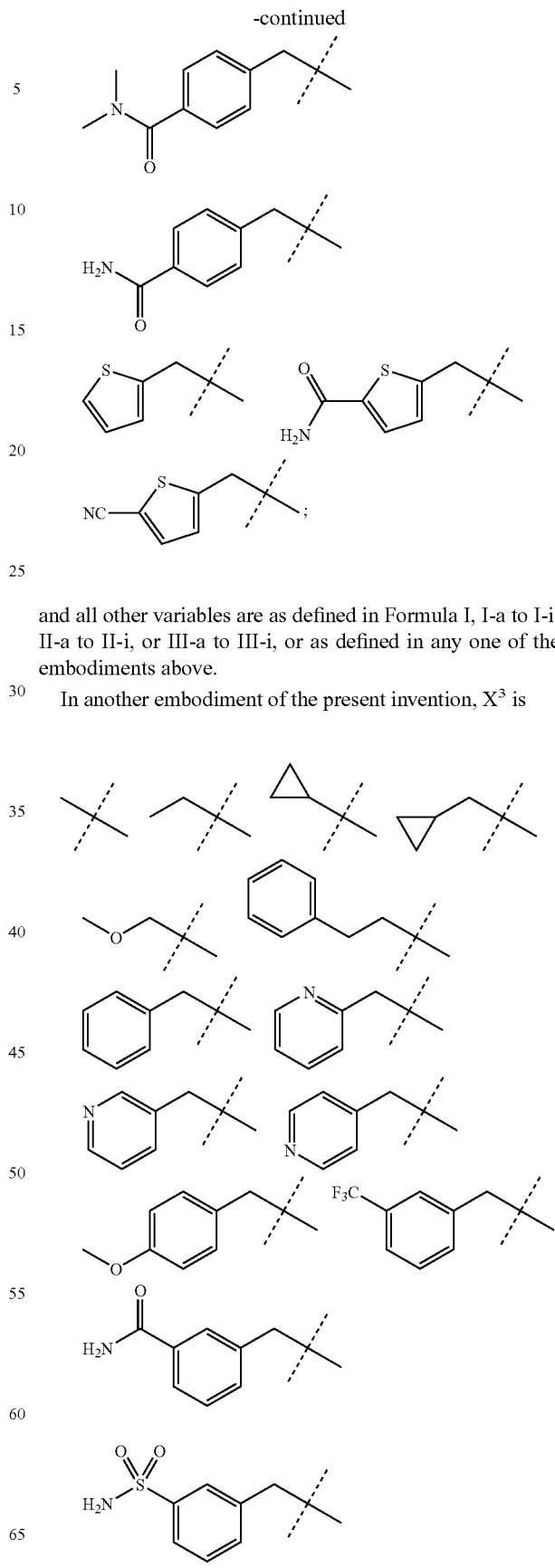
and all other variables are as defined in Formula I, I-a to I-i, II-a to II-i, or III-a to III-i, or as defined in any one of the embodiments above.
In another embodiment of the present invention, $X^3$ is

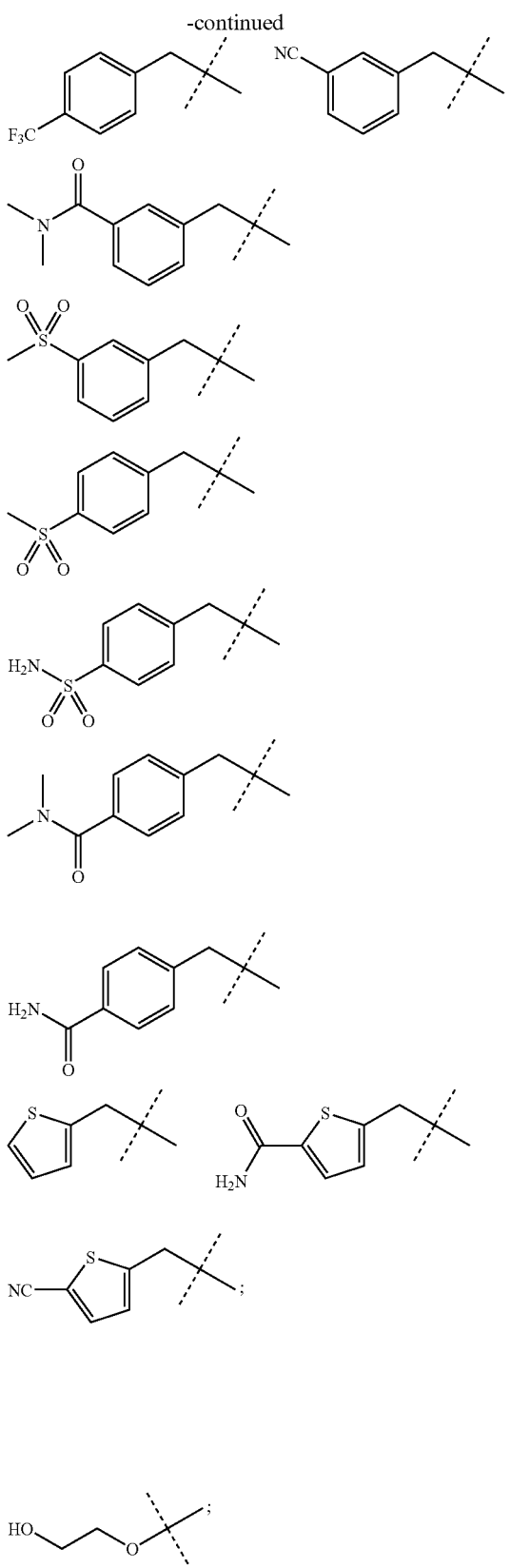

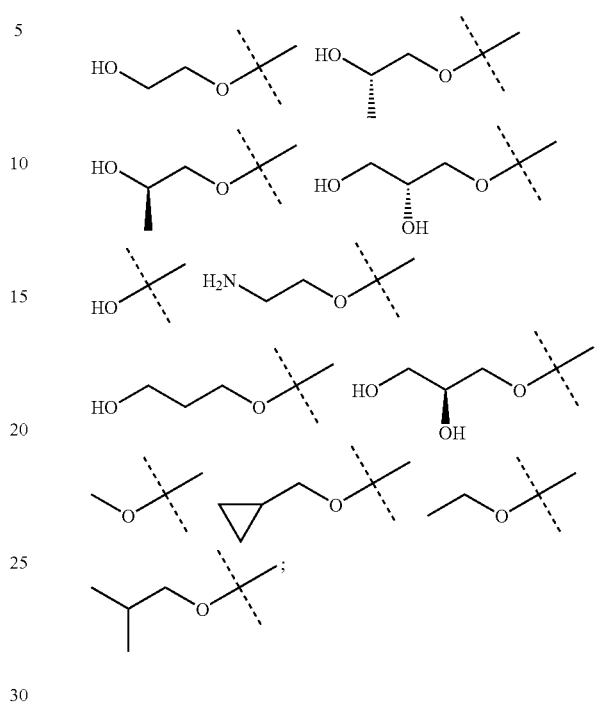

and all other variables are as defined in Formula I, I-a to I-i, or II-a to II-i, or as defined in any one of the embodiments above.

In another embodiment of the present invention, $X^3$ is other than H, $X^1$ is

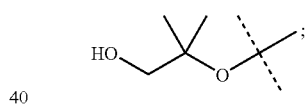

and all other variables are as defined in Formula I, I-a to I-i, or II-a to II-i, or as defined in any one of the embodiments above.

In another embodiment of the present invention, $X^3$ is other than H, $X^1$ is

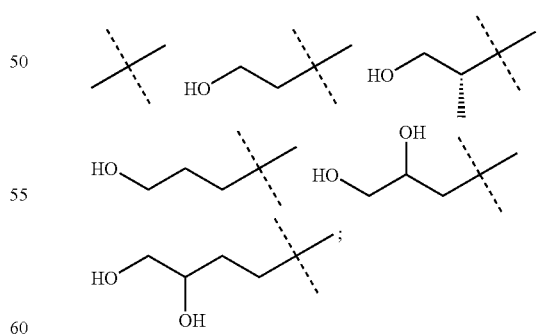

and all other variables are as defined in Formula I, or I-a to I-i, or as defined in any one of the embodiments above.

Another embodiment of the present invention includes compounds described in EXAMPLES 5-19 and compounds below

| 49 | 50 |
|---|---|
| 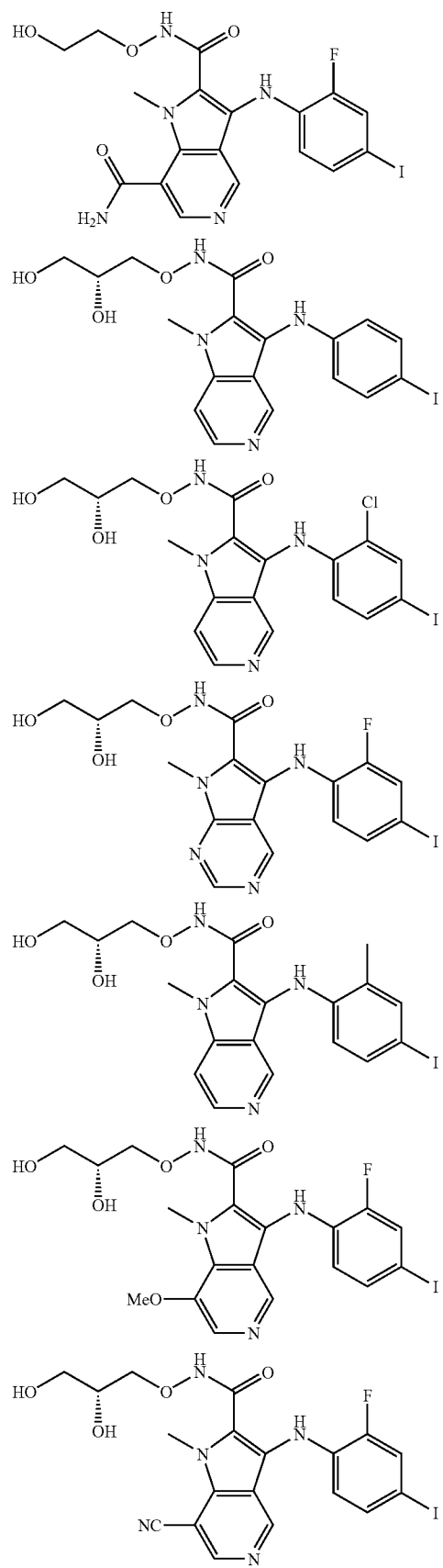 | 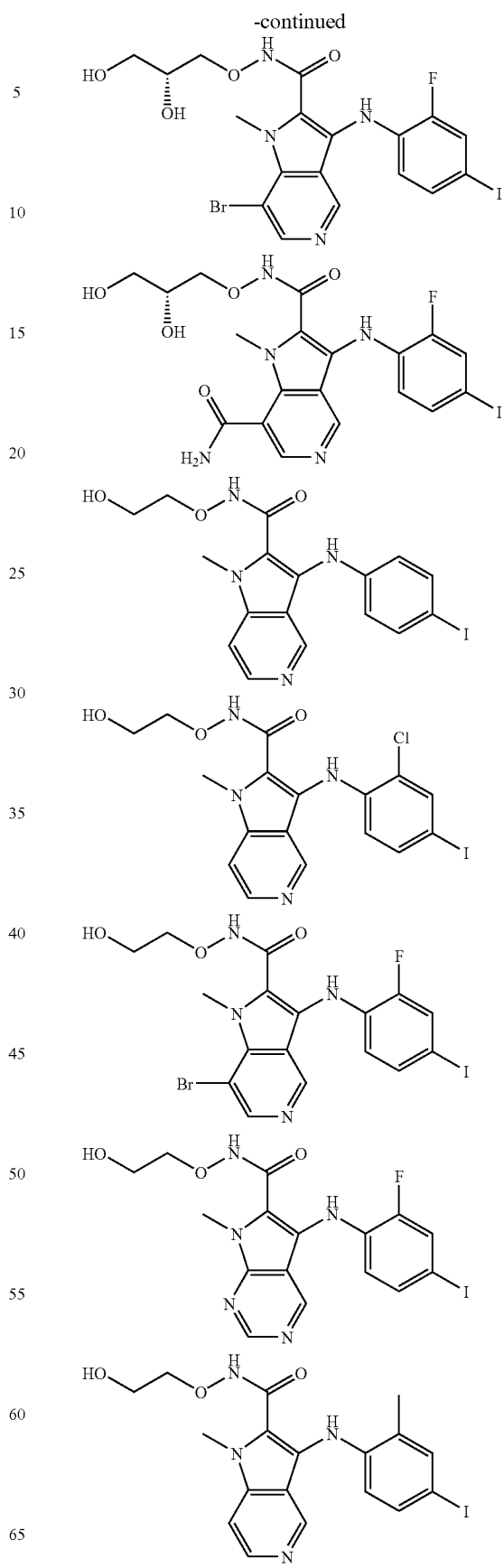
-continued |

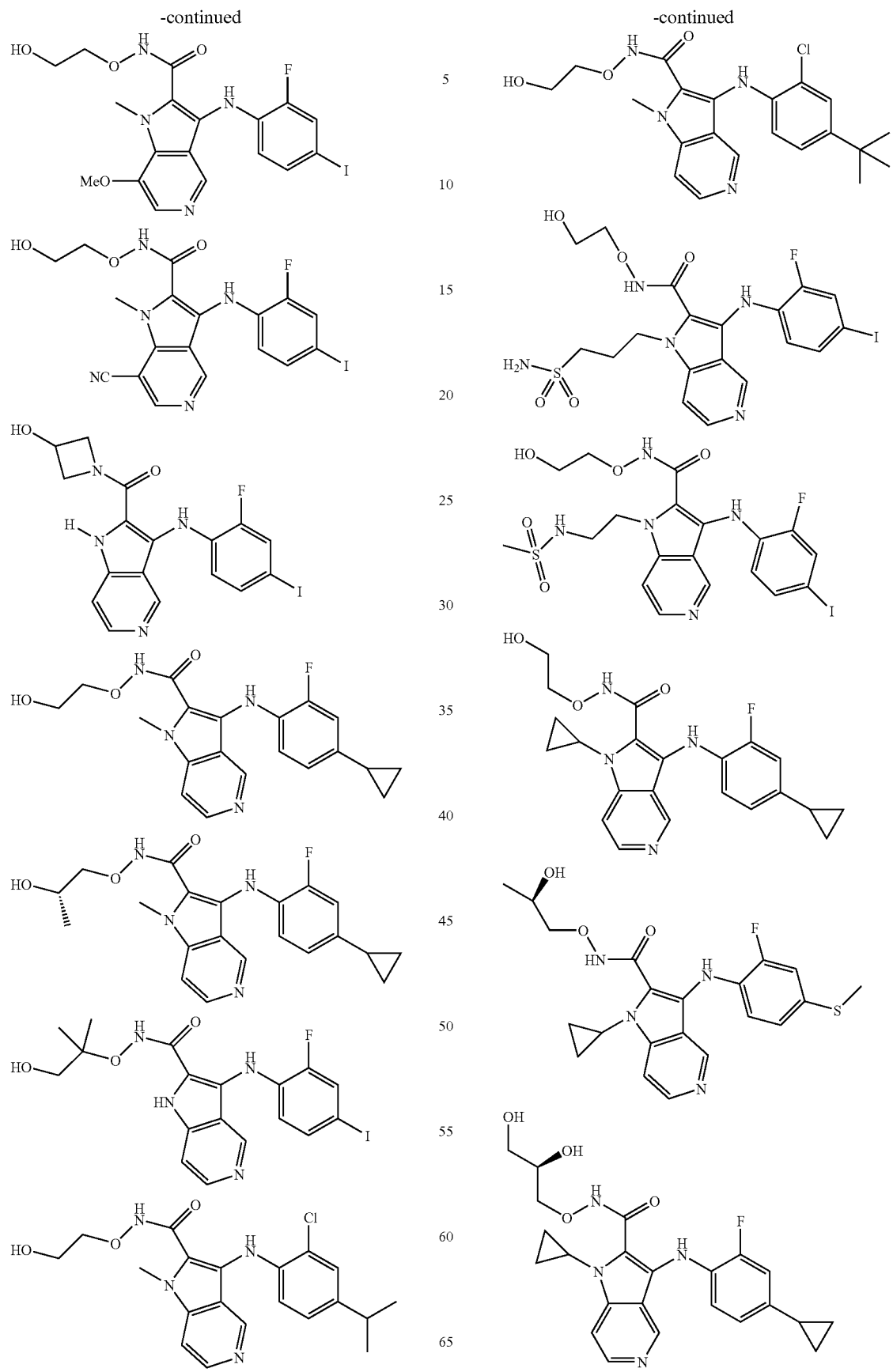

-continued

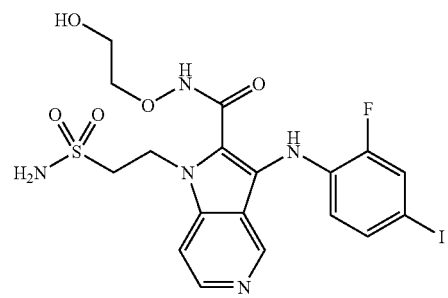

Preparation of Compounds of Formula I

The azaindolyl compounds of Formula I are prepared according to the procedures described below in the schemes and examples or by methods known in the art. The starting materials and various intermediates may be obtained from commercial sources, prepared from commercially available compounds, or prepared using well known synthetic methods (for example, those described in WO02/06213, WO 03/077855 and WO03/077914).

For example, 5-azaindoles of Formula (I-b), (II-b) or (III-b) may be prepared using the synthetic routes outlined in Scheme 1.

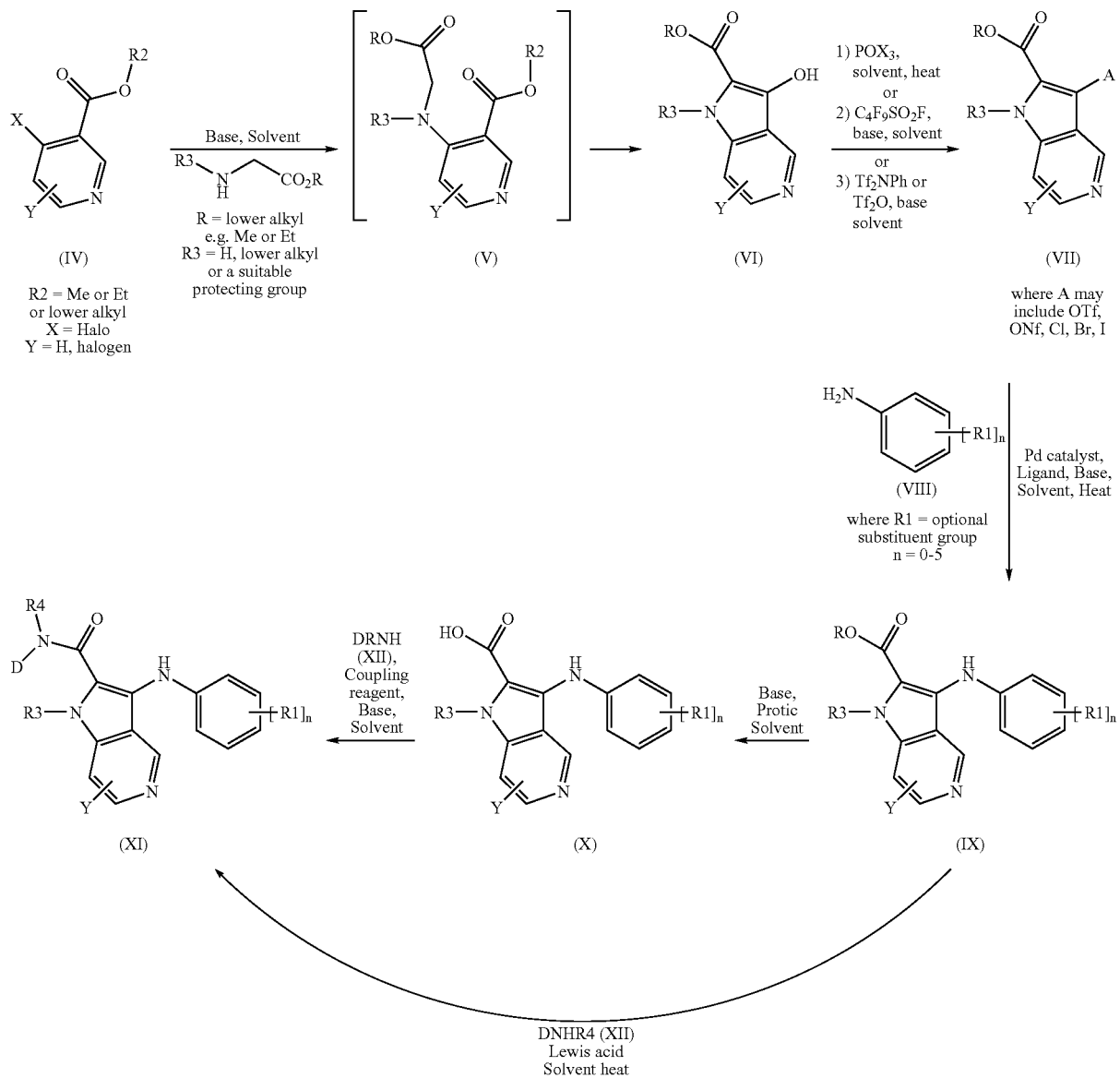

where $DNH_2$ may include, but is not limited to, a broad range of substituted and functionalised hydroxylamines and amines Compounds of formula (IV) may be prepared using published methods described in the literature. They may be reacted with glycine or a glycine derivative such as N-methyl glycine methyl or ethyl ester in the presence of a base, such as sodium hydride, in a suitable solvent, such as N,N-dimethylformamide or 1,2-dimethoxyethane, at a temperature of from −50° C. to room temperature, to obtain compounds of formula (VI). Alternatively compounds of general formula (IV) may be reacted with glycine or a glycine derivative such as glycine methyl or ethyl ester in the presence of a base such as sodium hydrogencarbonate in a solvent such as ethanol at a temperature of from −20° C. to 120° C. to provide intermediates of formula (V). Intermediates of formula (V) may then be cyclised in the presence of a base such as sodium ethoxide in a solvent such as ethanol at a temperature of from −40° C. to 120° C. to provide compounds of formula (VI).

Compounds of formula (VI) may be converted to compounds of formula (VII) by reaction with a halogenating agent such as phosphorus oxybromide, neat or in a suitable solvent such as toluene, at a temperature of from room temperature to 140° C. Alternatively, compounds of formula (VI) may be reacted with nonafluorobutane sulphonyl fluoride in the presence of a base such as diisopropylethylamine and a catalyst such as N,N-dimethyl-4-aminopyridine, in a solvent such as dichloromethane at room temperature, with N-phenyltrifluoromethanesulfonimide in the presence of a base such as diisopropylethylamine, in a suitable solvent such as 1,2-dimethoxyethane at a temperature from room temperature to the reflux temperature of the solvent. In addition, compounds of formula (VI) may be treated with trifluoromethanesulphonic acid anhydride in the presence of a base such as pyridine in a solvent such as dichloromethane at a temperature of from −20° C. to ambient temperature.

Compounds of formula (IX) may be obtained from compounds of formula (VII) by reaction with an aniline of formula (VIII) (incorporating appropriate substituents R1), in the presence of a catalyst such as tris(dibenzylideneacetone) dipalladium (0) or palladium acetate, a base such as potassium phosphate, sodium tert-butoxide, 1,8-diazabicyclo [5.4.1]undec-7-ene or cesium carbonate, a ligand such as 9,9'-dimethyl-4,5-bis(diphenylphosphino)xanthene, 2,2'-bis(diphenylphosphino)-1,1'-binaphthyl, 2-dicyclohexylphosphino-2'-(N,N-dimethylamino)biphenyl, 2-dicyclohexylphosphino-2',6'-(dimethoxy)biphenyl or tri-butyl-phosphine in a suitable solvent such as toluene, 1,2-dimethoxyethane, tetrahydrofuran or dioxane, at a temperature of from room temperature to the reflux temperature of the solvent, or under microwave irradiation at a temperature of from 70° C. to 150° C. Compounds of formula (X) can be obtained from compounds of formula (IX) by reaction with a base such as sodium hydroxide in a protic solvent such as ethanol or methanol, at a temperature of from room temperature up to reflux temperature.

Compounds of formula (X) can be reacted with a functionalised hydroxylamine of formula (XII) (commercially available or prepared according to Scheme 5) or an amine, and a suitable coupling agent, such as O-(7-aza-benzo-triazol-1-yl)-N,N,N',N'-tetra-methyluronium hexafluoro-phosphate, N-(3-dimethylaminopropyl)-N'-ethylcarbodiimide hydrochloride or N,N'-dicyclohexylcarbodiimide in the presence of N-hydroxy-1,2,3-benzotriazole, in the presence of a suitable base such as diisopropylethylamine or triethylamine in an inert solvent, such as tetrahydrofuran, N,N-dimethylformamide, or dichloromethane at a temperature of about room temperature, to obtain the compounds of formula (XI). Alternatively, compounds of formula (XI) can be obtained directly from compounds of formula (IX) by reaction with an amine or hydroxylamine DNHR in the presence of a Lewis acid such as trimethyl aluminium in a solvent such as DCM, at a temperature of from room temperature up to reflux temperature.

The substituent $R^3$ of compounds of general formula (XI) or any of the intermediates (VI) (VII) (IX) (X) may be manipulated at any stage of the synthesis. For example, compounds of general formula (IX) where R3=H may be alkylated with an alkyl halide such as iodomethane, using a base such as potassium carbonate, in a solvent such as DMF at a temperature of from 0° C. to 120° C. In a further example, compounds of general formula (VII) where $R^3$ is H may be appended with protecting groups such as SEM (trimethylsilyl ethoxy), using an alkylating agent such as SEM-chloride, in a solvent such as DMF in the presence of a base such as sodium hydride. Additionally compounds of general formula (XI) where R3 is a protecting group such as SEM may be deprotected using a reagent such as tetrabutylammonium fluoride in a solvent such as THF at a temperature of from −20° C. to 50° C. to provide compounds of formula (XI) where R3 is H.

Compounds of general formula (VI) may also be prepared according to the procedure shown in Scheme 2.

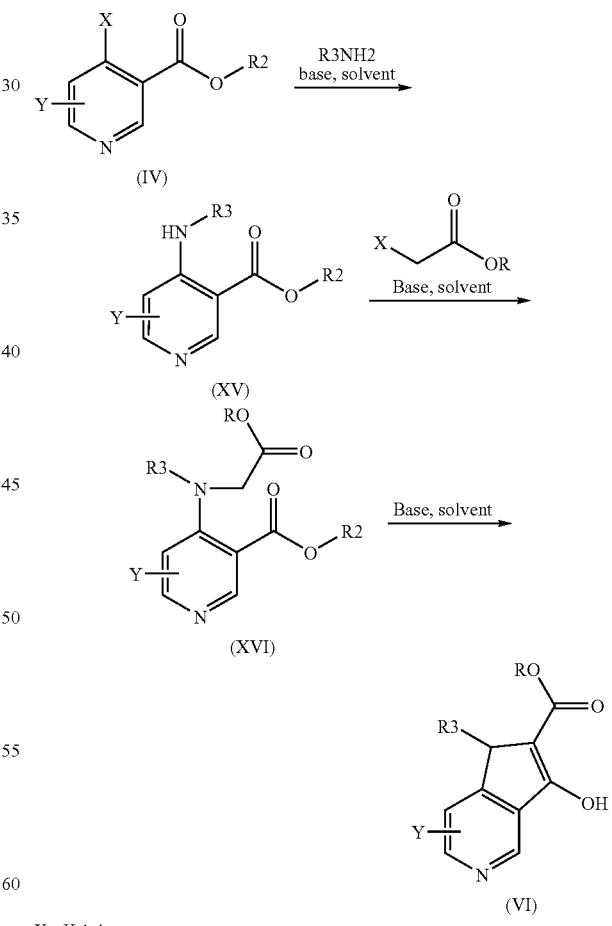

Y = H, halogen

Compounds of general formula (IV) may be prepared using published methods described in the literature. Compounds of formula (IV) may be reacted with amines such as methylamine, in a solvent such as ethanol, at a temperature of from 0° C. to reflux to give intermediates of general formula (XV). Compounds of formula (XV) may be alkylated with alkyl acetates such as bromo tert-butyl acetate, in the presence of a base such as sodium hydride, in a solvent such as DMF, to give compounds of general formula (XVI). Cyclisation of compounds of general formula (XVI) to give compounds of general formula (VI) may be achieved using a base such as sodium tert-butoxide, in a solvent such as THF, at a temperature of from −40° C. to reflux. Alternatively compounds of general formula (VI) may be prepared directly from compounds of general formula (XV) using more than one equivalent of base and prolonged reaction times or higher temperatures.

Alternatively, compounds of formula (IX) may be prepared according to Scheme 3.

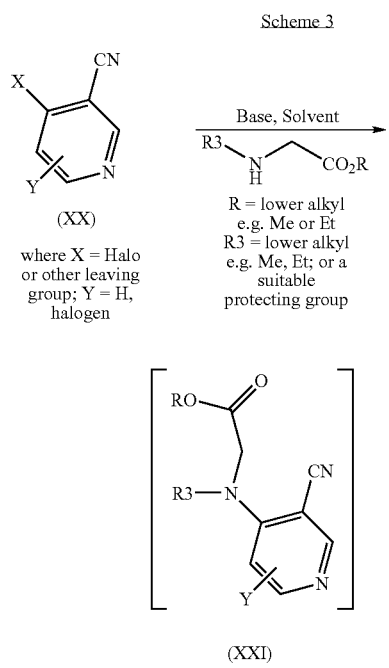

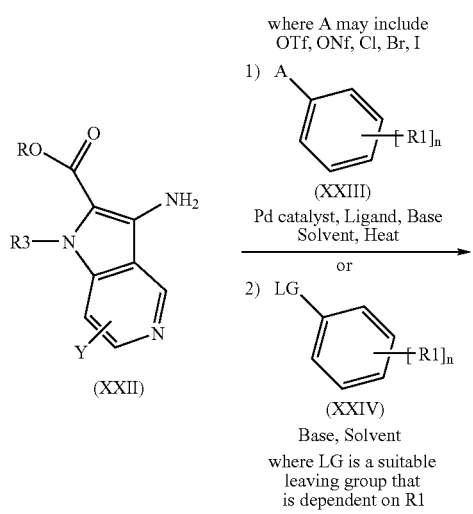

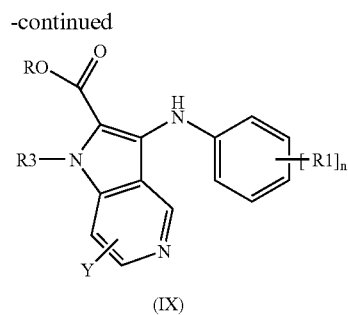

(IX)

where R1 = optional substituent group
n = 0-5

Compounds of formula (XX) may be prepared using published methods described in the literature. Compounds of formula (XXII) may be obtained from compounds of formula (XX) using methods described for the preparation of compounds of formula (VI) from compounds of formula (IV) in Scheme 1. Compounds of formula (IX) may be obtained from compounds of formula (XXII) by reaction with compounds of formula (XXIII) (incorporating appropriate substituents R1), using methods described for the preparation of compounds of formula (IX) from compounds of formula (VII) in Scheme 1. Alternatively, compounds of formula (IX) may be obtained from compounds of formula (XXII) by reaction with compounds of formula (XXIV) (incorporating appropriate substituents R1), in the presence of a base such as sodium hydride or lithium hexamethyldisilazane, in a suitable solvent such as tetrahydrofuran or N,N-dimethylformamide, at a temperature of from room temperature to 150° C.

Compounds of general formula (XXII) may also be prepared according to Scheme 4.

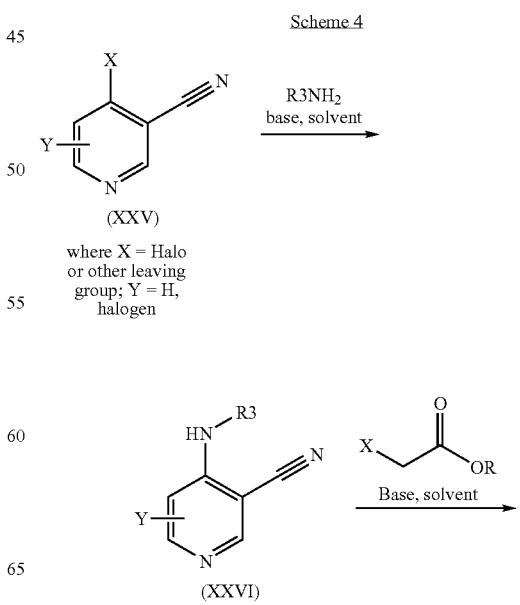

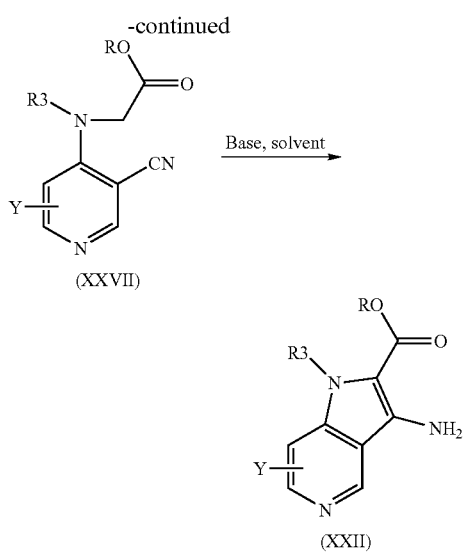

Compounds of general formula (XXV) may be prepared using published methods described in the literature. Compounds of formula (XXV) may be reacted with amines such as methylamine, in a solvent such as ethanol, at a temperature of from 0° C. to reflux to give intermediates of general formula (XXVI). Compounds of formula (XXVI) may be alkylated with alkyl acetates such as bromo tert-butyl acetate, in the presence of a base such as sodium hydride, in a solvent such as DMF to give compounds of general formula (XXVII). Compounds of formula (XXVII) may be cyclised to give compounds of general formula (XXII) using a base such as sodium tert-butoxide, in a solvent such as THF, at a temperature of from −40° C. to reflux. Alternatively, compounds of general formula (XXII) may be prepared directly from compounds of general formula (XXVI) using more than one equivalent of base and prolonged reaction times or higher temperatures. Pyrrolo[2,3-d]pyridazines of formula I-h, II-h and III-h and pyrrolo[3,2-c]pyridazines of formula I-g, II-g, and III-g may be prepared using the synthetic routes outlined in Scheme 5.

Scheme 5

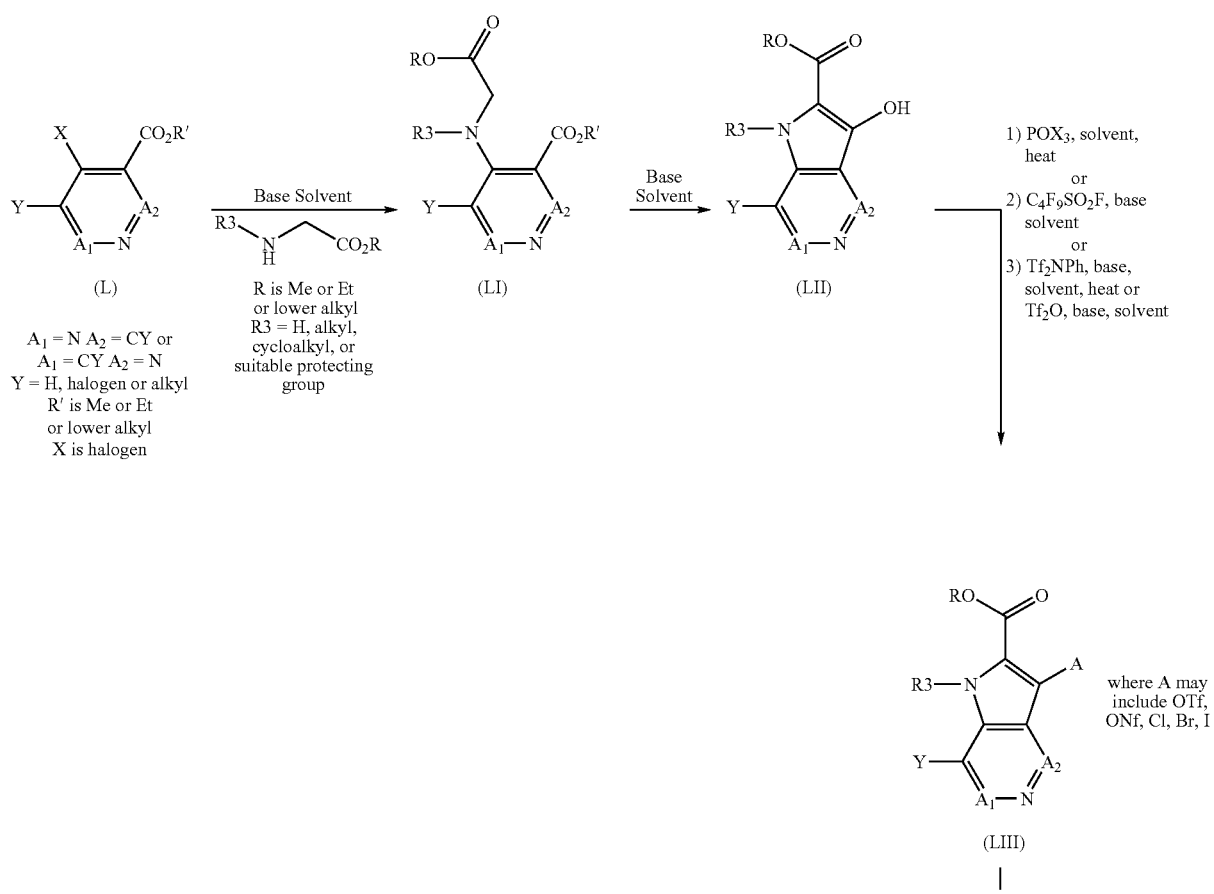

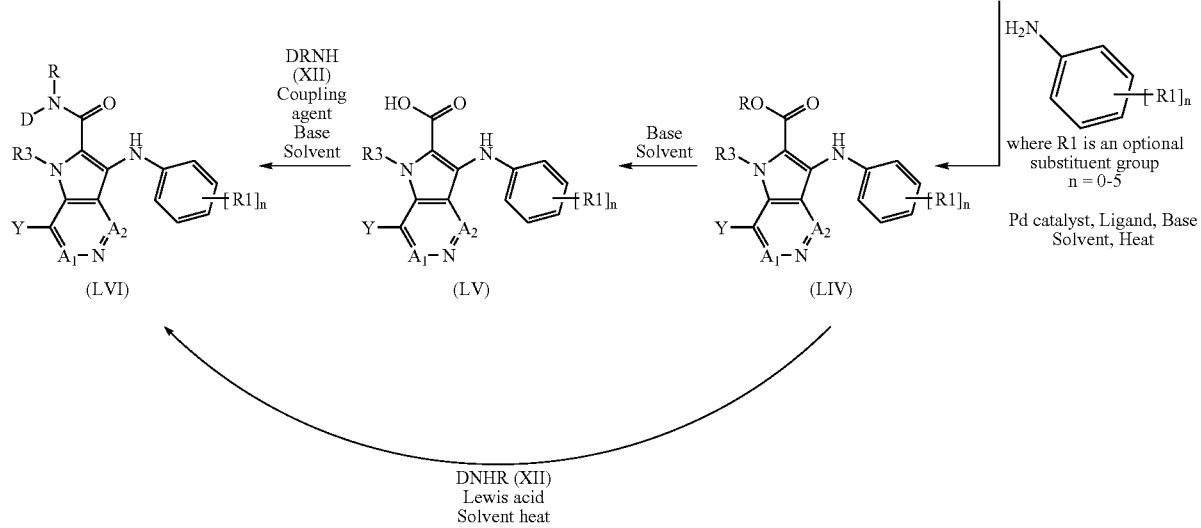

Compounds of formula (L) may be prepared according to methods described in the literature. Compounds of formula (LVI) may be obtained from compounds of formula (L) using similar methods to the ones described for the preparation of compounds of formula (XI) from compounds of formula (IV), as shown in Scheme 1. Alternatively, compounds of formula (LIV) may be prepared according to Scheme 6.

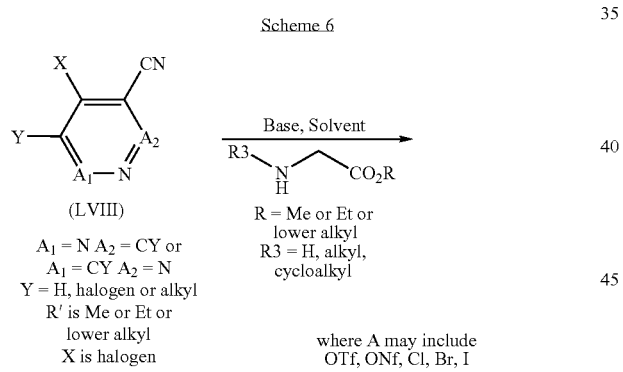

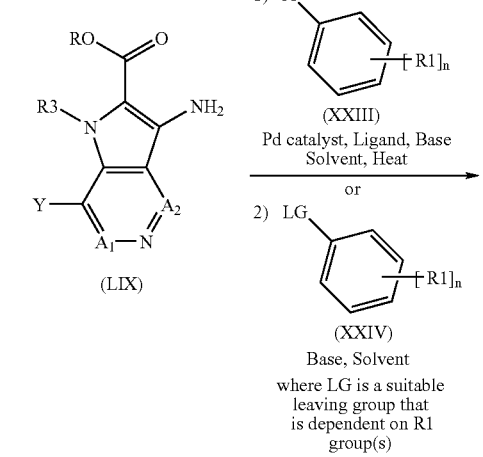

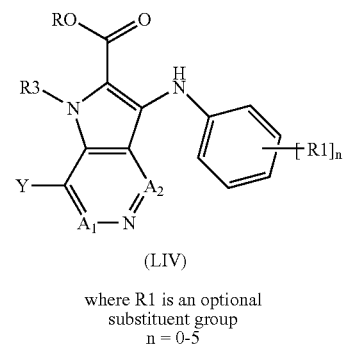

Compounds of formula (LVIII) may be prepared using published methods described in the literature. Compounds of general formula (LIV) can be prepared from compounds of formula (LIX) using methods described above for the preparation of compounds of formula (IX) from compounds of formula (XX) in Scheme 3.

Hydroxylamines of formula (XII) may be prepared using methods described in the literature or the synthetic route outlined in Scheme 7.

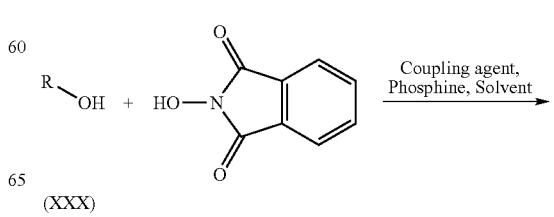

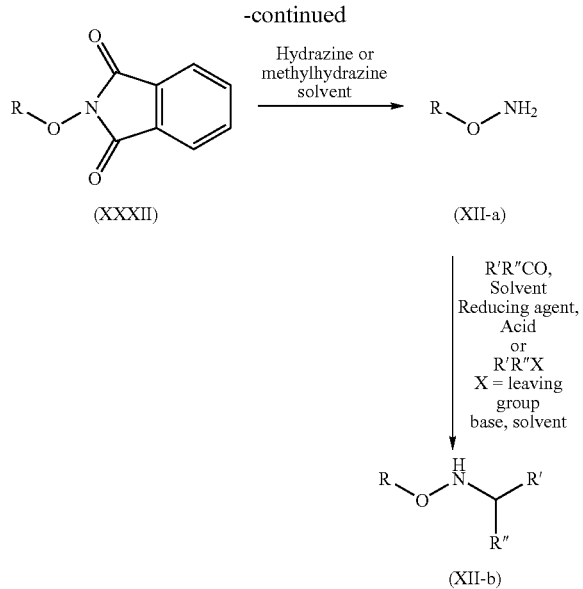

Primary or secondary alcohols of general formula (XXX) may be prepared using methods described in the literature. They may be reacted with N-hydroxy phthalimide using a phosphine such as triphenyl phosphine and coupling reagent such as diethyl azodicarboxylate to provide compounds of general formula (XXXII).

Compounds of general formula (XXXII) may be deprotected using hydrazine or methyl hydrazine to provide hydroxylamines of general formula (XII-a). Compounds of formula (XII-a) may be further modified by reductive amination with aldehydes or ketones using a reducing agent such as sodium triacetoxy borohydride, sodium cyanoborohydride, or borane-pyridine in a solvent such as dichloroethane at a temperature of from ambient temperature to reflux. In addition, compounds of formula (XII-a) may be further modified by alkylation with an alkyl halide in the presence of a base such as triethylamine, in a solvent such as dichloromethane, to provide hydroxylamines of general formula (XII-b).

Anilines of general formula (XXXIX) used in cross-coupling reactions described above may be prepared by using methods described in the literature or according to Scheme 8.

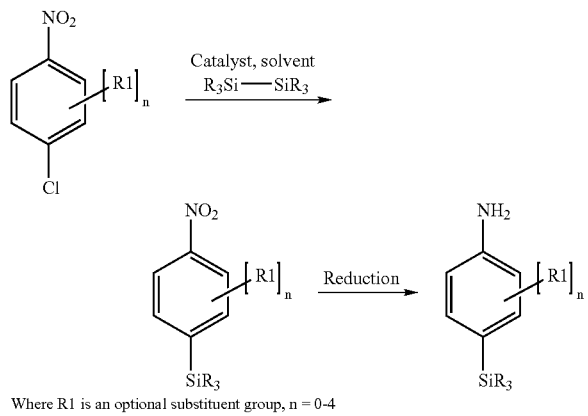

Where R1 is an optional substituent group, n = 0-4

Substituted 4-chloro-nitro benzene may be reacted with hexamethyldisilane in a solvent such as xylene, using a catalyst such as tetrakis(triphenylphosphine)palladium, at a temperature of from room temperature to reflux. The nitro group may be reduced using methods described in the literature such as reaction under an atmosphere of hydrogen, at a pressure of from 1 to 5 atmospheres, in the presence of a catalyst such as palladium on carbon, and in a solvent such as ethanol or ethyl acetate at room temperature.

Trifluoromethanesulfonyl esters of general formula (XL) used in cross-coupling reactions described above may be prepared by using methods described in the literature or according to Scheme 9.

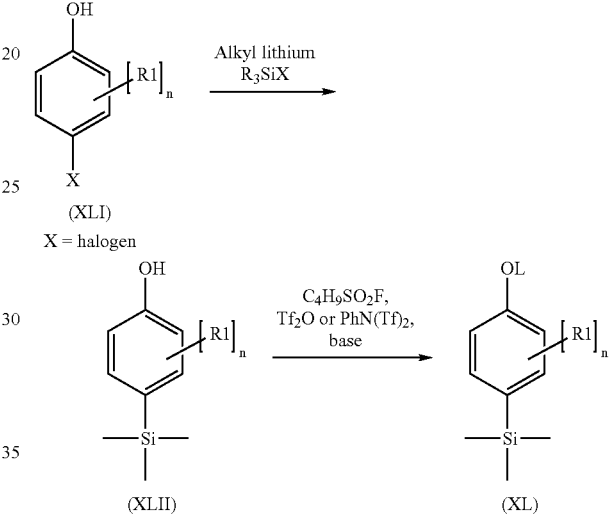

Where R1 is an optional substituent group, n = 0-4

Halo phenols of general structure (XLI) may be reacted with two equivalents of alkyllithium reagents such as n-butyl lithium in a solvent such as THF, followed by quenching with trialkylsilyl halide such as trimethylsilyl chloride to give trialkylsilyl phenols (XLII). Trialkylsilyl phenols may be further reacted using literature procedures to give trifluoromethane sulfonates or nonaflates of general structure (XL).

It will be appreciated that where appropriate functional groups exist, compounds of formula (I), (II), (III) or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

For example, aryl bromide or chloride groups may be converted to aryl iodides using a Finkelstein reaction employing an iodide source such as sodium iodide, a catalyst such as copper iodide and a ligand such as trans-N,N'-dimethyl-1,2-cyclohexane diamine in a solvent such as 1,4-dioxane and heating the reaction mixture at reflux temperature. Aryl trialkylsilanes may be converted to aryl iodides by treating the silane with an iodide source such as iodine monochloride in a solvent such as dichloromethane with or without Lewis acid such as silver tetrafluoroborate at a temperature from −40° C. to reflux.

In a further example, indole NH groups may be alkylated employing an alkyl halide such as benzyl bromide, a base such as potassium carbonate and a solvent such as DMF at a temperature of from room temperature to 80° C.

In a further example primary amine (—$NH_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—$NHSO_2R'$ or —$NR''SO_2R'$) groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N=C=O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e. —$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit MEK activity and activation (primary assays) and for their biological effects on growing cells (secondary assays) as described below. The compounds having $IC_{50}$ of less than 5 µM (more preferably less than 5 µM, even more preferably less than 1 µM, most preferably less than 0.5 µM) in the MEK activity assay of Example 1a or 1b, $IC_{50}$ of less than 5 µM (more preferably less than 0.1 µM, most preferably less than 0.01 µM) in the MEK activation assay of Example 2, $EC_{50}$ of less than 10 µM (more preferably less than 5 µM, most preferably less than 0.5 µM) in the cell proliferation assay of Example 3, and/or $EC_{50}$ of less than 10 µM (more preferably less than 1 µM, most preferably less than 0.1 µM) in the ERK phosphorylation assay of Example 4, are useful as MEK inhibitors.

The present invention includes a composition (e.g., a pharmaceutical composition) comprising a compound of Formula I (and/or solvates and/or salts thereof) and a carrier (a pharmaceutically acceptable carrier). The present invention also includes a composition (e.g., a pharmaceutical composition) comprising a compound of Formula I (and/or solvates and/or salts thereof) and a carrier (a pharmaceutically acceptable carrier), further comprising a second chemotherapeutic and/or a second anti-inflammatory agent such as those described herein. The present compositions are useful for inhibiting abnormal cell growth or treating a hyperproliferative disorder in a mammal (e.g., human). The present compositions are also useful for treating inflammatory diseases in a mammal (e.g., human).

The present compounds and compositions are also useful for treating an autoimmune disease, destructive bone disorder, proliferative disorders, infectious disease, viral disease, fibrotic disease or neurodegenerative disease in a mammal (e.g., human). Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV). Chronic pain, for purposes of the present invention includes, but is not limited to, idiopathic pain, and pain associated with chronic alcoholism, vitamin deficiency, uremia, hypothyroidism, inflammation, arthritis, and post-operative pain. Neuropathic pain is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The present compounds and compositions are also useful for treating pancreatitis or kidney disease (including proliferative glomerulonephritis and diabetes-induced renal disease) in a mammal (e.g., human).

The present compounds and compositions are also useful for the prevention of blastocyte implantation in a mammal (e.g., human).

The present invention includes a method of inhibiting abnormal cell growth or treating a hyperproliferative disorder in a mammal (e.g., human) comprising administering to said mammal a therapeutically effective amount of a compound of Formula I (and/or solvates and/or salts thereof) or a composition thereof. Also included in the present invention is a method of treating an inflammatory disease in a mammal (e.g., human) comprising administering to said mammal a therapeutically effective amount of a compound of Formula I (and/or solvates and/or salts thereof) or a composition thereof.

The present invention includes a method of inhibiting abnormal cell growth or treating a hyperproliferative disorder in a mammal (e.g., human) comprising administering to said mammal a therapeutically effective amount of a compound of Formula I (and/or solvates and/or salts thereof) or a composition thereof, in combination with a second chemotherapeutic agent such as those described herein. The present invention also includes a method of treating an inflammatory disease in a mammal (e.g., human) comprising administering to said mammal a therapeutically effective amount of a compound of Formula I (and/or solvates and/or salts thereof) or a composition thereof, in combination with a second anti-inflammatory agent such as those described herein.

The present invention includes a method of treating an autoimmune disease, destructive bone disorder, proliferative disorders, infectious disease, viral disease, fibrotic disease or neurodegenerative disease in a mammal (e.g., human) comprising administering to said mammal a therapeutically effective amount of a compound of Formula I (and/or solvates and salts thereof) or a composition thereof, and optionally further comprising a second therapeutic agent. Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV).

The present invention includes a method of treating pancreatitis or kidney disease (including proliferative glomerulonephritis and diabetes-induced renal disease) in a mammal (e.g., human) comprising administering to said mammal a therapeutically effective amount of a compound of Formula I (and/or solvates and salts thereof) or a composition thereof, and optionally further comprising a second therapeutic agent.

The present invention includes a method for preventing of blastocyte implantation in a mammal (e.g., human) comprising administering to said mammal a therapeutically effective amount of a compound of Formula I (and/or solvates and salts thereof) or a composition thereof, and optionally further comprising a second therapeutic agent.

The present invention includes a method of using the present compounds for in vitro, in situ, and in vivo diagnosis or treatment of mammalian cells, organisms, or associated pathological conditions.

It is also believed that the compounds of the present invention can render abnormal cells more sensitive to treatment with radiation for purposes of killing and/or inhibiting the growth of such cells. Accordingly, this invention further relates to a method for sensitizing abnormal cells in a mammal (e.g., human) to treatment with radiation which comprises administering to said mammal an amount of a compound of Formula I (and/or solvates and salts thereof) or a composition thereof, which amount is effective is sensitizing abnormal cells to treatment with radiation.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic or anti-inflammatory agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

Abbreviations

DBU 1,8-Diazabicyclo[5.4.0]undec-7-ene
DCM Dichloromethane
DIPEA Diisopropylethylamine
DMAP 4-Dimethylaminopyridine
DMF Dimethylformamide
EDCI 1-Ethyl-3-(3'-dimethylaminopropyl)carbodiimide
HCl Hydrochloric acid
HOBt 1-Hydroxybenzotriazole
HM-N Isolute® HM-N is a modified form of diatomaceous earth that can efficiently absorb aqueous samples
IMS Industrial methylated spirits
MeOH Methanol
$NaHCO_3$ Sodium bicarbonate
NaOH Sodium hydroxide
$NH_3$ Ammonia
$Pd_2dba_3$ Tris-(dibenzylideneacetone)dipalladium(0)
Si-PPC Pre-packed silica flash chromatography cartridge: Isolute® SPE, Biotage SNAP® or ISCO Redisep®
Si-SPE Pre-packed Isolute® silica flash chromatography cartridge
THF Tetrahydrofuran
Xantphos 9,9-Dimethyl-4,5-bis(diphenylphosphino)xanthene General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP1100 LC system with diode array detector. Uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes.

Method C: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 1.5 ml/minute flow rate. The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 1.5 minutes. The final solvent system was held constant for a further 1 minute.

Method D: Experiments performed on a PE Sciex API 150 EX quadrupole mass spectrometer linked to a Shimadzu LC-10AD LC system with diode array detector and 225 position autosampler using a Kromasil C18 50×4.6 mm column and a 3 ml/minute flow rate. The solvent system was a gradient starting with 100% water with 0.05% TFA (solvent A) and 0% acetonitrile with 0.0375% TFA (solvent B), ramping up to 10% solvent A and 90% solvent B over 4 minutes. The final solvent system was held constant for a further 0.50 minutes.

Microwave experiments were carried out using a Personal Chemistry Emrys Initiator™ or Optimizer™, which uses a single-mode resonator and dynamic field tuning, both of which give reproducibility and control. Temperature from 40-250° C. can be achieved, and pressures of up to 20 bar can be reached.

Method E: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 0.6 ml/minute flow rate. The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 9.0 minutes. The final solvent system was held constant for a further 1 minute.

Example 1a

MEK Assay

MEK Activity Assay

Constitutively activated human mutant MEK1 expressed in insect cells is used as source of enzymatic activity at a final concentration in the kinase assay of 62.5 nM.

The assay is carried out for 30 minutes in the presence of 50 µM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 1b

MEK Assay

MEK Activity Assay

Constitutively activated human mutant MEK1 expressed in insect cells is used as source of enzymatic activity at a final concentration in the kinase assay of 15 nM.

The assay is carried out for 30 minutes in the presence of 50 µM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. These are used at a final concentration of 4 µg/ml and 0.84 µg/ml respectively. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Compounds of Examples 5-19, 23-34, 36-65, and 68-71 exhibited an $IC_{50}$ of less than 5 µM in the assay described in either Example 1a or 1b.

Example 2 bRaf Assay

MEK Activation Assay

Constitutively activated bRaf mutant expressed in insect cells is used as source of enzymatic activity.

The assay is carried out for 30 minutes in the presence of 200 µM ATP using recombinant GST-MEK1 produced in *E. Coli* as substrate. Phosphorylation of the substrate is detected and quantified using HTRF, and reagents are supplied by Cisbio. These consist of an anti-GST antibody conjugated to allophycocyanin (XL665) and an anti-phospho (Ser217/Ser221) MEK antibody conjugated to europium-cryptate. The anti-phospho antibody recognises MEK dually phosphorylated on Ser217 and Ser221 or singly phosphorylated on Ser217. When both antibodies are bound to MEK (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multi-well fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

In this assay, compounds of Examples 5-6 exhibited an $IC_{50}$ of less than 5 μM.

Example 3

Cell Proliferation Assay

Compounds are tested in a cell proliferation assay using the following cell lines:

| | |
|---|---|
| HCT116 | human colorectal carcinoma (ATCC) |
| A375 | human malignant melanoma (ATCC) |

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 hours they are exposed to different concentrations of compounds in 0.83% DMSO. Cells are grown for a further 72 h, and an equal volume of CellTiter-Glo reagent (Promega) is added to each well. This lyses the cells and generates a luminescent signal proportional to the amount of ATP released (and therefore proportional to the number of cells in the well) that can be detected using a multi-well luminometer.

The $EC_{50}$ is defined as the concentration at which a given compound achieves 50% inhibition of control. $IC_{50}$ values are calculated using the XLfit software package (version 2.0.5).

In this assay, compounds of Examples 5-8, 10-11, 13, 15-16, 23-27, 31, 33, 36-49, 54, 56-59, 61 and 63-65 exhibited an $EC_{50}$ of less than 10 μM in either cell line.

Example 4

Phospho-ERK Cell-Based Assay

Compounds are tested in a cell-based phospho-ERK ELISA using the following cell lines:

| | |
|---|---|
| HCT116 | human colorectal carcinoma (ATCC) |
| A375 | human malignant melanoma (ATCC) |

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 h they are exposed to different concentrations of compounds in 0.83% DMSO. Cells are grown for a further 2 h or 24 h, fixed with formaldehyde (2% final) and permeabilised with methanol. Following blocking with TBST-3% BSA, fixed cells are incubated with primary antibody (anti-phospho ERK from rabbit) over-night at 4° C. Cells are incubated with Propidium Iodide (DNA fluorescent dye) and detection of cellular p-ERK is performed using an anti-rabbit secondary antibody conjugated to the fluorescent Alexa Fluor 488 dye (Molecular probes). The fluorescence is analysed using the Acumen Explorer (TTP Labtech), a laser-scanning microplate cytometer, and the Alexa Fluor 488 signal is normalised to the PI signal (proportional to cell number).

The $EC_{50}$ is defined as the concentration at which a given compound achieves a signal half way between the baseline and the maximum response. $EC_{50}$ values are calculated using the XLfit software package (version 2.0.5).

In this assay, compounds of Examples 5-8, 10-11, 13, 15-17, 23-31, 33, 34, 36-50, 54, 56-59 and 61-65 exhibited an $EC_{50}$ of less than 10 μM in either cell line.

Synthesis of Aza-Indolyl Cores 3-(4-Bromo-2-fluoro-phenylamino)-1-methyl-1H-pyrrolo[3,2-c]pyridine-2-carboxylic acid ethyl ester

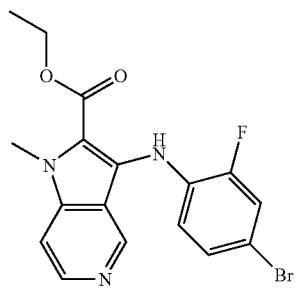

Step 1: Ethyl 4-chloro-nicotinate

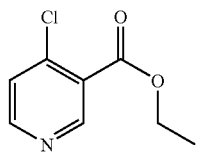

A suspension of 4-chloro-nicotinic acid (3.0 g, 19.0 mmol) in thionyl chloride (50 ml) was heated under reflux for 90 minutes. After cooling to ambient temperature, the solution was concentrated to dryness and then azeotroped with toluene (2×50 ml) to afford a solid. The resultant solid was added in portions to a cooled (0° C.) solution of ethanol (25 ml) and DIPEA (15 ml). The reaction was stirred at room temperature for 4 hours then concentrated in vacuo before water (75 ml) was added. The solution was extracted with ethyl acetate (2×75 ml) and the combined organic phases were dried over sodium sulfate, then concentrated to give the title compound as a brown oil (3.3 g, 94%). $^1$H NMR ($CDCl_3$, 400 MHz) 9.03 (s, 1H), 7.58 (d, J=5.4 Hz, 1H), 7.41 (dd, J=5.4 Hz, 0.5 Hz, 1H), 4.45 (q, J=7.3 Hz, 2H), 1.43 (t, J=7.3 Hz, 3H).

Step 2: 3-Hydroxy-1-methyl-1H-pyrrolo[3,2-c]pyridine-2-carboxylic acid ethyl ester

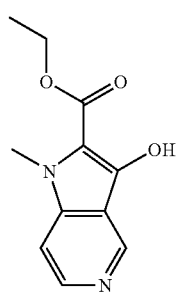

To a stirred solution of ethyl 4-chloro-nicotinate (2.05 g, 11.0 mmol) and sarcosine ethyl ester hydrochloride (4.75 g, 30.9 mmol) in anhydrous DMF (40 ml), under an argon atmosphere, was added sodium hydride (59.6 mmol, 60% in dispersion oil, 2.39 g) in portions over 20 minutes. On complete addition the mixture was heated at 80° C. for 1.5 hours. Potassium carbonate (1.52 g, 11.0 mmol) was then added and the mixture heated for a further 2 hours. The reaction mixture was then quenched by the addition of water (50 ml) and subsequently concentrated to provide a residue. The residue was partitioned between ethyl acetate (100 ml) and water (100 ml). The layers were separated, the aqueous phase was cooled to 0° C. and the pH adjusted to 7 by the addition of concentrated HCl. The aqueous phase was aged overnight and the resulting precipitate was filtered, washed with water and dried under vacuum at 60° C. to give a white solid (700 mg, 15%). LCMS (method B): $R_T$=1.82 min, $M+H^+$=221.

Step 3: 1-Methyl-3-(nonafluorobutane-1-sulfonyloxy)-1H-pyrrolo[3,2-c]pyridine-2-carboxylic acid ethyl ester

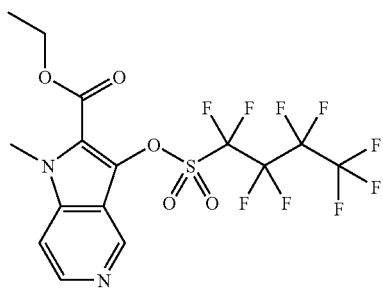

To a stirred solution of 3-hydroxy-1-methyl-1H-pyrrolo[3,2-c]pyridine-2-carboxylic acid ethyl ester (695 mg, 3.16 mmol) and DMAP (19 mg, 0.16 mmol) in DCM (10 ml) at 0° C. was added DIPEA (1.35 ml, 7.58 mmol) and nonafluorobutylsulfonyl fluoride (0.74 ml, 4.10 mmol). After 10 minutes the reaction was warmed to room temperature and stirred for an additional 4.5 hours. The reaction mixture was diluted with DCM (50 ml) and washed with water (30 ml). The organic phase was isolated, dried over sodium sulphate then filtered and evaporated to give a yellow oil. The oil was purified by flash chromatography (Si-PPC, pentane:ethyl acetate, gradient 100:0 to 60:40) to afford the title compound as a colourless oil which crystallised on standing (1.43 g, 90%). LCMS (method B): $R_T$=3.28 min, $M+H^+$=505.

Step 4: 3-(4-Bromo-2-fluoro-phenylamino)-1-methyl-1H-pyrrolo[3,2-c]pyridine-2-carboxylic acid ethyl ester A degassed solution of 1-methyl-3-(nonafluorobutane-1-sulfonyloxy)-1H-pyrrolo[3,2-c]pyridine-2-carboxylic acid ethyl ester (800 mg, 1.58 mmol), 4-bromo-2-fluoroaniline (360 mg, 1.89 mmol), $Pd_2dba_3$ (144 mg, 0.16 mmol), Xantphos (182 mg, 0.32 mmol) and DBU (538 μl, 3.79 mmol) in toluene (8 ml) was subjected to microwave irradiation at 120° C. for 5 minutes. The reaction mixture was cooled to ambient temperature then diluted with ethyl acetate (100 ml). The resultant solution was washed with water (50 ml), dried over sodium sulfate and concentrated in vacuo to give a solid residue. The solid residue was purified by flash chromatography (Si-PPC, pentane:ethyl acetate, gradient 100:0 to 60:40) to afford the title compound as a yellow solid (210 mg, 34%). LCMS (method B): $R_T$=2.33 min, M+H=392/394.

3-(2-Fluoro-4-iodo-phenylamino)-1-methyl-1H-pyrrolo[3,2-c]pyridine-2-carboxylic acid ethyl ester

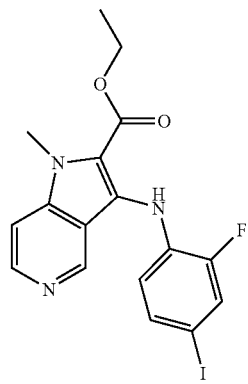

Step 1: 4-Methylamino-nicotinonitrile

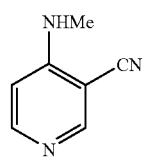

4-Chloronicotinonitrile (45.0 g, 324 mmol) was suspended in water (250 mL) and 41% aqueous methylamine solution (250 mL). The resultant mixture was heated, with stirring, at 90° C. for 1 hour before the mixture was cooled to room temperature and extracted with ethyl acetate (×2). The combined organic layers were washed with water, followed by brine then dried ($MgSO_4$) and evaporated to provide a residue. Trituration of the residue with diethyl ether gave the title compound (40.4 g, 93%) as a white solid. 1H NMR ($CDCl_3$) 2.98 (3H, d, J=5.1 Hz), 5.20 (1H, br s), 6.53 (1H, d, J=6.13 Hz), 8.35 (1H, d, J=6.13 Hz), 8.43 (1H, s).

Step 2: 3-Amino-1-methyl-1H-pyrrolo[3,2-c]pyridine-2-carboxylic acid ethyl ester

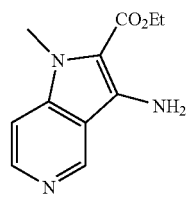

Sodium hydride (9.0 g, 60% dispersion, 225 mmol) was suspended in DMF (150 mL) and cooled to 0-5° C. A solution of 4-methylamino-nicotinonitrile (20.0 g, 150 mmol) in DMF (100 mL) was added dropwise over ca. 20 minutes and the resulting mixture stirred cold for 30 minutes and then treated with a solution of ethyl bromoacetate (34.0 g, 225 mmol) in DMF (50 mL). The solution was allowed to warm to room temperature over 1 hour. The mixture was partitioned between ethyl acetate and water and the aqueous further extracted with ethyl acetate. The combined organic layers were washed with water (×2), brine, dried (MgSO₄) and evaporated. Trituration of the resultant residue with ethyl acetate gave the title compound (12.2 g, 37%) as a yellow solid. ¹H NMR (CDCl₃) 1.44 (3H, t, J=7.1 Hz), 3.88 (3H, s), 4.43 (2H, q, J=7.1 Hz), 5.09 (2H, br s), 7.10 (1H, dd, 1H, J=6.1, 1.0 Hz), 8.35 (1H, d, J=6.1 Hz), 8.88 (1H, d, J=1.0 Hz).

Step 3: 3-(2-Fluoro-4-trimethylsilanyl-phenylamino)-1-methyl-1H-pyrrolo[3,2-c]pyridine-2-carboxylic acid ethyl ester

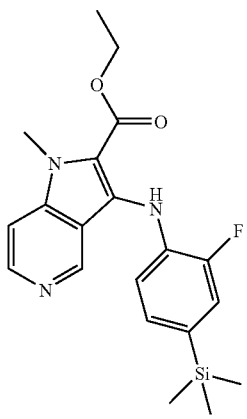

3-Amino-1-methyl-1H-pyrrolo[3,2-c]pyridine-2-carboxylic acid ethyl ester (25 g, 114 mmol), trifluoro-methane-sulfonic acid 2-fluoro-4-trimethylsilanyl-phenyl ester (47.0 g, 149 mmol), Pd₂(dba)₃ (5.0 g, 5.5 mmol), Xantphos (6.5 g, 11.3 mmol) and cesium carbonate (74.5 g, 228 mmol) were suspended in toluene (500 mL) and the flask evacuated and purged with argon. The reaction mixture was heated at reflux for 18 hours. The mixture was cooled and filtered through Celite® washing through with toluene. The filtrate was evaporated in vacuo and the residue subjected to flash chromatography (SiO₂, gradient 0-10% MeOH in DCM) to give the title compound (37.4 g, 85%) as a yellow solid. ¹H NMR (CDCl₃) 8.79 (1H, d, J=1.1 Hz), 8.39 (1H, d, J=6.1 Hz), 7.60 (1H, s, br), 7.25 (0.5H, s), 7.22 (1H, s), 7.21 (0.5H, d, J=1.0 Hz), 7.14-7.10 (2H, m), 4.42 (2H, q, J=7.0 Hz), 3.97 (3H, s), 1.44 (3H, t, J=7.0 Hz), 0.26 (9H, s).

Step 4: 3-(2-Fluoro-4-iodo-phenylamino)-1-methyl-1H-pyrrolo[3,2-c]pyridine-2-carboxylic acid ethyl ester A solution of 3-(2-fluoro-4-trimethylsilanyl-phenylamino)-1-methyl-1H-pyrrolo[3,2-c]pyridine-2-carboxylic acid ethyl ester (37.0 g, 96.0 mmol) in CH₂Cl₂ (500 mL) was cooled to 0-5° C. and treated dropwise with iodine monochloride solution (211 mL, 1M in CH₂Cl₂). The mixture was allowed to warm and stirring continued for 1 hour. The solution was washed with aqueous sodium thiosulfate solution, dried (MgSO₄) and evaporated in vacuo. The resultant residue was triturated with ethyl acetate to give the title compound (21.8 g, 52%) as a yellow solid. LCMS (method B): R$_T$=2.48 min, M+H⁺=440.

3-(2-Fluoro-4-iodo-phenylamino)-1-methyl-1H-pyrrolo[3,2-c]pyridine-2-carboxylic acid

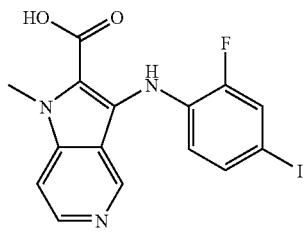

A mixture of 3-(2-fluoro-4-iodo-phenylamino)-1-methyl-1H-pyrrolo[3,2-c]pyridine-2-carboxylic acid ethyl ester (88 mg, 0.20 mmol), 1M aqueous sodium hydroxide solution (220 µl) and IMS (3 ml) was heated at 65° C. for 2 hours. After cooling to ambient temperature the solvent was evaporated, the resultant residue was dissolved in water and the pH of the solution was adjusted to 7 by the addition of 1N HCl solution. The precipitated solid was collected by filtration, washed with water (2 mL) then diethyl ether (2 mL) and left to air dry to provide the title compound as a yellow solid (80 mg, 92%). LCMS (method B): R$_T$=2.11 min, M+H⁺=412.

3-(2-Fluoro-4-iodo-phenylamino)-1-methyl-1H-pyrrolo[3,2-c]pyridine-2-carboxylic acid sodium salt

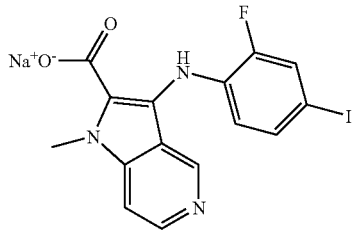

Sodium hydroxide (39 mg, 1.0 mmol) was added to a suspension of 3-(2-fluoro-4-iodo-phenylamino)-1-methyl-1H-pyrrolo[3,2-c]pyridine-2-carboxylic acid ethyl ester (400 mg, 0.91 mmol) in IMS (6 ml) and the reaction heated at 60° C. for 5 hours. The reaction mixture was concentrated in vacuo to yield the title compound as a yellow solid (439 mg, 100%). LCMS (method B): R$_T$=2.19 min, M-Na+H⁺=412.

3-(4-Bromo-2-chloro-phenylamino)-1-methyl-1H-pyrrolo[3,2-c]pyridine-2-carboxylic acid ethyl ester

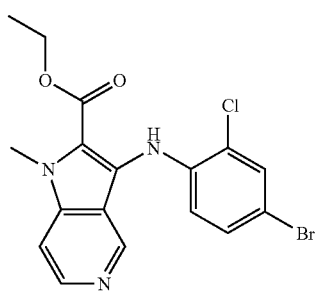

A degassed solution of 1-methyl-3-(nonafluorobutane-1-sulfonyloxy)-1H-pyrrolo[3,2-c]pyridine-2-carboxylic acid ethyl ester (500 mg, 0.99 mmol), 4-bromo-2-chloroaniline (246 mg, 1.19 mmol), Pd₂dba₃ (91 mg, 0.10 mmol), Xantphos (114 mg, 0.20 mmol) and DBU (352 µl, 2.48 mmol) in toluene (8 ml) was subjected to microwave irradiation at 120° C. for 5 minutes. The reaction mixture was cooled to ambient temperature then diluted with ethyl acetate (100 ml). The resultant solution was washed with water (30 ml), dried (Na₂SO₄) and concentrated in vacuo to give an oil. The oil was purified by flash chromatography (Si-PPC, cyclohexane:ethyl acetate, gradient 90:10 to 0:100) to afford the title compound as a yellow solid (140 mg, 35%). ¹H NMR (CDCl₃, 400 MHz) 8.75 (d, J=1.0 Hz, 1H), 8.41 (d, J=6.1 Hz, 1H), 7.68 (s, 1H), 7.54 (d, J=2.3 Hz, 1H), 7.19-7.27 (m, 2H), 6.94 (d, J=8.8 Hz, 1H), 4.44 (q, J=7.2 Hz, 2H), 3.99 (s, 3H), 1.44 (t, J=7.2 Hz, 3H).

3-(2-Fluoro-4-iodo-phenylamino)-1H-pyrrolo[3,2-c]pyridine-2-carboxylic acid ethyl ester

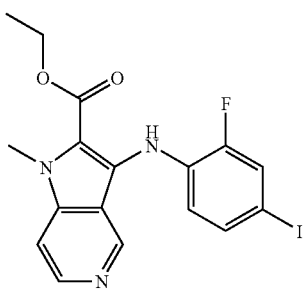

Step 1: Ethyl-(4-(3-cyanopyridine)glycinate

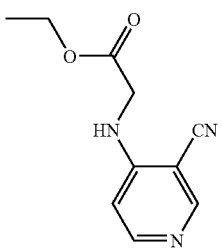

Ethyl glycinate hydrochloride (60.5 g, 432 mmol) and sodium hydrogen carbonate (25.5 g, 302 mmol) were suspended in 95% EtOH and the mixture was heated at reflux for 1 hour. 4-Chloronicotinonitrile (6.0 g, 43.2 mmol) was then added and the mixture was heated at reflux for a further 5 hours. The solvent was evaporated and the resultant residue was diluted with water (60 mL) and extracted with DCM (2×50 mL). The organic phases were combined then washed with water (20 mL), followed by brine (20 mL), dried (Na₂SO₄), filtered and evaporated to give a brown oil. The oil was purified by flash column chromatography (Si-PPC, DCM:MeOH, gradient 100:1 to 95:5). Appropriate fractions were collected, concentrated to dryness and the residue recrystallised (EtOAc/cyclohexane) to give the title compound as a white solid (3.99 g, 45%). ¹H NMR (CDCl₃, 400 MHz) 8.50 (s, 1H), 8.38 (dd, J=6.0 Hz, 0.6 Hz, 1H), 6.44 (d, J=6.0 Hz, 1H), 5.62 (br t, 1H), 4.30 (q, J=7.1 Hz, 2H), 4.02 (d, J=5.3 Hz, 2H), 1.33 (t, J=7.1 Hz, 3H).

Step 2:
3-Amino-1H-pyrrolo[3,2-c]pyridine-2-carboxylic acid ethyl ester

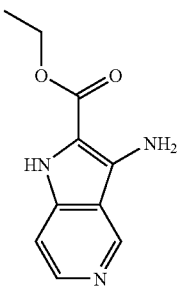

To a solution of ethyl-4-(3-cyanopyridine)glycinate (2.47 g, 12.1 mmol) under nitrogen in EtOH (60 mL) was added sodium ethoxide (0.90 g, 13.3 mmol) and the mixture was heated at reflux for 1 hour. The mixture was allowed to cool to ambient temperature then quenched by the addition of water (3 mL) and saturated ammonium chloride solution (5 mL). The solvent was concentrated in vacuo, to provide a residue that was diluted with water (30 mL), and extracted with EtOAc (2×40 mL). The combined organic layers were dried (Na₂SO₄), filtered and evaporated to give the title compound as a brown solid (1.35 g, 55%). LCMS (method B): R$_T$=0.61 min, M+H⁺=206.

Step 3: 3-(2-Fluoro-4-trimethylsilanyl-phenylamino)-1H-pyrrolo[3,2-c]pyridine-2-carboxylic acid ethyl ester

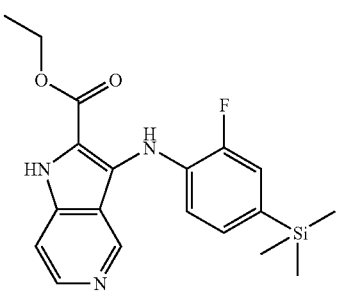

A degassed solution of 3-amino-1H-pyrrolo[3,2-c]pyridine-2-carboxylic acid ethyl ester (200 mg, 0.98 mmol), trifluoro-methanesulfonic acid 2-fluoro-4-trimethylsilanyl-phenyl ester (324 mg, 1.02 mmol), Pd₂dba₃ (44 mg, 0.048 mmol), Xantphos (56 mg, 0.098 mmol) and Cs₂CO₃ (636 mg, 1.95 mmol) in toluene (6 ml) was subjected to microwave irradiation at 150° C. for 20 minutes. The reaction mixture was cooled to ambient temperature then diluted with EtOAc (100 ml). The resultant solution was washed with water (60 ml), dried (Na₂SO₄) and concentrated in vacuo to give a black oil. The oil was purified by flash chromatography (Si-PPC, cyclohexane:EtOAc, gradient 90:10 to 20:80) to provide the title compound as a brown solid (152 mg, 42%). LCMS (method B): R$_T$=2.65 min, M+H⁺=372.

Step 4: 3-(2-Fluoro-4-iodo-phenylamino)-1H-pyrrolo[3,2-c]pyridine-2-carboxylic acid ethyl ester To a cooled (−10° C.) solution of 3-(2-fluoro-4-trimethylsilanyl-phenylamino)-1H-pyrrolo[3,2-c]pyridine-2-carboxylic acid ethyl ester (140 mg, 0.343 mmol) in DCM (5 mL) was added iodine monochloride (1M in DCM, 0.90 mL) dropwise over 10 minutes. On complete addition the mixture was allowed to stir at ambient temperature for 20 minutes then quenched by the addition of saturated sodium thiosulphate solution (3 mL). The solution was partitioned between DCM (50 mL) and water (10 mL). The organic layer was separated, dried ($Na_2SO_4$), filtered and evaporated to give a yellow solid. The solid was triturated with diethyl ether, filtered and left to air dry to provide the title compound as a yellow solid (148 mg, 85%). LCMS (method B): $R_T$=2.37 min, M+H$^+$=426.

3-(2-Fluoro-4-iodo-phenylamino)-1-(4-methoxy-benzyl)-1H-pyrrolo[3,2-c]pyridine-2-carboxylic acid

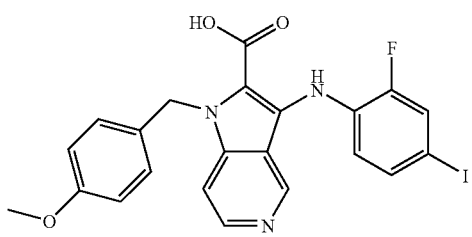

Step 1: 4-(4-Methoxy-benzylamino)-nicotinonitrile

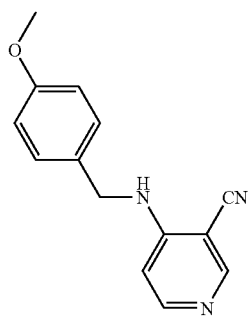

A solution of 4-chloronicotinonitrile (1.00 g, 7.22 mmol), 4-methoxybenzylamine (1.03 ml, 7.94 mmol) and potassium carbonate (1.20 g, 8.66 mmol) in propan-2-ol (20 mL) was heated under reflux for 18 hours. The solvent was concentrated in vacuo and the residue partitioned between EtOAc (150 mL) and water (50 mL). The organic phase was dried ($Na_2SO_4$), filtered and evaporated to give a brown oil. The oil was pre-adsorbed onto H-MN and purified by flash column chromatography (Si-PPC, cyclohexane:EtOAc, gradient 80:20 to 0:100) to provide the title compound as a white solid (1.61 g, 93%). 1H NMR (CDCl$_3$, 300 MHz) 8.46 (d, J=0.7 Hz, 1H), 8.30 (dd, J=6.1 Hz, 0.7 Hz, 1H), 7.24 (dd, J=8.6 Hz, 2.1 Hz, 2H), 6.92 (dd, J=8.6 Hz, 2.1 Hz, 2H), 6.55 (d, J=6.1 Hz, 1H), 5.35 (br t, 1H), 4.40 (d, J=5.6 Hz, 2H), 3.82 (s, 3H).

Step 2: 3-Amino-1-(4-methoxy-benzyl)-1H-pyrrolo[3,2-c]pyridine-2-carboxylic acid methyl ester

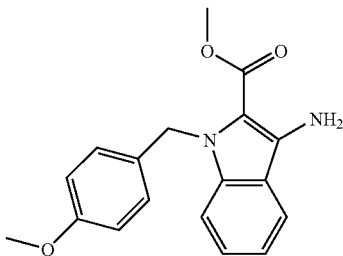

A cooled (0° C.) solution of 4-(4-methoxybenzylamino)-3-cyanopyridine (800 mg, 3.34 mmol) and methyl bromoacetate (0.37 mL, 4.02 mmol) in DMF was treated with sodium hydride (60% w/w in oil, 161 mg, 4.02 mmol) portionwise over 15 minutes. The mixture was allowed to warm to ambient temperature and stirred for 15 hours. The reaction was quenched by the addition of saturated ammonium chloride solution (10 mL) and the solvent evaporated. The resultant residue was partitioned between EtOAc (100 mL), water (50 mL) and saturated NaHCO$_3$ solution (5 mL). The organic phase was dried ($Na_2SO_4$), filtered and evaporated to give a brown oil. The oil was purified by flash column chromatography (Si-PPC, DCM:MeOH, gradient 100:0 to 85:15) to provide the title compound as an off white solid (401 mg, 39%). LCMS (method B): $R_T$=1.33 min, M+H$^+$=312.

Step 3: 3-(2-Fluoro-4-trimethylsilanyl-phenylamino)-1-(4-methoxy-benzyl)-1H-pyrrolo[3,2-c]pyridine-2-carboxylic acid methyl ester

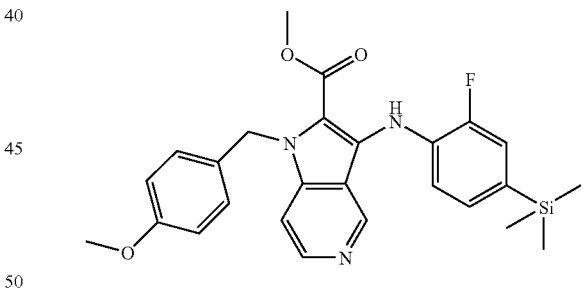

3-Amino-1-(4-methoxy-benzyl)-1H-pyrrolo[3,2-c]pyridine-2-carboxylic acid methyl ester (200 mg, 0.64 mmol) was dissolved in toluene (6 mL), to which Cs$_2$CO$_3$ (417 mg, 1.28 mmol) and trifluoro-methanesulfonic acid 2-fluoro-4-trimethylsilanyl-phenyl ester (263 mg, 0.83 mmol) were added and the mixture degassed with nitrogen before addition of Pd$_2$dba$_3$ (29 mg, 0.032 mmol) and Xantphos (37 mg, 0.064 mmol). The mixture was heated at 105° C. for 18 hours, allowed to cool to ambient temperature then partitioned between EtOAc (50 mL) and water (30 mL). The organic layer was isolated, dried (Na$_2$SO$_4$), filtered and evaporated to give a black oil. The oil was purified by flash column chromatography on silica (Si-PPC, cyclohexane:EtOAc, gradient 90:10 to 40:60) to provide the title compound as a pale brown solid (269 mg, 88%). LCMS (method B): $R_T$=2.81 min, M+H$^+$=478.

Step 4: 3-(2-Fluoro-4-iodo-phenylamino)-1-(4-methoxy-benzyl)-1H-pyrrolo[3,2-c]pyridine-2-carboxylic acid methyl ester

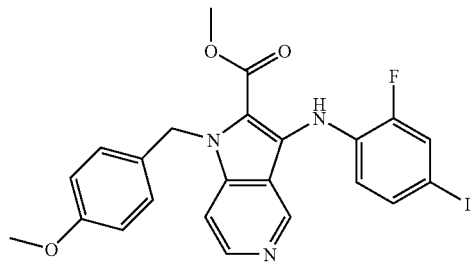

Iodine monochloride (1M in DCM, 1.13 mL) was added dropwise over 10 minutes to a cooled (−10° C.) solution of 3-(2-fluoro-4-trimethylsilanyl-phenylamino)-1-(4-methoxy-benzyl)-1H-pyrrolo[3,2-c]pyridine-2-carboxylic acid methyl ester (269 mg, 0.56 mmol) in DCM (5 mL). The mixture was allowed to warm to ambient temperature and stirred for 20 minutes then quenched by the addition of saturated sodium thiosulphate solution (1 mL). The solution was partitioned between DCM (30 mL) and water (20 mL), the organic layer was separated, dried ($Na_2SO_4$), filtered and evaporated to give an orange oil. The oil was purified by flash column chromatography on silica (Si-PPC, cyclohexane:EtOAc, gradient 90:10 to 40:60) to provide the title compound as a yellow solid (240 mg, 80%). LCMS (method B): $R_T$=2.59 min, M+H$^+$=532.

Step 5: 3-(2-Fluoro-4-iodo-phenylamino)-1-(4-methoxy-benzyl)-1H-pyrrolo[3,2-c]pyridine-2-carboxylic acid A mixture of 3-(2-fluoro-4-iodo-phenylamino)-1-(4-methoxy-benzyl)-1H-pyrrolo[3,2-c]pyridine-2-carboxylic acid ethyl ester (196 mg, 0.37 mmol), 1M aqueous sodium hydroxide solution (443 μl) and IMS (4 ml) was heated at 65° C. for 2.5 hours. After cooling to ambient temperature the solvent was evaporated, the residue was dissolved in water and the pH of the solution was adjusted to 7 by the addition of 1N HCl solution. The precipitated solid was collected by filtration, washed with water (5 mL), ethyl acetate (2 mL) and pentane (2 mL) then left to air dry to provide the title compound as a yellow solid (170 mg, 89%). LCMS (method A): $R_T$=7.22 min, M+H$^+$=518.

1-Ethyl-3-(2-fluoro-4-iodo-phenylamino)-1H-pyrrolo[3,2-c]pyridine-2-carboxylic acid ethyl ester

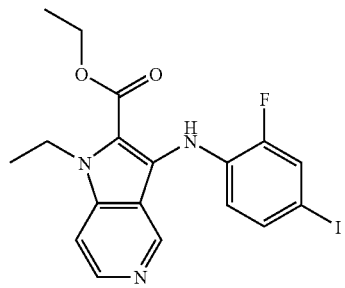

A mixture of 3-(2-fluoro-4-iodo-phenylamino)-1H-pyrrolo[3,2-c]pyridine-2-carboxylic acid ethyl ester (210 mg, 0.49 mmol), potassium carbonate (82 mg, 0.59 mmol) and ethyl iodide (44 μl, 0.54 mmol) in DMF was heated at 55° C. for 2 hours. The mixture was allowed to cool to ambient temperature then evaporated. The residue was partitioned between EtOAc (50 mL) and water (15 mL). The organic phase was separated, dried ($Na_2SO_4$), filtered and evaporated to give an oil. The oil was purified by flash column chromatography on silica (Si-PPC, pentane:EtOAc, gradient 100:0 to 40:60) to provide the title compound as a yellow solid (80 mg, 36%). LCMS (method B): $R_T$=2.52 min, M+H$^+$=454.

3-(2-Fluoro-4-iodo-phenylamino)-1-(2-methoxy-ethyl)-1H-pyrrolo[3,2-c]pyridine-2-carboxylic acid ethyl ester

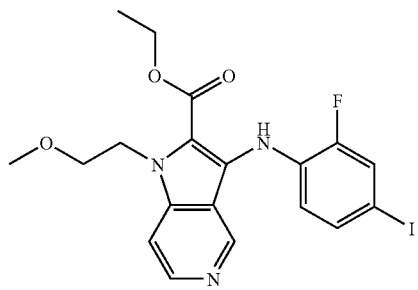

A mixture of 3-(2-Fluoro-4-iodo-phenylamino)-1H-pyrrolo[3,2-c]pyridine-2-carboxylic acid ethyl ester (234 mg, 0.55 mmol), potassium carbonate (91 mg, 0.66 mg), sodium iodide (103 mg, 0.69 mmol) and 1-bromo-2-methoxy-ethane (0.057 mL, 0.61 mmol) in DMF (5 mL) was stirred a 90° C. for 2 days. It was cooled to room temperature, diluted with water and extracted into ethyl acetate. The organic layer was separated then washed with water followed by brine, then dried ($Na_2SO_4$), filtered and concentrated to give a residue which was purified by flash chromatography (Si-PPC, ether:pentane, gradient 20:80 to 50:50) to provide the title compound as a yellow oil (44 mg, 16%). LCMS (method B): $R_T$=2.56 min, M+H$^+$=483.

3-(2-Fluoro-4-iodo-phenylamino)-1-(2-triisopropylsilanyloxy-ethyl)-1H-pyrrolo[3,2-c]pyridine-2-carboxylic acid methyl ester

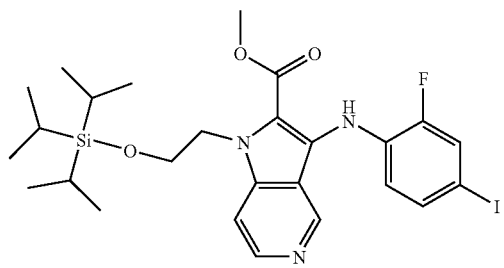

Step 1: 4-(2-Hydroxy-ethylamino)-nicotinonitrile

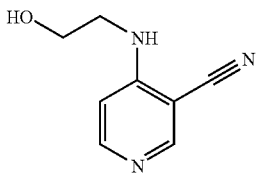

A mixture of ethanolamine (0.60 mL, 10.0 mmol), 4-chloronicotinonitrile (1.38 g, 10.0 mmol) and diisopropylethylamine (1.74 mL, 10.0 mmol) in isopropanol was heated at reflux for 2.5 hours. It was cooled to room temperature and loaded on to a 50 g SCX-2 cartridge preconditioned with methanol. The cartridge was eluted with methanol and then with a 2M solution of ammonia in methanol. Collecting appropriate fractions followed by evaporation of solvents gave the title compound as a beige solid (1.20 g, 74%). $^1$H NMR ($d_6$-DMSO, 400 MHz) 8.40 (s, 1H), 8.21 (d, J=6.3 Hz, 1H), 6.94 (bs, 1H), 6.77 (d, J=6.3 Hz, 1H), 4.84 (bs, 1H), 3.55 (t, J=6.0 Hz, 2H), 3.31 (dt, J=6.0 Hz, 6.0 Hz, 2H).

Step 2: 4-(2-Triisopropylsilanyloxy-ethylamino)-nicotinonitrile

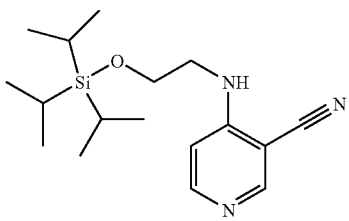

To a solution of 4-(2-hydroxy-ethylamino)-nicotinonitrile (500 mg, 3.07 mmol) and imidazole (250 mg, 3.68 mmol) in DMF (15 mL) was added triisopropylsilyl chloride (0.723 mL, 3.37 mmol). The reaction mixture stirred at room temperature for 2 hours. The mixture was then partitioned between ethyl acetate and water, the organic layer isolated and washed with brine, dried ($Na_2SO_4$), filtered and concentrated. The resultant residue was purified by flash chromatography (Si-PPC, pentane:ether, gradient 50:50 to 30:70) to provide the title compound as a white solid (753 mg, 77%). LCMS (method B): $R_T$=2.92 min, M+H$^+$=320.

Step 3: 3-Amino-1-(2-triisopropylsilanyloxy-ethyl)-1H-pyrrolo[3,2-c]pyridine-2-carboxylic acid methyl ester

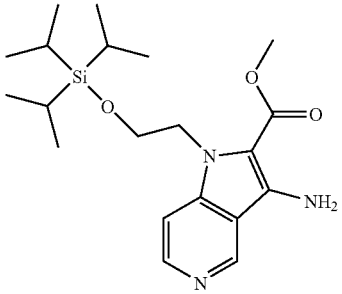

To a solution of 4-(2-triisopropylsilanyloxy-ethylamino)-nicotinonitrile (6.4 g, 20 mmol) in DMF at 0° C. under an inert atmosphere was added sodium hydride (60% dispersion in mineral oil, 880 mg, 22 mmol) in a stepwise manner over a 45 min period. The temperature was kept below 110° C. and the reaction mixture was stirred for 15 minutes. Methyl bromoacetate (2.0 mL, 22 mmol) was added to the reaction mixture which was allowed to reach room temperature and was stirred for 18 hours. Aqueous ammonium chloride (1M sltn. ca 100 mL) was added to the reaction mixture which extracted into ethyl acetate. The organic layer was separated, washed with water then brine, dried ($Na_2SO_4$), filtered and concentrated to give residue. The residue was purified by flash chromatography (Si-PPC, EtOAc:MeOH, gradient 100:0 to 90:10) to provide the title compound as a brown solid (1.19 g, 15%). LCMS (method B): $R_T$=2.79 min, M+H$^+$=392.

Step 4: 3-(2-Fluoro-4-trimethylsilanyl-phenylamino)-1-(2-triisopropylsilanyloxy-ethyl)-1H-pyrrolo[3,2-c]pyridine-2-carboxylic acid methyl ester

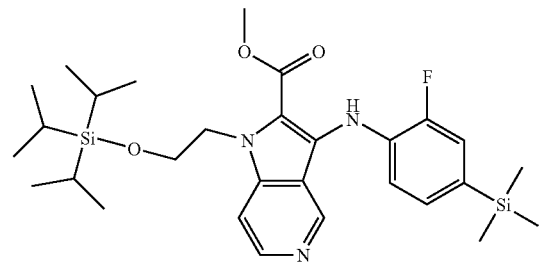

A degassed solution of 3-amino-1-(2-triisopropylsilanyloxy-ethyl)-1H-pyrrolo[3,2-c]pyridine-2-carboxylic acid methyl ester (1.41 g, 3.61 mmol), trifluoro-methanesulfonic acid 2-fluoro-4-trimethylsilanyl-phenyl ester (1.48 g, 4.69 mmol), $Pd_2dba_3$ (165 mg, 0.18 mmol), Xantphos (208 mg, 0.36 mmol) and $Cs_2CO_3$ (2.35 g, 7.21 mmol) in toluene (30 ml) was heated to reflux then stirred for 16 hours. The reaction mixture was cooled to ambient temperature then diluted with EtOAc and filtered through a pad of celite. The resultant solution was concentrated in vacuo to give a black oil. The oil was purified by flash chromatography (Si-PPC, pentane: ether, gradient 100:0 to 0:100) to provide the title compound as a yellow oil (1.78 g, 88%). LCMS (method B): $R_T$=3.76 min, M+H$^+$=558.

Step 5: 3-(2-Fluoro-4-iodo-phenylamino)-1-(2-triisopropylsilanyloxy-ethyl)-1H-pyrrolo[3,2-c]pyridine-2-carboxylic acid methyl ester To a cooled (0° C.) solution of 3-(2-fluoro-4-trimethylsilanyl-phenylamino)-1-(2-triisopropylsilanyloxy-ethyl)-1H-pyrrolo[3,2-c]pyridine-2-carboxylic acid methyl ester (1.78 g, 3.20 mmol) in DCM (35 mL) was added iodine monochloride (1M in DCM, 6.40 mL) dropwise over 10 minutes. The mixture was stirred for 1 hour then quenched by the addition of saturated sodium thiosulphate solution. The solution was partitioned between ethyl acetate and an saturated solution of sodium hydrogencarbonate. The organic layer was separated, washed with water then brine, dried ($Na_2SO_4$), filtered and evaporated to give a residue. The residue was purified by flash chromatography (Si-PPC, cyclohexane:ethylacetate, gradient 100:0 to 0:100) to provide the title compound as a yellow oil (1.52 g, 79%). LCMS (method B): $R_T$=3.47 min, M+H$^+$=612.

7-Chloro-3-(2-fluoro-4-iodo-phenylamino)-1-methyl-1H-pyrrolo[3,2-c]pyridine-2-carboxylic acid ethyl ester

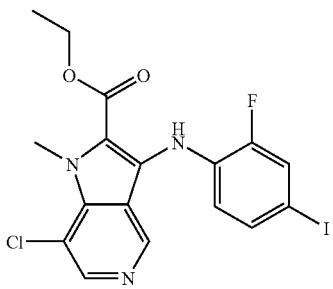

Step 1: 4,5-Dichloropyridine-3-carbaldehyde

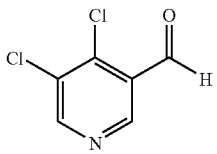

To a solution of diisopropylamine (10.73 ml, 75.9 mmol) in THF (60 ml) at −40° C., was added n-butyllithium (47.45 ml, 75.9 mmol, 1.6M in hexanes) and the solution was stirred for 15 min at −40° C., before cooling to −70° C. A solution of 3,4-dichloropyridine (10.7 g, 72.3 mmol) in THF (30 ml) was added dropwise to maintain the temperature below −65° C. The reaction was stirred at −70° C. for 2 hours before the addition of DMF (6.74 ml, 86.8 mmol). The reaction was then stirred at −40° C. for 1 hours and then allowed to warm to −5° C. before the careful addition of saturated ammonium chloride solution (50 ml) with rapid stirring over 3 min. The mixture was then partitioned between saturated ammonium chloride (150 ml) and dichloromethane (150 ml) and the layers separated. The aqueous layer was extracted with dichloromethane (2×100 ml) and the combined organic layers were dried over magnesium sulfate, then concentrated in vacuo. Purification of the resultant residue by flash chromatography (Si-PPC, dichloromethane:ethyl acetate gradient 100:0 to 94:6) afforded the title compound as white waxy solid (8.01 g, 63%).

Step 2: 4,5-Dichloropyridine-3-carbaldehyde oxime

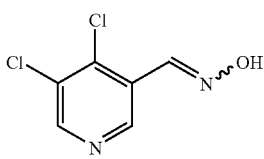

A solution of 4,5-dichloropyridine-3-carbaldehyde (8.01 g, 45.51 mmol) in ethanol (50 ml) was added to a rapidly stirred solution of hydroxylamine hydrochloride (3.48 g, 50.06 mmol) in water (50 ml). The reaction was stirred at room temperature for 45 min then partitioned between ethyl acetate (100 ml) and water (100 ml). The aqueous layer was extracted with ethyl acetate (2×50 ml) and the combined organic layers were dried over magnesium sulfate before being concentrated in vacuo to afford the title compound as a white solid (8.3 g, 96%).

Step 3: 4,5-Dichloronicotinonitrile

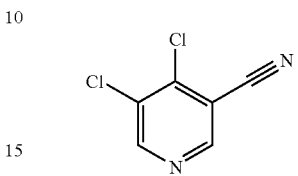

To a suspension of 4,5-dichloropyridine-3-carbaldehyde oxime (7.84 g, 41.05 mmol) in dichloromethane (150 ml) was added carbonyl diimidazole (7.99 g, 49.26 mmol). The mixture was then heated to reflux for 1.5 hours before cooling then washing with saturated aqueous sodium bicarbonate (70 ml) and water (70 ml). The organic layer was dried over magnesium sulfate and concentrated in vacuo. Purification of the resultant residue by flash chromatography (Si-PPC, cyclohexane:dichloromethane gradient 20:80 to 0:100) afforded the title compound as a white solid (0.53 g, 72%). LCMS (method B): $R_T$=2.86 min, no ion present.

Step 4: 5-Chloro-4-methylamino-nicotinonitrile

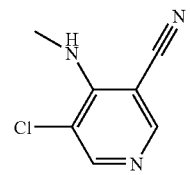

4,5-Dichloronicotinonitrile (500 mg, 2.89 mmol) was suspended in 41% aqueous methylamine solution (5 mL). The resultant mixture was heated, with stirring, up to 60° C. over ca. 30 min. The mixture was cooled to room temperature and extracted with ethyl acetate. The organic layer was washed with water, followed by brine then dried ($MgSO_4$) and evaporated to provide the title compound (340 mg, 70%) as a white solid. $^1$H NMR ($CDCl_3$) 8.39 (1H, s), 8.29 (1H, s), 5.50 (1H, s, br), 3.43 (3H, d, J=5.5 Hz).

Step 5: 3-Amino-7-chloro-1-methyl-1H-pyrrolo[3,2-c]pyridine-2-carboxylic acid ethyl ester

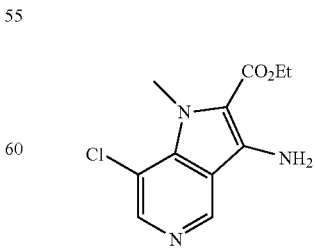

5-Chloro-4-methylamino-nicotinonitrile (340 mg, 2.02 mmol) was dissolved in DMF (5 mL) and the solution cooled in an ice-bath. This solution was treated portionwise with sodium hydride (120 mg, 60% in oil, 3.03 mmol). The ice-bath was removed and stirring continued for 15 minutes at room temperature before treating the mixture with ethyl bromoacetate (508 mg, 3.03 mmol). The reaction mixture was then partitioned between ethyl acetate and water. The organic layer was isolated, washed with water followed by brine then dried (MgSO$_4$) and evaporated to give a solid. Trituration of the resultant solid with diethyl ether gave the title compound (308 mg, 60%) as a cream solid. $^1$H NMR (CDCl$_3$) 8.90 (1H, s), 8.26 (1H, s), 8.26 (1H, s, br), 4.43 (2H, q, J=7.0 Hz), 4.28 (3H, s), 1.44 (3H, t, J=7.0 Hz)

Step 6: 7-Chloro-3-(2-fluoro-4-trimethylsilanyl-phenylamino)-1-methyl-1H-pyrrolo[3,2-c]pyridine-2-carboxylic acid ethyl ester

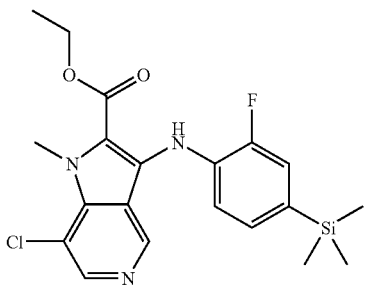

A degassed solution of 3-amino-7-chloro-1-methyl-1H-pyrrolo[3,2-c]pyridine-2-carboxylic acid ethyl ester (300 mg, 1.18 mmol), trifluoro-methanesulfonic acid 2-fluoro-4-trimethylsilanyl-phenyl ester (486 mg, 1.53 mmol), Pd$_2$dba$_3$ (54 mg, 0.06 mmol), Xantphos (68 mg, 0.118 mmol) and Cs$_2$CO$_3$ (770 mg, 2.36 mmol) in toluene (10 ml) was heated to reflux then stirred for 16 hours. The reaction mixture was cooled to ambient temperature then filtered through a pad of Celite® washing with toluene. The resultant solution was concentrated in vacuo to give an oil. The oil was purified by flash chromatography (SiO$_2$, cyclohexane:ethyl acetate, gradient 95:5 to 90:10) to provide the title compound as a gum (370 mg, 74%). $^1$H NMR (CDCl$_3$) 8.64 (1H, s), 8.31 (1H, s), 7.47 (1H, s, br), 7.23 (1H, dd, J=1.5, 110. Hz), 7.10 (1H, dd, J=1.0, 8.0 Hz), 6.97 (1H, t, J=8.0 Hz), 4.42 (2H, q, J=7.0 Hz), 4.35 (3H, s), 1.43 (3H, t, J=7.0 Hz), 0.29 (s, 9H).

Step 7: 7-Chloro-3-(2-fluoro-4-iodo-phenylamino)-1-methyl-1H-pyrrolo[3,2-c]pyridine-2-carboxylic acid ethyl ester To a cooled (0° C.) solution of 7-chloro-3-(2-fluoro-4-trimethylsilanyl-phenylamino)-1-methyl-1H-pyrrolo[3,2-c]pyridine-2-carboxylic acid ethyl ester (3.25 g, 7.74 mmol) in DCM (50 mL) was added iodine monochloride (1M in DCM, 17.0 mL) dropwise over 15 minutes. The mixture was allowed to warm to ambient temperature then partitioned between ethyl acetate and a saturated solution of sodium thiosulphate. The organic layer was separated, washed with water then brine, dried (Na$_2$SO$_4$), filtered and evaporated to give a residue. The residue was triturated with diethyl ether to provide the title compound as a yellow solid (2.62 g, 73%). LCMS (method B): R$_T$=3.95 min, M+H$^+$=474.

7-Chloro-3-(2-fluoro-4-iodo-phenylamino)-1H-pyrrolo[3,2-c]pyridine-2-carboxylic acid ethyl ester

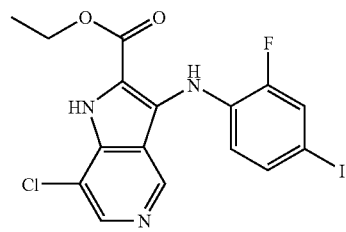

Step 1: 3-Amino-7-chloro-1H-pyrrolo[3,2-c]pyridine-2-carboxylic acid ethylester

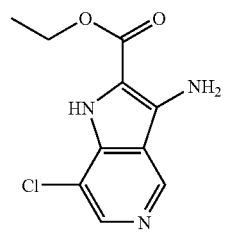

A mixture of 4,5-dichloronicotinonitrile (3.0 g, 17.3 mmol), glycine ethyl ester hydrochloride (7.2 g, 52.0 mmol) and sodium hydrogen carbonate (9.06 g, 104 mmol) in IMS (50 ml) was heated at reflux for 16 hours. The cooled reaction mixture was then partitioned between ethyl acetate and water, the organic layer washed with water then brine, dried (MgSO$_4$) filtered and concentrated in vacuo. The resultant residue was triturated in diethyl ether to give the title compound as a buff solid (3.58 g, 86%). $^1$H NMR (CDCl$_3$) 8.80 (1H, s), 8.36 (1H, s), 4.97 (2H, s, br), 4.44 (2H, q, J=7.0 Hz), 1.44 (3H, t, J=7.0 Hz).

Step 2: 7-Chloro-3-(2-fluoro-4-trimethylsilanyl-phenylamino)-1H-pyrrolo[3,2-c]pyridine-2-carboxylic acid ethyl ester

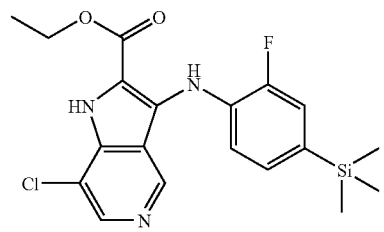

To a solution of 3-amino-7-chloro-1H-pyrrolo[3,2-c]pyridine-2-carboxylic acid ethyl ester (1.0 g, 4.18 mmol) and trifluoromethanesulfonic acid 2-fluoro-4-trimethylsilanyl-phenyl ester (1.45 g, 4.59 mmol) in toluene (18 ml) was added cesium carbonate (1.90 g, 5.85 mmol) before the mixture was degassed. Pd$_2$dba$_3$ (382 mg, 0.418 mmol) and Xantphos (482 mg, 0.835 mmol) were then added and the vessel was flushed with argon. The resultant reaction mixture was heated at 150°

C. under microwave irradiation for 31 min, cooled and filtered through Hyflo washing with ethyl acetate. The filtrate was washed with saturated sodium bicarbonate, the organic layer dried (MgSO$_4$) and concentrated in vacuo. Purification of the resultant residue by flash chromatography (Si-PPC, dichloromethane:ethyl acetate gradient 1:0 to 5:1) afforded the title compound as a pale yellow solid (0.84 g, 50%). LCMS (method B): R$_T$=3.75 min, M+H$^+$=406.

Step 3: 7-Chloro-3-(2-fluoro-4-iodo-phenylamino)-1H-pyrrolo[3,2-c]pyridine-2-carboxylic acid ethyl ester To a solution of 7-chloro-3-(2-fluoro-4-trimethylsilanyl-phenylamino)-1H-pyrrolo[3,2-c]pyridine-2-carboxylic acid ethyl ester (0.91 g, 2.25 mmol) in dichloromethane (20 ml) at −10° C. was added iodine monochloride (4.95 ml, 4.95 mmol, 1M solution in dichloromethane) and the resultant mixture was stirred at −10° C. to 0° C. for 2 h. A saturated solution of sodium thiosulfate (25 ml) was added and the mixture was poured into saturated sodium thiosulfate (40 ml). The aqueous layer was extracted with ethyl acetate (3×35 ml) and the combined organic layers were washed with brine, dried over magnesium sulfate and concentrated in vacuo. The resultant residue was triturated in dichloromethane:cyclohexane 1:4 to afford the title compound as a yellow solid (0.87 g, 84%). LCMS (method B): R$_T$=3.17 min, M+H$^+$=460.

7-Fluoro-3-(2-fluoro-4-iodo-phenylamino)-1-methyl-1H-pyrrolo[3,2-c]pyridine-2-carboxylic acid ethyl ester

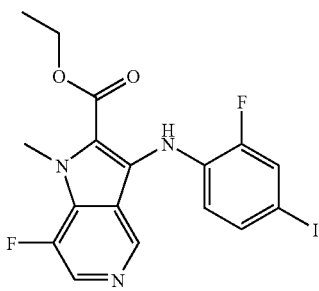

Step 1: 4-Chloro-5-fluoro-pyridine-3-carbaldehyde oxime

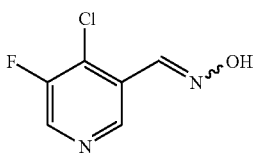

To a cooled (−78° C.) solution of 3-fluoro-4-chloro-pyridine (11.0 g, 84 mmol) in THF under nitrogen was added lithium diisopropylamide (1.8 M solution, 47 mL, 84 mmol) dropwise and the resultant solution stirred at −70 to −80° C. for 18 hours. DMF (7.68 g, 1.25 eq.) was added dropwise and stirring continued at −78° C. for 30 minutes before adding the reaction mixture to ice/2M HCl. The solution was extracted with diethyl ether and the organic layer back-extracted with 2M HCl, the two aqueous solutions held separately. The aqueous extracts were each treated with hydroxylamine hydrochloride (8.76 g, 126 mmol) and adjusted to pH 5 with potassium carbonate. After stirring for 1 hour the mixtures were extracted with ethyl acetate (×2), the combined organic extracts dried (Na$_2$SO$_4$), filtered and concentrated in vacuo to afford the title compound as a tan solid (11.07 g, 76%). LCMS (method B): R$_T$=2.49 min, M+H$^+$ 175.

Step 2: 4-Chloro-5-fluoronicotinonitrile

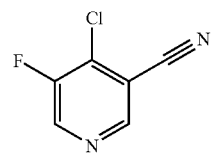

To a suspension of 4-chloro-5-fluoro-pyridine-3-carbaldehyde oxime (6.8 g, 39.0 mmol) in dichloromethane (150 ml) was added carbonyl diimidazole (9.5 g, 58.5 mmol). The mixture was then heated at reflux for 30 minutes before cooling to room temperature, before being washed with saturated aqueous sodium bicarbonate followed by water. The organic layer was dried over sodium sulfate and concentrated in vacuo and the resultant residue triturated in diethyl ether/cyclohexane to afford the title compound as a pale yellow solid (4.05 g, 79%). $^1$H NMR (CDCl$_3$) 8.71 (1H, d, J=0.4 Hz), 8.70 (1H, s).

Step 3: 5-Fluoro-4-methylamino-nicotinonitrile

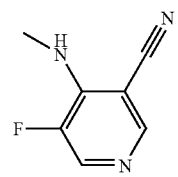

4-Chloro-5-fluoro-nicotinonitrile (3.5 g, 22.4 mmol) was suspended in 41% aqueous methylamine solution (35 mL). The resultant mixture was heated, with stirring, at 80° C. for 30 minutes. The mixture was cooled to room temperature and extracted with ethyl acetate. The organic layer was dried (Na$_2$SO$_4$) and concentrated in vacuo and the resultant residue triturated in diethyl ether to provide the title compound (2.35 g, 70%) as a white solid. 1H NMR (CDCl$_3$) 8.29 (1H, s), 8.18 (1H, d, J=4.0 Hz), 5.04 (1H, s, br), 3.34 (3H, dd, J=2.2, 5.5 Hz).

Step 4: 3-Amino-7-fluoro-1-methyl-1H-pyrrolo[3,2-c]pyridine-2-carboxylic acid ethyl ester

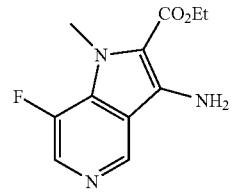

5-Fluoro-4-methylamino-nicotinonitrile (2.35 g, 15 mmol) was dissolved in DMF (50 mL) and the solution cooled in an ice-bath. This solution was treated portionwise with sodium hydride (900 mg, 60% in oil, 22.5 mmol). The mixture was allowed to warm to room temperature and stirring continued for 15 minutes at room temperature. Ethyl bromoacetate (2.49 ml, 22.5 mmol) was added and the mixture stirred for 30 minutes at room temperature The reaction mixture was quenched with water and extracted with ethyl acetate. The organic layer was isolated, dried (Na$_2$SO$_4$) and evaporated to give a solid. Trituration of the resultant solid with methanol gave the title compound (1.85 g, 52%) as a yellow solid. LCMS (method B): R$_T$=2.09 min, M+H$^+$ 238.

Step 5: 7-Fluoro-3-(2-fluoro-4-trimethylsilanyl-phenylamino)-1-methyl-1H-pyrrolo[3,2-c]pyridine-2-carboxylic acid ethyl ester

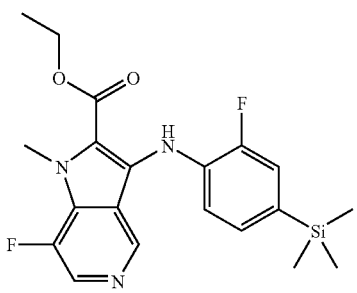

A degassed solution of 3-amino-7-fluoro-1-methyl-1H-pyrrolo[3,2-c]pyridine-2-carboxylic acid ethyl ester (900 mg, 3.8 mmol), trifluoro-methanesulfonic acid 2-fluoro-4-trimethylsilanyl-phenyl ester (1.44 mg, 4.56 mmol), Pd$_2$dba$_3$ (174 mg, 0.19 mmol), Xantphos (220 mg, 0.38 mmol) and Cs$_2$CO$_3$ (2.48 g, 7.6 mmol) in toluene (10 ml) was heated at 150° C. for 20 minutes using microwave irradiation. The reaction mixture was cooled to ambient temperature then filtered through a pad of Celite® washing with ethyl acetate. The filtrate was concentrated in vacuo and the resultant residue subjected to flash chromatography (Si-PPC, gradient 0-30% ethyl acetate in cyclohexane) to provide the title compound as a yellow/orange solid (2.12 g, 69%). LCMS (method B): R$_T$=4.15 min, M+H$^+$ 404.

Step 6: 7-Fluoro-3-(2-fluoro-4-iodo-phenylamino)-1-methyl-1H-pyrrolo[3,2-c]pyridine-2-carboxylic acid ethyl ester To a cooled (0° C.) solution of 7-fluoro-3-(2-fluoro-4-trimethylsilanyl-phenylamino)-1-methyl-1H-pyrrolo[3,2-c] pyridine-2-carboxylic acid ethyl ester (1.0 g, 2.48 mmol) in DCM (25 mL) was added iodine monochloride (1M in DCM, 4.96 mmol, 4.96 mL) dropwise. The mixture was stirred cold for 30 minutes then quenched by the addition of a saturated solution of sodium thiosulphate. The organic layer was separated, washed with a saturated solution of sodium thiosulphate, then dried (Na$_2$SO$_4$), filtered and evaporated to give a residue. The residue was triturated with diethyl ether to provide the title compound as a beige solid (805 mg, 71%). LCMS (method B): R$_T$=3.52 min, M+H$^+$ 458.

3-(2-Fluoro-4-iodo-phenylamino)-1-(3-triisopropyl-silanyloxy-propyl)-1H-pyrrolo[3,2-c]pyridine-2-carboxylic acid ethyl ester

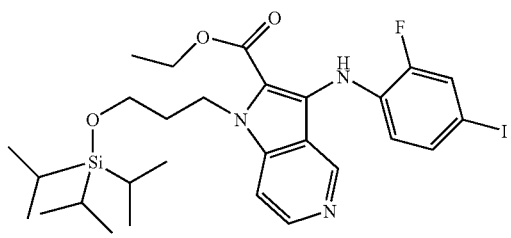

(3-Bromo-propoxy)-triisopropyl-silane (209 mg, 0.71 mmol) was dissolved in DMF (5 ml) and 3-(2-fluoro-4-iodophenylamino)-1H-pyrrolo[3,2-c]pyridine-2-carboxylic acid ethyl ester (250 mg, 0.59 mmol) was added, followed by cesium carbonate (250 mg, 0.77 mmol). The mixture was heated at 80° C. under nitrogen for 3 hours, then allowed to cool, diluted with water and extracted with dichloromethane (×2). The combined organic layers were washed with 20% aqueous lithium chloride solution, dried over magnesium sulfate then concentrated in vacuo. Purification of the resultant residue by flash chromatography (Si-PPC, dichloromethane:methanol gradient 1:0 to 99:1) gave the title compound as a yellow oil (109 mg, 44%). LCMS (method B): R$_T$ 3.41, M+H$^+$ 640.

7-Fluoro-3-(2-fluoro-4-iodo-phenylamino)-1H-pyrrolo[3,2-c]pyridine-2-carboxylic acid ethyl ester

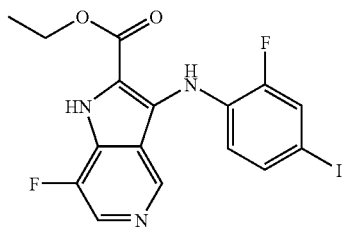

Step 1: 3-Amino-7-fluoro-1H-pyrrolo[3,2-c]pyridine-2-carboxylic acid ethyl ester

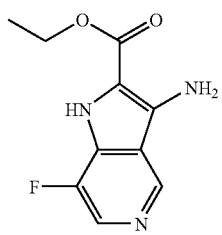

A mixture of 4-chloro-5-fluoro-nicotinonitrile (3.5 g, 22.4 mmol), glycine ethyl ester hydrochloride (9.4 g, 67.1 mmol) and sodium hydrogencarbonate (11.3 g, 134.2 mmol) in IMS (60 mL) was stirred at reflux for 18 hours. The reaction was then cooled to room temperature and partitioned between water and ethyl acetate. The organic layer was separated and washed with water and brine, dried over sodium sulphate, filtered and concentrated to give a solid which was triturated in diethyl ether. The mixture was aged at room temperature for 18 hours and the precipitate was filtered off and dried under vacuum at 60° C. to give the title compound as a beige solid (2.29 g, 46%). LCMS (method B): $R_T$=1.50 min, M+H$^+$=224.

Step 2: 7-Fluoro-3-(2-fluoro-4-trimethylsilanyl-phenylamino)-1H-pyrrolo[3,2-c]pyridine-2-carboxylic acid ethyl ester

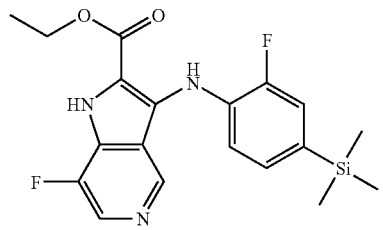

A degassed solution of 3-amino-7-fluoro-1H-pyrrolo[3,2-c]pyridine-2-carboxylic acid ethyl ester (1.0 g, 4.48 mmol), trifluoro-methanesulfonic acid 2-fluoro-4-trimethylsilanyl-phenyl ester (1.6 g, 4.93 mmol), Pd$_2$dba$_3$ (205 mg, 0.22 mmol), Xantphos (258 mg, 0.45 mmol) and cesium carbonate (2.0 g, 6.28 mmol) in toluene (20 ml) was subjected to microwave irradiation at 150° C. for 20 minutes. The reaction mixture was cooled to ambient temperature then diluted with ethyl acetate and filtered through a pad of Celite®. The filtrate was concentrated under reduced pressure to give a residue that was purified by flash chromatography (Si-PPC, pentane: diethyl ether, gradient 100:0 to 0:100) to afford the title compound as a yellow solid (505 mg, 29%). LCMS (method B): $R_T$=3.39 min, M+H$^+$=390.

Step 3: 7-Fluoro-3-(2-fluoro-4-iodo-phenylamino)-1H-pyrrolo[3,2-c]pyridine-2-carboxylic acid ethyl ester A solution of 7-fluoro-3-(2-fluoro-4-trimethylsilanyl-phenylamino)-1H-pyrrolo[3,2-c]pyridine-2-carboxylic acid ethyl ester (500 mg, 1.28 mmol) in CH$_2$Cl$_2$ (15 mL) was cooled to 0-5° C. and treated dropwise with iodine monochloride solution (2.6 mL, 1M in CH$_2$Cl$_2$). The mixture was stirred at 0-5° C. for one hour and then quenched by addition of a saturated aqueous sodium thiosulfate solution (10 mL). The mixture was diluted with water and dichloromethane. The precipitate formed was filtered off, washed with diethyl ether and dried under vacuum at 50° C. to give the title compound as a yellow solid (218 mg, 38%). LCMS (method B): $R_T$=2.87 min, M+H$^+$= 444.

3-(2-Chloro-4-methylsulfanyl-phenylamino)-1-methyl-1H-indole-2-carboxylic acid ethyl ester

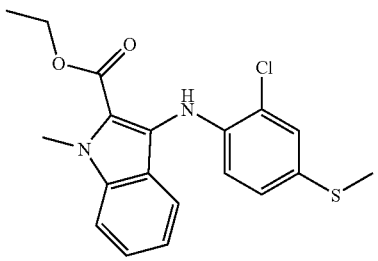

Step 1: 4-Bromo-3-chloro-benzenethiol

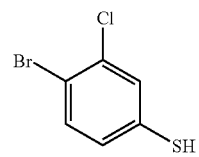

4-Bromo-3-chloro-benzenesulfonyl chloride (3.78 g, 13.0 mmol) was dissolved in dichloromethane (40 ml) and DMF (1.0 ml) was added. The mixture was cooled to 0° C. under argon and triphenylphosphine (10.26 g, 39.0 mmol) was added slowly, then the mixture was allowed to return to room temperature with stirring over 16 h. Hydrochloric acid (1 M, 75 ml) was added and the layers were separated. The organic layer was concentrated and the residue suspended in 1 M aqueous sodium hydroxide (75 ml) and filtered. The filtrate was extracted with Et$_2$O (×2), then neutralised (1 M HCl, 75 ml). The mixture was then extracted (Et$_2$O×3) and the combined organic layers were dried (Na$_2$SO$_4$) and concentrated to afford the title compound as a colourless oil (0.94 g, 32%). $^1$H NMR (CDCl$_3$ 400 MHz) 3.49 (1H, s), 7.02 (1H, dd, J=8.35, 2.24 Hz), 7.38 (1H, d, J=2.18 Hz), 7.45 (1H, d, J=8.35 Hz).

Step 2: 1-Bromo-2-chloro-4-methylsulfanyl-benzene

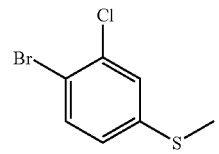

4-Bromo-3-chloro-benzenethiol (0.94 g, 4.21 mmol) was dissolved in tetrahydrofuran (10 ml) and cooled to 0° C. under argon. Sodium hydride (0.19 g, 4.63 mmol) was added and the mixture was stirred for 5 minutes, then iodomethane (0.28 ml, 4.42 mmol) was added. The mixture was allowed to warm, stirring for 30 minutes, then the reaction was quenched with saturated aqueous ammonium chloride. The mixture was extracted with dichloromethane (×2) and the combined organic layers were dried (MgSO$_4$) and concentrated. Purification of the resultant residue by flash chromatography (Si-PCC, pentane) afforded the title compound as a colourless oil (0.65 g, 65%). ¹H NMR (CDCl₃ 400 MHz) 2.47 (3H, s), 6.99 (1H, dd, J=8.45, 2.26 Hz), 7.30 (1H, d, J=2.25 Hz), 7.48 (1H, d, J=8.45 Hz).

Step 3: 3-(2-Chloro-4-methylsulfanyl-phenylamino)-1-methyl-1H-indole-2-carboxylic acid ethyl ester 3-Amino-1-methyl-1H-indole-2-carboxylic acid ethyl ester (200 mg, 0.91 mmol) and 1-bromo-2-chloro-4-methylsulfanyl-benzene (304 mg, 1.28 mmol) were dissolved in toluene (5 ml) and Pd₂(dba)₃ (42 mg, 0.05 mmol) was added, followed by Xantphos (53 mg, 0.09 mmol) and potassium phosphate tribasic (386 mg, 1.82 mmol). The mixture was degassed and purged with argon, then stirred under argon at 120° C. for 16 hours. After cooling, the mixture was filtered through celite then concentrated. Purification of the resultant residue by flash chromatography (Si-PCC, ether:pentane gradient 1:4 to 1:0) gave the title compound as a yellow oil (300 mg, 88%). LCMS (method B): R_T=2.64, M+H⁺ 376/378.

3-(2-Fluoro-4-methylsulfanyl-phenylamino)-1H-pyrrolo[3,2-c]pyridine-2-carboxylic acid ethyl ester

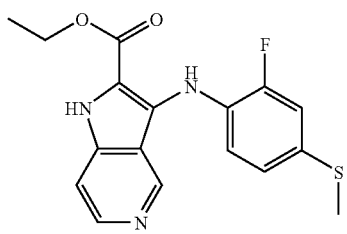

Step 1: 4-Bromo-3-fluoro-benzenethiol

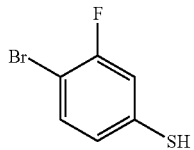

4-Bromo-3-fluoro-benzenesulfonyl chloride (324 µl, 2.19 mmol) was added dropwise to a solution of triphenylphosphine (1.73 g, 6.58 mmol) in a mixture of dimethylformamide (125 µl) and dichloromethane (5 ml). The solution was stirred at room temperature for 16 hours, then 1 M aqueous hydrochloric acid (5 ml) was added and the layers were separated. The organic layer was concentrated in vacuo and the resultant residue taken up in 1 M aqueous sodium hydroxide (10 ml). The resulting suspension was filtered through Celite® and the filtrate washed with ether (10 ml×3), then neutralised by addition of 1 M aqueous hydrochloric acid (10 ml). The solution was extracted with ether (10 ml×3) and the combined organic extracts were dried (Na₂SO₄) then concentrated in vacuo to afford the title compound as a colourless oil (225 mg, 50%). ¹H NMR (CDCl₃, 300 MHz) 7.47 (1H, dd, J=8.4, 7.5 Hz), 7.06 (1H, dd, J=8.9, 2.2 Hz), 6.93 (1H, ddd, J=8.4, 2.1, 0.7 Hz), 3.54 (1H, br s).

Step 2: 1-Bromo-2-fluoro-4-methylsulfanyl-benzene

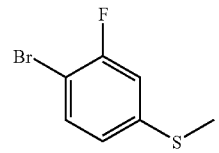

A solution of 4-bromo-3-fluoro-benzenethiol (225 mg, 1.09 mmol) in tetrahydrofuran (3 ml) was cooled to 0° C. Sodium hydride (60% dispersion in mineral oil, 52 mg, 1.31 mmol) was added and the mixture was stirred for 5 minutes. Iodomethane (78 µl, 1.25 mmol) was then added and the mixture was allowed to return to room temperature with stirring over 20 minutes. Dichloromethane (10 ml) was added and the reaction was quenched with 1 M aqueous hydrochloric acid. The layers were separated and the organic layer was washed with water, dried (MgSO₄), then concentrated in vacuo. The residue was purified by flash chromatography (Si-PPC, pentane:diethyl ether, gradient 100:0 to 90:10) to afford the title compound as a bright yellow oil (208 mg, 86%). ¹H NMR (CDCl₃, 400 MHz) 7.43 (1H, dd, J=8.4, 7.2), 7.00 (1H, dd, J=9.4, 2.3), 6.91 (1H, ddd, J=8.4, 2.1, 0.7), 2.48 (3H, s).

Step 3: 3-(2-Fluoro-4-methylsulfanyl-phenylamino)-1H-pyrrolo[3,2-c]pyridine-2-carboxylic acid ethyl ester A degassed solution of 3-amino-1H-pyrrolo[3,2-c]pyridine-2-carboxylic acid ethyl ester (0.610 g, 3 mmol), 1-bromo-2-fluoro-4-methylsulfanyl-benzene (1.13 g, 5.1 mmol), Pd₂dba₃ (0.14 g, 0.15 mmol), Xantphos (0.17 g, 0.3 mmol) and cesium carbonate (1.94 g, 6.0 mmol) in toluene (20 ml) was subjected to microwave irradiation at 150° C. for 2 hours. The reaction mixture was cooled to ambient temperature then diluted with ethyl acetate and filtered through a pad of Celite®. The filtrate was concentrated under reduced pressure to give a residue that was purified by flash chromatography (Si-PPC, ethyl acetate: DCM, gradient 0:100 to 40:100) to afford the title compound as a yellow solid (0.25 g, 24%). LCMS (method B): R_T=2.45 min, M+H⁺=346.

7-(2-Fluoro-4-iodo-phenylamino)-5-methyl-5H-pyrrolo[3,2-c]pyridazine-6-carboxylic acid ethyl ester

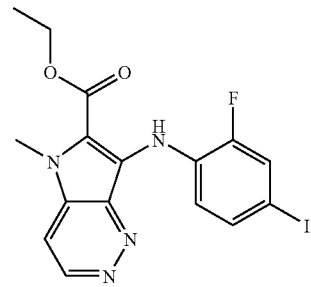

Step 1: 3-Chloro-7-hydroxy-5-methyl-5H-pyrrolo[3,2-c]pyridazine-6-carboxylic acid ethyl ester

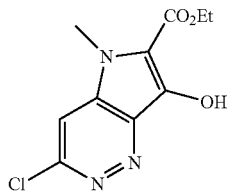

To a stirred solution of 4,6-dichloro-pyridazine-3-carboxylic acid methyl ester (2.9 g, 14 mmol) and sarcosine ethyl ester hydrochloride (2.15 g, 14 mmol) in acetonitrile (75 ml) was added triethylamine (4.9 mL, 35 mmol). The resultant reaction mixture was stirred at room temperature for 2 hours before adding further triethylamine (4.9 mL, 35 mmol) and heating the reaction mixture at 80° C. for 18 hours. After cooling to room temperature, the reaction mixture was concentrated in vacuo and the resultant residue treated with water and extracted with ethyl acetate (×3), the combined organic extracts dried (Na$_2$SO$_4$), filtered and concentrated in vacuo to give a solid. The solid was triturated in hot methanol to give the title compound as a yellow solid (1.6 g, 45%). LCMS (method B): R$_T$=2.64 min, M+H$^+$=256.

Step 2: 7-Hydroxy-5-methyl-5H-pyrrolo[3,2-c]pyridazine-6-carboxylic acid ethyl ester

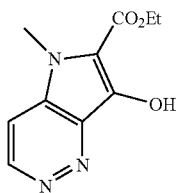

A suspension of 10% wt. palladium on carbon (150 mg) in ethanol was added to a de-gassed suspension of 3-chloro-7-hydroxy-5-methyl-5H-pyrrolo[3,2-c]pyridazine-6-carboxylic acid ethyl ester (1.6 g, 6.26 mmol) in ethanol (150 mL), the atmosphere evacuated and back-filled with nitrogen, re-evacuated and back-filled with hydrogen and the mixture stirred under hydrogen (1 atmosphere) for 3 days at room temperature. The resultant mixture was filtered through Celite® with DCM/methanol washings, the filtrate concentrated in vacuo to give the title compound as a yellow solid (1.4 g, quantitative). LCMS (method B): R$_T$=1.53/1.65 min, M+H$^+$=222.

Step 3: 7-Trifluoromethanesulfonyloxy-5-methyl-5H-pyrrolo[3,2-c]pyridazine-6-carboxylic acid ethyl ester

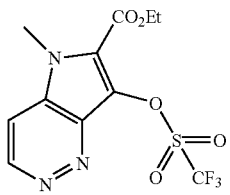

A suspension of 7-hydroxy-5-methyl-5H-pyrrolo[3,2-c]pyridazine-6-carboxylic acid ethyl ester (360 mg, 1.63 mmol), PhN(Tf)$_2$ (873 mg, 2.45 mmol), DIPEA (1.14 mL, 6.5 mmol) in ethyleneglycol dimethyl ether (15 ml) was heated at 90° C. for 3 hours. The cooled reaction mixture was concentrated in vacuo and the residue partitioned between ethyl acetate and water, the aqueous layer separated and extracted further with ethyl acetate. The combined organic extracts were dried (Na$_2$SO$_4$), filtered and concentrated in vacuo and the resultant residue subjected to flash chromatography (Si-PPC gradient 0:100 to 50:50 ethyl acetate:DCM) to give the title compound as a tan solid (248 mg, 43%). LCMS (method B): R$_T$=3.26 min, M+H$^+$=354.

Step 4: 7-(2-Fluoro-4-trimethylsilanyl-phenylamino)-5-methyl-5H-pyrrolo[3,2-c]pyridazine-6-carboxylic acid ethyl ester

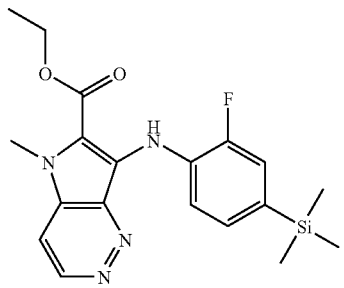

A degassed solution of 7-trifluoromethanesulfonyloxy-5-methyl-5H-pyrrolo[3,2-c]pyridazine-6-carboxylic acid ethyl ester (495 mg, 1.4 mmol), 2-fluoro-4-trimethylsiliyl aniline (333 mg, 1.82 mmol), Pd$_2$dba$_3$ (64 mg, 5 mol %), Xantphos (81 mg, 10 mol %) and cesium carbonate (912 mg, 2.8 mmol) in toluene (15 ml) was heated at 120° C. for 2 hours. The reaction mixture was cooled to ambient temperature then diluted with ethyl acetate and filtered through Celite® and the solution concentrated in vacuo to give a solid residue. The solid residue was purified by flash chromatography (Si-PPC, cyclohexane:ethyl acetate, gradient 100:0 to 40:60) to afford the title compound as an oily residue (242 mg, 45%). LCMS (method B): R$_T$=3.60 min, M+H$^+$=387.

Step 5: 7-(2-Fluoro-4-iodo-phenylamino)-5-methyl-5H-pyrrolo[3,2-c]pyridazine-6-carboxylic acid ethyl ester To a cooled (0° C.) solution 7-(2-fluoro-4-trimethylsilanyl-phenylamino)-5-methyl-5H-pyrrolo[3,2-c]pyridazine-6-carboxylic acid ethyl ester (242 mg, 0.626 mmol) in DCM (6 mL) was added iodine monochloride (1.25 mL 1M in DCM 17.0 mL) dropwise over 1 minute. The mixture was allowed to warm to ambient temperature, stirred for 1 hour, then partitioned between ethyl acetate and a saturated solution of sodium thiosulfate. The organic layer was separated, washed with water, dried (Na$_2$SO$_4$), filtered and evaporated to give a residue. The residue was subjected to flash chromatography (Si-PPC, 1:1 DCM:ethyl acetate eluent) to provide the title compound as an orange solid (242 g, 88%). LCMS (method B): R$_T$=3.03 min, M+H$^+$=441.

1-Cyclopropyl-3-(2-fluoro-4-iodo-phenylamino)-1H-pyrrolo[3,2-c]pyridine-2-carboxylic acid methyl ester

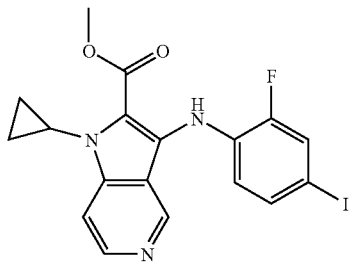

Step 1: 4-Cyclopropylamino-nicotinonitrile

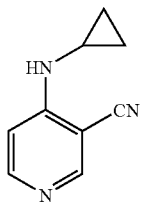

A mixture of 4-chloro-3-cyanopyridine (5.0 g, 36.1 mmol), cyclopropylamine (5.0 mL, 72.2 mmol, 2.0 eq), and potassium carbonate (5.2 g, 37.9 mmol, 1.05 eq) in isopropyl alcohol (130 mL) was stirred at 60° C. under $N_2$ for 20 h. The reaction was cooled to room temperature and the solvent was removed in vacuo. The residue was absorbed onto silica and purified by flash column chromatography (silica, ISCO, 45 mL/min, 10-100% ethyl acetate in hexane). Trituration from hexane afforded the title compound as an off-white solid (4.55 g, 79.3%). $^1$H-NMR (400 MHz; DMSO-$d_6$) δ ppm 8.43 (d, J=0.55 Hz, 1H), 8.29 (dd, J=6.10 Hz, 1H), 7.55 (s, 1H), 7.00-6.88 (m, 1H), 2.54 to 2.40 (m, 1H), 0.89-0.69 (m, 2H), 0.68-0.48 (m, 2H); LC-MS (method C): [M+H]$^+$=160.2, $R_T$=0.28 min.

Step 2: 3-Amino-1-cyclopropyl-1H-pyrrolo[3,2-c]pyridine-2-carboxylic acid methyl ester

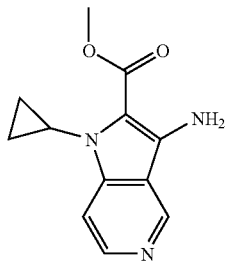

To a stirred solution of 4-cyclopropylamino-nicotinonitrile (2.15 g, 13.51 mmol) and methyl bromoacetate (1.53 mL, 16.21 mmol, 1.2 eq) at 0° C. was added sodium hydride (60% in mineral oil: 1.35 g, 33.78 mmol, 2.5 eq) portion wise over 15 min. After the evolution of hydrogen gas had subsided, the reaction mixture was warmed to ambient temperature and stirred under $N_2$ for 16 h. The reaction mixture was quenched with saturated NH$_4$Cl solution (10 mL) and poured into EtOAc. The biphasic layers were separated, and the organic layer was washed with 50% aq. brine, sat. NaHCO$_3$ solution, and brine. The organic layer was dried over Na$_2$SO$_4$, filtered, and concentrated in vacuo. The crude residue was absorbed onto silica and purified by flash column chromatography (silica, ISCO, 45 mL/min, 0 to 25% MeOH in EtOAc) to give the desired product as an orange solid (1.57 g, 50.3%). $^1$H-NMR (500 MHz, DMSO-$d_6$) δ ppm 9.01 (d, J=1.0 Hz, 1H), 8.24 (t, J=5.1 Hz, 1H), 7.29 (dd, J=6.0 Hz, J=1.0 Hz, 1H), 6.34-6.09 (br s, 2H), 3.85 (s, 3H), 3.35 (m, 1H), 1.14-1.03 (m, 2H), 0.80-0.70 (m, 2H); LC-MS (method D): [M+H]$^+$=232.0, $R_T$=1.31 min.

Step 3: 1-Cyclopropyl-3-(2-fluoro-4-trimethylsilanyl-phenylamino)-1H-pyrrolo[3,2-c]pyridine-2-carboxylic acid methyl ester

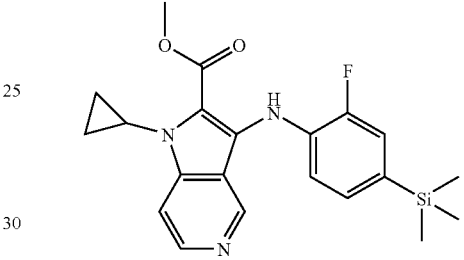

To a degassed suspension of 3-amino-1-cyclopropyl-1H-pyrrolo[3,2-c]pyridine-2-carboxylic acid methyl ester (215.0 mg, 0.93 mmol), and trifluoro-methanesulfonic acid 2-fluoro-4-trimethylsilanyl-phenyl ester (323.5 mg, 1.02 mmol, 1.1 eq) in anhydrous toluene (6.2 mL) was added Pd$_2$dba$_3$ (85.2 mg, 0.09 mmol, 0.1 eq), Xantphos (107.6 mg, 0.186 mmol, 0.2 eq) and Cs$_2$CO$_3$ (606.0 mg, 1.86 mmol, 2.0 eq). The reaction mixture was degassed with bubbling nitrogen for 10 minutes and stirred at 105° C. under $N_2$ for 17 h. The reaction mixture was cooled to room temperature and diluted with ethyl acetate (150 ml). The mixture was then filtered through a pad of Celite®. The celite pad was rinsed with EtOAc (2×50 mL), and the filtrate was concentrated under reduced pressure. The crude residue was then purified by flash column chromatography (silica, ISCO, 45 mL/min, 25 to 100% EtOAc in hexane) to afford the title compound as a yellow foam (265 mg, 71.7%). $^1$H-NMR (400 MHz, DMSO-$d_6$) δ ppm 8.52 (s, 1H), 8.33 (d, J=6.0 Hz, 1H), 7.86 (s, 1H), 7.55 (d, J=6.0 Hz, 1H), 7.29 (d, J=11.6 Hz, 1H), 7.13 (d, J=7.9 Hz, 1H), 6.90 (s, 1H), 3.82 (s, 3H), 3.57-3.46 (m, 1H), 1.27-1.03 (m, 2H), 0.96-0.71 (m, 2H), 0.23 (s, 9H); LC-MS (method D): [M+H]$^+$=398.2, $R_T$=2.69 min.

Step 4: 1-Cyclopropyl-3-(2-fluoro-4-iodo-phenylamino)-1H-pyrrolo[3,2-c]pyridine-2-carboxylic acid methyl ester To a stirred solution of 1-cyclopropyl-3-(2-fluoro-4-trimethylsilanyl-phenylamino)-1H-pyrrolo[3,2-c]pyridine-2-carboxylic acid methyl ester (265.0 mg, 0.67 mmol) in anhydrous DCM at −10° C. was added iodine monochloride (1.0 M in DCM, 0.80 mL, 0.80 mmol, 1.2 eq). The reaction mixture was then stirred at ambient temperature for 15 minutes then quenched with saturated aqueous sodium thiosulfate solution (3 mL). The reaction mixture was partitioned between ethyl acetate and water. The organic layer was washed with saturated aqueous NaHCO$_3$ solution, water, and brine, dried over Na$_2$SO$_4$, filtered, and concentrated under reduced pressure. The crude residue was purified by flash column chromatography (silica, ISCO, 45 mL/min, 25 to 100% ethyl acetate in hexane) to give the desired product as a yellow solid (159.0 mg, 52.9%). $^1$H-NMR (400 MHz, DMSO-d$_6$) δ ppm 8.53 (s, 1H), 8.33 (dd, J=6.0 Hz, J=1 Hz, 1H), 7.89 (s, 1H), 7.67-7.46 (m, 2H), 7.32 (m, 1H), 6.66 (dd, J=13.20 Hz, J=4.6 Hz, 1H), 3.81 (d, J=1.0 Hz, 3H), 3.61-3.41 (m, 1H), 1.22-1.10 (m, 2H), 0.90-0.79 (m, 2H); LC-MS (method C): [M+H]$^+$=452.0, R$_T$=0.79 min.

1-Cyclopropyl-3-(2-fluoro-4-methylsulfanyl-phenylamino)-1H-pyrrolo[3,2-c]pyridine-2-carboxylic acid methyl ester

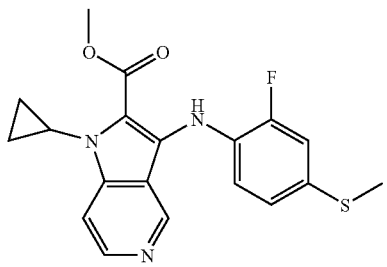

In a high-pressure tube was placed 3-amino-1-cyclopropyl-1H-pyrrolo[3,2-c]pyridine-2-carboxylic acid methyl ester (307.6 mg, 1.33 mmol), 2-fluoro-4-methylsulfanyl-phenylamine (500.0 mg, 2.26 mmol, 1.7 eq), 4,5-bis(diphenylphosphino)-9,9-dimethylxanthene (115.5 mg, 0.20 mmol, 1.5 eq), tris(dibenzylideneacetone)di-palladium(0) (91.4 mg, 0.10 mmol, 0.75 eq), and potassium phosphate (564.7 mg, 2.6 mmol, 2.0 eq) in degassed anhydrous toluene (21 mL). The tube was sealed tightly and the reaction mixture was heated to 100° C. for 17 h and cooled to room temperature. The reaction mixture was diluted with ethyl acetate (100 ml) and then filtered through a pad of Celite®. The celite pad was rinsed with EtOAc (2×50 mL), and the filtrate was concentrated under reduced pressure. The crude residue was then purified by flash column chromatography (silica, ISCO, 45 mL/min, 25 to 100% EtOAc in hexane) to afford the title compound as an orange glassy solid (339.6 mg, 68.7%). $^1$H-NMR (500 MHz, MeOD) δ ppm 8.36 (s, 1H), 8.24 (d, J=6.13 Hz, 1H), 7.59 (d, J=6.14 Hz, 1H), 7.14 (d, J=11.72 Hz, 1H), 7.08-6.93 (m, 2H), 3.95 (s, 3H), 3.59-3.47 (m, 1H), 2.47 (s, 3H), 1.25-1.21 (m, 2H), 0.92-0.89 (m, 2H); LC-MS (method C): [M+H]$^+$=371.8, R$_T$=0.80 min.

3-(2-Fluoro-4-iodo-phenylamino)-1-prop-2-ynyl-1H-pyrrolo[3,2-c]pyridine-2-carboxylic acid ethyl ester

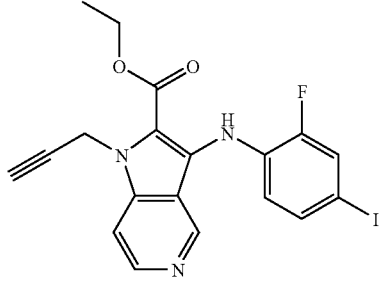

A mixture of 3-(2-fluoro-4-iodo-phenylamino)-1H-pyrrolo[3,2-c]pyridine-2-carboxylic acid ethyl ester (70.0 mg, 0.164 mmol), propargyl bromide (80% in xylene, 45.5 μL, 0.41 mmol, 2.5 eq), DBU (3.2 mL), and anhydrous THF (3.2 mL) was stirred at 50° C. under N$_2$ for 1 h, and then at ambient temperature for 17 h. The solvent was evaporated and the resultant residue was diluted with ethyl acetate (75 mL). The organic layer was washed with water (20 mL), followed by brine (20 mL), dried (Na$_2$SO$_4$), filtered and evaporated to give a brown oil. The oil was purified by flash column chromatography (silica, ISCO, 45 mL/min, Hexane:EtOAc, gradient 100:1 to 1:100). Crystallization from EtOAc-hexane gave the desired compound as a yellow solid (34.5 mg, 45.3%). $^1$H NMR (400 MHz, CDCl$_3$) δ ppm 8.74 (s, 1H), 8.44 (d, J=5.87 Hz, 1H), 7.60 (s, 1H), 7.45 (dd, J=10.26 Hz, 2.0 Hz, 1H), 7.37-7.27 (m, 2H), 6.87 (t, J=9.20 Hz, 1H), 5.29 (s, 2H), 4.46 (q, J=7.14 Hz, 2H), 2.29 (t, J=2.47 Hz, 1H), 1.49-1.40 (t, J=7.20 Hz, 3H); LC-MS (method D): [M+H]$^+$=464.0, R$_T$=2.40 min.

3-(2-Fluoro-4-iodo-phenylamino)-1-[4-(tetrahydro-pyran-2-yloxy)-but-2-ynyl]-1-H-pyrrolo[3,2-c]pyridine-2-carboxylic acid ethyl ester

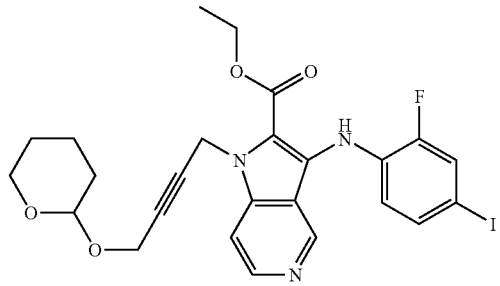

Step 1: 2-(4-Chloro-but-2-ynyloxy)-tetrahydro-pyran

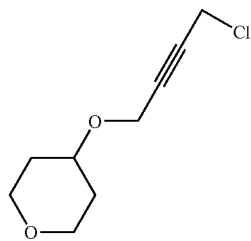

A solution of 4-chloro-but-2-yn-1-ol (2.16 g, 20.66 mmol), 3,4-dihydro-2H-pyran (2.83 mL, 30.99 mmol, 1.5 eq), and pyridinium p-toluenesulfonate (528.0 mg, 0.21 mmol, 0.10 eq) in anhydrous dichloromethane (50 mL) was stirred at room temperature under N$_2$ for 17 h. The reaction mixture was diluted with water (100 mL) and extracted with EtOAc (2×150 mL). The combined organic layers were washed with brine, dried (Na$_2$SO$_4$), filtered and evaporated in vacuo to give 3.80 g (97.4%) of the desired product as clear oil. $^1$H NMR (400 MHz, CDCl$_3$) δ ppm 4.80 (t, J=4.0 Hz, 1H), 4.39-4.22 (m, 2H), 4.19 (t, J=2.0 Hz, 2H), 3.88-3.80 (m, 1H), 3.57-3.51 (m, 1H), 1.89-1.70 (m, 2H), 1.68-1.50 (m, 4H).

Step 2: 3-(2-Fluoro-4-iodo-phenylamino)-1-[4-(tetrahydro-pyran-2-yloxy-but-2-ynyl]-1-H-pyrrolo[3,2-c]pyridine-2-carboxylic acid ethyl ester A mixture of 3-(2-fluoro-4-iodo-phenylamino)-1H-pyrrolo[3,2-c]pyridine-2-carboxylic acid ethyl ester (200.0 mg, 0.47 mmol), 2-(4-chloro-but-2-ynyloxy)-tetrahydro-pyran (133.0 mg, 0.70 mmol, 1.5 eq), and potassium carbonate (78.0 mg, 0.56 mmol, 1.2 eq) in anhydrous DMF (4.7 mL) was stirred at 75° C. under $N_2$ for 20 h. The reaction mixture was cooled to ambient temperature and diluted with ethyl acetate (50 mL). The organic layer was washed with 50% brine (20 mL), brine (20 mL), dried ($Na_2SO_4$), filtered, and evaporated to give a brown oil. The oil was purified by flash column chromatography (silica, ISCO, 45 mL/min, Hexane:EtOAc, gradient 75:25 to 1:100). Appropriate fractions were collected to give the desired compound as an orange solid (99.1 mg, 36.5%). $^1$H NMR (400 MHz, $CDCl_3$) δ ppm 8.58 (d, J=0.89 Hz, 1H), 8.34 (d, J=6.16 Hz, 1H), 7.62 (dd, J=6.19, 1.20 Hz, 1H), 7.52 (dd, J=10.60, 6.0 Hz, 1H), 7.36 (ddd, J=8.49, 1.60, 1.20 Hz, 1H), 6.80 (t, J=8.71 Hz, 1H), 5.44 (t, J=1.84 Hz, 2H), 4.67 (t, J=3.59 Hz, 1H), 4.41 (q, J=7.13 Hz, 2H), 4.19 (t, J=1.57 Hz, 2H), 3.78-3.68 (m, 1H), 3.43-3.34 (m, 1H), 1.75 (d, J=9.12 Hz, 1H), 1.68-1.41 (m, 5H), 1.37 (t, J=7.13 Hz, 3H); LC-MS (method C): [M+H]$^+$=578.0, $R_T$=0.926 min.

2-Fluoro-4-trimethylsilanyl-phenol

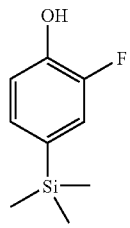

A solution 4-bromo-2-fluoro-phenol (75 g, 0.39 mol) in THF (750 mL) was cooled to −78° C. and treated dropwise with n-butyllithium (471 mL, 2.5M solution) over 1 hour keeping the internal temperature below −60° C. After stirring for a further 30 minutes the mixture was treated with chlorotrimethylsilane (128 g, 1.18 mol) in THF (150 mL) over 30 minutes keeping the internal temperature below −60° C. After the addition the mixture was allowed to warm to 0° C. over 40 minutes. The mixture was poured into 1M hydrochloric acid and the layers separated. The aqueous layer was extracted with diethyl ether (×2) and the combined organic layers were washed with water, brine, dried ($MgSO_4$) and concentrated in vacuo to give a colourless liquid. The liquid was dissolved in THF (750 mL) and treated with tetrabutylammonium fluoride (393 mL, 1M solution in THF). After 5 minutes the solution was poured into water and the layers separated. The aqueous layer was extracted with diethyl ether (×2) and the combined organic layers washed with water, brine, dried ($MgSO_4$) and evaporated to a straw-coloured oil. The oil was dissolved in DCM/cyclohexane (1:1, 500 mL) and stirred with silica (15 g) and filtered. The filtrate was evaporated to give the title compound as an oil which solidified on standing (72 g, 100% yield). $^1$H NMR ($CDCl_3$) 7.04-6.92 (2H, m), 6.92-6.76 (1H, m), and 0.077 (9H, s).

Trifluoro-methanesulfonic acid 2-fluoro-4-trimethylsilanyl-phenyl ester

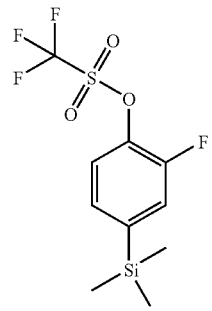

2-Fluoro-4-trimethylsilanyl-phenol (78.5 g, 0.43 mol) was dissolved in $CH_2Cl_2$ (500 mL) and pyridine (101 g, 1.28 mmol) added. The solution was cooled to 0-5° C. and treated dropwise with trifluoromethanesulfonic anhydride (126.3 g, 0.45 mol) in $CH_2Cl_2$ (100 mL) over 30 minutes and the resulting mixture was stirred cold for a further 15 minutes. The yellow solution was poured into 2M hydrochloric acid and the layers separated. The organic layer was washed with water, aqueous $NaHCO_3$ solution, brine, dried ($MgSO_4$) and solvent evaporated in vacuo. The resultant residue was dissolved in cyclohexane and stirred with flash silica and filtered. The filtrate was concentrated in vacuo to yield the title compound as a colourless liquid (123 g, 91% yield). $^1$H NMR ($CDCl_3$) 7.35 (1H, m), 7.30-7.27 (2H, m), and 0.29 (9H, s).

2-Fluoro-4-Trimethylsilanyl-Phenylamine

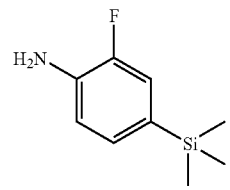

4-Chloro-2-fluoronitrobenzene (6.0 g, 34.2 mmol) was added to a 100 mL round bottom flask, followed by hexamethyldisilane (18.9 g, 129.0 mmol, 26.4 mL) and xylene (13 mL). The mixture was magnetically stirred while nitrogen was bubbled into the solution via glass pipette for 10 minutes or until the entire solid had dissolved.

Tetrakis(triphenylphosphine)palladium(0) (1.0 g, 0.9 mmol) was added, the flask fitted with a reflux condenser, and the reaction was heated at reflux for 24-48 hours while a slow stream of nitrogen was passed through a rubber septum placed in the top of the condenser. After cooling to room temperature, the reaction mixture was diluted with ethyl ether (40 mL) and filtered through a plug of silica gel (30 mL of $SiO_2$/ethyl ether slurry packed into a 60 mL fritted glass funnel). The filter cake was washed with ethyl ether (60 mL) and the combined organics were concentrated in vacuo to an orange oil, which was purified by flash chromatography (250 mL silica gel, 98:1:1 hexane-$CH_2Cl_2$-ethyl ether), yielding the 2-fluoro-4-trimethylsilylnitrobenzene (5.45 g, 75%) as a yellow-orange oil.

The 2-fluoro-4-trimethylsilylnitrobenzene (5.45 g, 25.6 mmol) was then dissolved in ethanol (100 mL), transferred to a Parr shaker bottle, flushed with nitrogen, then charged with 10% Pd—C (0.4 g). The reaction mixture was hydrogenated for 1 h on the Parr apparatus (45 psi $H_2$), and then filtered through a plug of Celite. The filter cake was washed with ethanol, and the combined filtrates were concentrated. The resulting residue was purified by flash chromatography (250 mL silica gel, 95:5 hexane-ethyl ether), to afford the title compound as a tan oil (4.31 g, 92%).

Compounds Prepared by General Methods

Pyrrolo[3,2-c]pyridine-1-NH alkylation general method 3-(2-Fluoro-4-iodo-phenylamino)-1H-pyrrolo[3,2-c]pyridine-2-carboxylic acid ethyl ester, potassium carbonate (1.2 eq) and the appropriate alkyl iodide, alkyl bromide or benzyl chloride (1.2 eq) in DMF was heated at 55° C. On completion of the reaction the mixture was allowed to cool to ambient temperature then evaporated. The resultant residue was dissolved in ethyl acetate and washed with water before the organic layer was isolated, dried over sodium sulfate, then concentrated in vacuo. The resultant residue was then subjected to purification.

Purification General Methods:

Method A: Si-PPC, ethyl acetate/cyclohexane gradient

Method B: Si-PPC, ethyl acetate/DCM gradient

Method C: Si-PPC, methanol/DCM gradient

Method D: Si-PPC, ether/pentane gradient then methanol/ether gradient

| Structure/Name | Purification method | LCMS# $R_T$/M+ | $^1$H NMR |
|---|---|---|---|
| 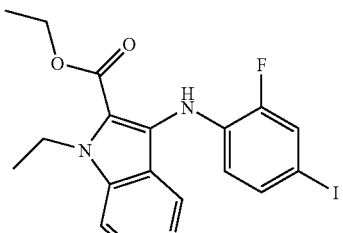<br>1-Ethyl-3-(2-fluoro-4-iodo-phenylamino)-1H-pyrrolo[3,2-c]pyridine-2-carboxylic acid ethyl ester | A | 2.52, 454 | — |
| 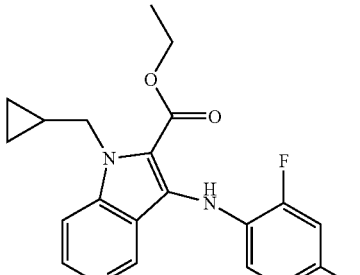<br>1-Cyclopropylmethyl-3-(2-fluoro-4-iodo-phenylamino)-1H-pyrrolo[3,2-c]pyridine-2-carboxylic acid ethyl ester | A | 2.61, 480 | — |
| 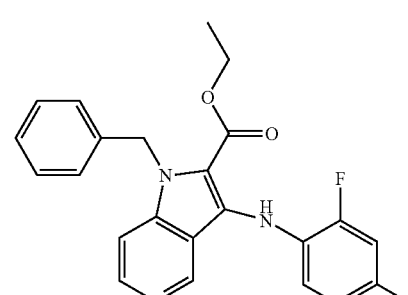<br>1-Benzyl-3-(2-fluoro-4-iodo-phenylamino)-1H-pyrrolo[3,2-c]pyridine-2-carboxylic acid ethyl ester | B | 2.83, 516 | — |

| Structure/Name | Purification method | LCMS# R$_T$/M+ | $^1$H NMR |
|---|---|---|---|
| 3-(2-Fluoro-4-iodo-phenylamino)-1-pyridin-4-ylmethyl-1H-pyrrolo[3,2-c]pyridine-2-carboxylic acid ethyl ester | C | — | (CDCl$_3$) 1.28 (3 H, t, J = 7.1 Hz), 4.33 (2 H, t, J = 7.1 Hz), 5.71 (2 H, s), 6.93 (3 H, m), 7.18 (1 H, dd, J = 6.1, 1.0 Hz), 7.36 (1 H, d, J = 8.4), 7.49 (1 H, dd, J = 10.1, 1.9 Hz), 7.66 (1 H, s), 8.41 (1 H, d, J = 6.1 Hz), 8.54 (2 H, d, J = 5.1 Hz), 8.79 (1 H, d, J = 1.0 Hz) |
| 3-(2-Fluoro-4-iodo-phenylamino)-1-pyridin-3-ylmethyl-1H-pyrrolo[3,2-c]pyridine-2-carboxylic acid ethyl ester | C | 2.24, 517 | — |
| 1-(2-Fluoro-benzyl)-3-(2-fluoro-4-iodo-phenylamino)-1H-pyrrolo[3,2-c]pyridine-2-carboxylic acid ethyl ester | A | — | (CDCl$_3$) 1.28 (3 H, t, J = 7.1 Hz), 4.35 (2 H, t, J = 7.1 Hz), 5.77 (2 H, s), 6.63 (1 H, t, J = 7.6 Hz), 7.00 (3H, m), 7.26 (2 H, m), 7.34 (1 H, d, J = 7.8 Hz), 7.47 (1 H, dd, J = 10.2, 1.9 Hz), 7.72 (1 H, s), 8.39 (1 H, d, J = 6.1 Hz), 8.77 (1 H, d, J = 1.0 Hz) |
| 3-(2-Fluoro-4-iodo-phenylamino)-1-(3-trifluoromethyl-benzyl)-1H-pyrrolo[3,2-c]pyridine-2-carboxylic acid ethyl ester | A | — | (CDCl$_3$) 1.28 (3 H, t, J = 7.1 Hz), 4.34 (2 H, t, J = 7.1 Hz), 5.74 (2 H, s), 7.11 (1 H, d, J = 7.8 Hz), 7.20 (1 H, dd, J = 6.1, 1.0 Hz), 7.37 (4 H, m), 7.47 (1 H, dd, J = 10.2, 1.9 Hz), 7.52 (1 H, d, J = 7.8 Hz), 7.65 (1 H, s), 8.41 (1 H, d, J = 6.1 Hz), 8.79 (1 H, d, J = 1.0 Hz) |

-continued

| Structure/Name | Purification method | LCMS# $R_T$/M+ | $^1$H NMR |
|---|---|---|---|
| 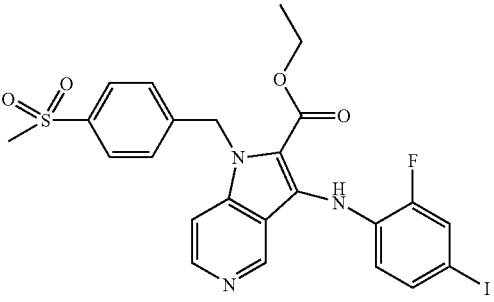<br>3-(2-Fluoro-4-iodo-phenylamino)-1-(4-methanesulfonyl-benzyl)-1H-pyrrolo[3,2-c]pyridine-2-carboxylic acid ethyl ester | A | — | (CDCl$_3$) 1.30 (3 H, t, J = 7.1 Hz), 4.34 (2 H, t, J = 7.1 Hz), 5.79 (2 H, s), 6.93 (1 H, t, J = 8.8 Hz), 7.21 (3 H, m), 7.35 (1 H, d, J = 8.4), 7.48 (1 H, dd, J = 10.1, 1.9 Hz), 7.61 (1 H, s), 7.87 (2 H, d, J = 8.3 Hz), 8.41 (1 H, d, J = 6.1 Hz), 8.80 (1 H, d, J = 1.0 Hz) |
| 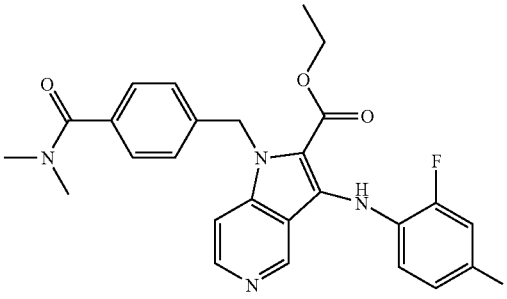<br>1-(4-Dimethylcarbamoyl-benzyl)-3-(2-fluoro-4-iodo-phenylamino)-1H-pyrrolo[3,2-c]pyridine-2-carboxylic acid ethyl ester | C | 2.57, 587 | — |
| 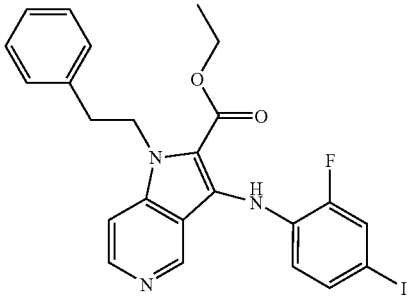<br>3-(2-Fluoro-4-iodo-phenylamino)-1-phenethyl-1H-pyrrolo[3,2-c]pyridine-2-carboxylic acid ethyl ester | A | — | (CDCl3) 1.33 (3 H, t, J = 7.1 Hz), 3.04 (2 H, t, J = 7.2 Hz), 4.43 (2 H, t, J = 7.1 Hz), 4.68 (2 H, t, J = 7.2 Hz), 6.83 (1 H, t, J = 8.8 Hz), 7.03 (1 H, dd, J = 6.1, 1.0 Hz), 7.08 (2 H, m), 7.26 (4 H, m), 7.45 (1 H, dd, J = 10.2, 1.8 Hz), 7.53 (1 H, s), 8.28 (1 H, d, J = 6.1 Hz), 8.72 (1 H, d, J = 1.0 Hz). |
| 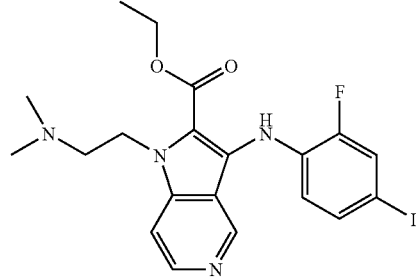<br>1-(2-Dimethylamino-ethyl)-3-(2-fluoro-4-iodo-phenylamino)-1H-pyrrolo[3,2-c]pyridine-2-carboxylic acid ethyl ester | J | 1.85, 497 | — |

-continued

| Structure/Name | Purification method | LCMS# R$_T$/M+ | $^1$H NMR |
|---|---|---|---|
| 1-(4-Fluoro-benzyl)-3-(2-fluoro-4-iodo-phenylamino)-1H-pyrrolo[3,2-c]pyridine-2-carboxylic acid ethyl ester | A | 2.87, 534 | — |
| 3-(2-Fluoro-4-iodo-phenylamino)-1-(4-trifluoromethyl-benzyl)-1H-pyrrolo[3,2-c]pyridine-2-carboxylic acid ethyl ester | B | 3.06, 584 | — |
| 1-(4-Cyano-benzyl)-3-(2-fluoro-4-iodo-phenylamino)-1H-pyrrolo[3,2-c]pyridine-2-carboxylic acid ethyl ester | B | 2.76, 541 | — |
| 1-(3-Dimethylcarbamoyl-benzyl)-3-(2-fluoro-4-iodo-phenylamino)-1H-pyrrolo[3,2-c]pyridine-2-carboxylic acid ethyl ester | C | 2.71, 587 | — |

-continued

| Structure/Name | Purification method | LCMS# R_T/M+ | ¹H NMR |
|---|---|---|---|
| 1-(3-Cyano-benzyl)-3-(2-fluoro-4-iodo-phenylamino)-1H-pyrrolo[3,2-c]pyridine-2-carboxylic acid ethyl ester | B | 2.75, 541 | — |
| 1-(4-Dimethylsulfamoyl-benzyl)-3-(2-fluoro-4-iodo-phenylamino)-1H-pyrrolo[3,2-c]pyridine-2-carboxylic acid ethyl ester | C | 2.77, 623 | — |
| 1-(4-Dimethylcarbamoyl-benzyl)-3-(2-fluoro-4-iodo-phenylamino)-1H-pyrrolo[3,2-c]pyridine-2-carboxylic acid ethyl ester | A | 2.56, 587 | — |
| 1-(5-Cyano-thiophen-2-ylmethyl)-3-(2-fluoro-4-iodo-phenylamino)-1H-pyrrolo[3,2-c]pyridine-2-carboxylic acid ethyl ester | A | 2.88, 547 | — |

-continued

| Structure/Name | Purification method | LCMS# $R_T$/M+ | $^1$H NMR |
|---|---|---|---|
| 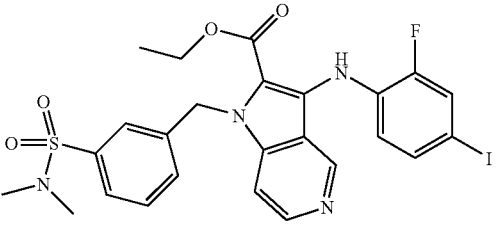 1-(3-Dimethylsulfamoyl-benzyl)-3-(2-fluoro-4-iodo-phenylamino)-1H-pyrrolo[3,2-c]pyridine-2-carboxylic acid ethyl ester | A | 2.33, 623 | — |

Footnotes to tabulated data, #LCMS method B

Synthesis of Selected Hydroxylamines

Cyclopropylmethylhydroxylamine Hydrochloride

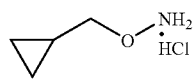

Prepared according to Marquez et al (2005) Synth. Comm. 35(17):2265-2269

O—((R)-2,2-dimethyl-[131]dioxolan-4-ylmethyl) hydroxylamine

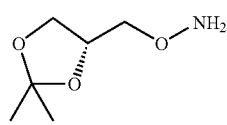

Prepared according to Bailey et al (1991) J. Med. Chem. 34(1):57-65

O-(2-Vinyloxy-ethyl)-hydroxylamine

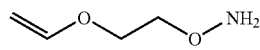

Prepared according to WO 0206213

N-Methyl-O-(2-vinyloxy-ethyl)-hydroxylamine

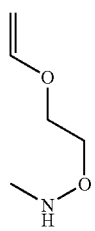

Formaldehyde (37% w/w in water, 80 μL, 1.0 mmol) was added to a cooled (0° C.) solution of O-(2-vinyloxy-ethyl)-hydroxylamine (105 mg, 1.0 mmol) in ethanol (1 mL). The mixture was stirred for 30 minutes before addition of pyridiniumpara-toluene sulfonate (250 mg, 1.0 mmol) and sodium cyanoborohydride (70 mg, 1.1 mmol). The resultant suspension was allowed to warm to ambient temperature and stirred for 20 hours. The solvent was evaporated and the residue was dissolved in ethyl acetate (25 mL) then washed with brine (20 mL). The organic extract was dried (MgSO$_4$), filtered and evaporated to provide the desired product as an oil (84 mg, 71%). $^1$H NMR (CDCl$_3$, 400 MHz) 6.44-6.55 (m, 1H), 4.98 (s, 1H), 4.16-4.24 (m, 1H), 3.98-4.06 (m, 1H), 3.82-3.96 (m, 4H), 2.59 (s, 3H).

4-(tert-Butyl-dimethyl-silanyloxy)-isoxazolidine

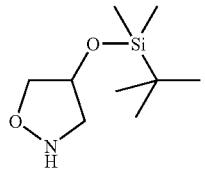

tert-Butyl-dimethyl-chlorosilane (0.5 g, 3.21 mmol) was added to a stirred solution of isoxazolidin-4-ol hydrochloride (0.40 g, 3.18 mmol) in DMF (3 mL). The mixture was left to stir at ambient temperature for 2.5 hours before the solvent was evaporated and the resultant residue partitioned between ethyl acetate (50 mL) and water (20 mL). The organic phase was separated and washed with water (3×20 mL) then brine (20 mL), dried (MgSO$_4$), filtered and evaporated to provide the desired product as a colourless oil (0.62 g, 96%). $^1$H NMR (CDCl$_3$, 400 MHz) 5.52 (s, 1H), 4.60-4.65 (m, 1H), 3.45-3.62 (m, 1H), 3.80-4.05 (m, 1H), 2.80-3.05 (m, 2H), 0.80 (s, 9H), 0.08 (s, 6H).

(S)-3-Aminooxy-pyrrolidine-1-carboxylic acid tert-butylester

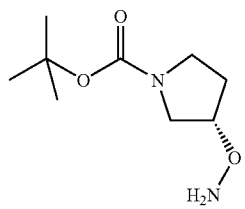

Step 1: (S)-3-(1,3-Dioxo-1,3-dihydro-isoindol-2-yloxy-pyrrolidine carboxylic acid tert-butyl ester

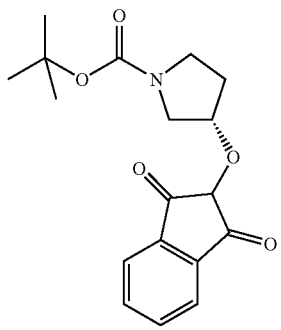

(R)-3-Hydroxy-pyrrolidine-1-carboxylic acid tert-butyl ester (1.37 g, 7.31 mmol) was dissolved in THF (20 mL) then 2-hydroxy-isoindole-1,3-dione (1.19 g, 7.31 mmol) and triphenyl phosphine (1.92 g, 7.31 mmol) were added. Diisopropyl azodicarboxylate (1.33 mL, 8.04 mmol) was added dropwise over 10 minutes. The reaction mixture was allowed to stir at ambient temperature for 18 hours then the solvent was evaporated. The resultant residue was purified by flash column chromatography (Si-PPC, DCM:EtOAc, gradient 100:0 to 80:20) to provide the title compound as a colourless oil (1.43 g, 59%). $^1$H NMR (CDCl$_3$, 400 MHz) 7.86 (m, 2H), 7.77 (m, 2H), 4.94-5.02 (m, 1H), 3.66-3.84 (m, 2H), 3.50-3.65 (m, 2H), 2.24-2.32 (m, 1H), 1.93-2.05 (m, 1H), 1.49 (s, 9H).

Step 2: (S)-3-Aminooxy-pyrrolidine-1-carboxylic acid tert-butylester

Methyl hydrazine (0.23 mL, 4.40 mmol) was added dropwise over 5 minutes to a solution of (S)-3-(1,3-dioxo-1,3-dihydro-isoindol-2-yloxy)-pyrrolidine-1-carboxylic acid tert-butyl ester (1.43 g, 4.3 mmol) in DCM (12 mL). The mixture was stirred at ambient temperature for 1 hour then evaporated. The resultant residue was suspended in diethyl ether (10 mL) and the solid was filtered. The filtrate was concentrated to provide the title compound as a colourless oil (0.86 g, 99%). $^1$H NMR (CDCl$_3$, 400 MHz) 4.24-4.26 (m, 1H), 3.60-3.66 (m, 1H), 3.44-3.54 (m, 1H), 3.30-3.42 (m, 2H), 2.03-2.12 (m, 1H), 1.84-1.96 (m, 1H), 1.46 (s, 9H).

Example 5

3-(2-Fluoro-4-iodo-phenylamino)-1-methyl-1H-pyrrolo[3,2-c]pyridine-2-carboxylic acid ((R)-2,3-dihydroxy-propoxy)-amide

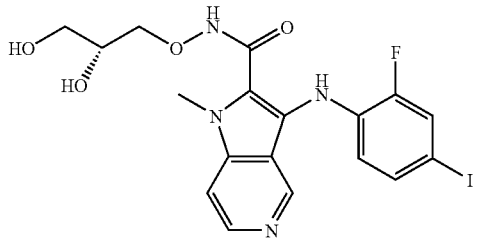

Step 1: 3-(2-Fluoro-4-iodo-phenylamino)-1-methyl-1H-pyrrolo[3,2-c]pyridine-2-carboxylic acid ((R)-2,2-dimethyl-[1,3]dioxolan-4-ylmethoxy)-amide

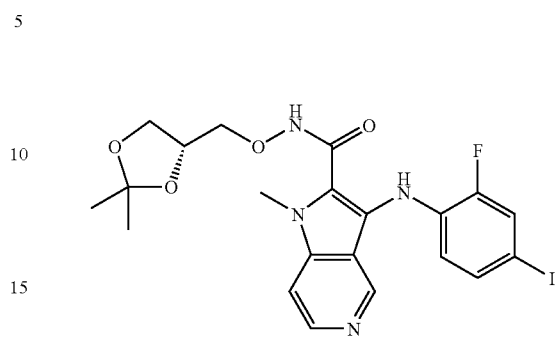

A mixture of 3-(2-fluoro-4-iodo-phenylamino)-1-methyl-1H-pyrrolo[3,2-c]pyridine-2-carboxylic acid ethyl ester (90 mg, 0.21 mmol), 1N aqueous NaOH solution (0.22 ml, 0.22 mmol) and ethanol (3 ml) were heated at 65° C. for 2.5 hours. The reaction mixture was concentrated and then azeotroped with toluene (2×5 ml) to give a solid residue. The solid residue was dissolved in anhydrous THF (5 ml) and O—((R)-2,2-dimethyl-[1,3]dioxolan-4-ylmethyl)hydroxylamine (49 mg, 0.41 mmol), EDCI (49 mg, 0.26 mmol), HOBt (39 mg, 0.29 mmol) and DIPEA (109 µl, 0.62 mmol) were added. After stirring for 19 hours the solvent was evaporated and the residue was partitioned between ethyl acetate (30 ml) and water (20 ml). The organic layer was isolated, dried over sodium sulphate then filtered and evaporated to give a yellow oil. The oil was purified by flash chromatography (Si-PPC, pentane: ethyl acetate, gradient 50:50 to 0:100) to afford the title compound as a yellow solid (71 mg, 65%). LCMS (method B): $R_T$=2.87 min, M+H$^+$=542.

Step 2: 3-(2-Fluoro-4-iodo-phenylamino)-1-methyl-1H-pyrrolo[3,2-c]pyridine-2-carboxylic acid ((R)-2,3-dihydroxy-propoxy)-amide 3-(2-Fluoro-4-iodo-phenylamino)-1-methyl-1H-pyrrolo[3,2-c]pyridine-2-carboxylic acid ((R)-2,2-dimethyl-[1,3]dioxolan-4-ylmethoxy)-amide (71 mg, 0.13 mmol) was dissolved in methanol (0.5 ml) and loaded onto an Isolute® SCX-2 cartridge (5 g). The cartridge was then washed with methanol (15 ml) and the desired product was subsequently eluted using 2M NH$_3$ in MeOH. The eluant was collected and concentrated to give a residue. The residue was purified by flash chromatography (Si-PPC, dichloromethane:MeOH, gradient 100:0 to 90:10) followed by reversed phase HPLC (Phenomenex Luna 5 phenyl/hexyl, 0.1% TFA in water on a gradient of acetonitrile 100:0 to 40:60) to afford the title compound as a white solid (12 mg, 15%). LCMS (method A): $R_T$=4.83 min, M+H$^+$=501. $^1$H NMR (d$_4$-MeOH, 400 MHz) 8.61 (s, 1H), 8.30 (d, J=6.0 Hz, 1H), 7.59 (d, J=6.0 Hz, 1H), 7.44 (dd, J=11.0 Hz, 1.8 Hz, 1H), 7.18-7.23 (m, 1H), 6.37 (dd, J=9.0 Hz, 9.0 Hz, 1H), 3.99 (s, 3H), 3.89-3.95 (m, 1H), 3.77-3.86 (m, 2H), 3.47-3.59 (m, 2H).

Example 6

3-(2-Fluoro-4-iodo-phenylamino)-1-methyl-1H-pyrrolo[3,2-c]pyridine-2-carboxylic acid (2-hydroxyethoxy)-amide

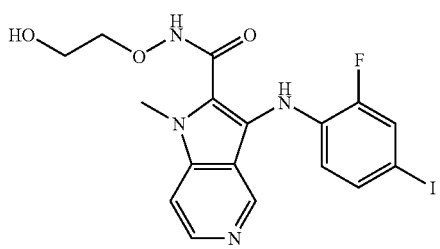

Step 1: 3-(2-Fluoro-4-iodo-phenylamino)-1-methyl-1H-pyrrolo[3,2-c]pyridine-2-carboxylic acid (2-vinyloxy-ethoxy)-amide

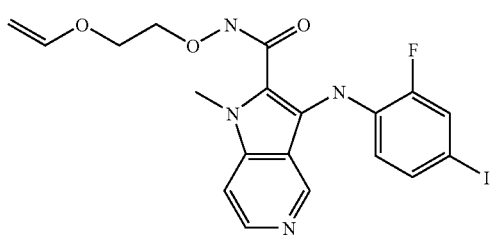

A mixture of ethyl 3-(2-fluoro-4-iodo-phenylamino)-1-methyl-1H-pyrrolo[3,2-c]pyridine-2-carboxylic acid ethyl ester (100 mg, 0.23 mmol), 1N aqueous sodium hydroxide (0.25 ml) and MeOH (3.0 ml) was heated at 65° C. for 1.5 hours. The reaction mixture was concentrated and azeotroped with toluene (2×2 ml) to give a solid residue. The solid residue was dissolved in anhydrous THF (4 ml) and O-(2-vinyloxy-ethyl)-hydroxylamine (47 mg, 0.46 mmol), EDCI (55 mg, 0.29 mmol), HOBt (43 mg, 0.32 mmol) and DIPEA (119 µl, 0.68 mmol) were added. After stirring for 72 hours at ambient temperature, the mixture was evaporated and the residue was partitioned between ethyl acetate (30 ml) and water (20 ml). The organic layer was isolated, dried over sodium sulphate, then filtered and evaporated to give a yellow oil. The oil was purified by flash chromatography (Si-PPC, dichloromethane:methanol, gradient 100:0 to 90:10) to afford the title compound as a yellow solid (64 mg, 57%). LCMS (method B): $R_T$=2.20 min, M+H$^+$=497.

Step 2: 3-(2-Fluoro-4-iodo-phenylamino)-1-methyl-1H-pyrrolo[3,2-c]pyridine-2-carboxylic acid (2-hydroxy-ethoxy)-amide A mixture of 3-(2-fluoro-4-iodo-phenylamino)-1-methyl-1H-pyrrolo[3,2-c]pyridine-2-carboxylic acid (2-vinyloxy-ethoxy)-amide (64 mg, 0.13 mmol), 1N aqueous HCl (0.39 mL) and MeOH (4.0 ml) was stirred at room temperature for 20 hours. Sodium hydrogen carbonate (32 mg, 0.39 mmol) was added, stirring was continued for 10 minutes then the reaction mixture was concentrated under reduced pressure. The residue was absorbed onto HM-N and purified by flash chromatography (Si-PPC, dichloromethane:MeOH, gradient 100:0 to 85:15) followed by reversed phase HPLC (Phenomenex Luna 5 phenyl/hexyl, 0.1% TFA in water on a gradient of acetonitrile 95:5 to 50:50) to afford the title compound as a yellow solid (16 mg, 27%). LCMS (method A): $R_T$=5.75 min, M+H$^+$=471. $^1$H NMR (d$_4$-MeOH, 400 MHz) 8.55 (s, 1H), 8.24 (d, J=6.2 Hz, 1H), 7.52 (d, J=6.2 Hz, 1H), 7.39 (dd, J=10.8 Hz, 1.8 Hz, 1H), 7.14-7.19 (m, 1H), 6.35 (dd, J=8.7 Hz, 8.7 Hz, 1H), 3.94 (s, 3H), 3.88 (t, J=4.5 Hz, 2H), 3.64 (t, J=4.5 Hz, 2H).

Example 18

3-(2-Fluoro-4-iodo-phenylamino)-1-(2-hydroxyethyl)-1H-pyrrolo[3,2-c]pyridine-2-carboxylic acid amide

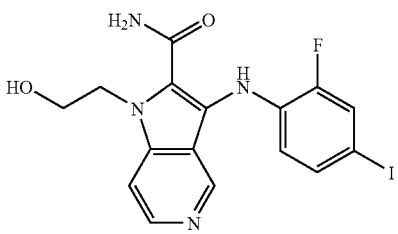

Step 1: 3-(2-Fluoro-4-iodo-phenylamino)-1-(2-triisopropylsilanyloxy-ethyl)-1H-pyrrolo[3,2-c]pyridine-2-carboxylic acid amide

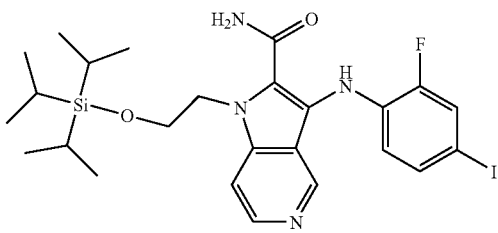

To a suspension of 3-(2-fluoro-4-iodo-phenylamino)-1-(2-triisopropylsilanyloxy-ethyl)-1H-pyrrolo[3,2-c]pyridine-2-carboxylic acid methyl ester (132 mg, 0.22 mmol) in ethanol (3 mL) was added a 1M aqueous solution of sodium hydroxide (0.23 mL, 0.23 mmol). The reaction mixture was heated at 65° C., stirred for 1 hour, cooled to room temperature, concentrated and azeotroped with toluene. The residue was suspended in DMF and ammonium chloride (24 mg, 0.44 mmol), diisopropylethylamine (0.15 mL, 0.88 mmol) then HATU (167 mg, 0.44 mmol) were added. The reaction mixture was stirred at room temperature for 16 hours before being partitioned between ethyl acetate and water. The organic layer was isolated and washed with water then a saturated solution of sodium hydrogencarbonate and then brine, dried (Na$_2$SO$_4$), filtered and evaporated to give the title compound as a yellow solid (105 mg, 80%). LCMS (method B): $R_T$=3.03 min, M+H$^+$=597.

Step 2: 3-(2-Fluoro-4-iodo-phenylamino)-1-(2-hydroxy-ethyl)-1H-pyrrolo[3,2-c]pyridine-2-carboxylic acid amide To a suspension of 3-(2-fluoro-4-iodo-phenylamino)-1-(2-triisopropylsilanyloxy-ethyl)-1H-pyrrolo[3,2-c]pyridine-2-carboxylic acid amide (100 mg, 0.17 mmol) in methanol was added a 1M solution of HCl (0.34 mL, 0.34 mmol). The reaction mixture was heated at reflux and stirred for 1 hour. After cooling to room temperature the reaction mixture was passed through a 5 g SCX-2 cartridge eluting with MeOH then 2M solution of ammonia in MeOH. The appropriate fractions were combined and concentrated to give a residue that was purified by flash chromatography (Si-PPC, MeOH:DCM, gradient 0:100 to 20:80) to provide the title compound as an off-white solid (40 mg, 53%). LCMS (method A): $R_T$=5.78 min, M+H$^+$=441. $^1$H NMR (DMSO-D$_6$) 3.70 (2H, q, J=5.3 Hz), 4.53 (2H, t, J=5.3 Hz), 4.94 (1H, t, J=5.3 Hz), 6.19 (1H, t, J=8.9 Hz), 7.20 (1H, m), 7.53 (1H, dd, J=11.0, 2.0 Hz), 7.60 (1H, dd, J=6.0, 1.0 Hz), 7.72 (1H, d, J=2.0 Hz), 7.81 (2H, s, br), 8.28 (1H, d, J=6.0 Hz), 8.52 (1H, d, J=1.0 Hz).

Example 19

3-(2-Fluoro-4-iodo-phenylamino)-1-(2-hydroxy-ethyl)-1H-pyrrolo[3,2-c]pyridine-2-carboxylic acid (2-hydroxy-ethoxy)-amide

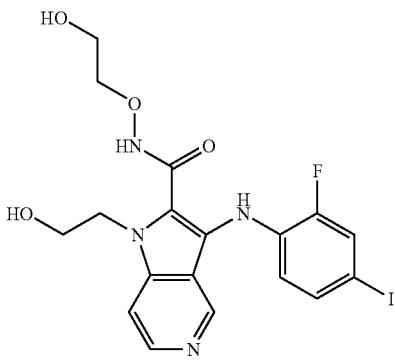

Step 1: 3-(2-Fluoro-4-iodo-phenylamino)-1-(2-triisopropylsilanyloxy-ethyl)-1H-pyrrolo[3,2-c]pyridine-2-carboxylic acid (2-vinyloxy-ethoxy)-amide

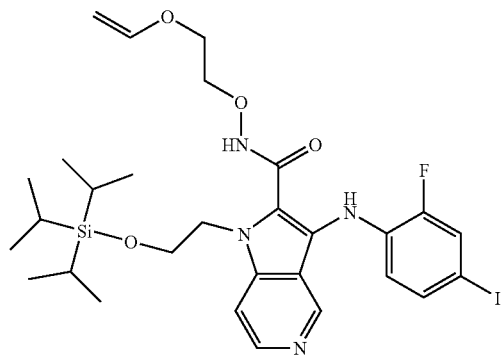

To a suspension of 3-(2-fluoro-4-iodo-phenylamino)-1-(2-triisopropylsilanyloxy-ethyl)-1H-pyrrolo[3,2-c]pyridine-2-carboxylic acid methyl ester (90 mg, 0.15 mmol) in ethanol (2 mL) was added a 1M aqueous solution of sodium hydroxide (0.15 mL, 0.15 mmol). The reaction mixture was heated at 65° C., stirred for 1 hour, cooled to room temperature, concentrated and azeotroped with toluene. The resultant residue was suspended in THF to which O-(2-vinyloxy-ethyl)-hydroxylamine (31 mg, 0.30 mmol), EDCI (37 mg, 0.19 mmol), HOBt (30 mg, 0.22 mmol) and DIPEA (105 µl, 0.60 mmol) were added. The reaction mixture was stirred at room temperature for 16 h then concentrated to give a residue which was purified by flash chromatography (Si-PPC, cyclohexane:EtOAc, gradient 100:0 to 0:100). The title compound was obtained as a yellow solid (58 mg, 57%). LCMS (method B): $R_T$=3.24 min, M+H$^+$=683.

Step 2: 3-(2-Fluoro-4-iodo-phenylamino)-1-(2-hydroxy-ethyl)-1H-pyrrolo[3,2-c]pyridine-2-carboxylic acid (2-hydroxy-ethoxy)-amide To a solution of 3-(2-fluoro-4-iodo-phenylamino)-1-(2-triisopropylsilanyloxy-ethyl)-1H-pyrrolo[3,2-c]pyridine-2-carboxylic acid (2-vinyloxy-ethoxy)-amide (58 mg, 0.085 mmol) in THF (2 mL) was added a 1M solution of tert-butylammonium fluoride in THF (0.1 mL, 0.1 mmol). The reaction mixture was stirred at room temperature for 1 hour and passed through a 5 g SCX-2 cartridge eluting with MeOH then 2M solution of ammonia in MeOH. The appropriate fractions were combined and concentrated to give a residue that was purified by flash chromatography (Si-PPC, MeOH:DCM, gradient 0:100 to 30:70). The title compound was obtained as a yellow solid (16 mg, 38%). LCMS (method A): $R_T$=5.13 min, M+H$^+$=501. $^1$H NMR (CDOD) 3.70 (2H, m), 3.90 (2H, t, J=5.3 Hz), 3.94 (2H, m), 4.60 (2H, t, J=5.3 Hz), 6.42 (1H, t, J=8.9 Hz), 7.2 (1H, m), 7.43 (1H, dd, J=10.9, 1.9 Hz), 7.60 (1H, dd, J=6.2, 0.9 Hz), 8.26 (1H, d, J=6.2 Hz), 8.58 (1H, d, J=0.9 Hz).

Example 20

3-(2-Fluoro-4-iodo-phenylamino)-1-methyl-1H-pyrrolo[3,2-c]pyridine-2-carboxylic acid ((S)-2-hydroxy-propoxy)-amide

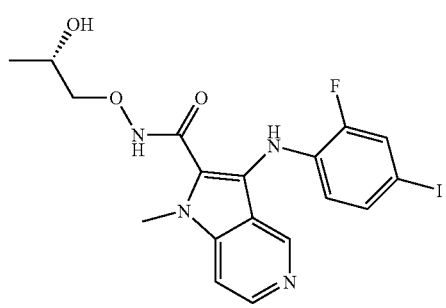

125

Step 1: 3-(2-fluoro-4-iodo-phenylamino)-1-methyl-1H-pyrrolo[3,2-c]pyridine-2-carboxylic acid [(S)-2-(tert-butyldimethylsilanyloxy)-propoxy]-amide

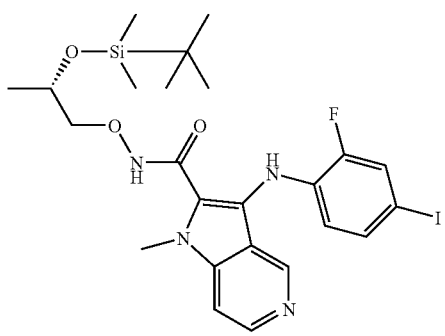

3-(2-Fluoro-4-iodo-phenylamino)-1-methyl-1H-pyrrolo[3,2-c]pyridine-2-carboxylic acid sodium salt (0.20 g, 0.46 mmol), O—[(S)-2-(tert-butyldimethylsilanyloxy)-propyl]-hydroxylamine (95 mg, 0.46 mmol), HOBT (69 mg, 0.51 mmol), EDCI (97 mg, 0.51 mmol) and DIPEA (0.08 ml, 0.46 mmol) were suspended in a mixture of THF (3 ml) and DMF (1 ml). The reaction was stirred at room temperature for 16 hours. The reaction mixture was concentrated in vacuo and the residue dissolved in ethyl acetate (20 ml) and washed with aqueous saturated sodium bicarbonate solution (20 ml). The aqueous layer was isolated and extracted with ethyl acetate (2×10 ml) and the combined organic layers dried, washed with brine and dried over magnesium sulfate before concentrating in vacuo. The crude residue was purified by flash chromatography (SiO$_2$, gradient 1-3% methanol in dichloromethane) to yield the title compound as an off-white solid (171 mg, 62%). LCMS (method B): R$_T$=3.00 min, M+H$^+$=599.

Step 2: 3-(2-Fluoro-4-iodo-phenylamino)-1-methyl-1H-pyrrolo[3,2-c]pyridine-2-carboxylic acid ((S)-2-hydroxy-propoxy)-amide TBAF (1.71 ml, 1N solution in THF, 1.71 mmol) was added to a solution of 3-(2-fluoro-4-iodo-phenylamino)-1-methyl-1H-pyrrolo[3,2-c]pyridine-2-carboxylic acid [(S)-2-(tert-butyldimethylsilanyloxy)-propoxy]-amide (171 mg, 0.29 mmol) in THF (3 ml) and the reaction heated at 45° C. for 4.5 hours. The reaction was concentrated in vacuo and the resultant residue purified by flash chromatography (SiO$_2$, gradient 0-10% methanol in dichloromethane) to yield the title compound as a yellow solid (35 mg, 25%). $^1$H NMR (DMSO-D$_6$, 400 MHz) 8.54 (1H, s), 8.27 (1H, d, J=5.7 Hz), 7.56-7.50 (2H, m), 7.48 (1H, dd, J=11.0, 2.1 Hz), 7.16-7.13 (1H, m), 6.18 (1H, t, J=8.9 Hz), 3.81 (3H, s), 3.74-3.67 (1H, m), 3.57-3.55 (2H, m), 0.95 (3H, d, J=5.99 Hz). LCMS (method A): R$_T$=5.82 min, M+H$^+$=485.

126

Example 59

3-(2-Fluoro-4-methylsulfanyl-phenylamino)-1H-pyrrolo[3,2-c]pyridine-2-carboxylic acid (2-hydroxy-1,1-dimethyl-ethoxy)-amide semiformate

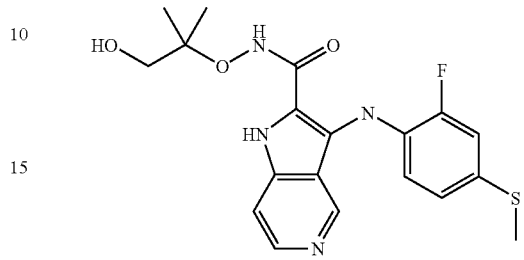

3-(2-Fluoro-4-methylsulfanyl-phenylamino)-1H-pyrrolo[3,2-c]pyridine-2-carboxylic acid ethyl ester (0.13 g, 0.38 mmol) was dissolved in IMS (5 ml) before 1M NaOH (0.45 ml, 0.45 mmol) was added and the mixture heated at 60° C. for 2 hours. The reaction mixture was concentrated in vacuo and the residue was re-dissolved in THF (3 ml). 2-Aminooxy-2-methyl-propan-1-ol (100 mg, 0.56 mmol), DIPEA (0.20 ml, 1.1 mmol) and HATU (210 mg, 0.56 mmol) were added and the mixture stirred at room temperature. On completion of the reaction, the solvent was removed in vacuo and the residue was partitioned between ethyl acetate and water. The organic extract was washed with water, dried (MgSO$_4$), and concentrated in vacuo. The resultant residue was purified by flash chromatography (Si-PPC, DCM:MeOH, gradient 99:1 to 90:10) to give an orange solid. The orange solid was then purified by reversed phase HPLC (Phenomenex Luna 5 phenyl/hexyl 0.1% HCO$_2$H in water on a gradient of acetonitrile) to provide the title compound (semiformate) as a yellow solid (7 mg, 5%). LCMS (method A): R$_T$=5.87 min, M+H$^+$=405. $^1$H NMR (d$_6$-DMSO, 400 MHz) 1.10 (6H, s), 2.42 (3H, s), 3.20 (2H, s), 6.58 (1H, t, J=8.58 Hz), 6.91 (1H, dd, J=8.42, 2.06 Hz), 7.20 (1H, dd, J=12.05, 2.11 Hz), 7.37 (1H, dd, J=5.84, 1.11 Hz), 7.81 (1H, s), 8.23 (1H, d, J=5.83 Hz), 8.52 (1H, d, J=1.07 Hz).

Example 60

7-(2-Fluoro-4-iodo-phenylamino)-5-methyl-5H-pyrrolo[3,2-c]pyridazine-6-carboxylic acid (2-hydroxy-ethoxy)-amide

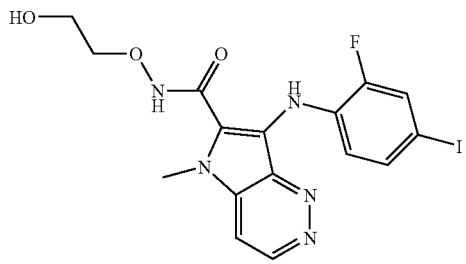

Step 1: 7-(2-Fluoro-4-iodo-phenylamino)-5-methyl-5H-pyrrolo[3,2-c]pyridazine-6-carboxylic acid (2-vinyloxy-ethoxy)-amide

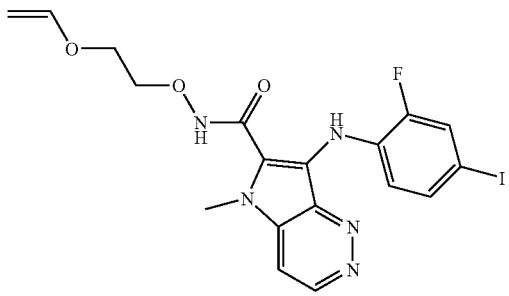

Sodium hydroxide (0.9 mL, 1M) was added to a suspension of 7-(2-fluoro-4-iodo-phenylamino)-5-methyl-5H-pyrrolo[3,2-c]pyridazine-6-carboxylic acid ethyl ester (242 mg, 0.55 mmol) in IMS (10 ml) and the reaction heated at 70° C. for 2 hours. The reaction mixture was concentrated in vacuo and the residue azeotroped with toluene (×3) to give a solid. The resultant crude solid was suspended in THF and HOBT (103 mg, 0.77 mmol), EDCI (136 mg, 0.69 mmol), DIPEA (0.144 ml, 0.83 mmol) and O-(2-vinyloxy-ethyl)-hydroxylamine (85 mg, 0.825 mmol) were then added and the reaction stirred at room temperature for 72 hours. The mixture was then concentrated in vacuo and the resultant residue dissolved in ethyl acetate (20 ml) and washed with water. The organic layer was separated, dried (Na$_2$SO$_4$), and filtered before concentrating in vacuo. The crude residue was purified by flash chromatography (Si-PPC, gradient 0-90% ethyl acetate in cyclohexane then 20% methanol in ethyl acetate) to yield the title compound as an orange solid (148 mg, 54%). LCMS (method B): R$_T$=2.64 min, M+H$^+$=498.

Step 2: 7-(2-Fluoro-4-iodo-phenylamino)-5-methyl-5H-pyrrolo[3,2-c]pyridazine-6-carboxylic acid (2-hydroxy-ethoxy)-amide To a solution of 7-(2-fluoro-4-iodo-phenylamino)-5-methyl-5H-pyrrolo[3,2-c]pyridazine-6-carboxylic acid (2-vinyloxy-ethoxy)-amide (148 mg, 0.3 mmol) in methanol (5 mL) was added concentrated hydrochloric acid (3 drops) and the reaction mixture stirred at room temperature for 10 minutes. The reaction mixture was concentrated in vacuo and the resultant residue dissolved in acetonitrile/water, neutralised with triethylamine and subjected to reverse-phase HPLC (Phenomenex Luna 5 phenyl/hexyl, 0.1% HCO$_2$H in water on a gradient of acetonitrile 90:10 to 15:85) to give the title compound as an orange solid (82 mg, 52%). LCMS (method A): R$_T$=5.89 min, M+H$^+$=471. $^1$H NMR (d$_6$-DMSO, 400 MHz) 3.58 (2H, s), 3.91 (2H, s), 3.95 (3H, s), 6.44 (1H, t, J=8.85 Hz), 7.18 (1H, d, J=8.56 Hz), 7.53 (1H, dd, J=11.02, 1.92 Hz), 7.94 (1H, s), 8.43 (1H, d, J=6.27 Hz), 9.31 (1H, d, J=6.52 Hz), 12.09 (1H, s).

Example 61

1-Cyclopropyl-3-(2-fluoro-4-iodo-phenylamino)-1H-pyrrolo[3,2-c]pyridine-2-carboxylic acid (2-hydroxy-ethoxy)-amide

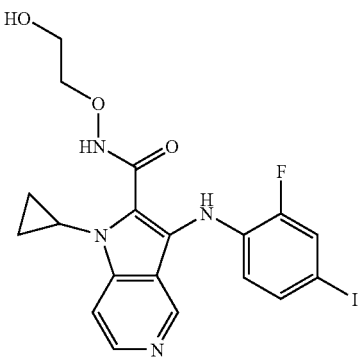

Step 1: 1-Cyclopropyl-3-(2-fluoro-4-iodo-phenylamino)-1H-pyrrolo[3,2-c]pyridine-2-carboxylic acid (2-vinyloxy-ethoxy)-amide

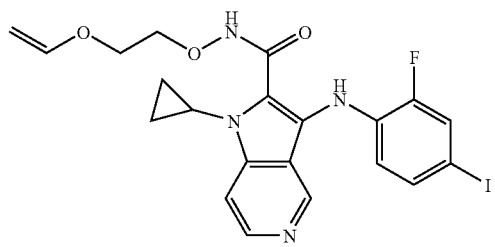

To a stirred solution of 1-cyclopropyl-3-(2-fluoro-4-iodo-phenylamino)-1H-pyrrolo[3,2-c]pyridine-2-carboxylic acid methyl ester (150.0 mg, 0.33 mmol) in anhydrous THF (3.5 mL) and anhydrous methanol (1.0 mL) under N$_2$ was added freshly prepared 1N aqueous sodium hydroxide (0.66 ml, 2.0 eq). The reaction mixture was stirred at 65° C. for 1 h. The resultant reaction mixture was evaporated in vacuo and azeotroped with toluene (3×5 ml) to give a yellow solid. The yellow solid was redissolved in anhydrous THF (6.6 ml). EDCI (127.0 mg, 0.66 mmol, 2.0 eq) and HOBT (89.7 mg, 0.66 mmol, 2.0 eq) were added. The reaction mixture was stirred at room temperature. After 5 minutes O-(2-vinyloxy-ethyl)-hydroxylamine (68.5 mg, 0.66 mmol, 2.0 eq) and DIPEA (0.12 mL, 0.66 mmol, 2.0 eq) were added, and the reaction mixture was stirred at ambient temperature under N$_2$ for 16 h. The reaction mixture was absorbed onto silica and purified by flash column chromatography (silica, ISCO, 45 mL/min, 0 to 20% EtOH in DCM) to give the desired product as a pale yellow solid (57.5 mg, 33.1%). $^1$H-NMR (400 MHz, CD$_3$OD) δ ppm 8.72 (s, 1H), 8.24 (d, J=6.0 Hz, 1H), 7.54-7.32 (m, 2H), 7.21 (ddd, J=8.5, 1.1 Hz, 1H), 6.61-6.39 (m, 1H), 3.86-3.70 (m, 2H), 3.62 (t, J=6.0 Hz, 2H), 3.35-3.24 (m, 1H), 3.34-3.32 (m, 1H), 3.14-3.00 (m, 2H), 1.42-1.27 (m, 2H), 0.94-0.78 (m, 2H); LC-MS (method D): [M+H]$^+$=523.2, R$_T$=2.21 min.

Step 2: 1-Cyclopropyl-3-(2-fluoro-4-iodo-phenylamino)-1H-pyrrolo[3,2-c]pyridine-2-carboxylic acid (2-hydroxy-ethoxy)-amide To a stirred solution of 1-cyclopropyl-3-(2-fluoro-4-iodo-phenylamino)-1H-pyrrolo[3,2-c]pyridine-2-carboxylic acid (2-vinyloxy-ethoxy)-amide (57.0 mg, 0.109 mmol) in anhydrous MeOH (5.5 mL) and anhydrous THF (2.7 mL) under $N_2$ was added 4 M HCl in dioxane (817 μL, 0.327 mmol, 3.0 eq), and the reaction mixture was stirred at room temperature. After 1 h the solvent was removed in vacuo and the residue was redissolved in acetonitrile (2.0 mL) and loaded onto Phenomenex Strata-X cartridge (5 g). The cartridge was washed with water (10 mL) and methanol (15 ml). The desired product was then eluted using 2M ammonia in MeOH. Trituration from DCM-hexane afforded the title compound as a tan solid (32.9 mg, 60.8%). $^1$H-NMR (400 MHz, DMSO-$d_6$) δ ppm 8.54 (s, 1H), 8.32 (d, J=5.9 Hz, 1H), 7.70-7.41 (m, 3H), 7.20 (dd, J=8.50 Hz, 1H), 6.26 (t, J=9.6 Hz, 1H), 4.78 (br s, 1H), 3.87 (dd, J=6.31 Hz, 2H), 3.70-3.39 (m, 3H), 1.27 (br s, 1H), 1.18-1.03 (m, 2H), 0.90-0.67 (m, 2H); LC-MS (method C): [M+H]$^+$=497.0, $R_T$=0.57 min.

Example 62

1-Cyclopropyl-3-(2-fluoro-4-methylsulfanyl-phenylamino)-1H-pyrrolo[3,2-c]pyridine-2-carboxylic acid (2-hydroxy-ethoxy)-amide

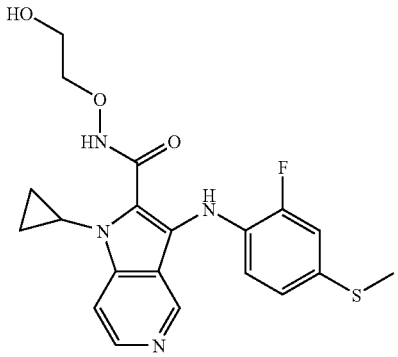

Step 1: 1-Cyclopropyl-3-(2-fluoro-4-methylsulfanyl-phenylamino)-1H-pyrrolo[3,2-c]pyridine-2-carboxylic acid (2-vinyloxy-ethoxy)-amide

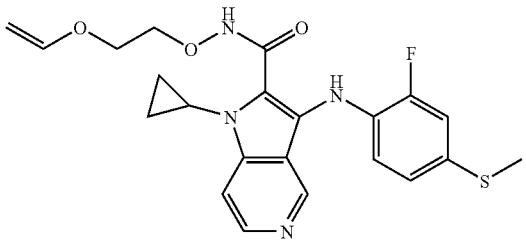

This compound was prepared in an analogous fashion to 1-cyclopropyl-3-(2-fluoro-4-iodo-phenylamino)-1H-pyrrolo[3,2-c]-pyridine-2-carboxylic acid (2-vinyloxy-ethoxy)-amide, using 1-cyclopropyl-3-(2-fluoro-4-methylsulfanyl-phenylamino)-1H-pyrrolo[3,2-c]pyridine-2-carboxylic acid methyl ester as the starting material. $^1$H-NMR (500 MHz, CDCl$_3$) δ ppm 9.50 (br s, 1H), 8.60 (d, J=0.88 Hz, 1H), 8.38 (d, J=5.97 Hz, 1H), 7.46 (dd, J=5.98 Hz, 1H), 7.10 (dd, J=11.45 Hz, 1H), 6.89 (dd, J=8.41 Hz, 1H), 6.66 (t, J=8.67 Hz, 1H), 6.42 (dd, J=14.33 Hz, 1H), 6.33 (br s, 1H), 4.29-4.22 (m, 2H), 4.18 (dd, J=14.33 Hz, 1H), 4.04 (dd, J=6.82 Hz, 1H), 3.98-3.90 (m, 2H), 3.61-3.53 (m, 1H), 2.44 (s, 3H), 1.33-1.20 (m, 2H), 1.01-0.96 (m, 2H); LC-MS (method D): [M+H]$^+$=443.3, $R_T$=2.17 min.

Step 2: 1-Cyclopropyl-3-(2-fluoro-4-methylsulfanyl-phenylamino)-1H-pyrrolo[3,2-c]pyridine-2-carboxylic acid (2-hydroxy-ethoxy)-amide This compound was prepared in an analogous fashion to 1-cyclopropyl-3-(2-fluoro-4-iodo-phenylamino)-1H-pyrrolo[3,2-c]pyridine-2-carboxylic acid (2-hydroxy-ethoxy)-amide, using 1-cyclopropyl-3-(2-fluoro-4-methylsulfanyl-phenylamino)-1H-pyrrolo[3,2-c]pyridine-2-carboxylic acid (2-vinyloxy-ethoxy)-amide as the starting material. $^1$H-NMR (400 MHz, DMSO-$d_6$) δ ppm 8.54 (s, 1H), 8.32 (d, J=5.9 Hz, 1H), 7.70-7.41 (m, 3H), 7.20 (dd, J=8.50 Hz, 1H), 6.26 (t, J=9.6 Hz, 1H), 4.78 (br s, 1H), 3.87 (dd, J=6.31 Hz, 2H), 3.70-3.39 (m, 3H), 1.27 (br s, 1H), 1.18-1.03 (m, 2H), 0.90-0.67 (m, 2H); LC-MS (method D): [M+H]$^+$=417.0, $R_T$=1.61 min.

Example 63

1-Cyclopropyl-3-(2-fluoro-4-iodo-phenylamino)-1H-pyrrolo[3,2-c]pyridine-2-carboxylic acid (2,3-dihydroxy-propoxy)-amide

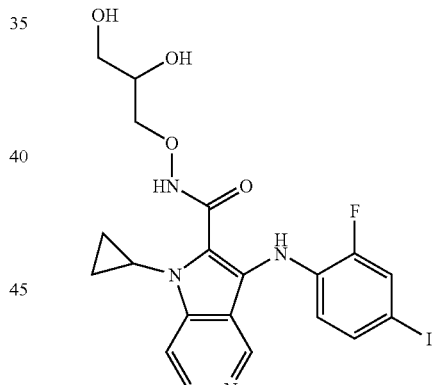

Step 1: 1-Cyclopropyl-3-(2-fluoro-4-iodo-phenylamino)-1H-pyrrolo[3,2-c]pyridine-2-carboxylic acid

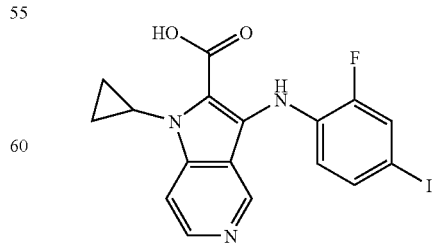

To a stirred solution of 1-cyclopropyl-3-(2-fluoro-4-iodo-phenylamino)-1H-pyrrolo[3,2-c]pyridine-2-carboxylic acid methyl ester (150.0 mg, 0.33 mmol) in anhydrous THF (3.5 mL) and anhydrous methanol (1.0 mL) under $N_2$ was added freshly prepared 1N aqueous sodium hydroxide (0.66 ml, 2.0 eq). The reaction mixture was stirred at 65° C. for 1 h. The resultant reaction mixture was evaporated in vacuo and azeotroped with toluene (3×5 ml) to give a yellow solid. The yellow solid was redissolved in water (5 mL), and concentrated. Acetic acid (2 drops) was added. A yellow solid precipitated out, and the solid was filtered, rinsed well with water, and dried on high-vacuum pump to give 243.6 mg (77.4%) of the product. $^1$H-NMR (500 MHz, DMSO-$d_6$) δ ppm 8.54 (s, 1H), 8.32 (d, J=6.0 Hz, 1H), 7.95 (br s, 1H), 7.65-7.52 (m, 2H), 7.33 (d, J=8.4 Hz, 1H), 6.67 (t, J=9.6 Hz, 1H), 3.53-3.28 (m, 1H), 1.20-1.07 (m, 2H), 0.85 (m, 2H); LC-MS (method C): [M+H]$^+$=438.0, $R_T$=0.67 min.

Step 2: 1-cyclopropyl-3-(2-fluoro-4-iodo-phenylamino)-1H-pyrrolo[3,2-c]pyridine-2-carboxylic acid (2,2-dimethyl-[1,3]dioxolan-4-ylmethoxy)-amide

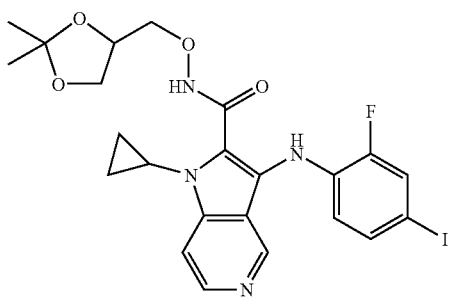

To a heterogeneous mixture of 1-cyclopropyl-3-(2-fluoro-4-iodo-phenylamino)-1H-pyrrolo[3,2-c]pyridine-2-carboxylic acid (160.0 mg, 0.37 mmol) and O-(2,2-dimethyl-[1,3]dioxolan-4-ylmethyl)-hydroxylamine (113.1 mg, 0.77 mmol, 2.1 eq) in anhydrous N,N-dimethylformamide (5.7 mL) was added N,N,N',N'-tetramethyl-O-(7-azabenzotriazol-1-yl)uronium hexafluorophosphate (278.3 mg, 0.74 mmol, 2.0 eq) and N,N-diisopropylethylamine (0.25 mL, 1.46 mmol, 4.0 eq), and the resulting homogeneous reaction mixture was stirred under $N_2$ at RT for 16 h. The reaction mixture was quenched with MeOH (2 mL), and the crude material was absorbed onto silica. The crude mixture was purified by flash column chromatography (silica, ISCO, 45 mL/min, 25 to 100% EtOAc in hexane) to afford the product as an orange waxy solid (75.4 mg; 36.4%). LC-MS (method C): [M+H]$^+$=567.2, $R_T$=0.73 min.

Step 3: 1-Cyclopropyl-3-(2-fluoro-4-iodo-phenylamino)-1H-pyrrolo[3,2-c]pyridine-2-carboxylic acid (2,3-dihydroxy-propoxy)-amide To 1-cyclopropyl-3-(2-fluoro-4-iodo-phenylamino)-1H-pyrrolo[3,2-c]-pyridine-2-carboxylic acid (2,2-dimethyl-[1,3]dioxolan-4-ylmethoxy)-amide (65.0 mg, 0.12 mmol) in anhydrous methanol (1.8 mL) was added 4 M Hydrogen chloride in 1,4-Dioxane (1.0 mL), and the reaction mixture was stirred at ambient temperature for 17 h. The solvent was removed in vacuo and the residue was redissolved in acetonitrile (2.0 mL) and loaded onto a Phenomenex Strata-X cartridge (5 g). The cartridge was washed with water (10 mL) and methanol (15 ml). The desired product was then eluted using 2M ammonia in MeOH. Methanol was removed in vacuo to give a brown oil, which was purified by HPLC to obtain 3.3 mg (5.5%) of the desired product as the TFA salt. $^1$H-NMR (500 MHz, MeOD.) δ ppm 8.96 (s, 1H), 8.45 (d, J=6.81 Hz, 1H), 8.18 (d, J=6.77 Hz, 1H), 7.48 (dd, J=10.76 Hz, 1H), 7.28 (d, J=8.50 Hz, 1H), 6.56 (t, J=9.6, 1H), 4.01-3.86 (m, 1H), 3.85-3.75 (m, 2H), 3.75-3.64 (m, 1H), 3.63-3.47 (m, 2H), 1.34-1.29 (m, 2H), 1.09-1.04 (m, 2H); LC-MS (method D): [M+H]$^+$=527.0, $R_T$=3.33 min.

Example 64

3-(2-Fluoro-4-iodo-phenylamino)-1-prop-2-ynyl-1H-pyrrolo[3,2-c]pyridine-2-carboxylic acid (2-hydroxy-ethoxy)-amide

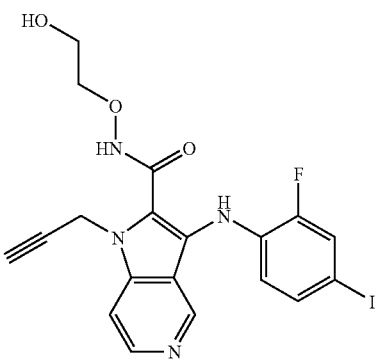

Step 1: 3-(2-Fluoro-4-iodo-phenylamino)-1-prop-2-ynyl-1-H-pyrrolo[3,2-c]pyridine-2-carboxylic acid (2-vinyloxy-ethoxy)-amide

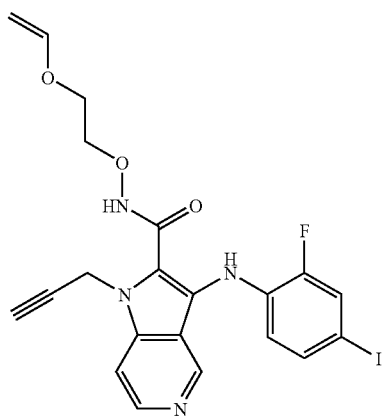

To a stirred solution of 3-(2-fluoro-4-iodo-phenylamino)-1-prop-2-ynyl-1H-pyrrolo[3,2-c]pyridine-2-carboxylic acid ethyl ester (55.0 mg, 0.12 mmol) in anhydrous THF (1.0 mL) and MeOH (0.5 mL) under $N_2$ was added freshly prepared 1N aqueous sodium hydroxide (0.24 ml, 2.0 eq). The reaction mixture was stirred at 65° C. for 1 h. The resultant reaction mixture was evaporated in vacuo and azeotroped with toluene (3×5 ml) to give a tan solid. The tan solid was redissolved in anhydrous THF (2.4 ml). EDCI (45.2 mg, 0.24 mmol, 2.0 eq) and HOBT (35.0 mg, 0.26 mmol, 2.2 eq) were added. The reaction mixture was stirred at room temperature. After 5 minutes O-(2-vinyloxy-ethyl)-hydroxylamine (14.6 mg, 0.14 mmol, 1.2 eq) and DIPEA (82.2 µL, 0.47 mmol, 4.0 eq) were added, and the reaction mixture was stirred at ambient temperature under $N_2$ for 24 h. The reaction mixture was absorbed onto silica and purified by flash column chromatography (silica, ISCO, 45 mL/min, EtOAc:MeOH, gradient 100:1 to 50:50) to give the desired product as a yellow solid (34.4 mg, 56.0%). $^1$H-NMR (400 MHz, DMSO-$d_6$) δ ppm 11.72 (s, 1H), 8.60 (s, 1H), 8.37 (d, J=6.4 Hz, 1H), 7.79-7.47 (m, 3H), 7.24 (d, J=10.0 Hz, 1H), 6.50 (dd, J=14.0 Hz, 8.0 Hz, 1H), 6.35-6.15 (m, 1H), 5.31 (s, 2H), 4.27-4.11 (m, 1H), 4.11-3.90 (m, 4H), 3.92-3.70 (m, 2H); LC-MS (method D): $[M+H]^+=521.0$, $R_T=2.18$ min.

Step 2: 3-(2-Fluoro-4-iodo-phenylamino)-1-prop-2-ynyl-1H-pyrrolo[3,2-c]pyridine-2-carboxylic acid (2-hydroxy-ethoxy)-amide To a stirred solution of 3-(2-fluoro-4-iodo-phenylamino)-1-prop-2-ynyl-1-H-pyrrolo[3,2-c]pyridine-2-carboxylic acid (2-vinyloxy-ethoxy)-amide (35.0 mg, 0.067 mmol) in anhydrous MeOH (6.7 mL) and anhydrous THF (3.4 mL) under $N_2$ was added 4 M HCl in dioxane (50 µL, 0.20 mmol, 3.0 eq), and the reaction mixture was stirred at room temperature. After 3 h the solvent was removed in vacuo and the residue was redissolved in acetonitrile (2.0 mL) and loaded onto Phenomenex Strata-X cartridge (5 g). The cartridge was washed with water (10 mL) and MeOH (15 ml). The desired product was then eluted using 2M ammonia in MeOH. Trituration from DCM-hexane afforded the title compound as a yellow solid (32.7 mg, 98.5%). $^1$H-NMR (400 MHz, DMSO-$d_6$) δ ppm 8.58 (d, J=0.82 Hz, 1H), 8.36 (d, J=5.93 Hz, 1H), 7.79-7.62 (m, 2H), 7.60-7.47 (m, 1H), 7.30-7.15 (m, 1H), 6.34-6.15 (m, 1H), 5.33 (s, 2H), 4.77 (broad s, 1H), 3.84 (t, J=4.54 Hz, 2H), 3.61-3.50 (m, 2H), 3.42-3.34 (m, 2H); LC-MS (method E): $[M+H]^+=495.1$, $R_T=3.54$ min.

Example 65

3-(2-Fluoro-4-iodo-phenylamino)-1-(4-hydroxy-but-2-ynyl)-1-H-pyrrolo[3,2-c]pyridine-2-carboxylic acid (2-hydroxy-ethoxy)-amide

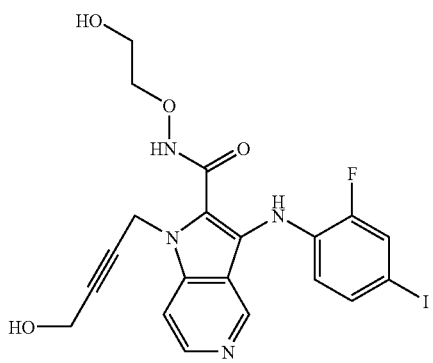

Step 1: 3-(2-Fluoro-4-iodo-phenylamino)-1-[4-(tetrahydro-pyran-2-yloxy)-but-2-ynyl]-1-H-pyrrolo[3,2-c]pyridine-2-carboxylic acid (2-vinyloxy-ethoxy)-amide

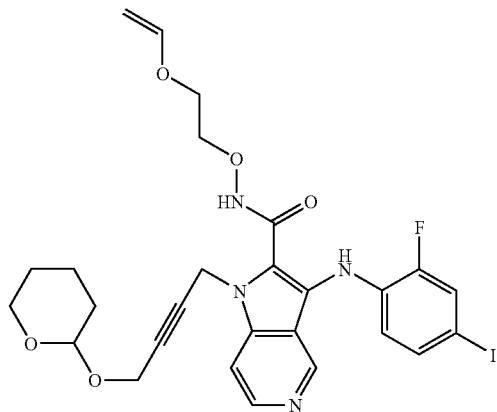

To a stirred solution of 3-(2-fluoro-4-iodo-phenylamino)-1-[4-(tetrahydro-pyran-2-yloxy)-but-2-ynyl]-1-H-pyrrolo[3,2-c]pyridine-2-carboxylic acid ethyl ester (147.0 mg, 0.25 mmol) in anhydrous THF (1.0 mL) and MeOD (3.0 mL) under $N_2$ was added freshly prepared 1N aqueous sodium hydroxide (0.51 ml, 2.0 eq). The reaction mixture was stirred at 65° C. for 1 h. The resultant reaction mixture was evaporated in vacuo and azeotroped with toluene (3×5 ml) to give a yellow foam. The yellow foam was redissolved in anhydrous THF (7.9 ml). EDCI (103.3 mg, 0.54 mmol, 2.2 eq) and HOBT (72.8 mg, 0.54 mmol, 2.2 eq) were added. The reaction mixture was stirred at room temperature. After 5 minutes O-(2-vinyloxy-ethyl)-hydroxylamine (50.5 mg, 0.49 mmol, 2.0 eq) and DIPEA (0.19 mL, 1.10 mmol, 4.5 eq) were added, and the reaction mixture was stirred at ambient temperature under $N_2$ for 17 h. The reaction mixture was absorbed onto silica and purified by flash column chromatography (silica, ISCO, 45 mL/min, Hexane:EtOAc, gradient 100:1 to 1:100) to give the desired product as a yellow solid (47.2 mg, 30.3%). $^1$H-NMR (400 MHz, $CDCl_3$) δ ppm 8.60 (s, 1H), 8.40 (d, J=5.95 Hz, 1H), 7.54-7.36 (m, 2H), 7.21 (d, J=8.48 Hz, 1H), 6.43-6.34 (m, 2H), 6.20 (broad s, 1H), 5.49 (s, 2H), 4.71 (m, 1H), 4.26-4.11 (m, 4H), 4.03 (dd, J=6.80, 2.4 Hz, 1H), 3.93-3.86 (m, 2H), 3.80-3.72 (m, 1H), 3.48 (m, 3H), 1.82-1.64 (m, 2H), 1.62-1.44 (m, 4H); LC-MS (method C): $[M+H]^+=635.1$, $R_T=0.839$ min.

Step 2: 3-(2-Fluoro-4-iodo-phenylamino)-1-(4-hydroxy-but-2-ynyl)-1-H-pyrrolo[3,2-c]pyridine-2-carboxylic acid (2-hydroxy-ethoxy)-amide To a stirred solution of 3-(2-fluoro-4-iodo-phenylamino)-1-[4-(tetrahydro-pyran-2-yloxy)-but-2-ynyl]-1-H-pyrrolo[3,2-c]pyridine-2-carboxylic acid (2-vinyloxy-ethoxy)-amide (47.0 mg, 0.075 mmol) in anhydrous MeOH (3.0 mL) under $N_2$ was added 4 M HCl in dioxane (0.10 mL, 0.40 mmol, 5.5 eq), and the reaction mixture was stirred at room temperature. After 3 h the solvent was removed in vacuo and the residue was redissolved in acetonitrile (2.0 mL) and loaded onto Phenomenex Strata-X cartridge (5 g). The cartridge was washed with water (10 mL) and methanol (15 ml). The desired product was then eluted using 2M ammonia in MeOH. Trituration from DCM-hexane afforded the title compound as a yellow solid (14.1 mg, 36.3%). ¹H-NMR (400 MHz, DMSO-d₆) δ ppm 11.66 (broad s, 1H), 8.58 (s, 1H), 8.36 (d, J=5.86 Hz, 1H), 7.70 (d, J=6.8 Hz, 1H), 7.63 (m, 1H), 7.55 (dd, J=11.03, 1.6 Hz, 1H), 7.26-7.17 (m, 1H), 6.23 (t, J=8.8 Hz, 1H), 5.35 (s, 2H), 5.18 (t, J=5.96 Hz, 1H), 4.80-4.74 (m, 1H), 4.02 (d, J=4.25 Hz, 2H), 3.85 (t, J=4.76 Hz, 2H), 3.60-3.48 (m, 2H); LC-MS (method D): [M+H]⁺=525.1, R$_T$=1.59 min.

Example 66

1-Cyclopropyl-3-(2-fluoro-4-iodo-phenylamino)-1-H-pyrrolo[3,2-c]pyridine-2-carboxylic acid ((R)-2,3-dihydroxy-propoxy)-amide

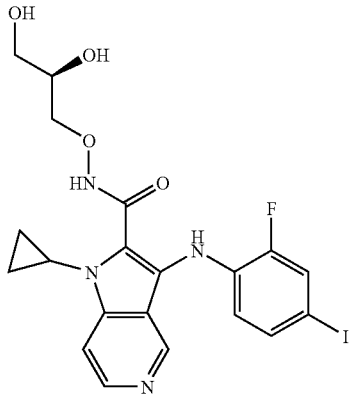

The title compound was prepared in an analogous fashion to 1-cyclopropyl-3-(2-fluoro-4-iodo-phenylamino)-1H-pyrrolo[3,2-c]pyridine-2-carboxylic acid (2,3-dihydroxy-propoxy)-amide, replacing O-(2,2-dimethyl-[1,3]dioxolan-4-ylmethyl)-hydroxylamine with O—((R)-2,2-dimethyl-[1,3]dioxolan-4-ylmethyl)-hydroxylamine. ¹H-NMR (500 MHz, DMSO-d₆) δ ppm 11.60 (s, 1H), 8.53 (s, 1H), 8.32 (d, J=5.86 Hz, 1H), 7.57 (d, J=5.69 Hz, 1H), 7.53-7.48 (m, 2H), 7.20 (d, J=8.06 Hz, 1H), 6.26 (t, J=8.81 Hz, 1H), 4.87 (d, J=4.05 Hz, 1H), 4.60 (t, J=5.43 Hz, 1H), 3.94 (dd, J=9.88, 2.80 Hz, 1H), 3.76 (t, J=8.0 Hz, 1H), 3.70 (broad s, 1H), 3.56-3.45 (m, 1H), 3.40-3.34 (m, 2H), 1.15-1.08 (m, 2H), 0.88-0.83 (m, 2H); LC-MS (method E): [M+H]⁺=527.1, R$_T$=7.31 min.

Example 67

1-Cyclopropyl-3-(2-fluoro-4-methylsulfanyl-phenylamino)-1-H-pyrrolo[3,2-c]pyridine-2-carboxylic acid ((R)-2,3-dihydroxy-propoxy)-amide

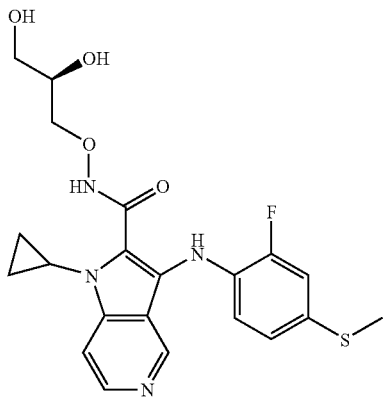

The title compound was prepared in an analogous fashion to 1-cyclopropyl-3-(2-fluoro-4-methylsulfanyl-phenylamino)-1H-pyrrolo[3,2-c]pyridine-2-carboxylic acid (2-hydroxy-ethoxy)-amide, replacing O-(2-vinyloxy-ethyl)-hydroxylamine with O—((R)-2,2-dimethyl-[1,3]dioxolan-4-ylmethyl)-hydroxylamine. ¹H-NMR (500 MHz, DMSO-d₆). δ ppm 11.58 (broad s, 1H), 8.51 (d, J=0.83 Hz, 1H), 8.31 (d, J=5.87 Hz, 1H), 7.56 (dd, J=5.88, 1.20 Hz, 1H), 7.36 (s, 1H), 7.18 (dd, J=12.13, 2.50 Hz, 1H), 6.87 (dd, J=8.46, 2.50 Hz, 1H), 6.45 (t, J=8.99 Hz, 1H), 4.94-4.78 (m, 1H), 4.62-4.53 (m, 1H), 3.94 (dd, J=9.91 Hz, 1H), 3.76 (dd, J=9.85, 7.0 Hz, 1H), 3.73-3.66 (m, 1H), 3.56-3.47 (m, 1H), 3.42-3.31 (m, 2H), 2.41 (s, 3H), 1.15-1.08 (m, 2H), 0.87-0.83 (m, 2H); LC-MS (method C): [M+H]⁺=447.2, R$_T$=0.479 min.

Example 68

[3-(2-Fluoro-4-iodo-phenylamino)-1H-pyrrolo[3,2-c]pyridin-2-yl]-((R)-3-hydroxy-pyrrolidin-1-yl)-methanone

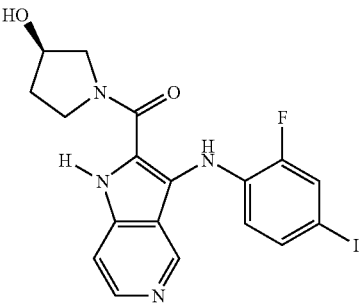

A mixture of 3-(2-fluoro-4-iodo-phenylamino)-1H-pyrrolo[3,2-c]pyridine-2-carboxylic acid ethyl ester (100 mg, 0.23 mmol), 1N aqueous sodium hydroxide (0.50 mL, 2.2 eq), THF (1.50 mL) and MeOH (0.5 mL) was heated at 75° C. for 1.0 hour. The reaction mixture was concentrated and azeotroped with toluene (3×2 ml) to give the sodium salt intermediate as foam. The crude residue was dissolved in anhydrous THF (4.7 ml). (R)-Pyrrolidin-3-ol hydrochloride (58.1 mg, 0.4 mmol), EDCI (94.6 mg, 0.48 mmol, 2.1 eq), HOBt (66.7 mg, 0.48 mmol, 2.1 eq) and DIPEA (164 μL, 0.94 mmol, 4.0 eq) were then added. After stirring for 16 hours at ambient temperature, the reaction mixture was absorbed onto silica. The title compound was purified by flash chromatography (silica, ISCO, 45 mL/min, EtOAc:MeOH, gradient 100:0 to 60:40). Crystallization from dichloromethane:hexane afforded the title compound as a yellow solid (93.1 mg, 85%). ¹H NMR (400 MHz, MeOD.) δ ppm 8.62 (s, 1H), 8.23 (d, J=5.99 Hz, 1H), 7.46 (m, 2H), 7.23 (ddd, J=8.54, 2.0, 1.11 Hz, 1H), 6.55 (t, J=8.84 Hz, 1H), 4.54-4.28 (m, 1H), 3.73 (broad s, 2H), 3.58-3.37 (m, 2H), 1.93 (m, 2H); LC-MS (method E): [M+H]⁺=467.1, R$_T$=3.60 min.

Example 69

[3-(2-Fluoro-4-iodo-phenylamino)-1H-pyrrolo[3,2-c]pyridin-2-yl]-((2S,4R)-4-hydroxy-2-hydroxymethyl-pyrrolidin-1-yl)-methanone

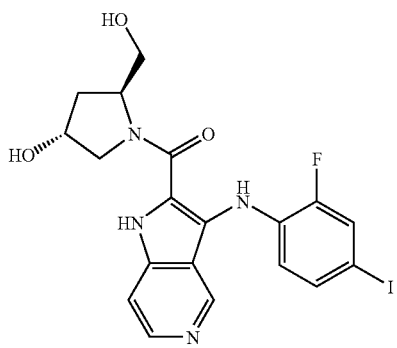

The title compound was prepared in an analogous fashion to [3-(2-fluoro-4-iodo-phenylamino)-1H-pyrrolo[3,2-c]pyridin-2-yl]-((R)-3-hydroxy-pyrrolidin-1-yl)-methanone, replacing (R)-pyrrolidin-3-ol hydrochloride with (3R,5S)-5-hydroxymethyl-pyrrolidin-3-ol hydrochloride. $^1$H-NMR (400 MHz, MeOD) δ ppm 8.62 (d, J=1.02 Hz, 1H), 8.23 (d, J=5.99 Hz, 1H), 7.52-7.35 (m, 2H), 7.34-7.16 (m, 1H), 6.60 (t, J=8.8 Hz, 1H), 4.59-4.42 (m, 1H), 4.35-4.17 (m, 1H), 3.71-3.44 (m, 4H), 2.19-1.90 (m, 2H); LC-MS (method E): [M+H]$^+$=497.1, R$_T$=3.37 min.

Example 70

[3-(2-Fluoro-4-iodo-phenylamino)-1H-pyrrolo[3,2-c]pyridin-2-yl]-(3-hydroxy-azetidin-1-yl)-methanone

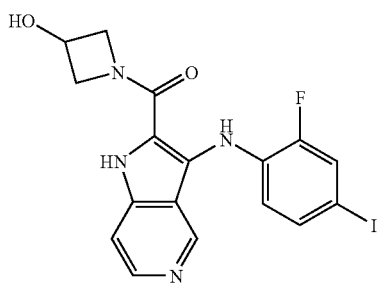

The title compound was prepared in an analogous fashion to [3-(2-fluoro-4-iodo-phenylamino)-1H-pyrrolo[3,2-c]pyridin-2-yl]-((R)-3-hydroxy-pyrrolidin-1-yl)-methanone, replacing (R)-pyrrolidin-3-ol hydrochloride with azetidin-3-ol hydrochloride. $^1$H-NMR (400 MHz, MeOD) δ ppm 8.84 (s, 1H), 8.34 (d, J=6.55 Hz, 1H), 7.77 (d, J=6.58 Hz, 1H), 7.50 (dd, J=10.88 Hz, 1H), 7.29 (d, J=8.54 Hz, 1H), 6.62 (t, J=8.83 Hz, 1H), 4.60-4.52 (m, 1H), 4.50-4.31 (m, 2H), 4.19-3.82 (m, 2H); LC-MS (method E): [M+H]$^+$=453.1, R$_T$=3.55 min.

Example 71

3-(2-Chloro-4-isopropyl-phenylamino)-1-methyl-1H-pyrrolo[3,2-c]pyridine-2-carboxylic acid (2-hydroxy-ethoxy)-amide

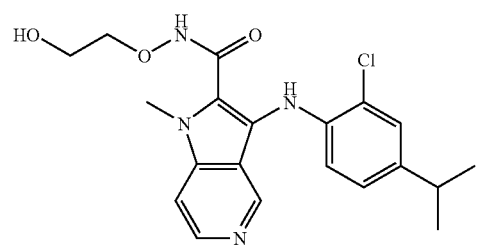

Step 1: Trifluoro-methanesulfonic acid 2-chloro-4-isopropyl-phenyl ester

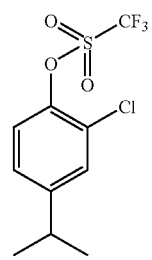

Trifluoromethanesulfonic anhydride (2.14 g, 7.6 mmol) was dissolved in DCM (5 ml) and cooled to 5° C. To this was added 2-chloro-4-isopropyl-phenol (1.23 g, 7.2 mmol), in 10 ml DCM and 1.75 ml pyridine, dropwise. The reaction mixture was stirred at 110° C. for 2 hours. The resultant dark solution was washed with 1M HCl (20 ml), water (20 ml) and saturated aqueous NaHCO$_3$ (20 ml). The DCM extract was dried and concentrated in vacuo to provide the title compound as a dark orange oil (1.71 g, 78%). $^1$H NMR (CDCl$_3$) 1.22-1.29 (6H, d, J=6.87 Hz), 2.88-3.00 (1H, sept, J=6.89 Hz), 7.15-7.20 (1H, m), 7.24 (1H, d, J=8.36 Hz), 7.36 (1H, d, J=2.17 Hz).

Step 2: 3-(2-Chloro-4-isopropyl-phenylamino)-1-methyl-1H-pyrrolo[3,2-c]pyridine-2-carboxylic acid ethyl ester

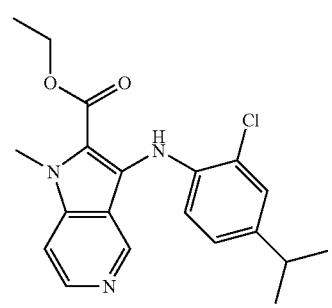

A degassed solution of 3-amino-1-methyl-1H-pyrrolo[3,2-c]pyridine-2-carboxylic acid ethyl ester (300 mg, 1.4 mmol), trifluoro-methanesulfonic acid 2-chloro-4-isopropyl-phenyl ester (700 mg, 2.3 mmol), Pd$_2$dba$_3$ (63 mg, 0.068 mmol), Xantphos (79 mg, 0.14 mmol) and K$_3$PO$_4$ (0.58 g, 2.7 mmol) in toluene (10 ml) was heated at 120° C. for 18 hours. The reaction mixture was cooled to ambient temperature then filtered through a pad of Celite®. The filtrate was concentrated in vacuo to give a brown gum. The gum was purified by flash chromatography (Si-SPE, DCM:EtOAc, 90:10) to provide the title compound as a yellow gum (120 mg, 24%). LCMS (method B): R$_T$=2.82 min, M+H$^+$=372.

Step 3: 3-(2-Chloro-4-isopropyl-phenylamino)-1-methyl-1H-pyrrolo[3,2-c]pyridine-2-carboxylic acid

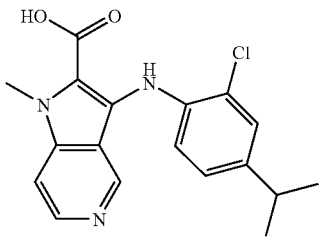

A solution of 3-(2-chloro-4-isopropyl-phenylamino)-1-methyl-1H-pyrrolo[3,2-c]pyridine-2-carboxylic acid ethyl ester (230 mg, 0.62 mmol) and 1M NaOH (0.74 ml, 7.4 mmol) in IMS (5 ml) was heated at 60° C. for 3 hours. The reaction mixture was cooled to ambient temperature then acidified to pH 5 using 1M HCl. The fine yellow suspension was filtered to provide the title compound as a yellow solid (220 mg, 100%). LCMS (method B): R$_T$=2.53 min, M+H$^+$=344.

Step 4: 3-(2-Chloro-4-isopropyl-phenylamino)-1-methyl-1H-pyrrolo[3,2-c]pyridine-2-carboxylic acid (2-hydroxy-ethoxy)-amide A suspension of 3-(2-chloro-4-isopropyl-phenylamino)-1-methyl-1H-pyrrolo[3,2-c]pyridine-2-carboxylic acid (0.22 g, 0.65 mmol), O-(2-vinyloxy-ethyl)-hydroxylamine (0.10 g, 0.98 mmol), HATU (0.37 g, 0.98 mmol) and DIPEA (0.33 ml, 1.9 mmol) in THF (2 ml) was stirred at ambient temperature for 18 hours. The mixture was concentrated in vacuo and the resultant residue was purified by flash chromatography (Si-PPE, DCM:MeOH, gradient 99:1 to 90:10) to give an orange gum (337 mg). This material was dissolved in IMS (5 ml) and 1M aqueous hydrochloric acid (5 ml) was added. The mixture was stirred for 1 hour, then the crude product was isolated using an SCX-2 cartridge (gradient 0:100 then 100:02M NH$_3$ in MeOH:MeOH), the appropriate fractions combined and concentrated in vacuo. Purification of the resultant residue by flash chromatography (Si-PPC, dichloromethane:methanol gradient 100:0 to 92:8) gave the title compound as a glassy yellow oil (21 mg, 8% over two steps). LCMS (method A): R$_T$ 6.14, M+H$^+$ 403. $^1$H NMR (CDCl$_3$) 8.58 (1H, s), 8.41-8.36 (1H, m), 7.30 (1H, d, J=6.08 Hz), 7.26 (1H, d, J=1.99 Hz), 6.87 (1H, dd, J=8.33, 2.02 Hz), 6.47 (1H, dd, J=8.34, 3.82 Hz), 5.85 (1H, s), 4.11 (3H, s), 3.97-3.90 (2H, m), 3.71 (2H, dd, J=5.23, 3.41 Hz), 2.78 (1H, m), 1.22-1.13 (6H, m).

Example 72

3-(4-Cyclopropyl-2-fluoro-phenylamino) 1-methyl-1H-pyrrolo[3,2-c]pyridine-2-carboxylic acid (2-vinyloxy-ethoxy)-amide

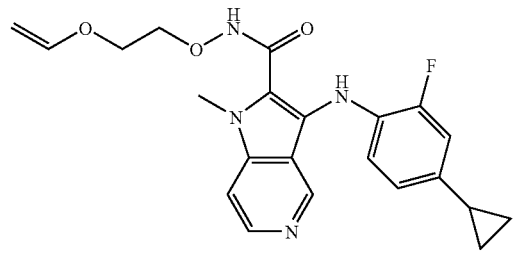

Step 1: 4-Cyclopropyl-2-fluoro-1-iodo-benzene

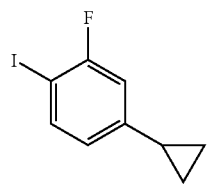

4-Cyclopropyl-2-fluoro-phenylamine (400 mg, 2.65 mmol) was dissolved in water (5 ml) and cooled to 0° C. Concentrated sulfuric acid (1.6 ml) was added dropwise slowly, followed by a solution of sodium nitrite (0.18 ml, 2.65 mmol) in water (1 ml). The resulting mixture was added to a solution of potassium iodide (0.43 g, 5.30 mmol) in water (1 ml). The mixture was heated at 60° C. for 2 hours, then allowed to cool and extracted with dichloromethane (×2). The combined organic extracts were dried (Na$_2$SO$_4$) and concentrated in vacuo. Purification of the resultant residue by flash chromatography (Si-PPC, pentane) afforded the title compound as a pale yellow oil (490 mg, 71%). $^1$H NMR (CDCl$_3$) 0.60-0.77 (2H, m), 0.94-1.06 (2H, m), 1.81-1.90 (1H, m), 6.64 (1H, dd, J=8.17, 2.01 Hz), 6.74-6.96 (1H, m), 7.53-7.64 (1H, m).

Step 2: 3-(4-Cyclopropyl-2-fluoro-phenylamino)-1-methyl-1H-pyrrolo[3,2-c]pyridine-2-carboxylic acid ethyl ester

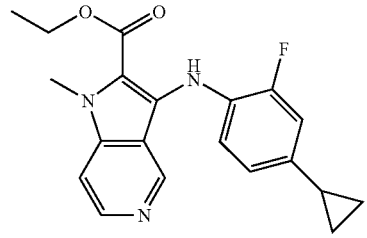

A degassed solution of 3-amino-1-methyl-1H-pyrrolo[3,2-c]pyridine-2-carboxylic acid ethyl ester (521 mg, 2.4 mmol), 4-cyclopropyl-2-fluoro-1-iodo-benzene (810 mg, 3.09 mmol), Pd$_2$dba$_3$ (154 mg, 0.168 mmol), Xantphos (194 mg, 0.336 mmol) and cesium carbonate (1.95 g, 6.0 mmol) in toluene (5 ml) was heated at 110° C. for 18 hours. The reaction mixture was cooled to ambient temperature then filtered through a pad of Celite®. The filtrate was washed with water and brine, dried over magnesium sulphate and concentrated in vacuo to give a brown gum. The gum was purified by flash chromatography (Si-PPC, DCM:MeOH, 90:10) to provide the title compound as an orange oil (197 mg, 23%). LCMS (method B): $R_T$=2.65 min, M+H$^+$=354.

Step 3: 3-(4-Cyclopropyl-2-fluoro-phenylamino)-1-methyl-1H-pyrrolo[3,2-c]pyridine-2-carboxylic acid

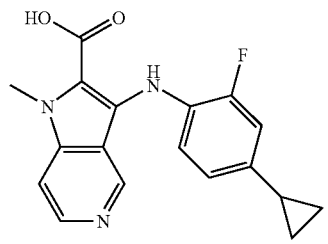

A solution of 3-(4-cyclopropyl-2-fluoro-phenylamino)-1-methyl-1H-pyrrolo[3,2-c]pyridine-2-carboxylic acid ethyl ester (197 mg, 0.50 mmol) and 1M NaOH (1.02 ml, 1.02 mmol) in IMS (3 ml) was heated at 60° C. for 2 hours. The reaction mixture was cooled to ambient temperature then acidified to pH 4 using acetic acid. The brown solid was filtered off, the residue dried to provide the title compound (161 mg, 97%). LCMS (method B): $R_T$=2.18 min, M+H$^+$=326.

Step 4: 3-(4-Cyclopropyl-2-fluoro-phenylamino)1-methyl-1H-pyrrolo[3,2-c]pyridine-2-carboxylic acid (2-vinyloxy-ethoxy)-amide A suspension of 3-(4-cyclopropyl-2-fluoro-phenylamino)-1-methyl-1H-pyrrolo[3,2-c]pyridine-2-carboxylic acid (88 mg, 0.25 mmol), O-(2-vinyloxy-ethyl)-hydroxylamine (028 mg, 0.28 mmol), HATU (114 mg, 0.30 mmol) and DIPEA (0.052 ml, 0.30 mmol) in THF (3 ml) was stirred at ambient temperature for 18 hours. On completion of the reaction, the mixture was concentrated in vacuo then re-dissolved in DCM. The solution was washed with saturated aqueous NaHCO$_3$ and brine, dried over magnesium sulphate then concentrated in vacuo. The resultant residue was purified by flash chromatography (Si-PPC, DCM:MeOH, gradient 99:1 to 90:10) to give a yellow solid (34 mg, 33%). LCMS (method B): $R_T$=2.46 min, M+H$^+$=411. $^1$H NMR (CDCl$_3$): 8.58 (1H, s), 8.41-8.36 (1H, m), 7.30 (1H, d, J=6.08 Hz), 7.26 (1H, d, J=1.99 Hz), 6.87 (1H, dd, J=8.33, 2.02 Hz), 6.47 (1H, dd, J=8.34, 3.82 Hz), 5.85 (1H, s), 4.11 (3H, s), 3.97-3.90 (2H, m), 3.71 (2H, dd, J=5.23, 3.41 Hz), 2.78 (1H, m), 1.22-1.13 (6H, m).

Compounds Prepared by General Methods

Amides and hydroxamates were prepared from the appropriate acid by using the coupling general method described below. In some cases the intermediate acid was not isolated, the coupling reaction performed on the crude carboxylate salt produced by following the saponification general method.

Saponification General Method

A mixture of carboxylic acid ester, 1N aqueous NaOH (1-2 eq.) and EtOH was heated at 70° C. for 1-4 hours. The reaction mixture was concentrated in vacuo and azeotroped with toluene to give the crude carboxylate salt.

Coupling General Methods

Method A: The appropriate carboxylic acid or carboxylate salt was suspended in anhydrous THF before the appropriate hydroxylamine or amine (1-4 eq.), EDCI (1-1.5 eq.), HOBt (1-1.5 eq.) and DIPEA (2-4 eq.) were added. After stirring at ambient temperature until the reaction was complete (LCMS/TLC), the reaction mixture was concentrated in vacuo. The resultant residue was dissolved in ethyl acetate and washed with water before the organic layer was isolated, dried over sodium sulfate, then concentrated in vacuo. The resultant residue was subjected to purification.

Method B: The appropriate carboxylic acid or carboxylate salt was dissolved in DMF before the appropriate amine or hydroxylamine (2-4 eq.), DIPEA (2-4 eq.) and HATU (1-2 eq.) were added. On completion of the reaction, the solution was diluted with water and the resultant solid precipitate filtered off or extracted with ethyl acetate. The ethyl acetate extract was washed with water, dried (Na$_2$SO$_4$), and concentrated in vacuo. The resultant residue was subjected to purification.

Deprotection General Methods

Method A: Aqueous HCl was added to a mixture of the protected substrate in an appropriate solvent at ambient temperature. The mixture was stirred until analysis (TLC/LCMS) showed complete consumption of starting material. The reaction mixture was neutralized, concentrated in vacuo and subjected to purification.

Method B: A solution of the substrate in methanol was loaded onto an Isolute® SCX-2 cartridge. The cartridge was then washed with methanol before the desired product was eluted using 2M ammonia in MeOH and the eluent collected then concentrated to give a residue. The residue was subjected to purification.

Method C: TBAF in THF was added to a solution of the silyl ether, the mixture stirred at ambient temperature until analysis (TLC/LCMS) showed complete consumption of starting material. The reaction mixture was concentrated in vacuo and subjected to purification.

Method D: TFA was added to the substrate either neat or as a solution in DCM. The reaction mixture was stirred at ambient temperature until analysis (TLC/LCMS) showed complete consumption of starting material. The reaction mixture was concentrated in vacuo, and subjected to purification.

Method E: An aliquot (3 mol equivalents) of freshly prepared HCl in methanol solution [concentrated HCl (0.14 ml) in methanol (25 ml)] was added to the coupled substrate at ambient temperature. The mixture was stirred until analysis (TLC/LCMS) showed complete consumption of starting material. The contents were evaporated to dryness and the residue was dissolved in dichloromethane and treated with triethylamine (3 mol equivalents) at room temperature for 10 min. The mixture was then concentrated in vacuo and the residue subjected to purification.

Purification General Methods

Method A: Si-PPC, ethyl acetate/cyclohexane gradient

Method B: Si-PPC, ethyl acetate/DCM gradient

Method C: Si-PPC, methanol/DCM gradient

Method D: Si-PPC, ether/pentane gradient then methanol/ether gradient

Method E: reversed phase HPLC Phenomenex Luna 5 phenyl/hexyl, 0.1% TFA in water on a gradient of methanol Method F: reversed phase HPLC Phenomenex Luna 5 phenyl/hexyl, 0.1% TFA in water on a gradient of acetonitrile Method G: reversed phase HPLC Phenomenex Luna 5 phenyl/hexyl, 0.1% HCO₂H in water on a gradient of methanol Method H: reversed phase HPLC Phenomenex Luna 5 phenyl/hexyl, 0.1% HCO₂H in water on a gradient of acetonitrile Method I: A solution of the substrate in methanol was loaded onto an Isolute® SCX-2 cartridge. The cartridge was then washed with methanol before the desired product was eluted using 2M ammonia in MeOH.

Method J: NH₂-PPC, methanol/ether or methanol/DCM gradient

Analogs Prepared by Coupling Method A

Footnotes to tabulated data, deviations from general methods:

*LCMS method A; ¹triturated in methanol/ethyl acetate; ²recrystallised from methanol/water then triturated in ethyl acetate; ³triturated in ethyl acetate; ⁴triturated in 5% methanol in DCM; ⁵triturated in methanol, recrystallised from chloroform/methanol; ⁶triturated in methanol; ⁷reaction temperature 45° C.; ⁸C18 reverse phase column used; ⁹triturated in acetonitrile; ¹⁰deprotection reaction run at 50° C.; ¹¹triturated in ethyl acetate/DCM; ¹²reaction run in THF

TABLE 1

| | | | | | | |
|---|---|---|---|---|---|---|
| | | Analogs prepared by coupling method A | | | | |
| EXAMPLE # | Structure/Name | Intermediate purification method(s) | Deprotection method | Purification method(s) | LCMS* R$_T$/M+ | $^1$H NMR (ppm) |
| 7 | 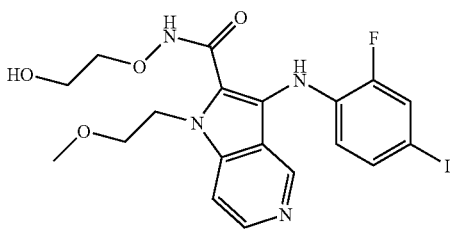<br>3-(2-Fluoro-4-iodo-phenylamino)-1-(2-methoxy-ethyl)-1H-pyrrolo[3,2-c]pyridine-2-carboxylic acid (2-hydroxy-ethoxy)-amide | C | B | C | 5.78, 515 | (DMSO-D$_6$) 1.73 (2 H, m), 1.87 (2 H, m), 2.93 (2 H, m), 3.19 (2 H, m), 3.86 (3 H, s), 4.01 (1 H, m), 6.22 (1 H, t, J = 8.9 Hz), 7.20 (1 H, m), 7.52 (1 H, dd, J = 11.1, 1.9 Hz), 7.61 (1 H, dd, J = 5.9, 1.0 Hz), 7.63 (1 H, s), 8.33 (1 H, d, J = 5.9 Hz), 8.61 (1 H, d, J = 1 Hz), 9.2 (2 H, s, br) |
| 8 | 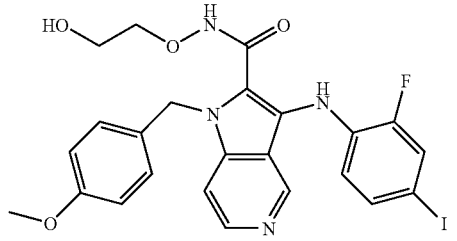<br>3-(2-Fluoro-4-iodo-phenylamino)-1-(4-methoxy-benzyl)-1H-pyrrolo[3,2-c]pyridine-2-carboxylic acid (2-hydroxy-ethoxy)-amide | A | A, IMS | I, C | 6.08, 577 | (CD$_3$OD) 3.56 (2 H, m), 3.73 (3 H, s), 3.78 (2 H, m), 5.61 (2 H, s), 6.38 (1 H, t, J = 8.8 Hz), 6.82 (2 H, m), 7.08 (2 H, m), 7.22 (1 H, m), 7.43 (1 H, dd, J = 10.9, 1.9 Hz), 7.65 (1 H, dd, J = 6.1, 1.0 Hz), 8.28 (1 H, d, J = 6.1 Hz), 8.63 (1 H, d, J = 1.0 Hz) |
| 9 | 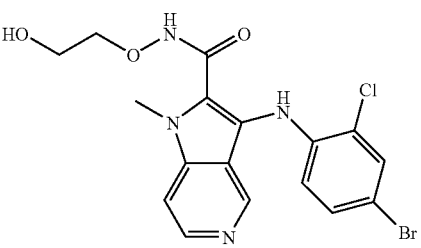<br>3-(4-Bromo-2-chloro-phenylamino)-1-methyl-1H-pyrrolo[3,2-c]pyridine-2-carboxylic acid (2-hydroxy-ethoxy)-amide | 1 | A, IMS 40° C. | 2 | 5.36, 439/441 | (CD$_3$OD) 3.66 (2 H, m), 3.92 (2 H, m), 3.98 (3 H, s), 6.42 (1 H, d, J = 8.8 Hz), 7.15 (1 H, dd, J = 8.8, 2.3 Hz), 7.53 (1 H, d, J = 2.3 Hz), 7.60 (1 H, dd, J = 6.2, 1.0 Hz), 8.31 (1 H, d, J = 6.2 Hz), 8.58 (1 H, s) |

TABLE 1-continued

Analogs prepared by coupling method A

| EXAMPLE # | Structure/Name | Intermediate purification method(s) | Deprotection method | Purification method(s) | LCMS* $R_T$/M+ | $^1$H NMR (ppm) |
|---|---|---|---|---|---|---|
| 10 | 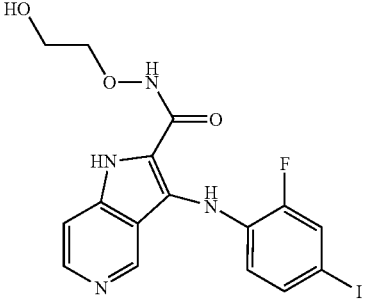<br>3-(2-Fluoro-4-iodo-phenylamino)-1H-pyrrolo(3,2-c]pyridine-2-carboxylic acid (2-hydroxy-ethoxy)-amide | C | B | 4 | 5.49, 457 | (CD$_3$OD) 3.71 (2 H, t, J = 4.5 Hz), 3.99 (2 H, t, J = 4.5 Hz), 6.45 (1 H, t, J = 8.9 Hz), 7.26 (1 H, m), 7.47 (1 H, d, J = 5.9 Hz), 7.48 (1 H, dd, J = 10.8, 1.9 Hz), 8.24 (1 H, d, J = 5.9 Hz), 8.56 (1 H, s) |
| 11 | 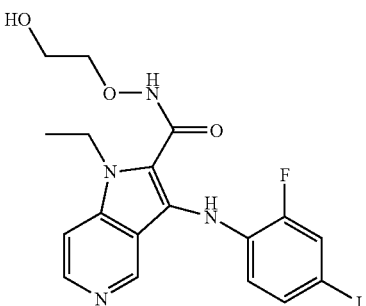<br>1-Ethyl-3-(2-fluoro-4-iodo-phenylamino)-1H-pyrrolo[3,2-c]pyridine-2-carboxylic acid (2-hydroxy-ethoxy)-amide | C$^5$ | B | — | 5.76, 485 | (CD$_3$OD) 1.41 (3 H, t, J = 7.1 Hz), 3.66 (2 H, m), 3.90 (2 H, m), 4.54 (2 H, q, J = 7.1 Hz), 6.36 (1 H, t, J = 8.7 Hz), 7.21 (1 H, ddd, J = 8.7, 1.9, 1.0 Hz), 7.44 (1 H, dd, J = 10.8, 1.9 Hz), 7.60 (1 H, dd, J = 6.1, 1.0 Hz), 8.29 (1 H, d, J = 6.1 Hz), 8.61 (1 H, d, J = 1.0 Hz) |
| 12 | 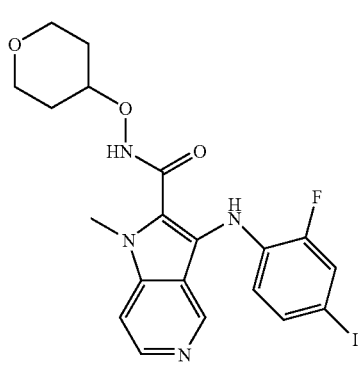<br>3-(2-Fluoro-4-iodo-phenylamino)-1-methyl-1H-pyrrolo[3,2-c]pyridine-2-carboxylic acid (tetrahydro-pyran-4-yloxy)-amide | — | — | I, D | 5.84, 511 | (DMSO-D$_6$) 1.44 (2 H, m), 1.73 (2 H, m), 3.25 (2 H, m), 3.78 (2 H, dt, J = 11.8, 4.2 Hz), 3.86 (3 H, s), δ 3.87 (1 H, m), 6.21 (1 H, t, J = 9.0 Hz), 7.19 (1 H, m), 7.52 (1 H, dd, J = 11.1, 1.9 Hz), 7.56 (1 H, s, br), 7.59 (1 H, dd, J = 5.9, 1.0 Hz), 8.32 (1 H, d, J = 5.9 Hz), 8.63 (1 H, d, J = 1.0 Hz), 11.39 (1 H, s, br) |

TABLE 1-continued

Analogs prepared by coupling method A

| EX-AMPLE # | Structure/Name | Intermediate purification method(s) | Deprotection method | Purification method (s) | LCMS* $R_T$/M+ | $^1$H NMR (ppm) |
|---|---|---|---|---|---|---|
| 13 | 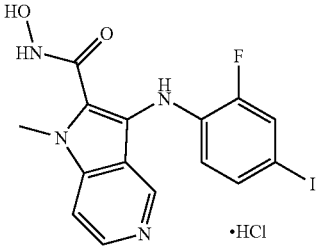<br>3-(2-Fluoro-4-iodo-phenylamino)-1-methyl-1H-pyrrolo[3,2-c]pyridine-2-carboxylic acid hydroxyamide mono hydrochloride salt | D | A, IMS | 6 | 5.31, 427 | (DMSO-D$_6$) 3.99 (3 H, s), 6.32 (1 H, t, J = 8.7 Hz), 7.20 (1 H, d, J = 8.7 Hz), 7.56 (1 H, dd, J = 11.0, 1.9 Hz), 7.82 (1 H, s), 8.21 (1 H, dd, J = 6.8, 1.4 Hz), 8.54 (1 H, d, J = 6.8 Hz), 9.03 (1 H, s), 9.61 (1 H, s), 11.41 (1 H, s), 15.00 (1 H, s, br) |
| 14 | 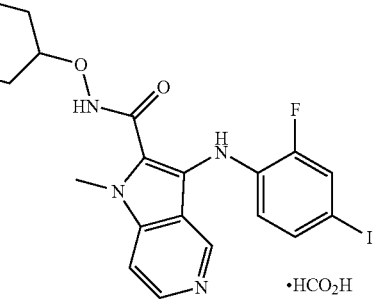<br>3-(2-Fluoro-4-iodo-phenylamino)-1-methyl-1H-pyrrolo[3,2-c]pyridine-2-carboxylic acid (piperidin-4-yloxy)-amide mono formate salt | D | A, MeOH | H | 3.96, 510 | (DMSO-D$_6$) 1.73 (2 H, m), 1.87 (2 H, m), 2.93 (2 H, m), 3.19 (2 H, m), 3.86 (3 H, s), 4.01 (1 H, m), 6.22 (1 H, t, J = 8.9 Hz), 7.20 (1H, m), 7.52 (1 H, dd, J = 11.1, 1.9 Hz), 7.61 (1 H, dd, J = 5.9, 1.0 Hz), 7.63 (1 H, s), 8.33 (1 H, d, J = 5.9 Hz), 8.61 (1 H, d, J = 1 Hz), 9.2 (2 H, s, br) |
| 15 | 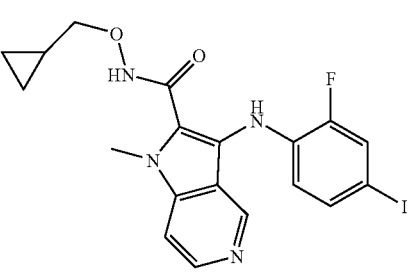<br>3-(2-Fluoro-4-iodo-phenylamino)-1-methyl-1H-pyrrolo[3,2-c]pyridine-2-carboxylic acid cyclopropylmethoxy-amide | — | — | C | 5.80, 411 | (DMSO-D$_6$) 0.19 (2 H, m), 0.48 (2 H, m), 1.00 (1 H, m), 3.55 (2 H, d, J = 7.2 Hz), 3.91 (3 H, s), 6.31 (1 H, t, J = 8.9 Hz), 7.21 (1 H, m), 7.54 (1 H, dd, J = 11.1, 1.9 Hz), 7.74 (1 H, s), 7.88 (1 H, d, J = 6.3 Hz), 8.42 (1 H, d, J = 6.3 Hz), 8.83 (1 H, s), 11.66 (1 H, s) |
| 21 | 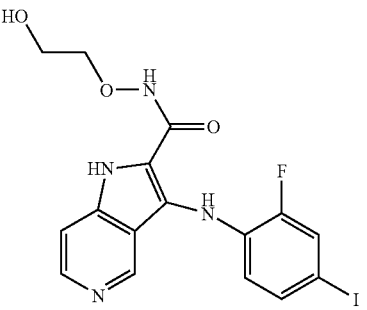<br>3-(2-Fluoro-4-iodo-phenylamino)-1H-pyrrolo[3,2-c]pyridine-2-carboxylic acid (2-hydroxy-ethoxy)-amide | C | B | 4 | 5.49, 457 | (CD$_3$OD) 3.71 (2 H, t, J = 4.5 Hz), 3.99 (2 H, t, J = 4.5 Hz), 6.45 (1 H, t, J = 8.9 Hz), 7.26 (1 H, m), 7.47 (1 H, d, J = 5.9 Hz), 7.48 (1 H, dd, J = 10.8, 1.9 Hz), 8.24 (1 H, d, J = 5.9 Hz), 8.56 (1 H, s) |

TABLE 1-continued

Analogs prepared by coupling method A

| EX- AM- PLE # | Structure/Name | Intermediate purification method(s) | Deprotection method | Purification method (s) | LCMS* $R_T$/M+ | $^1$H NMR (ppm) |
|---|---|---|---|---|---|---|
| 22 | 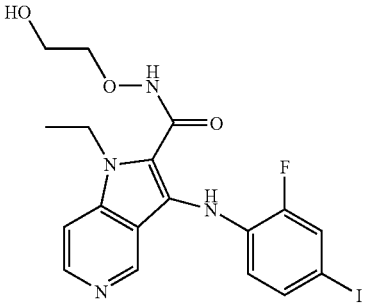<br>1-Ethyl-3-(2-fluoro-4-iodo-phenylamino)-1H-pyrrolo[3,2-c]pyridine-2-carboxylic acid (2-hydroxy-ethoxy)-amide | C⁶ | B | — | 5.76, 485 | (CD₃OD) 1.41 (3 H, t, J = 7.1 Hz), 3.66 (2 H, m), 3.90 (2 H, m), 4.54 (2 H, q, J = 7.1 Hz), 6.36 (1 H, t, J = 8.7 Hz), 7.21 (1 H, ddd, J = 8.7, 1.9, 1.0 Hz), 7.44 (1 H, dd, J = 10.8, 1.9 Hz), 7.60 (1 H, dd, J = 6.1, 1.0 Hz), 8.29 (1 H, d, J = 6.1 Hz), 8.61 (1 H, d, J = 1.0 Hz) |
| 23 | 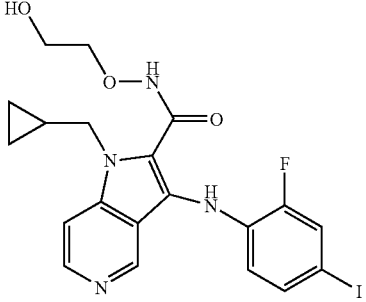<br>1-Cyclopropylmethyl-3-(2-fluoro-4-iodo-phenylamino)-1H-pyrrolo[3,2-c]pyridine-2-carboxylic acid (2-hydroxy-ethoxy)-amide | C | B | I, C | 6.16, 511 | (CD₃OD) 0.41 (2 H, m), 0.51 (2 H, m), 1.26 (1 H, m), 3.66 (2 H, m), 3.90 (2 H, m), 4.42 (2 H, d, J = 7.0 Hz), 6.36 (1 H, t, J = 8.8 Hz), 7.20 (1 H, m), 7.43 (1 H, dd, J = 10.9, 2.0 Hz), 7.62 (1 H, dd, J = 6.2, 1.0 Hz), 8.27 (1 H, d, J = 6.2 Hz), 8.61 (1 H, d, J = 1.0 Hz) |
| 24 | 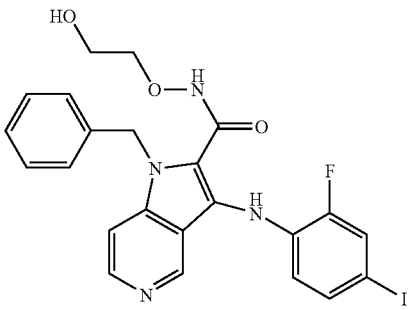<br>1-Benzyl-3-(2-fluoro-4-iodo-phenylamino)-1H-pyrrolo[3,2-c]pyridine-2-carboxylic acid (2-hydroxy-ethoxy)-amide | B | A | H | 6.49, 547 | (DMSO-D₆) 3.44 (2 H, t, J = 4.7 Hz), 3.71 (2 H, t, J = 4.7 Hz), 5.67 (2 H, s), 6.27 (1 H, t, J = 8.9 Hz), 7.10 (2 H, m), 7.26 (4 H, m), 7.53 (1 H, dd, J = 11.1, 2.0 Hz), 7.57 (1 H, s, br), 7.68 (1 H, d, J = 6.0 Hz), 8.30 (1 H, d, J = 6.0 Hz), 8.58 (1 H, s) |

TABLE 1-continued

Analogs prepared by coupling method A

| EXAMPLE # | Structure/Name | Intermediate purification method(s) | Deprotection method | Purification method (s) | LCMS* $R_T$/M+ | $^1$H NMR (ppm) |
|---|---|---|---|---|---|---|
| 25 | 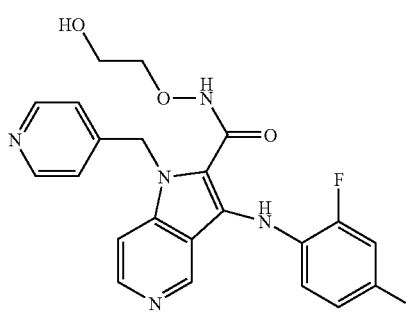<br>3-(2-Fluoro-4-iodo-phenylamino)-1-pyridin-4-ylmethyl-1H-pyrrolo[3,2-c]pyridine-2-carboxylic acid (2-hydroxy-ethoxy)-amide | C | A | I | 4.26, 548 | (CD$_3$OD) 3.55 (2 H, m), 3.77 (2 H, m), 5.84 (2 H, s), 6.46 (1 H, t, J = 8.8 Hz), 7.11 (2 H, m), 7.25 (1 H, m), 7.46 (1 H, dd, J = 10.9, 2.0 Hz), 7.57 (1 H, d, J = 6.1 Hz), 8.31 (1 H, d, J = 6.1 Hz), 8.45 (2 H, m), 8.68 (1 H, s) |
| 26 | 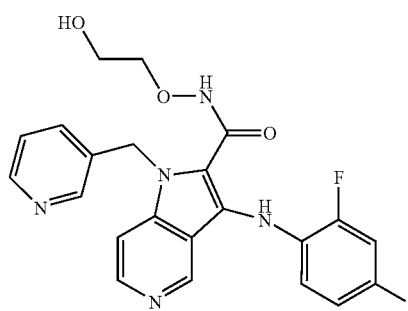<br>3-(2-Fluoro-4-iodo-phenylamino)-1-pyridin-3-ylmethyl-1H-pyrrolo[3,2-c]pyridine-2-carboxylic acid (2-hydroxy-ethoxy)-amide | C | A | H | 4.95, 548 | (CD$_3$OD) 3.57 (2 H, m), 3.79 (2 H, m), 5.83 (2 H, s), 6.43 (1 H, t, J = 8.8 Hz), 7.24 (1 H, m), 7.38 (1 H, dd, J = 8.0, 4.8 Hz), 7.46 (1 H, dd, J = 10.8, 2.0 Hz), 7.61 (1 H, m), 7.69 (1 H, d, J = 6.0 Hz), 8.33 (1 H, d, J = 6 Hz), 8.39 (1 H, s), 8.44 (1 H, d, J = 4.8 Hz), 8.68 (1 H, s) |
| 27 | 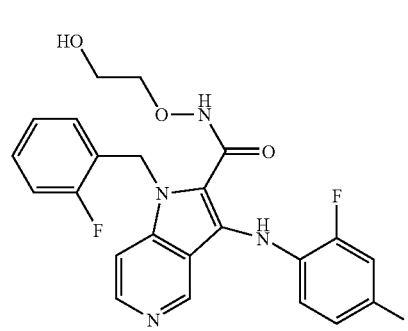<br>1-(2-Fluoro-benzyl)-3-(2-fluoro-4-iodo-phenylamino)-1H-pyrrolo[3,2-c]pyridine-2-carboxylic acid (2-hydroxy-ethoxy)-amide | A | B | I, C | 6.62, 565 | (CD$_3$OD) 3.57 (2 H, m), 3.78 (2 H, m), 5.83 (2 H, s), 6.40 (1 H, t, J = 8.8 Hz), 6.95 (1 H, m), 7.08 (2 H, m), 7.23 (1 H, m), 7.29 (1 H, m), 7.44 (1 H, dd, J = 10.8, 2.0 Hz), 7.61 (1 H, d, J = 6.1 Hz), 8.29 (1 H, d, J = 6.1 Hz), 8.64 (1 H, s) |

TABLE 1-continued

Analogs prepared by coupling method A

| EX- AM- PLE # | Structure/Name | Intermediate purification method(s) | Deprotection method | Purification method(s) | LCMS* $R_T$/M+ | $^1$H NMR (ppm) |
|---|---|---|---|---|---|---|
| 28 | 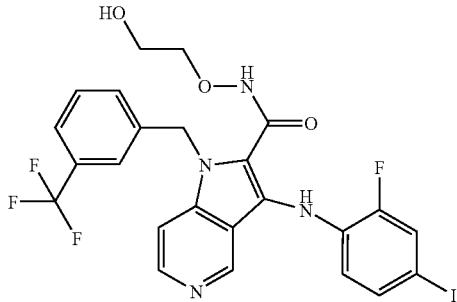<br>3-(2-Fluoro-4-iodo-phenylamino)-1-(3-trifluoromethyl-benzyl)-1H-pyrrolo[3,2-c]pyridine-2-carboxylic acid (2-hydroxy-ethoxy)-amide | C | B | I, C | 7.06, 615 | (CD$_3$OD) 3.56 (2 H, m), 3.78 (2 H, m), 5.85 (2 H, s), 6.41 (1 H, t, J = 8.8 Hz), 7.23 (1 H, m), 7.35 (1 H, d, J = 7.8 Hz), 7.44 (1 H, dd, J = 11.1, 2.0 Hz), 7.47 (1 H, s), 7.49 (1 H, t, J = 7.8 Hz), 7.56 (1 H, d, J = 7.8 Hz), 7.62 (1 H, d, J = 6.2 Hz), 8.30 (1 H, d, J = 6.2 Hz), 8.66 (1 H, s) |
| 29 | 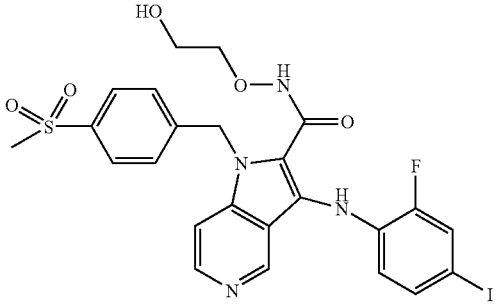<br>3-(2-Fluoro-4-iodo-phenylamino)-1-(4-methanesulfonyl-benzyl)-1H-pyrrolo[3,2-c]pyridine-2-carboxylic acid (2-hydroxy-ethoxy)-amide | C | B | I, C | 6.10, 625 | (CD$_3$OD) 3.07 (3 H, s), 3.55 (2 H, m), 3.77 (2 H, m), 5.88 (2 H, s), 6.45 (1 H, t, J = 8.8 Hz), 7.24 (1 H, m), 7.34 (2 H, m), 7.45 (1 H, dd, J = 10.9, 2.0 Hz), 7.59 (1 H, dd, J = 6.1, 1.0 Hz), 7.88 (2 H, m), 8.29 (1 H, d, J = 6.1 Hz), 8.66 (1 H, d, J = 1.0 Hz) |
| 30 | 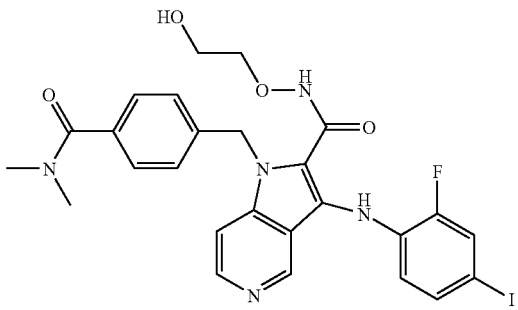<br>1-(4-Dimethylcarbamoyl-benzyl)-3-(2-fluoro-4-iodo-phenylamino)-1H-pyrrolo[3,2-c]pyridine-2-carboxylic acid (2-hydroxy-ethoxy)-amide | C | B | I, C | 6.07, 618 | (CD$_3$OD) 3.27 (6 H, s), 3.52 (2 H, m), 3.74 (2 H, m), 5.82 (2 H, s), 6.38 (1 H, t, J = 8.8 Hz), 7.19 (1 H, m), 7.32 (1 H, d, J = 7.7 Hz), 7.40 (1 H, dd, J = 10.9, 2.0 Hz), 7.46 (3 H, m), 7.59 (1 H, d, J = 6.1 Hz), 8.27 (1 H, d, J = 6.1 Hz), 8.63 (1 H, d, J = 1.0 Hz) |

TABLE 1-continued

Analogs prepared by coupling method A

| EX-AM-PLE # | Structure/Name | Intermediate purification method(s) | Deprotection method | Purification method (s) | LCMS* $R_T$/M+ | $^1$H NMR (ppm) |
|---|---|---|---|---|---|---|
| 31 | 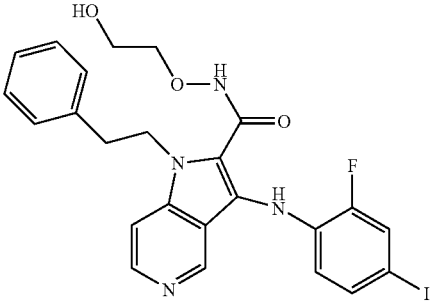<br>3-(2-Fluoro-4-iodo-phenylamino)-1-phenethyl-1H-pyrrolo[3,2-c]pyridine-2-carboxylic acid (2-hydroxy-ethoxy)-amide | A | B | I, C | 6.90, 561 | (CDCl$_3$) 3.12 (2 H, t, J = 7.2 Hz), 3.73 (2 H, m), 3.97 (2 H, m), 4.85 (2 H, t, J = 7.2 Hz), 5.71 (1 H, d, J = 3 Hz), 6.23 (1 H, t, J = 8.8 Hz), 7.08 (2 H, m), 7.21 (5 H, m), 7.48 (1 H, dd, J = 10.3, 1.9 Hz), 8.35 (1 H, d, J = 6.1 Hz), 8.60 (1 H, d, J = 1.0 Hz), 10.20 (1 H, s, br) |
| 32 | 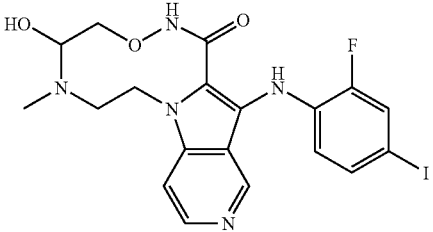<br>1-(2-Dimethylamino-ethyl)-3-(2-fluoro-4-iodo-phenylamino)-1H-pyrrolo[3,2-c]pyridine-2-carboxylic acid (2-hydroxy-ethoxy)-amide | J | B | J | 4.03, 528 | (CDCl$_3$) 8.70 (1 H, s), 8.39 (1 H, d, J = 5.8 Hz), 7.64 (1 H, s), 7.40 (1 H, dd, J = 10.2, 2.0 Hz), 7.25-7.20 (1 H, m), 7.12 (1 H, d, J = 6.2 Hz), 6.70 (1 H, t, J = 9.0 Hz), 4.35 (2 H, t, J = 5.0 Hz), 4.04 (2 H, t, J = 4.5 Hz), 3.76 (2 H, t, J = 4.5 Hz), 2.93 (2 H, t, J = 5.0 Hz), 2.32 (6 H, s). |
| 33 | 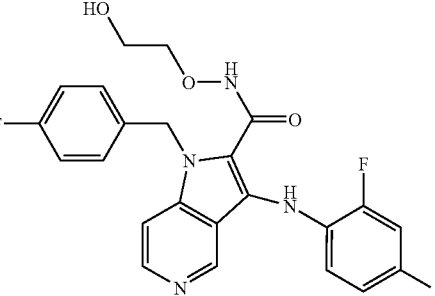<br>1-(4-Fluoro-benzyl)-3-(2-fluoro-4-iodo-phenylamino)-1H-pyrrolo[3,2-c]pyridine-2-carboxylic acid (2-hydroxy-ethoxy)-amide | C | B | C | 6.76, 565 | (CD$_3$OD) 8.61 (1 H, d, J = 0.9 Hz), 8.26 (1 H, d, J = 6.1 Hz), 7.60 (1 H, dd, J = 6.1, 1.2 Hz), 7.41 (1 H, dd, J = 11.0, 2.1 Hz), 7.20 (1 H, ddd, J = 8.4, 1.8, 1.0 Hz), 7.15-7.11 (m, 2 H), 7.01-6.95 (m, 2 H), 6.37 (1 H, t, J = 8.9 Hz), 5.69 (2 H, s), 3.75 (2 H, t, J = 4.5 Hz), 3.53 (2 H, t, J = 4.5 Hz) |
| 34 | 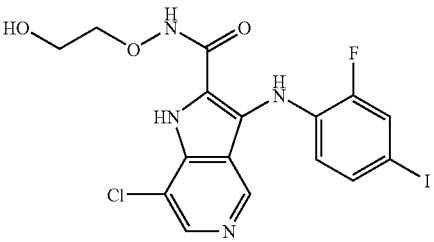<br>7-Chloro-3-(2-fluoro-4-iodo-phenylamino)-1H-pyrrolo[3,2-c]pyridine-2-carboxylic acid (2-hydroxy-ethoxy)-amide | B | E | B/D | 6.36, 491 | (CD$_3$OD) 3.79 (2 H, t, J = 4.7 Hz), 4.03 (2 H, t, J = 4.6 Hz), 6.57 (1 H, t, J = 8.7 Hz), 7.27 (1 H, d, J = 8.2 Hz), 7.45 (1 H, t, J = 11.0 Hz), 8.23 (1 H, s), 8.46 (1 H, s) |

TABLE 1-continued

Analogs prepared by coupling method A

| EXAMPLE # | Structure/Name | Intermediate purification method(s) | Deprotection method | Purification method(s) | LCMS* R$_T$/M+ | $^1$H NMR (ppm) |
|---|---|---|---|---|---|---|
| 35 | 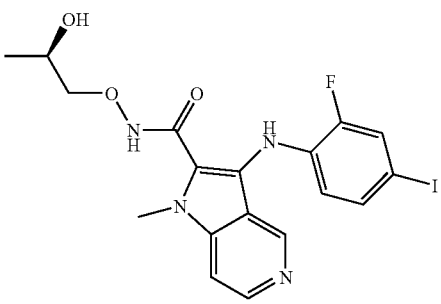 3-(2-Fluoro-4-iodo-phenylamino)-1-methyl-1H-pyrrolo[3,2-c]pyridine-2-carboxylic acid ((R)-2-hydroxy-propoxy)-amide | C | C$^7$ | C | 5.87, 485 | (DMSO-D$_6$) 8.54 (1 H, s), 8.27 (1 H, d, J = 5.5 Hz), 7.56-7.50 (2 H, m), 7.48 (1 H, dd, J = 11.0, 2.0 Hz), 7.16-7.13 (1 H, m), 6.18 (1 H, t, J = 9.0 Hz), 3.81 (3 H, s), 3.74-3.67 (1 H, m), 3.57-3.55 (2 H, m), 0.95 (3 H, d, J = 6.0 Hz) |
| 36 | 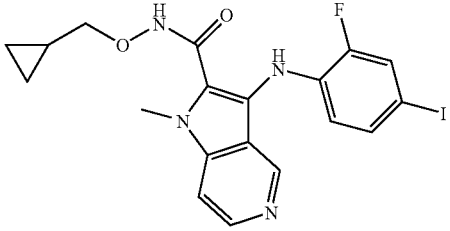 3-(2-Fluoro-4-iodo-phenylamino)-1-methyl-1H-pyrrolo[3,2-c]pyridine-2-carboxylic acid cyclopropyl-methoxy-amide | — | — | C$^6$ | 6.92, 481 | (DMSO-D$_6$) 0.19 (2 H, m), 0.47 (2 H, m), 0.99 (1 H, m), 3.54 (2 H, d, J = 7.0 Hz), 3.91 (3 H, s), 6.31 (1 H, t, J = 8.8 Hz), 7.20 (1 H, dd, J = 7.4, 1.3 Hz), 7.54 (1 H, dd, J = 11.0, 1.7 Hz), 7.74 (1 H, s), 7.88 (1 H, d, J = 6.4 Hz), 8.42 (1 H, d, J = 6.5 Hz), 8.82 (1 H, s), 11.66 (1 H, s) |
| 37 | 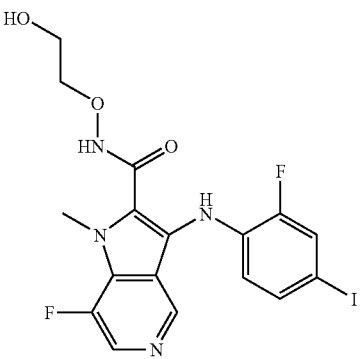 7-Fluoro-3-(2-fluoro-4-iodo-phenylamino)-1-methyl-1H-pyrrolo[3,2-c]pyridine-2-carboxylic acid (2-hydroxy-ethoxy)-amide | A | B | 6 | 5.95, 489 | (DMSO-D$_6$) 8.45 (1 H, d, J = 2.5 Hz), 8.17 (1 H, d, J = 6.3 Hz), 7.44 (1 H, dd, J = 2.6, 14.5 Hz), 7.21 (1 H, ddd, J = 1.5, 2.7, 11.2 Hz), 6.37 (1 H, t, J = 11.6 Hz), 4.14 (3 H, d, J = 1.4 Hz), 3.89 (2 H, m), 3.66 (2 H, m) |

TABLE 1-continued

Analogs prepared by coupling method A

| EX-AMPLE # | Structure/Name | Intermediate purification method(s) | Deprotection method | Purification method(s) | LCMS* R$_T$/M+ | $^1$H NMR (ppm) |
|---|---|---|---|---|---|---|
| 38 | 3-(2-Fluoro-4-iodo-phenylamino)-1H-pyrrolo[3,2-c]pyridine-2-carboxylic acid cyclopropylmethoxy-amide monoformate | — | — | H | 6.53, 467 | (CD$_3$OD) 8.56 (1 H, s), 8.33 (1 H, s), 8.22 (1 H, d, J = 6.5 Hz), 7.48 (1 H, d, J = 6.0 Hz), 7.22 (1 H, m), 6.39 (1 H, t, J = 8.0 Hz), 3.67 (2 H, d, J = 8.0 Hz), 1.04 (1 H, m), 0.48 (2 H, m), 0.21 (2 H, m) |
| 39 | 7-Chloro-3-(2-fluoro-4-iodo-phenylamino)-1-methyl-1H-pyrrolo[3,2-c]pyridine-2-carboxylic acid (2-hydroxy-ethoxy)-amide | 6 | D | A | 6.44, 505 | (DMSO-D$_6$) 11.63 (1 H, s, br), 8.47 (1 H, s), 8.25 (1 H, s), 7.55 (1 H, s, br), 7.47 (1 H, dd, J = 2.0, 10.0 Hz), 7.14 (1 H, dd, J = 2.0, 8.0 Hz), 6.18 (1 H, t, J = 9.0 Hz), 4.70 (1 H, s, br), 4.06 (3 H, s), 3.78 (2 H, t, J = 4.0 Hz), 3.48 (2 H, t, J = 4.0 Hz) |
| 40 | 3-(2-Fluoro-4-iodo-phenylamino)-1H-pyrrolo[3,2-c]pyridine-2-carboxylic acid tert-butoxy-amide monoformate | — | — | H | 7.05, 469 | (DMSO-D$_6$) 11.95 (1 H, s, br), 10.49 (1 H, s, br), 8.53 (1 H, d, J = 1.0 Hz), 8.21 (1 H, d, J = 6.0 Hz), 8.10 (1 H, s), 7.71 (1 H, s, br), 7.50 (1 H, dd, J = 1.5, 9.0 Hz), 7.34 (1 H, dd, J = 6.0, 10.0 Hz), 7.18 (1 H, d, J = 8.0 Hz), 6.23 (1 H, t, J = 9.0 Hz), 1.08 (9 H, s) |
| 41 | 3-(2-Fluoro-4-iodo-phenylamino)-1-(3-hydroxy-propyl)-1H-pyrrolo[3,2-c]pyridine-2-carboxylic acid (2-hydroxy-ethoxy)-amide | — | — | I, C | 5.14, 515 | (DMSO-D$_6$) 1.84 (2 H, quin, J = 6.7 Hz), 3.54 (2 H, s, br), 3.83 (2 H, t, J = 4.7 Hz), 4.44 (2 H, t, J = 7.0 Hz), 4.65 (1 H, s, br), 4.75 (1 H, s, br), 6.23 (1 H, t, J = 8.9 Hz), 7.20 (1 H, dd, J = 8.4, 1.4 Hz), 7.52 (1 H, dd, J = 11.2, 2.0 Hz), 7.56 (1 H, s, br), 7.59 (1 H, dd, J = 5.9 Hz), 8.30 (1 H, d, J = 5.9 Hz), 8.55 (1 H, d, J = 0.9 Hz), 11.54 (1 H, s, br) |

TABLE 1-continued

Analogs prepared by coupling method A

| EX-AMPLE # | Structure/Name | Intermediate purification method(s) | Deprotection method | Purification method (s) | LCMS* $R_T$/M+ | $^1$H NMR (ppm) |
|---|---|---|---|---|---|---|
| 42 | 1-(4-Dimethylcarbamoyl-benzyl)-3-(2-fluoro-4-iodo-phenylamino)-1H-pyrrolo[3,2-c]pyridine-2-carboxylic acid (2-hydroxy-ethoxy)-amide | A | A | C | 6.07, 618 | (CH$_3$OH-D$_4$) 2.94 (3 H, s), 3.05 (3 H, s), 3.53-3.58 (2 H, m), 3.77 (2 H, t, J = 4.58 Hz), 5.80 (2 H, s), 6.42 (1 H, t, J = 8.80 Hz), 7.19 (2 H, d, J = 8.03 Hz), 7.18-7.25 (1H, m), 7.34 (2 H, d, J = 8.21 Hz), 7.41-7.46 (1 H, m), 7.60 (1 H, dd, J = 6.13, 1.03 Hz), 8.24-8.30 (1 H, m), 8.64 (1 H, d, J = 0.98 Hz). |
| 43 | 3-(2-Fluoro-4-iodo-phenylamino)-1-(4-trifluoromethyl-benzyl)-1H-pyrrolo[3,2-c]pyridine-2-carboxylic acid (2-hydroxy-ethoxy)-amide | B | A | H$^8$ | 7.40, 615 | (DMSO-D$_6$) 3.40 (2 H, t, J = 4.73 Hz), 3.67 (2 H, t, J = 4.68 Hz), 5.75 (2 H, s), 6.29 (1 H, t, J = 8.88 Hz), 7.18-7.25 (1 H, m), 7.27 (2 H, d, J = 8.05 Hz), 7.52 (1 H, dd, J = 11.01, 1.94 Hz), 7.61 (1 H, s), 7.60-7.71 (3 H, m), 8.30 (1 H, t, J = 5.95 Hz), 8.59 (1 H, d, J = 0.97 Hz). |
| 44 | 1-(4-Cyano-benzyl)-3-(2-fluoro-4-iodo-phenylamino)-1H-pyrrolo[3,2-c]pyridine-2-carboxylic acid (2-hydroxy-ethoxy)-amide | B | A | H$^8$ | 6.47, 572 | (DMSO-D$_6$) 3.56 (2 H, d, J = 4.95 Hz), 5.87 (2 H, s), 6.49 (1 H, t, J = 8.84 Hz), 7.26 (3 H, dd, J = 13.43, 8.07 Hz), 7.56 (1 H, dd, J = 10.97, 1.95 Hz), 7.80 (2 H, d, J = 8.33 Hz), 7.95-8.04 (1 H, m), 8.23 (1 H, t, J = 6.75 Hz), 8.51-8.57 (1 H, m), 9.15 (1 H, s), 11.94 (1 H, s). |
| 45 | 1-(3-Dimethylcarbamoyl-benzyl)-3-(2-fluoro-4-iodo-phenylamino)-1H-pyrrolo[3,2-c]pyridine-2-carboxylic acid (2-hydroxy-ethoxy)-amide | C | A | H$^8$ | 6.12, 618 | (DMSO-D$_6$) 2.79 (3 H, s), 2.92 (3 H, s), 3.42 (2 H, t, J = 4.72 Hz), 3.70 (2 H, t, J = 4.63 Hz), 5.70 (2 H, s), 6.27 (1 H, t, J = 8.84 Hz), 7.08 (1 H, s), 7.14-7.24 (2 H, m), 7.26 (1 H, d, J = 7.58 Hz), 7.35 (1 H, t, J = 7.63 Hz), 7.52 (1 H, dd, J = 11.00, 1.93 Hz), 7.60-7.72 (1 H, m), 8.29 (1 H, d, J = 5.90 Hz), 8.57 (1 H, s). |

TABLE 1-continued

Analogs prepared by coupling method A

| EXAMPLE # | Structure/Name | Intermediate purification method(s) | Deprotection method | Purification method (s) | LCMS* $R_T$/M+ | $^1$H NMR (ppm) |
|---|---|---|---|---|---|---|
| 46 | 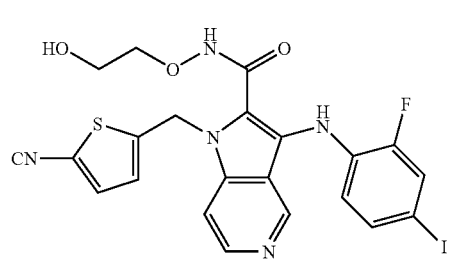<br>1-(5-Cyano-thiophen-2-ylmethyl)-3-(2-fluoro-4-iodo-phenylamino)-1H-pyrrolo[3,2-c]pyridine-2-carboxylic acid (2-hydroxy-ethoxy)-amide | A | A | I, C | 6.59, 578 | (CH$_3$OH-D$_4$) 3.60-3.65 (2 H, m), 3.84-3.89 (2 H, m), 6.00 (2 H, s), 6.40 (1 H, t, J = 8.78 Hz), 7.17 (1 H, d, J = 3.86 Hz), 7.21-7.24 (1 H, m), 7.44 (1 H, dd, J = 10.82, 1.94 Hz), 7.59 (1 H, d, J = 3.84 Hz), 7.71 (1 H, d, J = 6.11 Hz), 8.32 (1 H, d, J = 6.08 Hz), 8.62 (1 H, s). |
| 47 | 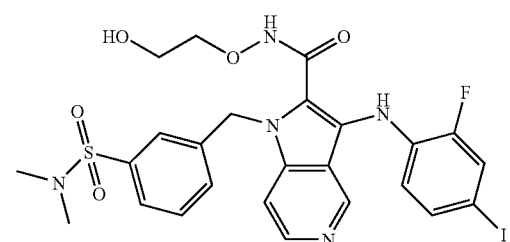<br>1-(3-Dimethylsulfamoyl-benzyl)-3-(2-fluoro-4-iodo-phenylamino)-1H-pyrrolo[3,2-c]pyridine-2-carboxylic acid (2-hydroxy-ethoxy)-amide | C | A | I, C | 6.74, 654 | (CH$_3$OH-D$_4$) 2.55 (6 H, s), 3.53-3.58 (2 H, m), 3.76-3.81 (2 H, m), 5.88 (2 H, s), 6.41 (1 H, t, J = 8.79 Hz), 7.24 (1 H, ddd, J = 8.50, 1.93, 1.07 Hz), 7.40 (1 H, s), 7.44 (1 H, dd, J = 10.84, 1.93 Hz), 7.49 (1 H, d, J = 7.85 Hz), 7.56 (1 H, t, J = 7.73 Hz), 7.60 (1 H, d, J = 6.11 Hz), 7.66 (1 H, d, J = 7.78 Hz), 8.29 (1 H, d, J = 6.09 Hz), 8.67 (1 H, s). |
| 48 | 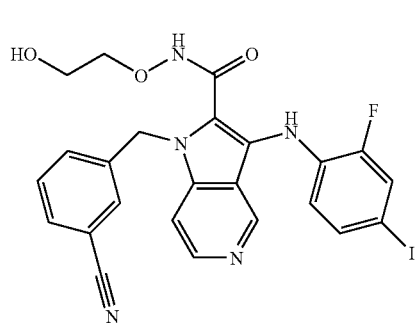<br>1-(3-Cyano-benzyl)-3-(2-fluoro-4-iodo-phenylamino)-1H-pyrrolo[3,2-c]pyridine-2-carboxylic acid (2-hydroxy-ethoxy)-amide | B | A | H$^8$ | 6.53, 572 | (DMSO-D$_6$) 3.42 (2 H, t, J = 4.69 Hz), 3.69 (2 H, t, J = 4.68 Hz), 5.70 (2 H, s), 6.31 (1 H, t, J = 8.88 Hz), 7.22 (1 H, dd, J = 8.48, 1.87 Hz), 7.41 (1 H, d, J = 7.98 Hz), 7.49-7.55 (3 H, m), 7.62 (1 H, s), 7.61-7.70 (1 H, m), 7.73 (1 H, dd, J = 7.54, 1.54 Hz), 8.27-8.32 (1 H, m), 8.59 (1 H, d, J = 0.97 Hz). |

TABLE 1-continued

Analogs prepared by coupling method A

| EX-AM-PLE # | Structure/Name | Intermediate purification method(s) | Deprotection method | Purification method(s) | LCMS* R$_T$/M+ | $^1$H NMR (ppm) |
|---|---|---|---|---|---|---|
| 49 | 7-Fluoro-3-(2-fluoro-4-iodo-phenylamino)-1H-pyrrolo[3,2-c]pyridine-2-carboxylic acid (2-hydroxy-ethoxy)-amide | C | B | C | 5.92, 475 | (DMSO-D$_6$) 3.57 (2 H, t, J = 4.81 Hz), 3.87 (2 H, t, J = 4.83 Hz), 6.43 (1 H, t, J = 8.80 Hz), 7.23-7.27 (1 H, m), 7.55 (1 H, dd, J = 10.95, 1.94 Hz), 7.91 (1 H, s), 8.22 (1 H, d, J = 3.01 Hz), 8.36 (1 H, d, J = 2.28 Hz). |
| 50 | 1-(4-Dimethylsulfamoyl-benzyl)-3-(2-fluoro-4-iodo-phenylamino)-1H-pyrrolo[3,2-c]pyridine-2-carboxylic acid (2-hydroxy-ethoxy)-amide | C | A | H$^8$ | 6.67, 654 | (DMSO-D$_6$) 2.57 (6 H, d, J = 1.91 Hz), 3.40 (2 H, t, J = 4.91 Hz), 3.67 (2 H, t, J = 4.66 Hz), 5.80 (2 H, s), 6.34 (1 H, t, J = 8.77 Hz), 7.21-7.25 (1 H, m), 7.28 (2 H, d, J = 8.18 Hz), 7.53 (1 H, dd, J = 10.99, 1.96 Hz), 7.63 (1 H, d, J = 6.19 Hz), 7.67 (2 H, d, J = 8.20 Hz), 8.29 (1 H, d, J = 5.90 Hz), 8.58 (1 H, s). |
| 51 | [7-Fluoro-3-(2-fluoro-4-iodo-phenylamino)-1H-pyrrolo[3,2-c]pyridin-2-yl]-((R)-3-hydroxy-pyrrolidin-1-yl)-methanone | — | — | B, C | 5.76, 485 | (CH$_3$OH-D$_4$) 1.90-2.01 (2 H, m), 3.40-3.80 (3 H, m), 4.37 (1 H, s), 6.54 (1 H, t, J = 8.82 Hz), 7.23 (1 H, ddd, J = 8.52, 1.94, 1.09 Hz), 7.42 (1 H, dd, J = 10.90, 1.94 Hz), 8.15 (1 H, d, J = 3.33 Hz), 8.47 (1 H, d, J = 1.94 Hz). |

TABLE 1-continued

Analogs prepared by coupling method A

| EXAMPLE # | Structure/Name | Intermediate purification method(s) | Deprotection method | Purification method (s) | LCMS* $R_T$/M+ | $^1$H NMR (ppm) |
|---|---|---|---|---|---|---|
| 52 | [7-Fluoro-3-(2-fluoro-4-iodo-phenylamino)-1H-pyrrolo[3,2-c]pyridin-2-yl]-((2S,4R)-4-hydroxy-2-hydroxymethyl-pyrrolidin-1-yl)-methanone | — | — | B, C[9] | 5.15, 515 | (CH$_3$OH-D$_4$) 1.99-2.07 (2 H, m), 3.45-3.60 (4 H, m), 4.29 (1 H, m), 4.44-4.52 (1 H, m), 6.57 (1 H, t, J = 8.81 Hz), 7.25 (1 H, ddd, J = 8.51, 1.94, 1.08 Hz), 7.42 (1 H, dd, J = 10.91, 1.94 Hz), 8.15 (1 H, d, J = 3.33 Hz), 8.46 (1 H, d, J = 1.94 Hz). |
| 53 | [7-Fluoro-3-(2-fluoro-4-iodo-phenylamino)-1H-pyrrolo[3,2-c]pyridin-2-yl]-(4-hydroxy-isoxazolidin-2-yl)-methanone | — | — | C, B | 6.11, 487 | (DMSO-D$_6$) 3.60 (1 H, d, J = 11.51 Hz), 3.82-3.96 (3 H, m), 4.65 (1 H, s), 5.46 (1 H, s), 6.55 (1 H, t, J = 8.87 Hz), 7.28 (1 H, d, J = 8.56 Hz), 7.54 (1 H, dd, J = 10.97, 1.93 Hz), 7.97 (1 H, s), 8.24 (1 H, d, J = 3.04 Hz), 8.40 (1 H, d, J = 2.23 Hz), 12.33 (1 H, s). |
| 54 | 7-Fluoro-3-(2-fluoro-4-iodo-phenylamino)-1-methyl-1H-pyrrolo[3,2-c]pyridine-2-carboxylic acid ((S)-2-hydroxy-propoxy)-amide | A | C[10] | A, C | 6.50, 503 | (CH$_3$OH-D$_4$) 1.06 (3 H, d, J = 6.46 Hz), 3.58 (1 H, dd, J = 10.70, 8.13 Hz), 3.68 (1 H, dd, J = 10.69, 3.27 Hz), 3.82-3.88 (1 H, m), 4.14 (3 H, d, J = 1.01 Hz), 6.36 (1 H, t, J = 8.81 Hz), 7.21 (1 H, ddd, J = 8.51, 1.92, 1.09 Hz), 7.43 (1 H, dd, J = 10.87, 1.93 Hz), 8.16 (1 H, d, J = 4.65 Hz), 8.47 (1 H, d, J = 1.73 Hz). |

TABLE 1-continued

Analogs prepared by coupling method A

| EXAMPLE # | Structure/Name | Intermediate purification method(s) | Deprotection method | Purification method(s) | LCMS* R$_T$/M+ | ¹H NMR (ppm) |
|---|---|---|---|---|---|---|
| 55 | 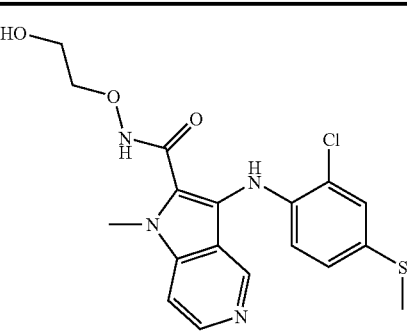<br>3-(2-Chloro-4-methylsulfanyl-phenylamino)-1-methyl-1H-pyrrolo[3,2-c]pyridine-2-carboxylic acid (2-hydroxy-ethoxy)-amide | C | A | I, C¹¹ | 5.49, 407 | (DMSO-D$_6$) 2.39 (3 H, s), 3.54 (2 H, t, J = 4.76 Hz), 3.82-3.88 (5 H, m), 6.31 (1 H, d, J = 8.56 Hz), 7.00 (1 H, d, J = 8.56, 2.19 Hz), 7.30 (1 H, s), 7.35 (1 H, d, J = 2.17 Hz), 7.60 (1 H, d, J = 5.98 Hz), 8.31 (1 H, d, J = 5.93 Hz), 8.49 (1 H, s). |
| 56 | 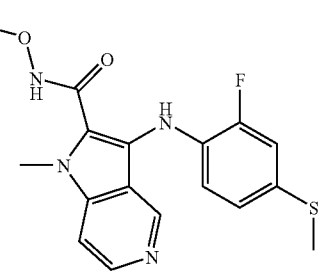<br>3-(2-Fluoro-4-methylsulfanyl-phenylamino)-1-methyl-1H-pyrrolo[3,2-c]pyridine-2-carboxylic acid (2-hydroxy-ethoxy)-amide | B | A | H⁸ | 5.01, 391 | (CHCl$_3$-D$_3$) 2.45 (3 H, s), 3.74-3.78 (2 H, m), 3.98-4.02 (2 H, m), 4.14 (3 H, s), 5.68 (1 H, s), 6.50 (1 H, t, J = 8.66 Hz), 6.85-6.88 (1 H, m), 7.13 (1 H, dd, J = 11.47, 2.05 Hz), 7.36 (1 H, d, J = 6.11 Hz), 8.43 (1 H, d, J = 6.09 Hz), 8.63 (1 H, s). |

TABLE 2

Analogs prepared by coupling method B

| EXAMPLE # | Structure/Name | Intermediate purification method(s) | Deprotection method | Purification method (s) | LCMS* R$_T$/M+ | ¹H NMR (ppm) |
|---|---|---|---|---|---|---|
| 16 | 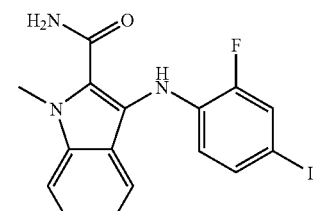<br>3-(2-Fluoro-4-iodo-phenylamino)-1-methyl-1H-pyrrolo[3,2-c]pyridine-2-carboxylic acid amide | — | — | C³ | 5.45, 411 | (CDCl$_3$) 4.15 (3 H, s), 5.91 (1 H, s), 6.33 (1 H, t, J = 8.8 Hz), 7.21 (1 H, m), 7.38 (1 H, d, J = 6.1 Hz), 7.45 (1 H, dd, J = 10.3, 1.9 Hz), 8.42 (1 H, d, J = 6.1 Hz), 8.67 (1 H, s) |

US 7,855,216 B2

TABLE 2-continued

Analogs prepared by coupling method B

| EXAMPLE # | Structure/Name | Intermediate purification method(s) | Deprotection method | Purification method (s) | LCMS* $R_T$/M+ | $^1$H NMR (ppm) |
|---|---|---|---|---|---|---|
| 17 | 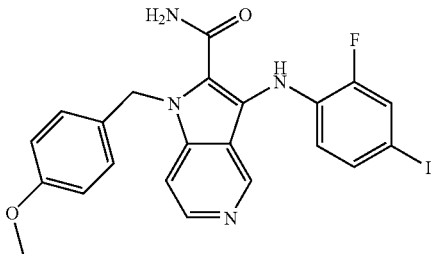　3-(2-Fluoro-4-iodo-phenylamino)-1-(4-methoxy-benzyl)-1H-pyrrolo[3,2-c]pyridine-2-carboxylic acid amide | — | — | I | 6.96, 517 | (DMSO-D$_6$) 3.69 (3 H, s), 5.70 (2 H, s), 6.18 (1 H, t, J = 8.7 Hz), 6.84 (2 H, m), 7.10 (2 H, m), 7.21 (1 H, dd, J = 8.7, 1.9 Hz), 7.53 (1 H, dd, J = 11.1, 1.9 Hz), 7.68 (2 H, m), 7.81 (2 H, s), 8.29 (1 H, d, J = 5.9 Hz), 8.54 (1 H, d, J = 0.8 Hz) |
| 57 | 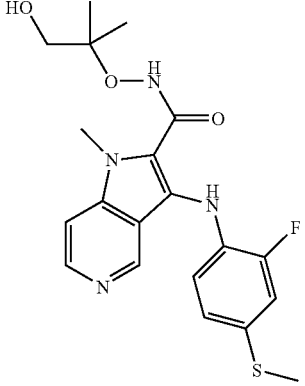　3-(2-Fluoro-4-methylsulfanyl-phenylamino)-1-methyl-1H-pyrrolo[3,2-c]pyridine-2-carboxylic acid (2-hydroxy-1,1-dimethyl-ethoxy)-amide | — | — | C, H | 5.79, 419 | (DMSO-D$_6$) 1.09 (6 H, s), 2.39 (3 H, s), 3.16 (2 H, s), 3.86 (3 H, s), 6.35 (1 H, t, J = 8.88 Hz), 6.85 (1 H, dd, J = 8.43, 2.05 Hz), 7.18 (1 H, dd, J = 12.16, 2.10 Hz), 7.39 (1 H, s), 7.60 (1 H, dd, J = 5.99, 1.04 Hz), 8.13 (1 H, s), 8.31 (1 H, d, J = 5.95 Hz), 8.54 (1 H, d, J = 1.00 Hz). |
| 58 | 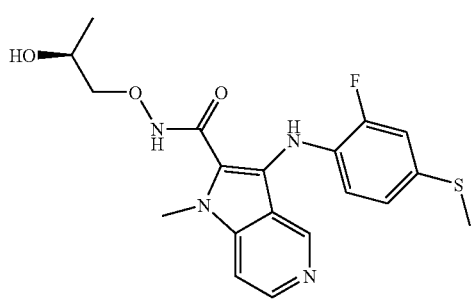　3-(2-Fluoro-4-methylsulfanyl-phenylamino)-1-methyl-1H-pyrrolo[3,2-c]pyridine-2-carboxylic acid ((S)-2-hydroxy-propoxy)-amide | C$^{12}$ | A | H | 5.34, 405 | (DMSO-D$_6$) 0.96-1.02 (3 H, m), 2.39 (3 H, s), 3.58 (2 H, dd, J = 19.89, 5.64 Hz), 3.70-3.79 (1 H, m), 3.85 (3 H, s), 6.38 (1 H, t, J = 8.82 Hz), 6.85 (1 H, dd, J = 8.43, 2.06 Hz), 7.18 (1 H, dd, J = 12.15, 2.10 Hz), 7.42 (1 H, s), 7.56-7.60 (1 H, m), 8.26-8.32 (1 H, m), 8.55 (1 H, s). |

We claim:
1. A compound selected from Formula I:

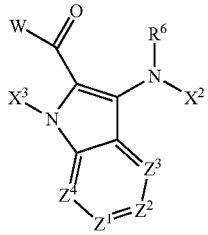

and pharmaceutically acceptable salts thereof, wherein:
$Z^1$ is $CR^1$;
$Z^2$ is N;
$Z^3$ is $CR^3$;
$Z^4$ is $CR^4$;
$R^1$, $R^3$ and $R^4$ are independently selected from H, halo, CN, $CF_3$, $-OCF_3$, $-NO_2$, $-(CR^{14}R^{15})_nC(=Y)R^{11}$, $-(CR^{14}R^{15})_nC(=Y)OR^{11}$, $-(CR^{14}R^{15})_nC(=Y)NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y)R^{11}$, $-(CR^{14}R^{15})_nNR^{12}C(=OR^{11}$, $-(CR^{14}R^{15})_nNR^{13}C(=Y)NR^{11}R^{12}$, $-(CR^{14}R^{15})_nNR^{12}SO_2R^{11}$, $-(CR^{14}R^{15})_nOC(=Y)R^{11}$, $-(CR^{14}R^{15})_nOC(=Y)OR^{11}$, $-(CR^{14}R^{15})_nOC(=Y)NR^{11}R^{12}$, $-(CR^{14}R^{15})_nOS(O)_2(OR^{11})$, $-(CR^{14}R^{15})_nOP(=Y)(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y)R^{11}$, $-(CR^{14}R^{15})_nSC(=Y)OR^{11}$, $-(CR^{14}R^{15})_nSC(=Y)NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;
W is

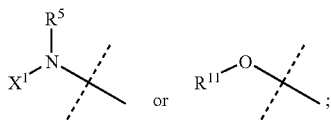

$R^5$ and $R^6$ are independently selected from H or $C_1$-$C_{12}$ alkyl;
$X^1$ is selected from $R^{11}$, $-OR^{11}$, $-NR^{11}R^{12}$, $-S(O)R^{11}$, and $-S(O)_2R^{11}$; when $X^1$ is $R^{11}$ or $-OR^{11}$, $R^{11}$ or $-OR^{11}$ of $X^1$ is optionally taken together with $-N-R^5$ of W to form a 4-7 membered saturated or unsaturated ring having 0-2 additional heteroatoms selected from O, S and N, wherein said ring is optionally substituted with one or more groups selected from halo, CN, $CF_3$, $-OCF_3$, $-NO_2$, oxo, $-Si(C_1$-$C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n$SR$^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;
$X^2$ is selected from carbocyclyl, heterocyclyl, aryl, and heteroaryl;
$X^3$ is selected from H, $-(CR^{23}R^{24})_pR^{12}$, $-(CR^{23}R^{24})_qNR^{11}R^{12}$, $-(CR^{23}R^{24})_qOR^{12}$, $-(CR^{23}R^{24})_pC(O)NR^{11}R^{12}$, $-(CR^{23}R^{24})(NR^{11}C(O)R^{12}$, $-(CR^{23}R^{24})_pS(O)_2NR^{11}R^{12}$, and $-(CR^{23}R^{24})_qNR^{11}S(O)_2R^{12}$;
$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl,
or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, $-OCF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO$_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);
$R^{14}$ and $R^{15}$ are independently selected from H, $C_1$-$C_{12}$ alkyl, aryl, carbocyclyl, heterocyclyl, and heteroaryl;
m and n are independently selected from 0, 1, 2, 3, 4, 5, or 6;
p is 0, 1, 2, or 3;
q is 2 or 3;
Y is independently O, $NR^{11}$, or S;
wherein each said alkyl, alkenyl, alkynyl, carbocyclyl, heterocyclyl, aryl and heteroaryl of $R^1$, $R^2$, $R^3$, $R^4$, $R^5$, $R^6$, $X^1$, $X^2$, $R^{11}$, $R^{12}$, $R^{13}$, $R^{14}$, and $R^{15}$ is independently optionally substituted with one or more groups independently selected from halo, CN, $CF_3$, $-OCF_3$, $-NO_2$, oxo, $-Si(C_1$-$C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n$SR$^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;
each $R^{16}$, $R^{17}$ and $R^{18}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, $-OCF_3$, $CF_3$, $-NO_2$, $C_1$-$C_6$ alkyl, $-OH$, $-SH$, $-O(C_1$-$C_6$ alkyl), $-S(C_1$-$C_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

or R$^{16}$ and R$^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{19}$ and R$^{20}$ are independently selected from H, C$_1$-C$_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

R$^{21}$ is C$_1$-C$_{12}$ alkyl, C$_2$-C$_8$ alkenyl, C$_2$-C$_8$ alkynyl, carbocyclyl, heterocyclyl, aryl, or heteroaryl, wherein each member of R$^{21}$ is optionally substituted with one or more groups selected from halo, oxo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

each Y' is independently O, NR$^{22}$, or S;

R$^{22}$ is H or C$_1$-C$_{12}$ alkyl; and

R$^{23}$ and R$^{24}$ are independently H or C$_1$-C$_6$ alkyl wherein said alkyl is optionally substituted with one or more groups selected from halo, CN, CF$_3$, —OCF$_3$, —NO$_2$, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl).

2. The compound of claim 1 wherein X$^1$ is selected from:

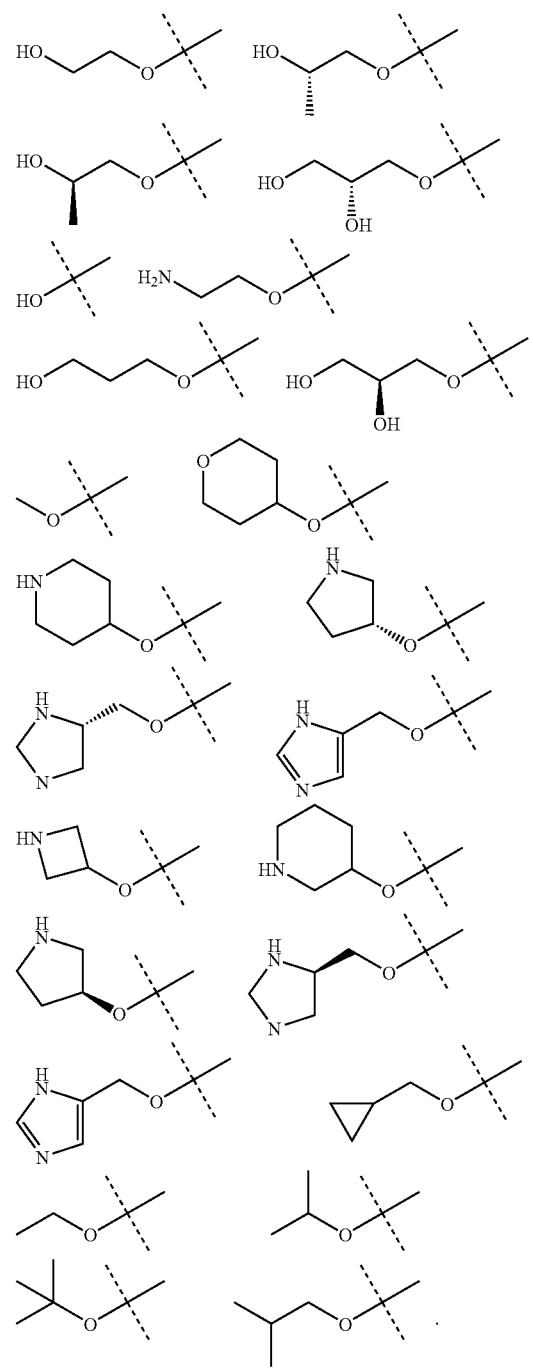

3. The compound of claim 1 wherein $X^3$ is other than H and $X^1$ is selected from:

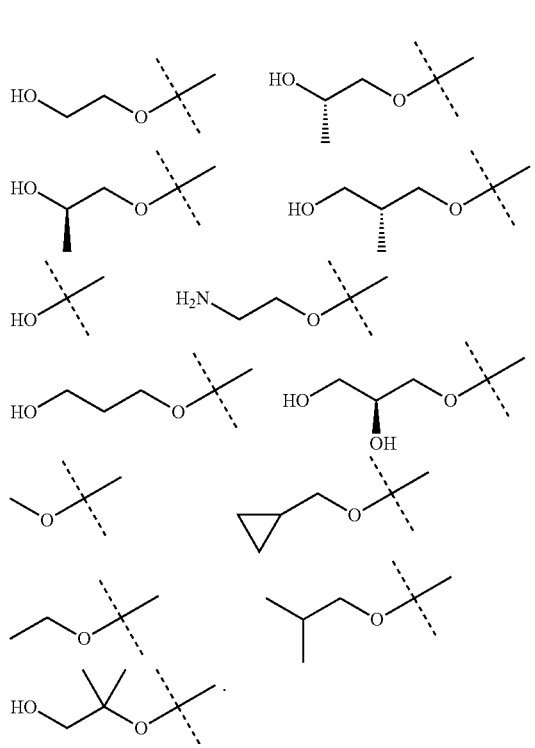

4. The compound of claim 1 wherein $R^5$ is H, $X^3$ is H and $X^1$ is selected from:

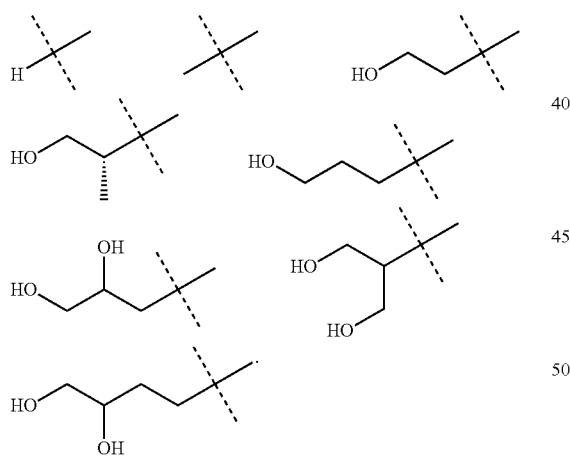

5. The compound of claim 1 wherein $R^5$ is methyl, $X^3$ is H and $X^1$ is selected from:

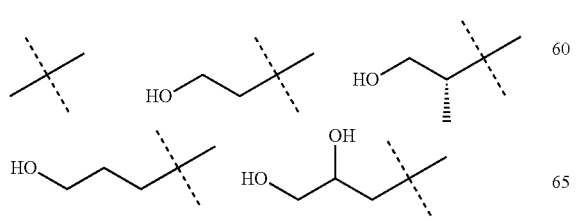

-continued

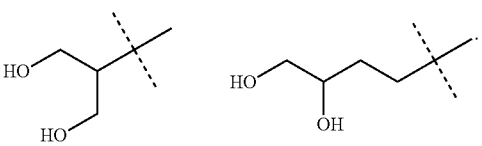

6. The compound of claim 1 wherein $R^5$ is methyl, $X^3$ is other than H and $X^1$ is selected from:

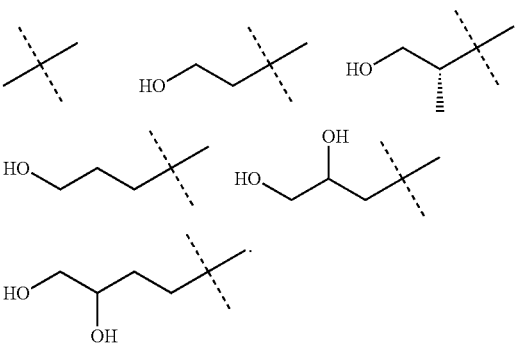

7. The compound of claim 1 wherein W is selected from:

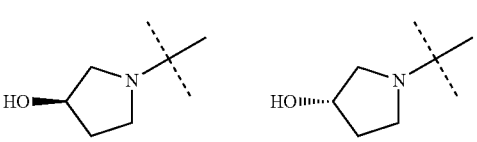

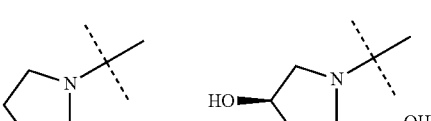

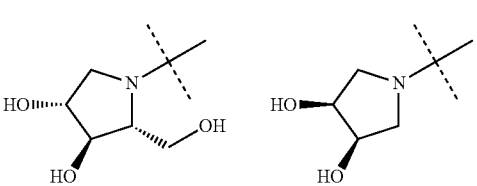

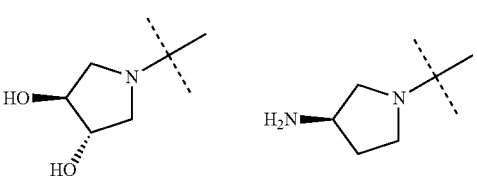

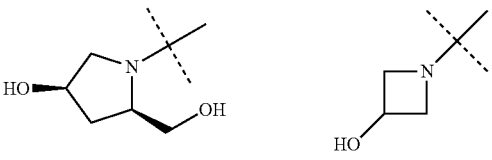

8. The compound of claim 1 wherein $X^2$ is selected from:
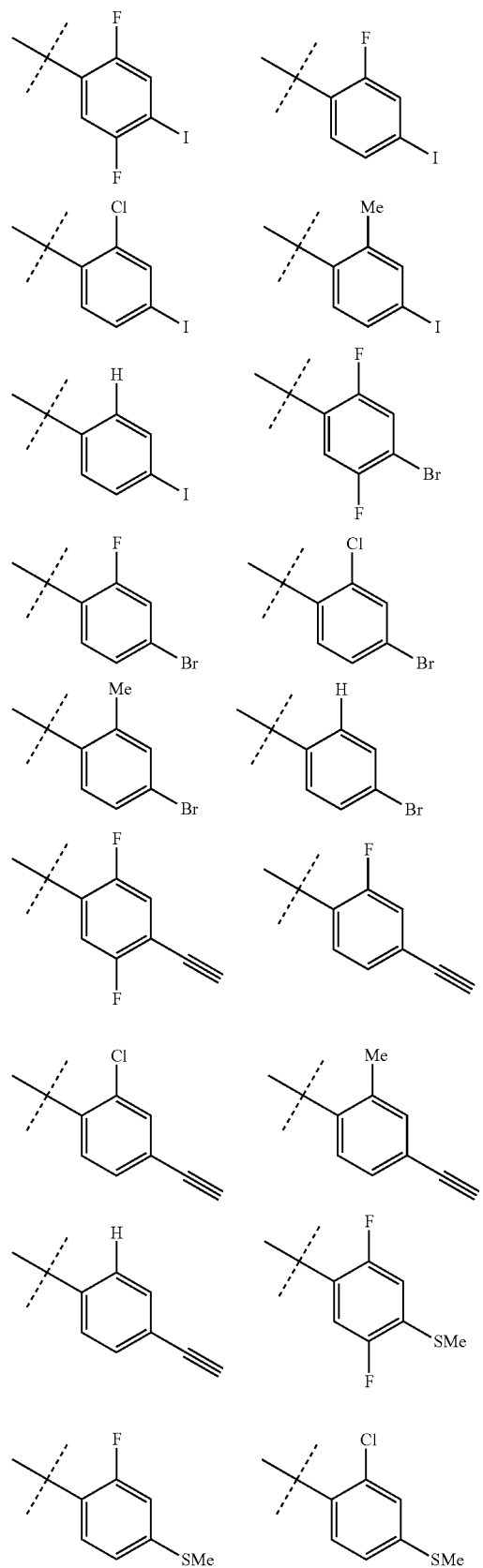
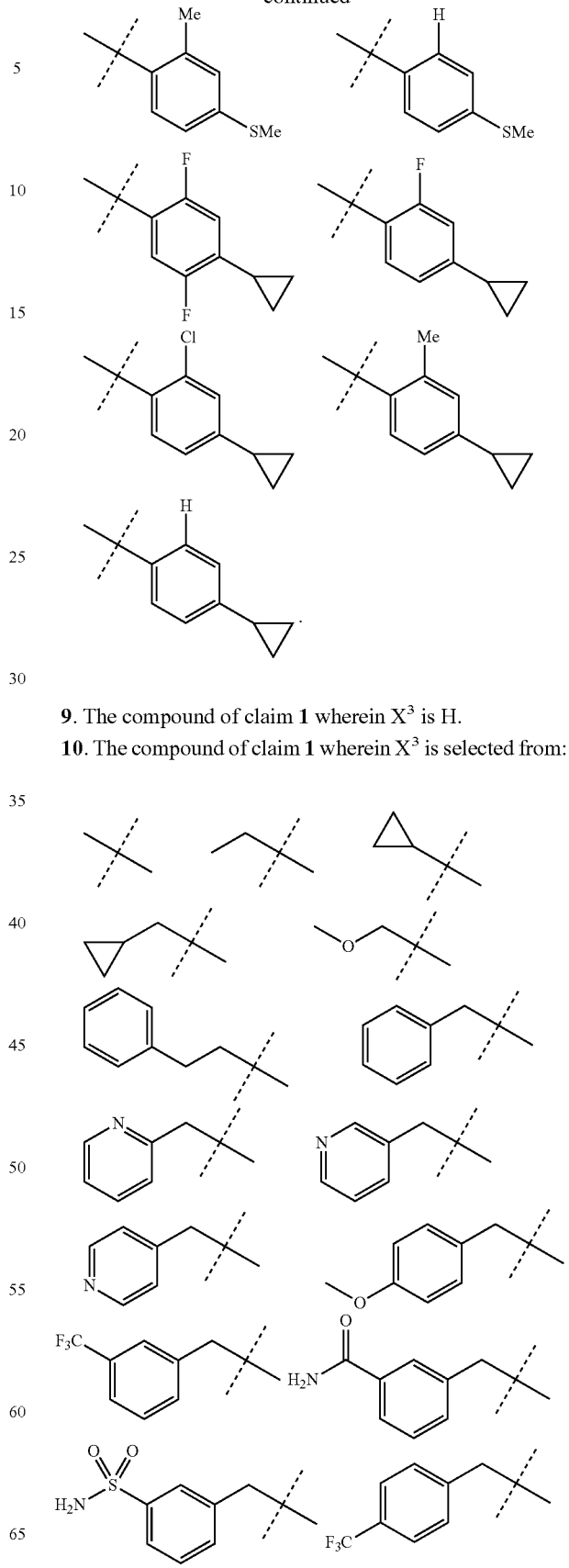
9. The compound of claim 1 wherein $X^3$ is H.
10. The compound of claim 1 wherein $X^3$ is selected from:

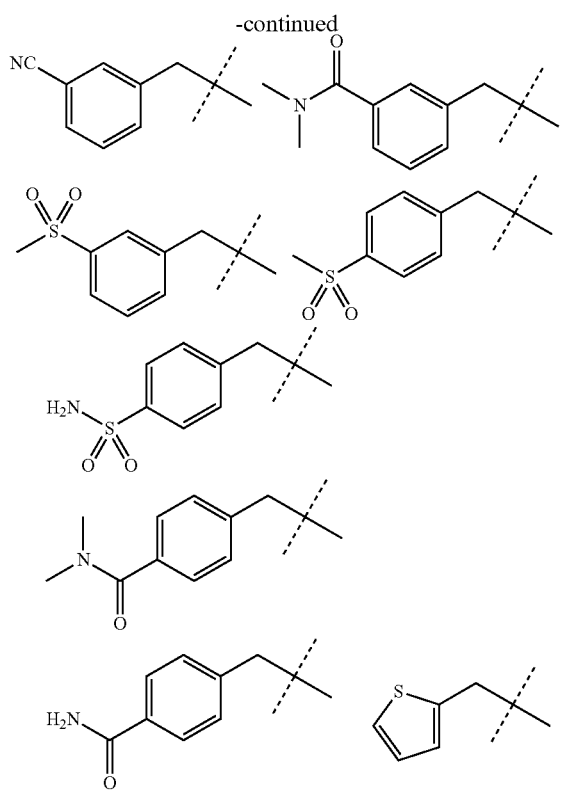

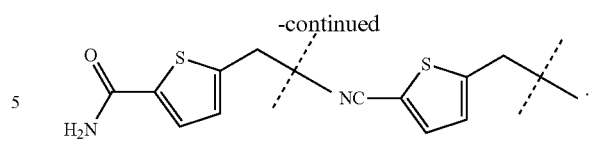

11. The compound of claim 10 wherein $X^3$ is methyl, ethyl or cyclopropyl.

12. The compound of claim 1 wherein $R^1$ is H, Cl, CN, $CF_3$, methyl, $-NH_2$, $-NH(CH_3)$, $-N(CH_3)_2$, $-OH$, or $-OCH_3$.

13. The compound of claim 12 wherein $R^1$ is Cl, CN, $CF_3$, methyl, $-NH_2$, $-NH(CH_3)$, $-N(CH_3)_2$, $-OH$, or $-OCH_3$.

14. The compound of claim 1 wherein $R^3$ is selected from H, F, Cl, $CF_3$, methyl or CN.

15. The compound of claim 14 wherein $R^3$ is H.

16. The compound of claim 1 wherein $R^4$ is selected from H, Cl, Br, Me, Et, F, $CHF_2$, or $CF_3$.

17. The compound of claim 16 wherein $R^4$ is H or F.

18. The compound of claim 1 wherein $R^5$ is H or methyl.

19. The compound of claim 1 wherein $R^6$ is H or methyl.

20. A pharmaceutical composition comprising a compound of claim 1, and a pharmaceutically acceptable carrier.

21. The pharmaceutical composition of claim 20, further comprising an additional chemotherapeutic agent.

22. The pharmaceutical composition of claim 20, further comprising an additional anti-inflammatory agent.

\* \* \* \* \*